(12) United States Patent
Jackson et al.

(10) Patent No.: US 10,188,432 B2
(45) Date of Patent: Jan. 29, 2019

(54) SNAP-ON MULTI-PLANAR AND MONO-PLANAR RECEIVER ASSEMBLIES HAVING INTEGRAL AND MULTI-PART MULTIPURPOSE POSITIONERS FOR PIVOTING AND NON-PIVOTING RETAINERS

(71) Applicant: Roger P. Jackson, Prairie Village, KS (US)

(72) Inventors: Roger P. Jackson, Prairie Village, KS (US); James L. Surber, Kansas City, KS (US)

( * ) Notice: Subject to any disclaimer, the term of this patent is extended or adjusted under 35 U.S.C. 154(b) by 0 days.

(21) Appl. No.: 15/521,163

(22) PCT Filed: Oct. 21, 2015

(86) PCT No.: PCT/US2015/056706
§ 371 (c)(1),
(2) Date: Apr. 21, 2017

(87) PCT Pub. No.: WO2016/065033
PCT Pub. Date: Apr. 28, 2016

(65) Prior Publication Data
US 2017/0333085 A1   Nov. 23, 2017

Related U.S. Application Data

(63) Continuation-in-part of application No. 14/674,517, filed on Mar. 31, 2015, now Pat. No. 9,522,021, and a continuation-in-part of application No. 14/731,064, filed on Jun. 4, 2015, now Pat. No. 9,597,119.

(60) Provisional application No. 62/212,253, filed on Aug. 31, 2015, provisional application No. 62/200,501, filed on Aug. 3, 2015, provisional application No.
(Continued)

(51) Int. Cl.
A61B 17/70 (2006.01)
A61B 17/86 (2006.01)
A61B 90/00 (2016.01)

(52) U.S. Cl.
CPC ........ *A61B 17/7037* (2013.01); *A61B 17/702* (2013.01); *A61B 17/7035* (2013.01); *A61B 17/7038* (2013.01); *A61B 17/863* (2013.01); *A61B 17/8605* (2013.01); *A61B 17/864* (2013.01); *A61B 2090/037* (2016.02)

(58) Field of Classification Search
CPC .................................................. A61B 17/7038
See application file for complete search history.

(56) References Cited

U.S. PATENT DOCUMENTS 9,492,204 B2 * 11/2016 Biedermann ...... A61B 17/7035
9,707,013 B2 * 7/2017 Rezach .............. A61B 17/7037
(Continued)

*Primary Examiner* — Jan Christopher Merene
(74) *Attorney, Agent, or Firm* — Polsinelli PC

(57) ABSTRACT

A receiver subassembly adapted to couple with a universal shank to form a bone anchor assembly. The universal shank having an integral upper capture structure with opposed spaced apart flat side surfaces. The receiver subassembly including a receiver including a distal opening for bottom loading of the capture structure of the universal shank there-through. The receiver supporting a retainer and a positioner within the receiver. The positioner supporting a position of the retainer within the receiver. The retainer configured to couple with the capture structure when the capture structure extends at least partially through the distal opening.

24 Claims, 67 Drawing Sheets

Related U.S. Application Data

62/200,491, filed on Aug. 3, 2015, provisional application No. 62/194,955, filed on Jul. 21, 2015, provisional application No. 62/137,707, filed on Mar. 24, 2015, provisional application No. 62/137,713, filed on Mar. 24, 2015, provisional application No. 62/078,154, filed on Nov. 11, 2014, provisional application No. 62/078,173, filed on Nov. 11, 2014, provisional application No. 62/066,813, filed on Oct. 21, 2014, provisional application No. 62/066,806, filed on Oct. 21, 2014.

(56) References Cited

U.S. PATENT DOCUMENTS

| | | | |
|---|---|---|---|
| 2011/0098755 A1* | 4/2011 | Jackson | A61B 17/7008 606/305 |
| 2012/0035670 A1* | 2/2012 | Jackson | A61B 17/7032 606/305 |
| 2012/0209336 A1* | 8/2012 | Jackson | A61B 17/7032 606/305 |
| 2015/0173816 A1* | 6/2015 | Biedermann | A61B 17/8605 606/308 |

* cited by examiner

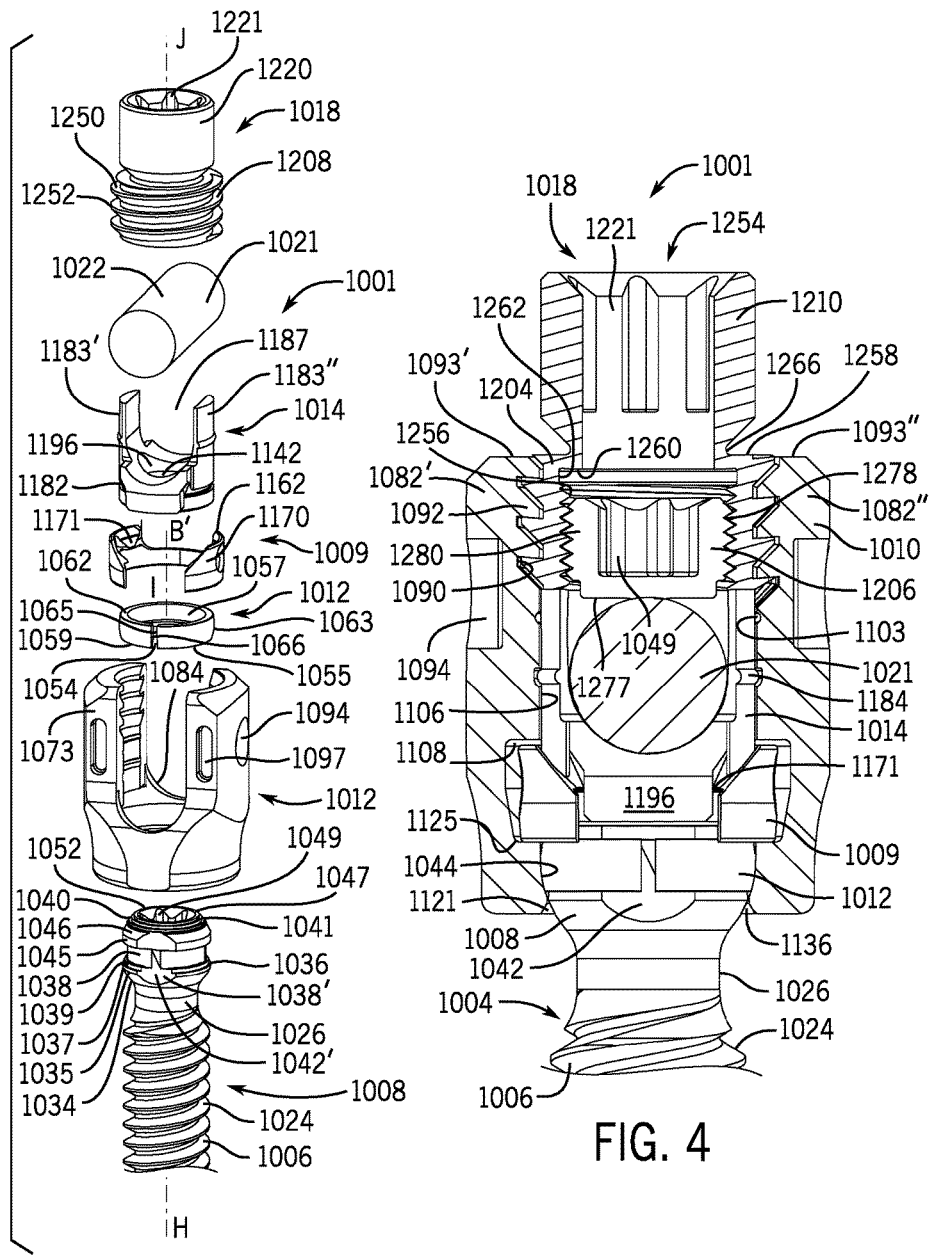

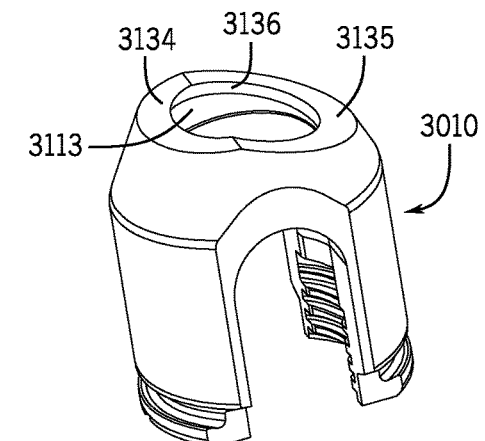
FIG. 8
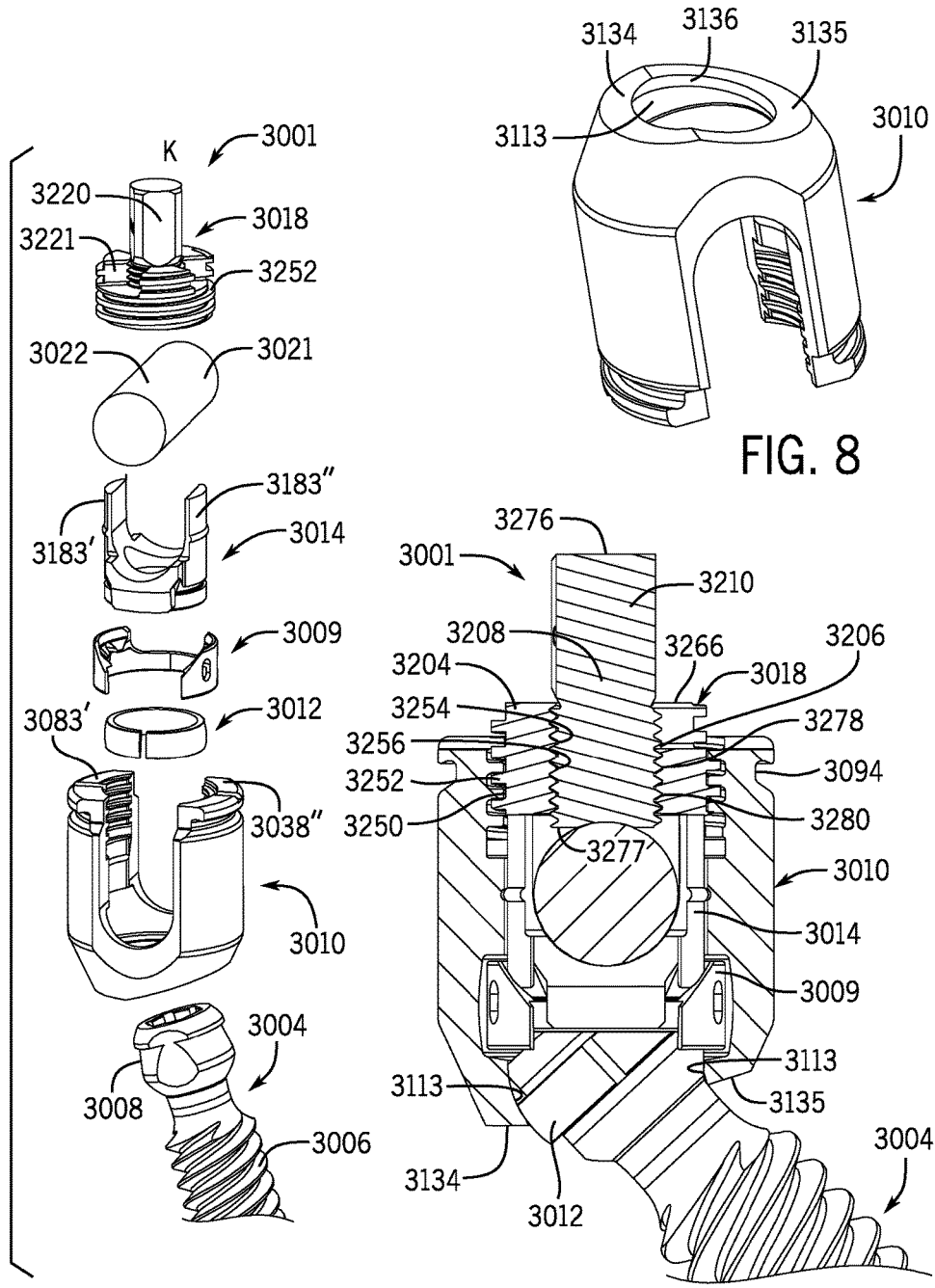
FIG. 7
FIG. 9

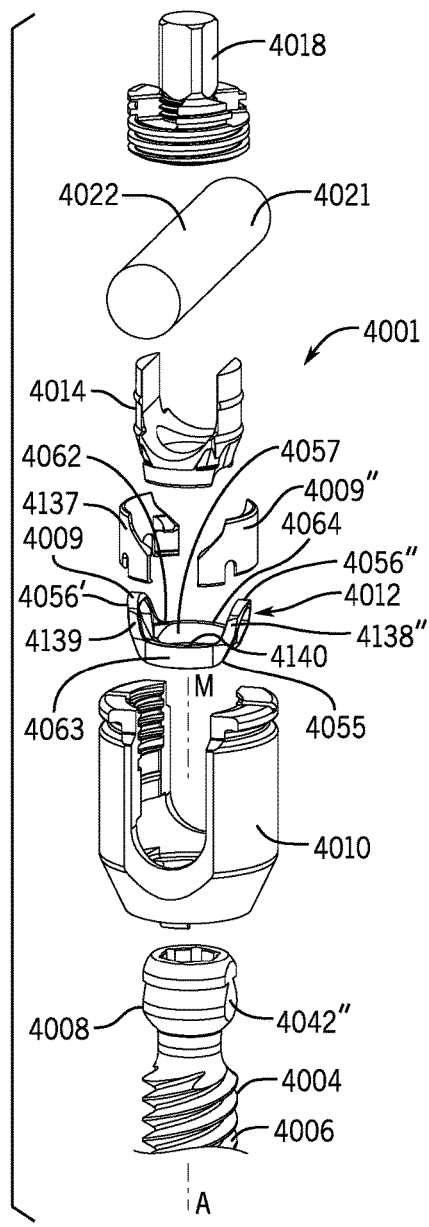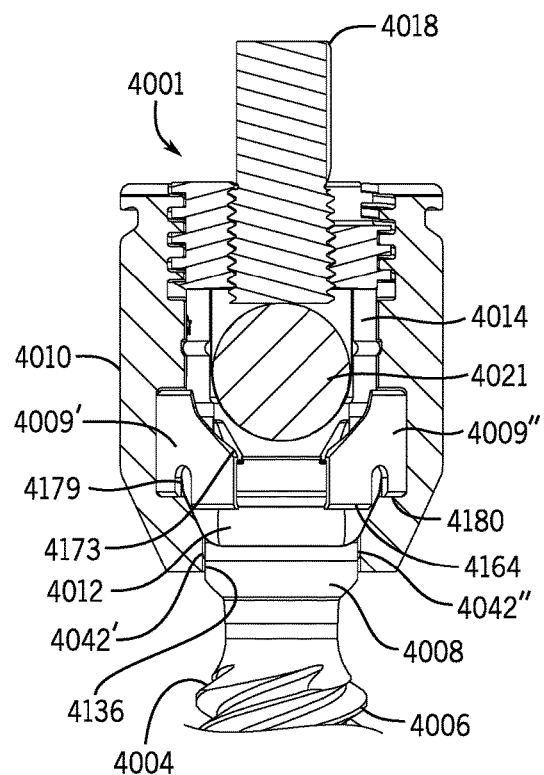
FIG. 10
FIG. 11

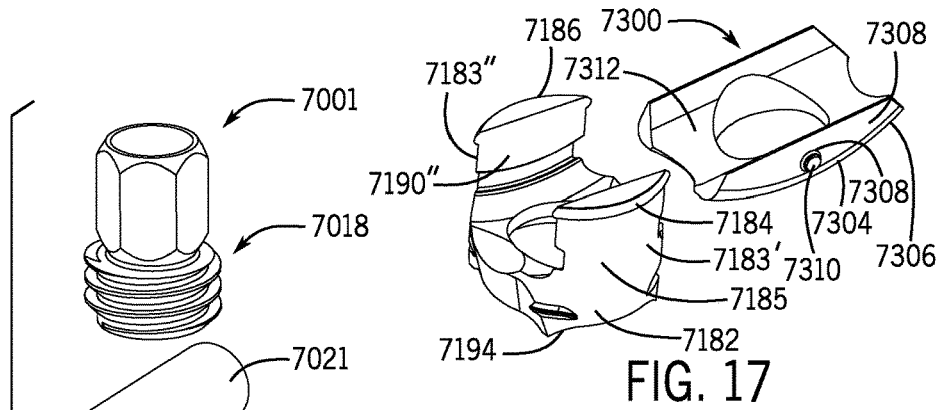
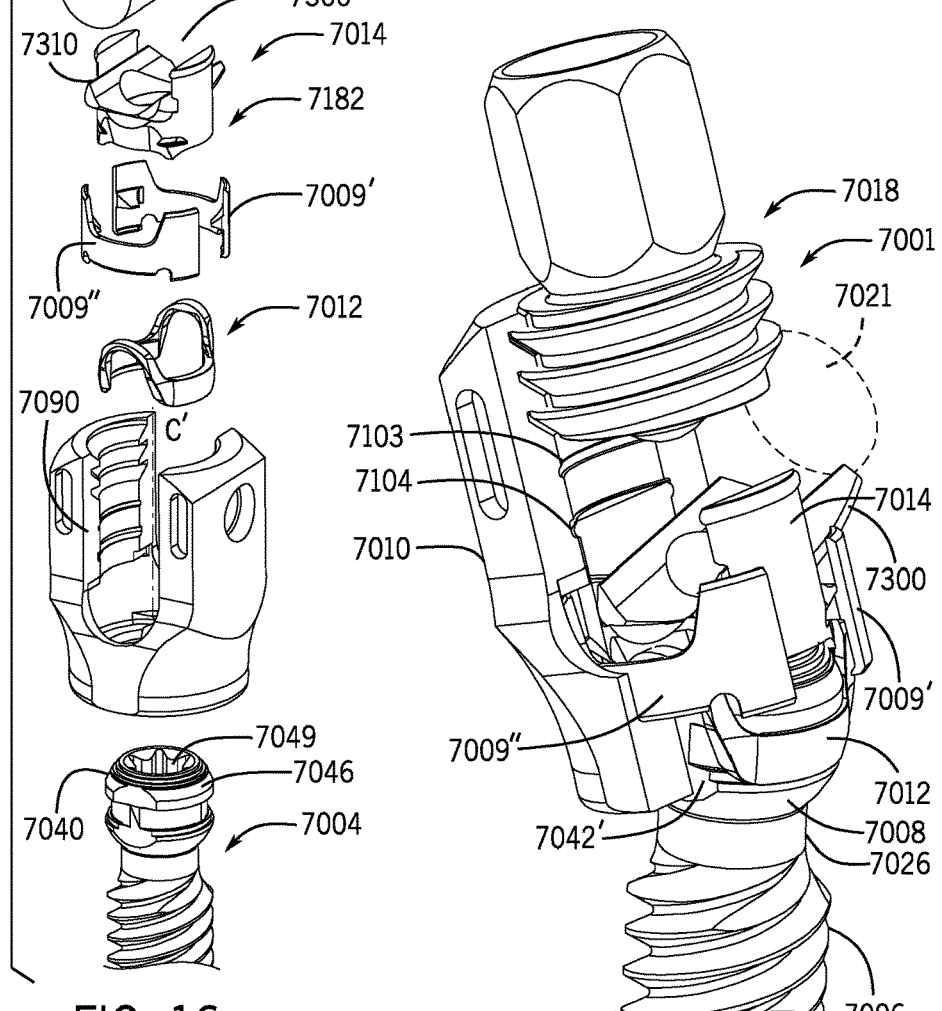

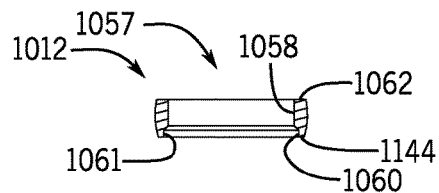
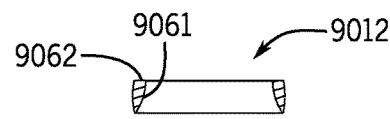
FIG. 20
FIG. 22
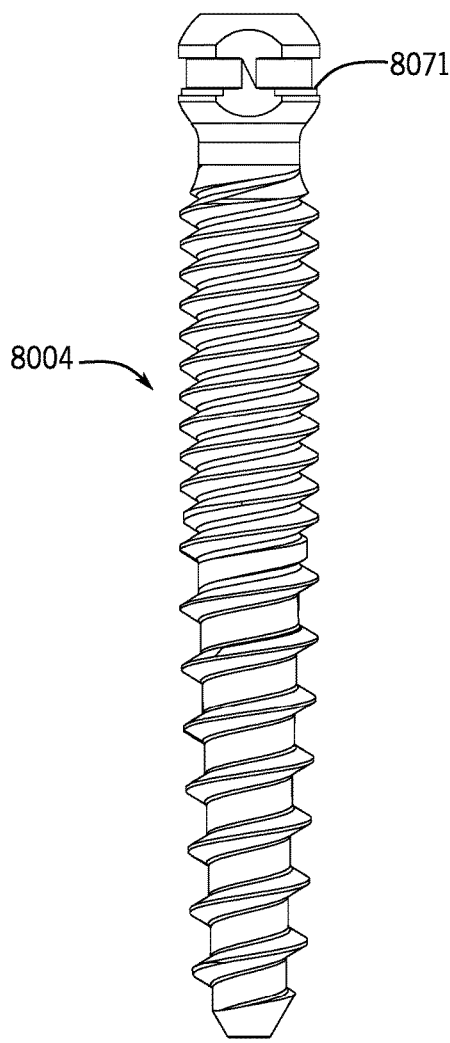
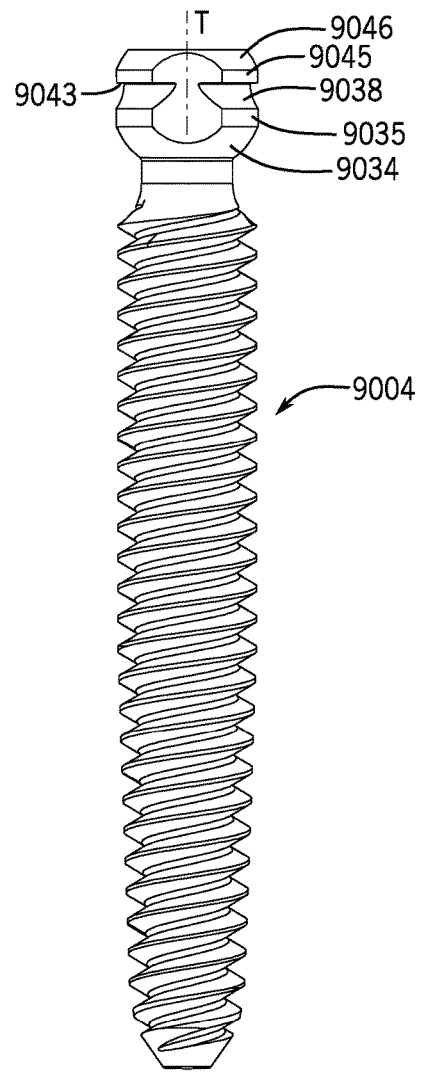
FIG. 19
FIG. 21

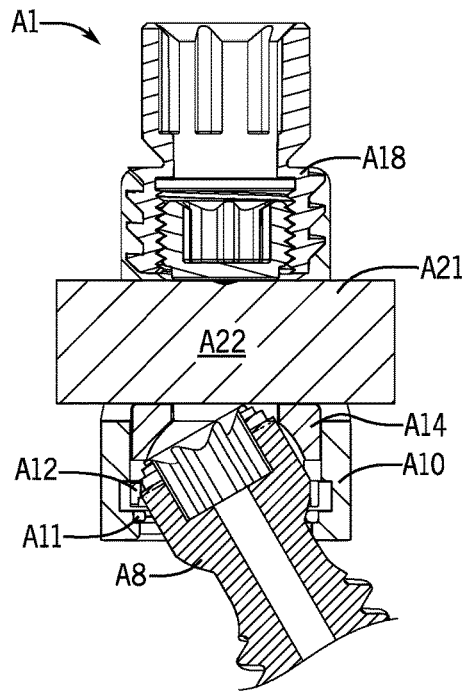
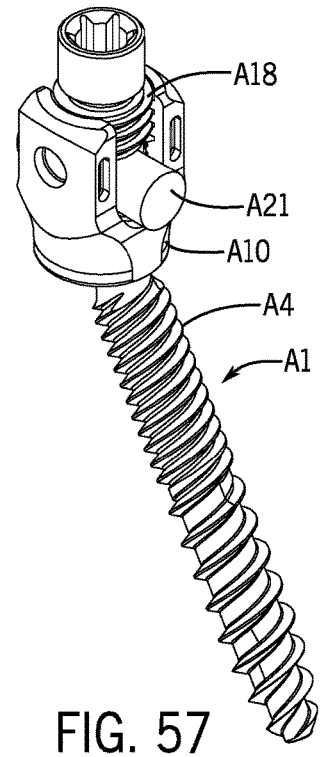
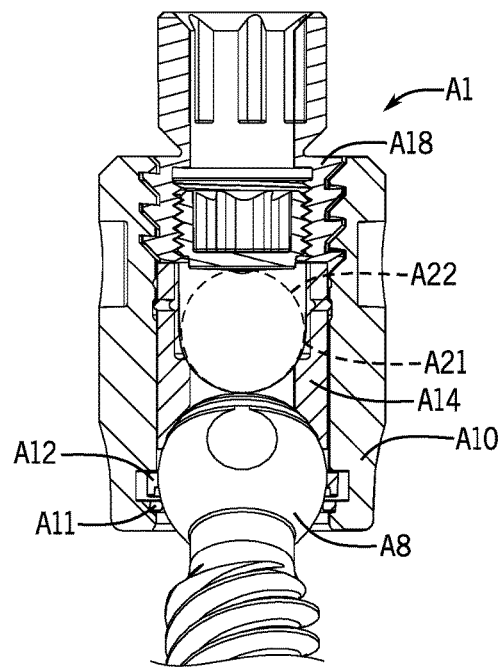
FIG. 58
FIG. 57
FIG. 59

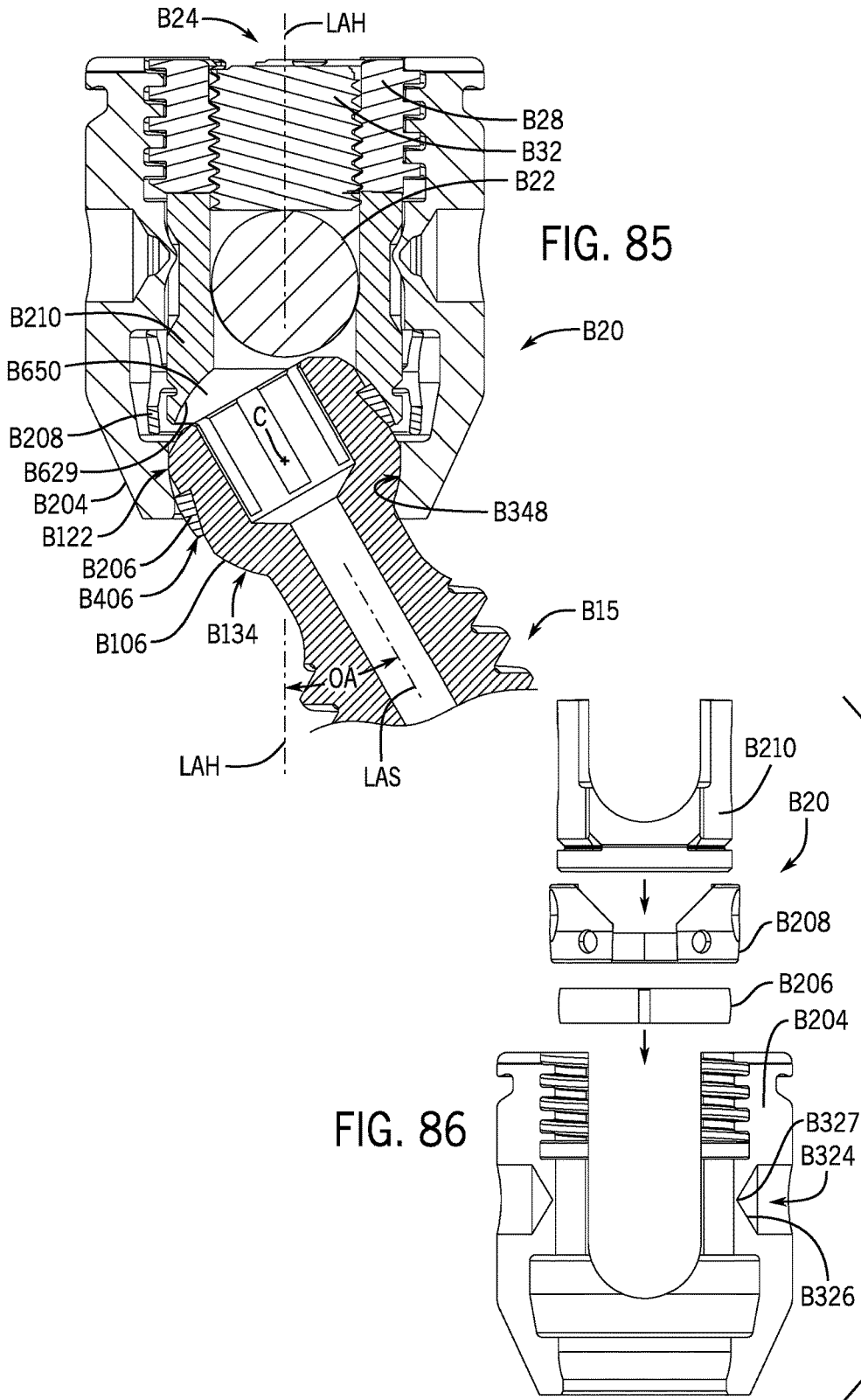

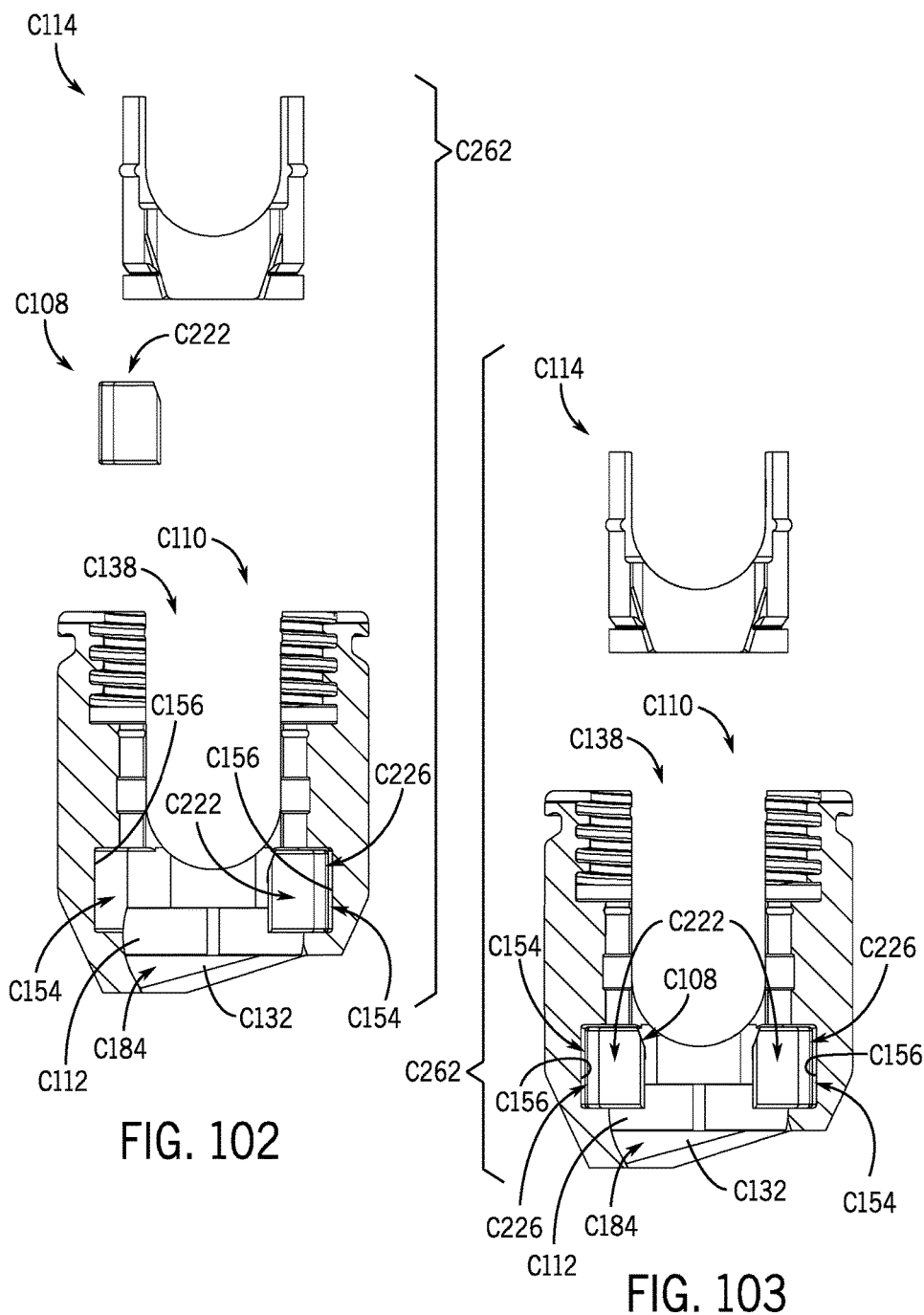

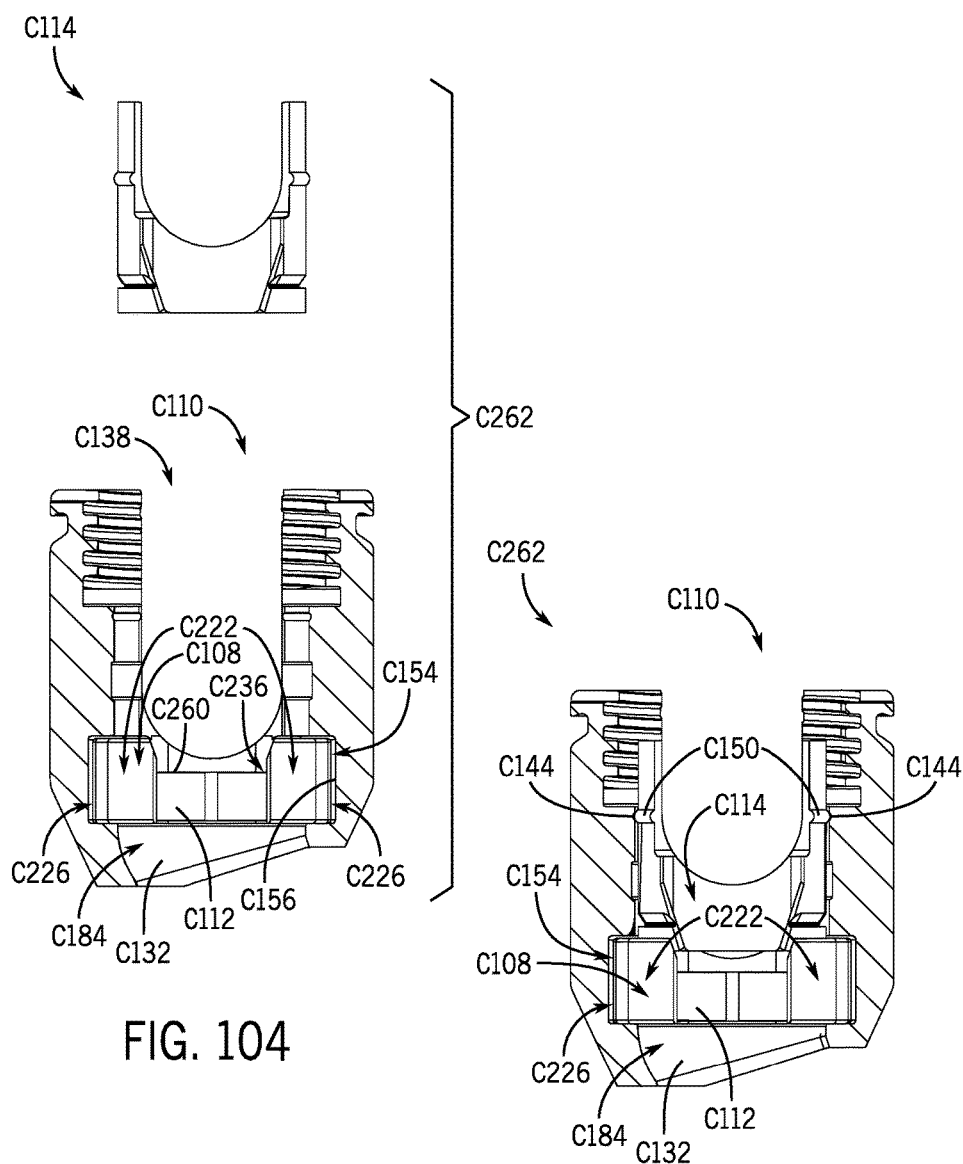

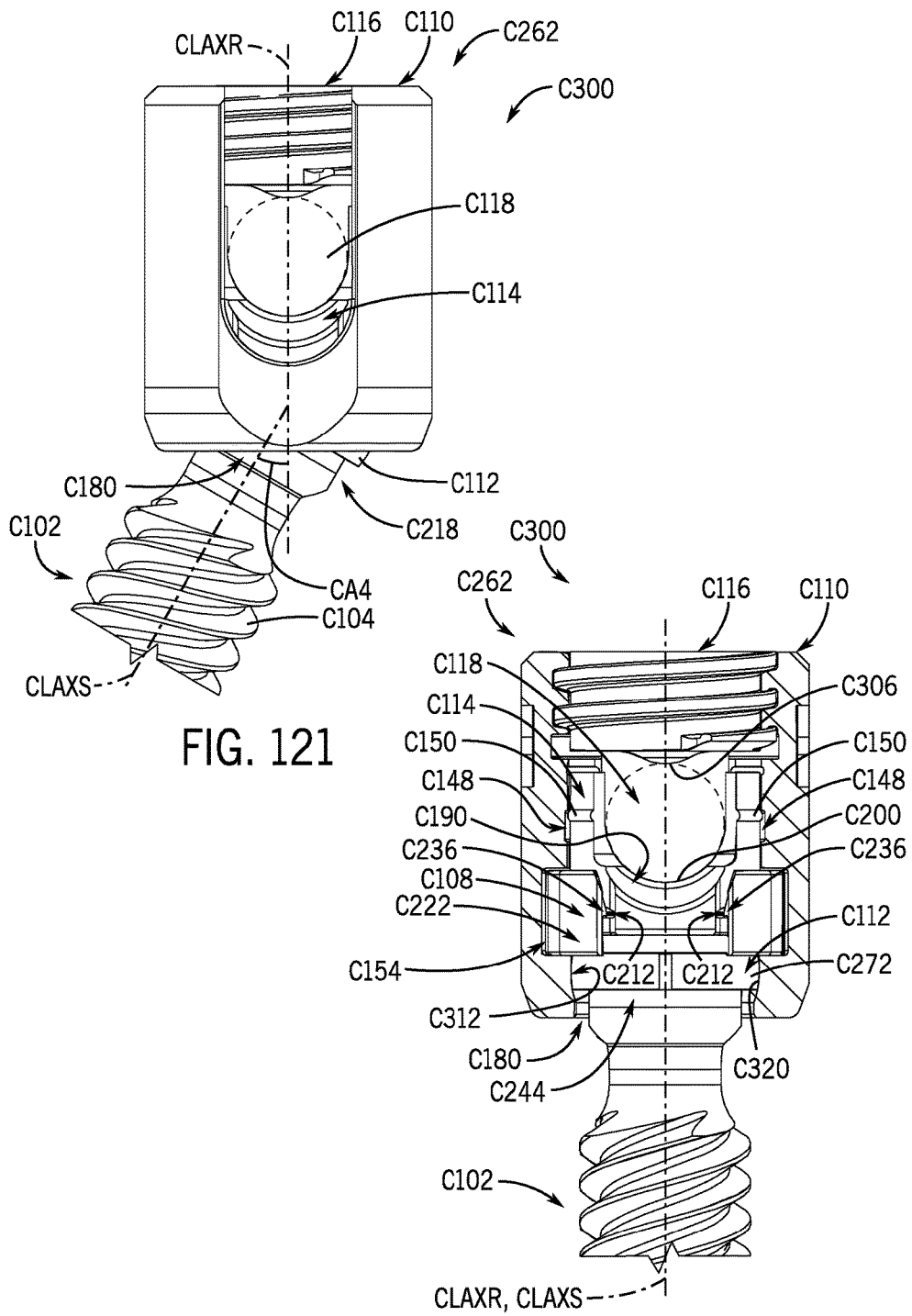

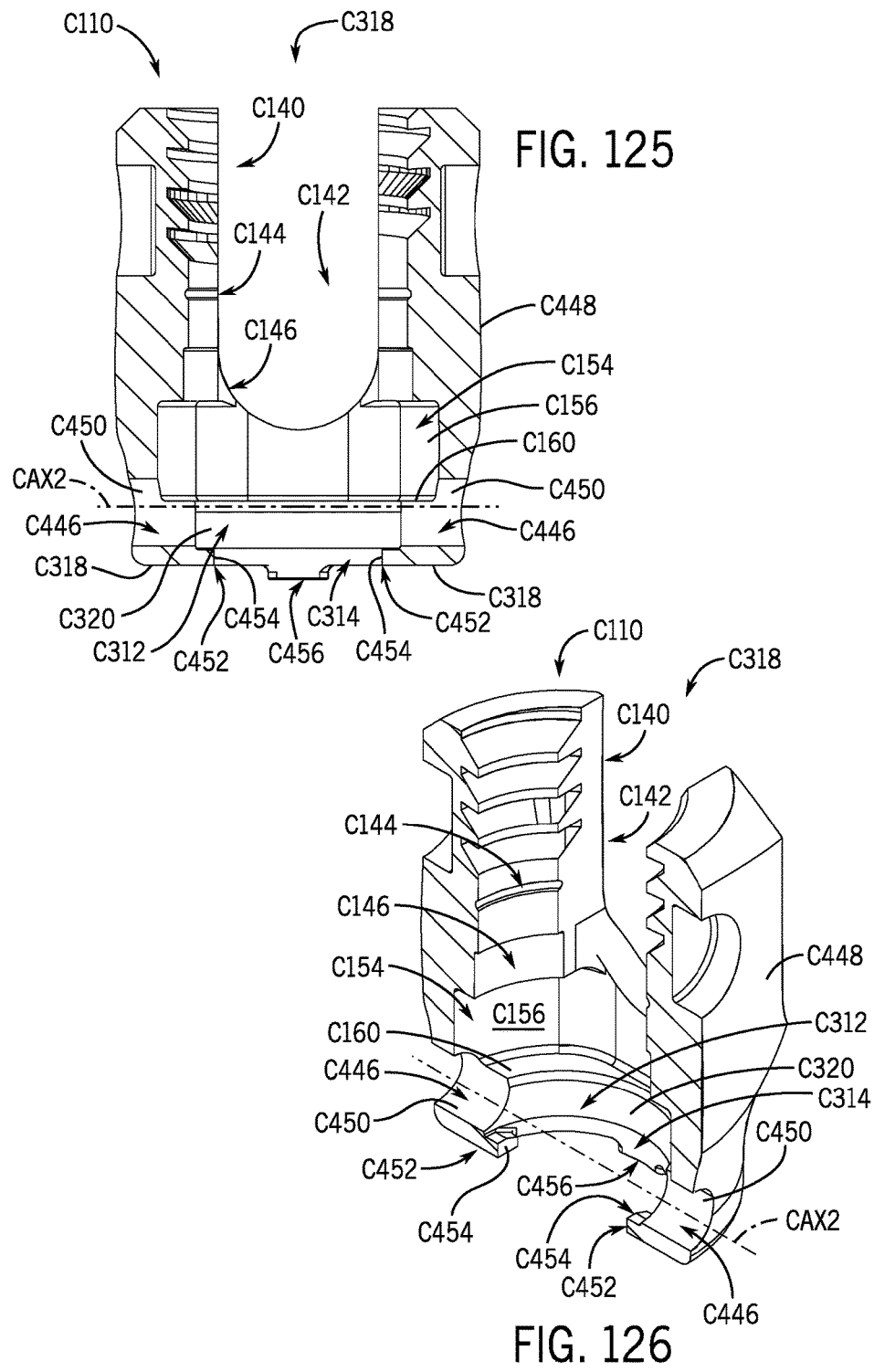

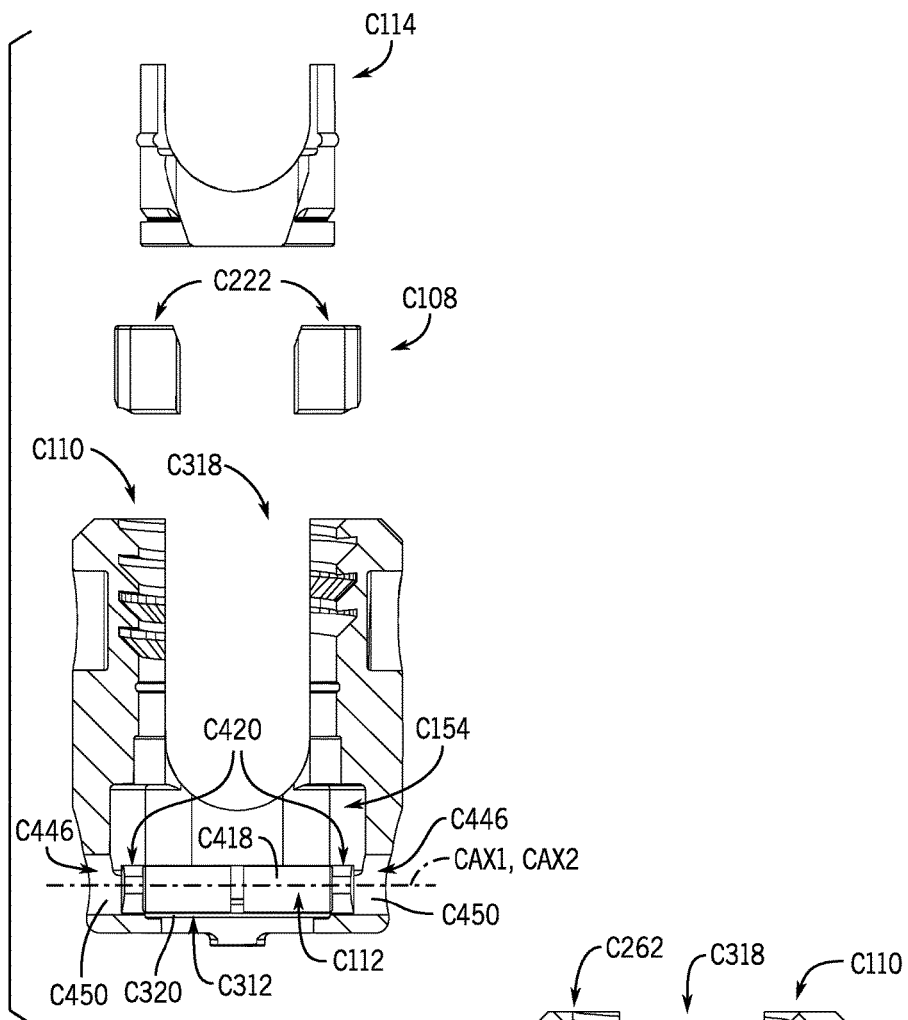
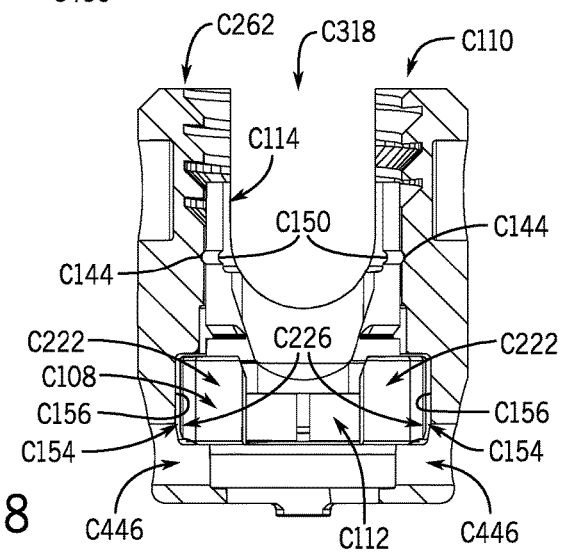
FIG. 127
FIG. 128

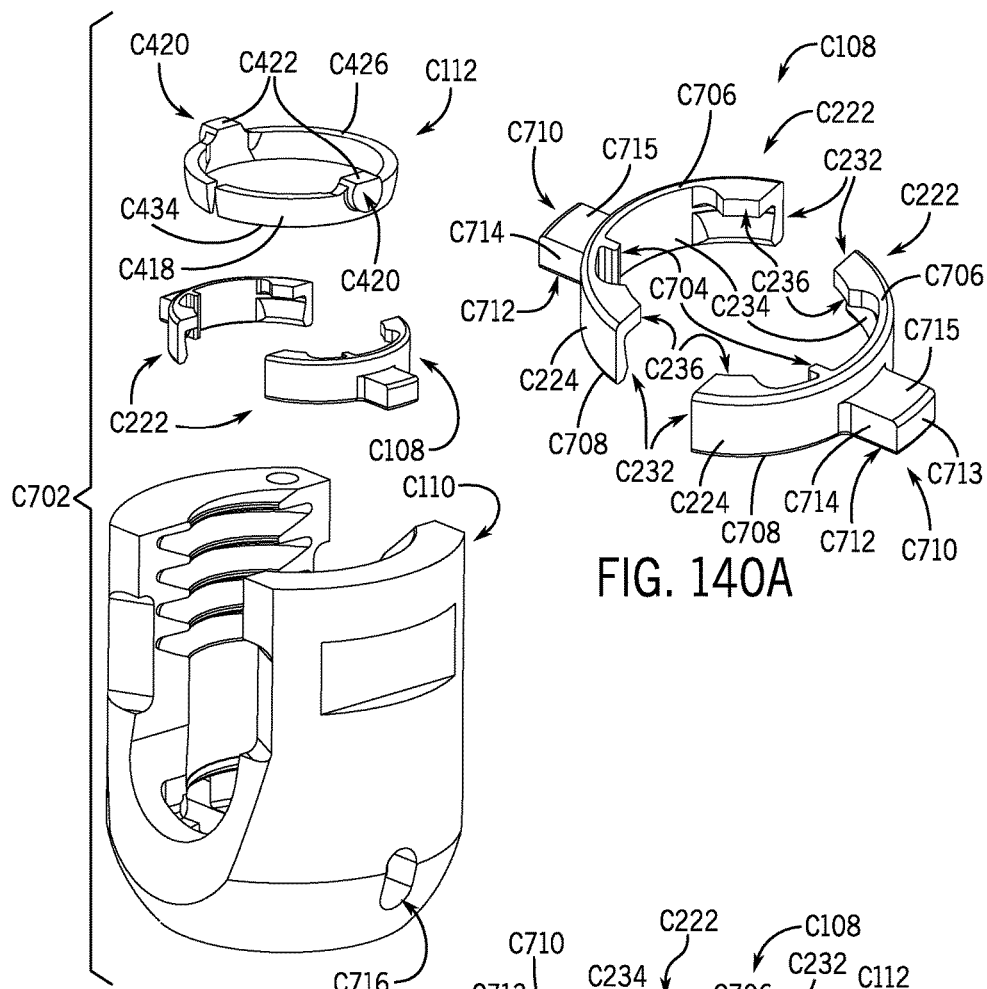
FIG. 140A
FIG. 139
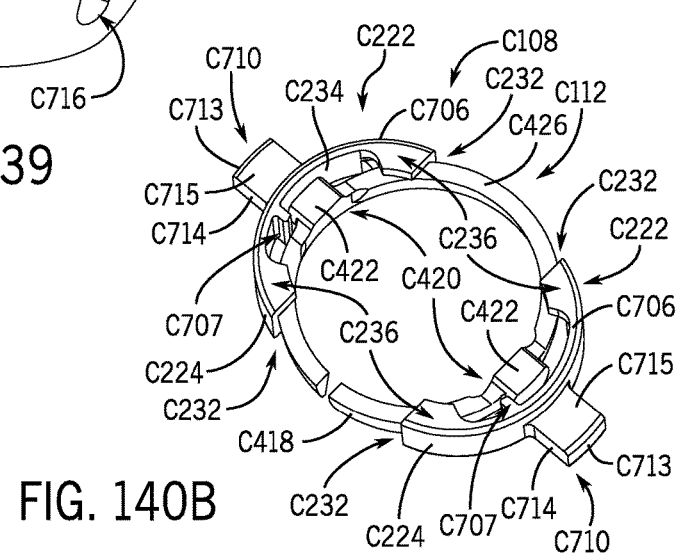
FIG. 140B

SNAP-ON MULTI-PLANAR AND MONO-PLANAR RECEIVER ASSEMBLIES HAVING INTEGRAL AND MULTI-PART MULTIPURPOSE POSITIONERS FOR PIVOTING AND NON-PIVOTING RETAINERS

CROSS-REFERENCE TO RELATED APPLICATIONS

This application is a national stage entry of PCT Application No. PCT/US2015/056706, filed Oct. 21, 2015.

PCT Application No. PCT/US2015/056706 claims priority to and the benefit of U.S. Provisional Patent Application No. 62/194,955, filed Jul. 21, 2015; titled "BONE ANCHOR ASSEMBLIES HAVING NON -PIVOTING RETAINERS AND PIVOTING SHANKS, SOME WITH PIVOTING RETAINERS," and is hereby incorporated by reference in its entirety into the present application.

PCT Application No. PCT/US2015/056706 also claims priority to and the benefit of U.S. Provisional Patent Application No. 62/137,713, filed Mar. 24, 2015; titled "BONE ANCHOR HAVING A SNAP-FIT ASSEMBLY COUPLING AN ANCHOR HEAD TO AN ANCHOR SHANK," and is hereby incorporated by reference in its entirety into the present application.

PCT Application No. PCT/US2015/056706 also claims priority to and the benefit of U.S. Provisional Patent Application No. 62/137,707, filed Mar. 24, 2015; titled "BONE ANCHOR HAVING A SNAP-FIT ASSEMBLY COUPLING AN ANCHOR HEAD TO AN ANCHOR SHANK," and is hereby incorporated by reference in its entirety into the present application.

PCT Application No. PCT/US2015/056706 also claims priority to and the benefit of U.S. Provisional Patent Application No. 62/078,173, filed Nov. 11, 2014; titled "BONE ANCHOR HAVING A SNAP-FIT ASSEMBLY COUPLING AN ANCHOR HEAD TO AN ANCHOR SHANK," and is hereby incorporated by reference in its entirety into the present application.

PCT Application No. PCT/US2015/056706 also claims priority to and the benefit of U.S. Provisional Patent Application No. 62/078,154, filed Nov. 11, 2014; titled "BONE ANCHOR HAVING A SNAP-FIT ASSEMBLY COUPLING AN ANCHOR HEAD TO AN ANCHOR SHANK," and is hereby incorporated by reference in its entirety into the present application.

PCT Application No. PCT/US2015/056706 also claims priority to and the benefit of U.S. Provisional Patent Application No. 62/066,813, filed Oct. 21, 2014; titled "POLYAXIAL PEDICLE SCREW HAVING A SNAP-FIT ASSEMBLY COUPLING A SCREW HEAD TO A SCREW SHANK," and is hereby incorporated by reference in its entirety into the present application.

PCT Application No. PCT/US2015/056706 also claims priority to and the benefit of U.S. Provisional Patent Application No. 62/066,806, filed Oct. 21, 2014; titled "POLYAXIAL PEDICLE SCREW HAVING A SNAP-FIT ASSEMBLY COUPLING A SCREW HEAD TO A SCREW SHANK," and is hereby incorporated by reference in its entirety into the present application.

PCT Application No. PCT/US2015/056706 also claims priority to and the benefit of U.S. Provisional Patent Application No. 62/200,491, filed Aug. 3, 2015; titled "MODULAR MULTI-FUNCTIONAL BONE ANCHOR RECEIVER ASSEMBLIES HAVING PRE-LOADED PIVOTING RETAINERS FOR CONNECTING WITH UNIVERSAL SHANK HEADS HAVING CYLINDRICAL, CONICAL, AND CURVATE CAPTURE STRUCTURES," and is hereby incorporated by reference in its entirety into the present application.

PCT Application No. PCT/US2015/056706 also claims priority to and the benefit of U.S. Provisional Patent Application No. 62/200,501, filed Aug. 3, 2015; titled "MODULAR MULTI-FUNCTIONAL BONE ANCHOR RECEIVER ASSEMBLIES HAVING NON-PIVOTING RETAINERS FOR CONNECTING WITH A UNIVERSAL SHANK HEAD," and is hereby incorporated by reference in its entirety into the present application.

PCT Application No. PCT/US2015/056706 also claims priority to and the benefit of U.S. Provisional Patent Application No. 62/212,253, filed Aug. 31, 2015; titled "BONE ANCHOR PIVOTING RECEIVER ASSEMBLIES WITH NON-PIVOTING RETAINER ALIGNED AND RELEASED BY A MULTI-PURPOSE POSITIONER," and is hereby incorporated by reference in its entirety into the present application.

PCT Application No. PCT/US2015/056706 is also a continuation-in-part of U.S. patent application Ser. No. 14/674,517, filed on Mar. 31, 2015; titled "POLYAXIAL BONE ANCHOR WITH RETAINER WITH NOTCH FOR MONO-AXIAL MOTION," and is hereby incorporated by reference in its entirety into the present application.

PCT Application No. PCT/US2015/056706 is also a continuation-in-part of U.S. patent application Ser. No. 14/731,064, filed Jun. 4, 2015; titled "POLYAXIAL BONE ANCHOR WITH POLYMER SLEEVE," and is hereby incorporated by reference in its entirety into the present application.

This application is a national stage entry of PCT Application No. PCT/US2015/056706, filed Oct. 21, 2015.

The following applications are related to the present application and hereby incorporated by reference in their entireties into the present application: U.S. patent application Ser. No. 14/181,998, filed on Feb. 17, 2014, titled "SAGITTAL ANGLE SCREW WITH INTEGRAL SHANK AND RECEIVER"; U.S. Provisional Patent Application No. 61/456,163, filed Nov. 2, 2010, titled "POLYAXIAL BONE ANCHOR WITH POP-ON SHANK AND PIVOTABLE RETAINER"; U.S. Provisional Patent Application No. 62/007,616, filed Jun. 4, 2014, titled "POLYAXIAL BONE ANCHOR WITH POLYMER SLEEVE"; U.S. Provisional Patent Application No. 61/336,911, filed Jan. 28, 2010, titled "POLYAXIAL BONE ANCHOR WITH NON-PIVOTABLE SNAP-ON SPRING RING AND FRICTION FIT INSERT"; U.S. patent application Ser. No. 13/317,969, filed Nov. 1, 2011, titled "POLYAXIAL BONE ANCHOR WITH POP-ON SHANK AND PIVOTABLE RETAINER"; U.S. patent application Ser. No. 14/164,882, filed on Jan. 27, 2014, titled "POLYAXIAL BONE ANCHOR WITH RECEIVER WITH SPHERIC EDGE FOR FRICTION FIT"; U.S. patent application Ser. No. 11/140,343, filed on May. 27, 2005, titled "POLYAXIAL BONE SCREW WITH SHANK ARTICULATION PRESSURE INSERT AND METHOD"; U.S. patent application Ser. No. 12/148,465, filed on Apr. 18, 2008, titled "DYNAMIC FIXATION ASSEMBLIES WITH PRE-TENSIONED CORD SEGMENTS"; U.S. patent application Ser. No. 13/573,516, filed Sep. 19, 2012, titled "POLYAXIAL BONE ANCHOR WITH POP-ON SHANK AND WINGED INSERT WITH FRICTION FIT COMPRESSIVE COLLET"; U.S. patent application Ser. No. 13/694,954, filed Jan. 22, 2013, titled "POLYAXIAL BONE ANCHOR WITH POP-ON SHANK AND WINGED INSERT WITH FRICTION FIT COM- PRESSIVE COLLET"; and, U.S. patent application Ser. No. 14/061,393, filed on Oct. 2013, titled "POLYAXIAL BONE ANCHOR WITH POP-ON MULTI-THREAD SHANK, SOME WITH DIAMETRIC INTERFERENCE FIT INSERTS."

TECHNICAL FIELD

The present disclosure relates to medical apparatus and methods. More specifically, the present disclosure relates to pivoting bone anchors and associated methods of manufacture and use.

BACKGROUND

Bone screws and related anchors of various types have been used for supporting rods and other elongate members in spinal surgery which are herein considered as a common group.

Bone screws are utilized in many types of spinal surgery in order to secure various implants to vertebrae along the spinal column for the purpose of stabilizing and/or adjusting spinal alignment. Although both closed-ended and open-ended bone screws are both used in spinal surgery, open-ended screws are particularly well suited for connections to rods or soft connecting members and connector arms, due to ease of use, because such rods or connecting members do not need to be passed through a closed bore, but rather can be laid or urged into an open channel within a receiver or head of such a screw.

Typical open-ended bone screws include a threaded shank with a pair of parallel projecting branches or arms which form a yoke with a U-shaped slot or channel to receive a rod. Hooks and other types of connectors, as are used in spinal fixation techniques, may also include similar open ends for receiving rods or portions of other structure.

Open-ended bone screws or anchors of this type may have a fixed or monoaxial head or a pivoting head or so called receiver at one end of the shank. In the fixed bone screws, the head cannot be moved relative to the shank and the rod must be favorably positioned in order for it to be placed within the open head. This is sometimes very difficult or impossible to do. Therefore, open ended bone screws or anchors are commonly preferred. Open-ended bone anchors or screws typically allow for a loose or floppy rotation of the head or receiver about the shank until a desired rotational and/or angular position of the receiver is achieved by fixing such position relative to the shank during a final stage of a medical procedure when a rod or other longitudinal connecting member is inserted into the receiver, followed by a locking screw or other closure.

One example of an open-ended bone screw or anchor is a multiaxial or polyaxial bone screw or anchor. In a multiaxial bone screw or anchor, the head or receiver is positionable in plurality of angular or axial positions about a spherical cone with respect to the shank. The range of angles of the multiaxial bone anchor is limited, in part, by the size of the opening at the bottom of the receiver or head.

Another example of an open-ended bone screw or anchor is a monoplanar or uniplanar bone screw or anchor. In a monoplanar bone screw or anchor, the head or receiver is positionable in plurality of angular or axial positions about a single plane with respect to the shank. The direction and range of angles of the monoplanar bone screw may be limited by the opening at the bottom of the receiver or head or by other structures or components within the receiver.

Some of these open-ended bone anchors with receivers utilize a lower pressure insert positioned within the receiver to transfer locking forces from a rod, longitudinal member, or other structure above the insert to a shank having an integral head, or a separate head or retainer that can pivot with the shank, located below the insert, so as to lock the shank in a fixed angular configuration with respect to the receiver, forming a receiver assembly or receiver subassembly. Again, the receiver assembles or subassemblies can be configured as a polyaxial or uniplanar.

Surgeries to stabilize the spine require a wide range of spinal implants involving these screws, hooks, and connectors. These implants must be available in an extensive array of sizes and shapes to accommodate a given patient's anatomy, pathology, and required procedure. This results in the need for a company to maintain and manage voluminous and expensive inventories and to frequently ship large quantities of implants and instruments across the globe. As a result and to help maintain cost efficiencies, the industry is moving toward more modular spinal systems, wherein the shanks (screw or hooks) that attach to the bone are separate from the head or receiver that connects to an elongate or longitudinal connecting member, such as a rod, positioned along the spine to help support and correct the spinal pathology and/or deformity afflicting the patient.

These modular separate components involving shanks of different sizes and receivers with different functionalities must be able to be easily and securely connected together, either at the company prior to shipping or at the hospital during the actual surgery when the surgical team has finally decided which type, length, and size of implant is needed at a given level in the patient's spine.

The connection of components needs to be quick, easy, and reliable. Generally, a snap-on mechanism is preferred, as opposed to screwing together, for example. With a snap-on approach or mechanism the separate receiver has several parts and is, therefore, a receiver assembly or subassembly when it is shipped from the vendor or manufacturer to the spinal company, or from the spinal company to the hospital.

The receiver assemblies are generally of two types concerning the capture mechanism for snapping on the upper capture portion or structure of the shank. One type has a non-pivoting retainer that holds the shank in the receiver, such that only the shank and not the retainer can pivot with respect to the receiver in one or more planes. The other type has a pivoting retainer that couples with the shank capture structure and pivots with the shank relative to the receiver in one or more planes.

The capture structure at the upper end of the shanks can have different geometries, such as spherical or ball shapes, conical, cylindrical, and curvate shapes, as well as other shapes or geometries. The shank capture structure can include one or more flat sides of surfaces.

The retainers, pivoting or non-pivoting, can also have different geometries, sizes, and shapes. Generally they have a slit of slot, so as to be open, wherein they can be snapped over the shank upper capture portion or structure. This can create some problems or difficulties for the retainers positioned within their receivers, as further discussed herein.

Generally, the receivers have a locking chamber and an expansion chamber for a retainer. These chambers communicate and allow the retainers to move around therein and therebetween. The retainers must be in the expansion chamber, so that they can expand enough to allow the shank capture structure to pass through an opening in the retainers.

Once captured, the retainer and shank must move into the locking chamber where at least the shank can then pivot with respect to the receiver.

If the retainer is allowed, or the receiver assembly is configured so that the retainer can return to the expansion chamber, it is possible the shank could come back out of the receiver, which in certain situations is not desirable.

Another problem with these types of bone anchors or screws is that the retainers can get out of plane or alignment within the receiver chambers. This can make the snap-on procedure difficult or unreliable at times and create problems.

There is a need to have the retainers, pivoting and non-pivoting, stay in alignment within the receiver, and once the shank is captured and the retainer and shank move down into the locking chamber, not have the retainer or the shank be able to go back up within the receiver assembly.

While the aforementioned systems are known in the art, there is a need for additional systems and tools to further advance surgical spinal procedures. Such systems and tools will be discussed herein and may include snap-on, bottom-loaded screws, hooks and other bone anchors that provide advantages over techniques, systems, and other bone anchors known in the art.

SUMMARY

An embodiment according to the disclosure includes: a pivotal bone screw or anchor apparatus or assembly that includes a shank having a capture structure and a first receiver subassembly having a cylindrical bottom opening, so as to allow a shank multi-planar motion and a second receiver subassembly having a bottom opening with radiused sides and adjacent two opposed opposite flat sides, so as to constrict a shank to mono-planar motion. The bone attachment structure is configured to work with a multitude of different receiver structures.

The shank head upper capture portion that cooperates with a retaining structure, and that pivots with flat sides, has at least these configurations for an interface surface: cylindrical, conical, frusto-conical, or curvate.

An embodiment of the disclosure includes a bone anchor assembly according to the disclosure and includes: a shank head having an upper capture portion configured as a partially spherically shaped structure with opposite parallel flat planar surfaces; a pivoting retainer whose function is the capture the upper capture portion within the receiver; a receiver having a centrally aligned lower aperture opening onto a bottom surface thereof, the lower aperture being capable of receiving and capturing the shank head; a compression insert engageable with the shank upper capture portion and located there above, and wherein a positioner or other similar structure stabilizes and controls the position and alignment of the pivoting retainer structure, both vertically and rotationally within the receiver.

The pivoting retainer is envisioned to be ring shaped and is expanded about the shank head upper capture portion and mated against an interface surface, the interface surface being sized and shaped to mate with an internal surface of the pivoting retainer. In some embodiments, the pivotal retainer may include arch extensions or structures on opposite sides thereof, the arch structures being substantially planar on a respective internal surface thereof and are angled away from a central axis, such that the shank and pivoting retainer in combination create a substantially spherical outer surface.

In several of the illustrated embodiments the upper cylindrical surface has a smaller diameter than the lower cylindrical surface.

In the illustrated embodiments the positioner is in spaced relation with respect to the shank head, but it is foreseen that the positioner and shank may engage in some embodiments.

It is envisioned that at least one of the receiver interior, the pivotal retainer, the positioner, the interface surface, and the outer surface of the shank includes a surface treatment, such as knurled, scored, roughened, grit blasted, and textured.

It is foreseen that the bone anchor assembly of the present disclosure may include bone screws, bone hooks, and other bone attachment structures, such as clamps and ligaments, in both monoplanar and multiplanar configurations.

It is foreseen that the lower compression insert has at least one surface engaging the receiver to block axial rotation therebetween, and wherein the insert can provide either a friction fit or floppy fit when the shank is in an unlocked orientation with respect to the receiver.

In some of the illustrated embodiments, the insert can be bottom loaded into the receiver and includes an outer structure that is sized and shaped to mate with a receiver aperture or groove located on a receiver internal surface, such that when the insert outer structure is mated with the receiver aperture, the insert is captured with respect to the receiver, and prevented from further moving up and down within the receiver until a force is applied to move the insert down.

In some of the illustrated embodiments, the insert further includes a saddle. The saddle allows the rod to be manipulated along a sagittal plane. It is foreseen that this insert will work with either mono-planar receiver subassemblies or multi-planar receiver subassemblies.

In an embodiment, a bone anchor assembly is provided. The bone anchor assembly includes a universal shank having an integral upper capture structure with opposed spaced apart flat sides. The bone anchor assembly also includes first and second receiver subassemblies. Each subassembly has a pre-loaded pivoting retainer within the respective receiver subassembly. Each pivoting retainer is configured to mate with the capture structure and pivot with the shank in combination with respect to the respective receiver subassembly. Each receiver subassembly includes a lower opening for bottom loading of the shank capture structure therethrough. The first receiver subassembly allows for multi-planar motion of the shank with respect to the first receiver member. The second receiver subassembly allows for motion of the shank about a single plane with respect to the second receiver member. The capture structure of the shank is equally capable of being captured in a selected one of the first and second receiver subassemblies.

In an embodiment, a bone anchor assembly is provided. The bone anchor assembly includes a universal shank having an integral upper capture structure with opposed spaced apart flat sides. The capture structure is equally capable of being snapped into at least first and second receiver subassemblies. Each receiver subassembly has first and second receiver members, each with a pre-loaded pivoting retainer within the respective receiver members. Each pivoting retainer is configured to mate with the capture structure and pivot with the shank in combination with respect to the respective receiver subassembly. The bone anchor assembly also includes a lower opening for bottom loading of the shank capture structure there-through. The first receiver subassembly allows for multi-planar motion of the shank with respect to the first receiver member. The second receiver subassembly allows for motion of the shank about a single plane with respect to the second receiver member.

In an embodiment, the pivoting retainer of the second receiver member includes structure so as to limit the motion of the shank to a single plane.

In an embodiment, each pivoting retainer is expanded about the shank upper portion and mated within an interface surface. The interface surface is sized and shaped to mate with an internal surface of the pivoting retainer.

In an embodiment, the interface surface is cylindrically shaped.

In an embodiment, the interface surface is conically shaped, such that the interface surface has a larger diameter near a top of the shank.

In an embodiment, the interface surface is frusto-conically shaped, such that the interface surface has a smaller diameter near a top of the shank.

In an embodiment, the interface surface is curved.

In an embodiment, at least one of the first and second receiver subassemblies further includes a positioner being positioned within a respective receiver expansion chamber, and located about the respective pivoting retainer.

In an embodiment, the shank is in spaced relation with respect to the positioner.

In an embodiment, at least one of the pivotal retainers and the positioner includes a surface that has been at least one of knurled, scored, roughened, grit blasted, and textured.

In an embodiment, the pivoting retainer of the second receiver member is a ring with opposite arch structures.

In an embodiment, at least one of the first and second receiver subassemblies further includes a compression insert in engagement with the shank upper portion and located above the shank upper portion.

In an embodiment, the insert has at least one surface engaging the shank in a friction fit manner when the shank is in an unlocked orientation with respect to the receiver.

In an embodiment, the insert includes an outer structure that is sized and shaped to mate with a respective receiver aperture located on a respective retainer internal surface, such that when the insert outer structure is mated with the respective receiver aperture, the insert is captured with respect to the respective receiver member.

In an embodiment, the first receiver subassembly includes a first positioner and the second receiver subassembly further including a second positioner.

In an embodiment, the second receiver subassembly further includes an insert having a separate saddle. The saddle is configured to allow a rod to be fixed in a plurality of angles about a sagittal plane.

To solve these problems, a multi-functional or multi-purpose positioner component or member has been disclosed herein to hold the retainer in alignment both vertically and rotationally within the receiver, typically in the expansion chamber prior to snapping on the shank. Thereafter, the positioner prevents the retainer from returning to the expansion chamber after it enters the locking chamber.

Embodiments of the present disclosure are directed to: a bone anchor assembly comprising: a shank having a bone attachment structure and an upper capture portion; a receiver having a centrally aligned lower aperture opening onto a bottom surface thereof, the lower aperture cooperating to receive and capture the shank upper capture portion within the receiver; an open retainer having a top surface; a multi-purpose positioner being located above the retainer and having a ledged surface that releasably mates with the top surface of the retainer to create a combination structure, and wherein the capture portion separates the combination structure, such that the retainer captures the upper capture portion within the receiver; and a compression insert in engagement with the shank upper portion and located above the shank upper portion.

In one embodiment of the disclosure involving a non-pivoting retainer, the retainer is held in the receiver expansion chamber and aligned therein by a multi-purpose positioner, such that the non-pivoting retainer is capable of expanding about the shank upper capture portion, so as to capture the shank, and thereafter, the retainer is released from the positioner and moved down into the receiver locking chamber, the positioner preventing the retainer from moving up out of the locking chamber.

In another embodiment of the invention, a retainer is configured to pivot with the shank during positioning of the shank, after the shank is captured by the retainer. The retainer in this embodiment also being held, aligned, contained, and restrained by a multi-purpose positioner.

In some embodiments, the positioner is a discontinuous ring with a slit extending from an interior surface to an exterior surface. The positioner may include a concave interior surface so as to mate with the shank upper capture portion. It is envisioned that at least one of the non-pivotal retainer and the positioner may include a surface that has been at least one of knurled, scored, roughened, grit blasted, and textured.

In one embodiment, the receiver has an insert with at least one surface engaging the shank in a friction fit manner when the shank is in an unlocked orientation with respect to the receiver. It is envisioned that the insert may engage the positioner and interact with it. The insert may include an outer structure that is sized and shaped to mate with a receiver aperture located on a retainer internal surface, such that when the insert outer structure is mated with the receiver aperture, the insert is captured with respect to the receiver member or head.

In another embodiment, the insert includes a separate sliding and/or pivoting saddle, the saddle configured to allow a rod to be fixed in a plurality of angles about a sagittal plane.

The bone anchor assembly is envisioned as being multi-axial or polyaxial, bi-planar along a sagittal and transverse plane, or mono-planar or uni-planar with shank motion limited to just one plane. The current disclosure is also envisioned with comprising dynamic components for soft stabilization, such as a tensionable cord or inner core, spacers, bumpers, blockers, and sleeves, with or without load-transferring saddles.

In an embodiment, a bone anchor assembly is provided. The bone anchor assembly includes a shank for attachment to a bone, a receiver having an internal cavity for receiving an upper end of the shank and a retainer for maintaining the shank in the receiver during use. The improvement includes a multi-purpose positioner positioned within an expansion chamber portion of the receiver cavity. The retainer is held by the positioner until capturing the shank. The positioner releases the retainer down into a locking chamber portion of the receiver cavity. The positioner also prevents the retainer from returning to the expansion chamber portion.

In an embodiment, the retainer is a non-pivoting retainer, wherein the non-pivoting retainer is prevented from pivoting with the shank during positioning of the shank.

In an embodiment, a bone anchor assembly is provided. The bone anchor assembly includes a shank having a bone attachment structure and an upper capture portion. The bone anchor assembly also includes a receiver having a centrally aligned lower aperture opening onto a bottom surface thereof. The lower aperture cooperates to receive and capture the shank upper capture portion within the receiver. The bone anchor assembly also includes an open retainer having a top surface and a multi-purpose positioner being located above the retainer and having a ledged surface that releasably mates with the top surface of the retainer to create a combination structure.

In an embodiment, the retainer is prevented from pivoting with the shank during positioning of the shank, the retainer being located firstly in a receiver first chamber and being expandable in a receiver second chamber, such that the non-pivoting retainer is capable of expanding about the shank upper capture portion, so as to capture the shank.

In an embodiment, the retainer is configured to pivot with the shank during positioning of the shank, the retainer being located firstly in a receiver first chamber and being expandable in a receiver second chamber, such that the retainer is capable of expanding about the shank upper capture portion, so as to capture the shank.

In an embodiment, the positioner is a discontinuous ring with a slit extending from an interior surface to an exterior surface.

In an embodiment, at least one of the non-pivotal retainer and the positioner includes a surface that has been at least one of knurled, scored, roughened, grit blasted, and textured.

In an embodiment, the positioner includes a concave interior surface so as to mate with the shank upper capture portion.

In an embodiment, the bone anchor assembly also includes a compression insert in engagement with the shank upper portion and located above the shank upper portion.

In an embodiment, the insert has at least one surface engaging the shank in a friction fit manner when the shank is in an unlocked orientation with respect to the receiver In an embodiment, the insert includes a separate saddle, the saddle configured to allow a rod to be fixed in a plurality of angles about a sagittal plane.

In an embodiment, the insert engages the positioner.

In an embodiment, the insert includes an outer structure that is sized and shaped to mate with a respective receiver aperture located on a respective retainer internal surface, such that when the insert outer structure is mated with the respective receiver aperture, the insert is captured with respect to the respective receiver member.

In an embodiment, the bone anchor assembly is multi-axial.

In an embodiment, the bone anchor assembly is monoplanar.

In an embodiment, the bone anchor assembly also includes a tensionable cord.

One implementation of the present disclosure may take the form of a bone anchor. In one embodiment, the bone anchor may include a shank and a head. The shank may include a shank distal end and a shank proximal end opposite the shank distal end. The head may include a head distal end and a head proximal end opposite the head distal end. The head may further include a receiver defining an opening that extends from the head proximal end to the head distal end, and an internal snap-fit assembly configured to reside within the receiver and facilitate coupling of the head and the shank. The snap-fit assembly may include an insert, a retainer ring, and a positioner configured to support a position of the retainer ring within the receiver. The head may be configured to couple to the shank via the snap-fit assembly in a bottom-loaded arrangement such that as the shank proximal end is at least partially received in the opening through the head distal end the retainer ring is caused to release from the positioner and engage with a feature defined on the shank proximal end such that the head and shank are coupled together.

In certain embodiments the retainer ring may include a conically shaped inner circumferential surface and a spherically shaped outer circumferential surface. In this and other embodiments, the feature defined on the shank proximal end may include a conically shaped recess that matingly matches the conically shaped inner circumferential surface of the retainer ring. In this and other embodiments, when the retainer ring is engaged with the feature defined on the shank proximal end, the spherically shaped outer circumferential surface may match a radius of a circumferential portion of the shank proximal end positioned proximally of the retainer ring.

In certain embodiments, the positioner supports a position of the retainer ring within the receiver. In this and other embodiments, the positioner may limit proximal displacement of the retainer ring from within the receiver during coupling of the head and shank.

In certain embodiments, the insert may include an insert distal end including a circumferential inner surface that is configured to contact a matching circumferential portion of the shank proximal end when the shank is coupled to the head.

In certain embodiments, the shank distal end is threaded.

In certain embodiments, the retainer ring and the positioner each include a gap defined therein, each gap being aligned with each other. In this and other embodiments, the retainer ring may be coaxially nested within the positioner.

In certain embodiments, the retainer ring and the positioner each include a gap defined therein, each gap being aligned with each other.

In certain embodiments, the retainer ring is coaxially nested within the positioner.

In certain embodiments, the shank distal end is a hook.

In certain embodiments, the head limits motion of the shank to a single plane.

Aspects of the present disclosure may also involve a receiver assembly for connecting to a capture structure of a proximal end of a bone anchoring member to form a bone anchor assembly configured to anchor a rod to patient bone. In one embodiment, the receiver assembly includes a receiver body, a retainer and a positioner. The receiver body includes a distal end, a proximal end and an inner volume. The distal end of the receiver body is configured to receive the proximal end of the bone anchoring member. The proximal end of the receiver body is configured to receive the rod. The retainer is located in the inner volume and configured to engage the capture structure in a manner that connects the proximal end of the bone anchoring member to the receiver assembly upon the proximal end of the bone anchoring member having been received by the distal end of the receiver body and the retainer having engaged the capture structure in a manner that prevents the proximal end from exiting the distal end of the receiver body. The positioner is located in the inner volume and configured to orient the retainer to engage the capture structure.

In one embodiment, the retainer includes a central opening that receives at least a portion of the proximal end of the bone anchoring member when the retainer engages the capture structure. The positioner orients the retainer such that the central opening of the retainer is generally coaxially aligned with a distal opening in the distal end of the receiver body. The positioner may orient the retainer to engage the capture structure only until the retainer engages the capture structure, the capture structure then becoming free to displace in an angular fashion relative to the positioner. The positioner can limit the proximal displacement of the retainer within the inner volume.

The positioner can be a unitary construction ring-like structure, or the positioner can include multiple separate segments that are arranged in a ring-like configuration. The retainer can be in the form of a ring-like structure.

Depending on the embodiment, the positioner is a separate and distinct structure from both the receiver body and the retainer, or the positioner is a separate and distinct structure from either the receiver body or the retainer. For example, in some embodiments, the positioner may be a structural extension of the receiver body, the retainer or both.

The receiver body may restrict distal-proximal displacement of the positioner. The receiver assembly may be in the form of a polyaxial configuration, a favored angle configuration, or a monoplanar configuration. The bone anchoring member may be in the form of a bone screw configuration, a nail configuration, or a hook configuration.

In one embodiment, the receiver assembly may further include a compression insert and a closure. The compression insert is proximal of the positioner and received in the receiver body. The closure is configured to secure the rod to the proximal end of the receiver body. The closure may drive the rod against the compression insert when the closure is used to secure the rod to the proximal end of the receiver body.

Aspects of the present disclosure may also involve a receiver assembly for connecting to a capture structure of a proximal end of a bone anchoring member to form a bone anchor assembly configured to anchor a rod to patient bone. In one embodiment, the receiver assembly includes a receiver body, a retainer and a positioner. The retainer resides within the receiver body and is configured to engage in a locking manner with the capture structure via the proximal end of the bone anchor member being inserted into the receiver body. The positioner resides in the receiver body and is configured to maintain an orientation of the retainer within the receiver body that facilitates the retainer engaging in the locking manner with the capture structure. The positioner is also configured to allow the retainer to change orientation within the receiver body when the retainer is engaged in the locking manner with the capture structure.

In one embodiment, the positioner is also configured to allow the retainer to change orientation relative to the positioner when the retainer is engaged in the locking manner with the capture structure. The positioner may orient the retainer such that a central opening of the retainer is generally coaxially aligned with a distal opening in a distal end of the receiver body. The positioner may limit the proximal displacement of the retainer within the inner volume.

Depending on the embodiment, the positioner may be a unitary construction ring-like structure, or the positioner may include multiple separate segments that are arranged in a ring-like configuration. The retainer may be in the form of a ring-like structure.

Depending on the embodiment, the positioner is a separate and distinct structure from both the receiver body and the retainer, or the positioner is a separate and distinct structure from either the receiver body or the retainer. For example, in some embodiments, the positioner may be a structural extension of the receiver body, the retainer or both.

The receiver body may restrict distal-proximal displacement of the positioner. The receiver assembly may be in the form of a polyaxial configuration, a favored angle configuration, or a monoplanar configuration. The bone anchoring member may be in the form of a bone screw configuration, a nail configuration, or a hook configuration.

In one embodiment, the receiver assembly may further include a compression insert and a closure. The compression insert is proximal of the positioner and received in the receiver body. The closure is configured to secure the rod to the proximal end of the receiver body. The closure may drive the rod against the compression insert when the closure is used to secure the rod to the proximal end of the receiver body.

Aspects of the present disclosure also involve a medical kit for use with the bone anchoring member discussed above or herein, wherein the capture structure of the proximal end of the bone anchoring member includes a universal configuration compatibly connectable with a variety of the embodiments of the receiver assembly described herein. In one embodiment, the medical kit includes first and second receiver assemblies of any of the embodiments discussed above and herein. The first receiver assembly includes a first configuration that is one of multi-planar, favored angle, or mono-planar, and the second receiver assembly includes a second configuration that is one of multi-planar, favored angle, or mono-planar, the first configuration being different than the second configuration. The medical kit also includes information conveying that both the first and second receiver assemblies are compatible for connecting to the capture structure of the proximal end of the bone anchoring member. The information may be provided on packaging surrounding the first and second receiver assemblies, on a document contained in or otherwise accompanying the packaging, or electronically via, for example, the internet or an electronic document.

This medical kit is advantageous for at least the reason that it can substantially reduce inventory and associated costs as the medical kit may contain different receiver assembly types (e.g., multi-planar, favored angle, mono-planar, or others) and the surgeon can intra-operatively select the appropriate receiver assembly and connect it to a universal capture structure of a bone anchor member, the universal capture structure being capable of connecting equally well to any of the different receiver assembly types (e.g., multi-planar, favored angle, mono-planar, or others) making up the medical kit.

Further disclosed herein is a surgical method of using a first receiver assembly of any of the embodiments disclosed above or herein and a second receiver assembly of any of the embodiments disclosed above or herein. The method includes: implanting the bone anchoring member into the patient bone with the capture structure proximally extending from the patient bone, the capture structure being of a universal configuration; and connecting a selected receiver assembly to the capture structure, the selected receiver assembly being selected intra-operatively from the first and second receiver assemblies, the first receiver assembly including a first configuration that is one of multi-planar, favored angle, or mono-planar, and the second receiver assembly including a second configuration that is one of multi-planar, favored angle, or mono-planar, the first configuration being different than the second configuration. The first and second receiver assemblies can be provided as part of the medical kit described herein.

While multiple embodiments are disclosed, still other embodiments of the present disclosure will become apparent to those skilled in the art from the following detailed description, which shows and describes illustrative embodiments of the disclosure. As will be realized, the various embodiments described herein are capable of modifications in various aspects, all without departing from the spirit and scope of the present disclosure. Accordingly, the drawings and detailed description are to be regarded as illustrative in nature and not restrictive.

BRIEF DESCRIPTION OF THE DRAWINGS

FIG. 3 is a fragmentary exploded perspective view of a second embodiment of a multiplanar bone screw assembly according to the present disclosure including a second embodiment of a shank, the receiver, a second embodiment of a pivoting retainer, the positioner, a second embodiment of a pressure insert and a closure shown in a second embodiment of an independent lock configuration, all shown in conjunction with a rod.

FIG. 4 is an enlarged fragmentary side elevation view of the bone screw assembly of FIG. 3 with portions of the receiver and closure cut away to show cooperation of the parts at a stage whereat the multiplanar bone screw assembly is fully locked by the closure.

FIG. 7 is a fragmentary exploded perspective view of a fourth embodiment of a multiplanar bone screw assembly according to the present disclosure including the first embodiment of the shank, the second embodiment of a receiver shown in an extended angle configuration, the first embodiment of the pivoting retainer, the positioner, the second embodiment of the pressure insert and a closure shown in a fourth embodiment of an independent lock with a castle drive configuration, all shown in conjunction with a rod.

FIG. 8 is an enlarged inverted perspective view of the second embodiment of the receiver.

FIG. 9 is an enlarged fragmentary side elevation view of the bone screw assembly of FIG. 7 with portions of the receiver and closure cut away to show cooperation of the parts at a stage whereat the multiplanar bone screw assembly is fully locked by the closure.

FIG. 10 is a fragmentary exploded perspective view of an embodiment of a monoplanar bone screw assembly according to the present disclosure including the first embodiment of the shank, a second embodiment of a receiver, a first embodiment of a pivoting retainer, a second embodiment of a positioner, a second embodiment of a pressure insert and a closure shown in a fourth embodiment of an independent lock configuration, all shown in conjunction with a rod.

FIG. 11 is an enlarged fragmentary side elevation view of the bone screw assembly of FIG. 10 with portions of the receiver and closure cut away to show cooperation of the parts at a stage whereat the monoplanar bone screw assembly is fully locked by the closure.

FIG. 16 is a fragmentary exploded perspective view of a second embodiment of a bi-planar bone screw assembly according to the present disclosure including the second embodiment of the shank, the second embodiment of the receiver, the second embodiment of a pivoting retainer, a second embodiment of a positioner, a fourth embodiment of a pressure insert and a sixth embodiment of a closure shown, all shown in conjunction with a rod.

FIG. 17 is an enlarged perspective view of the fourth embodiment of the insert of FIG. 16.

FIG. 18 is an enlarged side elevation view of the bone screw assembly of FIG. 16 with portions of the receiver and closure cut away to show cooperation of the parts at a stage whereat the bi-planar bone screw assembly is fully locked by the closure.

FIG. 19 is a side view of a third embodiment of a shank.

FIG. 20 is a transverse cross section of the retainer of FIG. 3.

FIG. 21 is a side view of a fourth embodiment of a shank.

FIG. 22 is a transverse cross section of a third embodiment of a pivoting retainer.

FIG. 57 is a perspective view of the entire assembly of FIG. 25 shown with the shank at an angle with respect to the receiver.

FIG. 58 is an enlarged and partial side elevation view of the assembly of FIG. 57 with portions broken away to show the detail thereof.

FIG. 59 is an enlarged and partial front elevation view of the assembly of FIG. 57 with portions broken away to show the detail thereof.

FIG. 85 is the same view as FIG. 84, except showing all of the components of the head and the shank proximal end portion secured in the head at a 30 degree angle relative to the longitudinal axis of the head by the compressing forces of the components of the plug and the implant rod.

FIG. 86 is an exploded ninety degree of sagittal side elevation view of the head, wherein the receiver is shown as a longitudinal cross section.

FIG. 102 is the same view as FIG. 101, except the positioner member is fully positioned within the expansion chamber of the receiver.

FIG. 103 is the same view as FIG. 102, except both positioner members are positioned within the expansion chamber of the receiver.

FIG. 104 is the same view as FIG. 103, except the retainer has been proximately displaced.

FIG. 105 depicts the head or receiver assembly in the shipping state.

FIG. 118 is a front exploded view of another embodiment of a bone anchor.

FIG. 119 depicts a front cross sectional view of the receiver.

FIG. 120 depicts a fully assembled state of the bone anchor with the receiver viewed in cross section.

FIG. 121 depicts the bone anchor with the shank angled relative to the receiver.

FIG. 122 is a front exploded view of another embodiment of a bone anchor.

FIG. 123 is an isometric view of the retainer.

FIG. 124A is a side view of the retainer.

FIG. 124B is an isometric view of the positioner.

FIG. 124C is an isometric view of the positioner and the retainer.

FIG. 125 is a front cross sectional view of the receiver.

FIG. 126 is a front isometric cross sectional view of the receiver.

FIG. 127 is a front view of the insert and the positioner with the retainer positioned within the receiver, which is viewed in cross section.

FIG. 128 is a front view of the shipping state of the head assembly with the receiver viewed in cross-section.

Figures 129, 130:
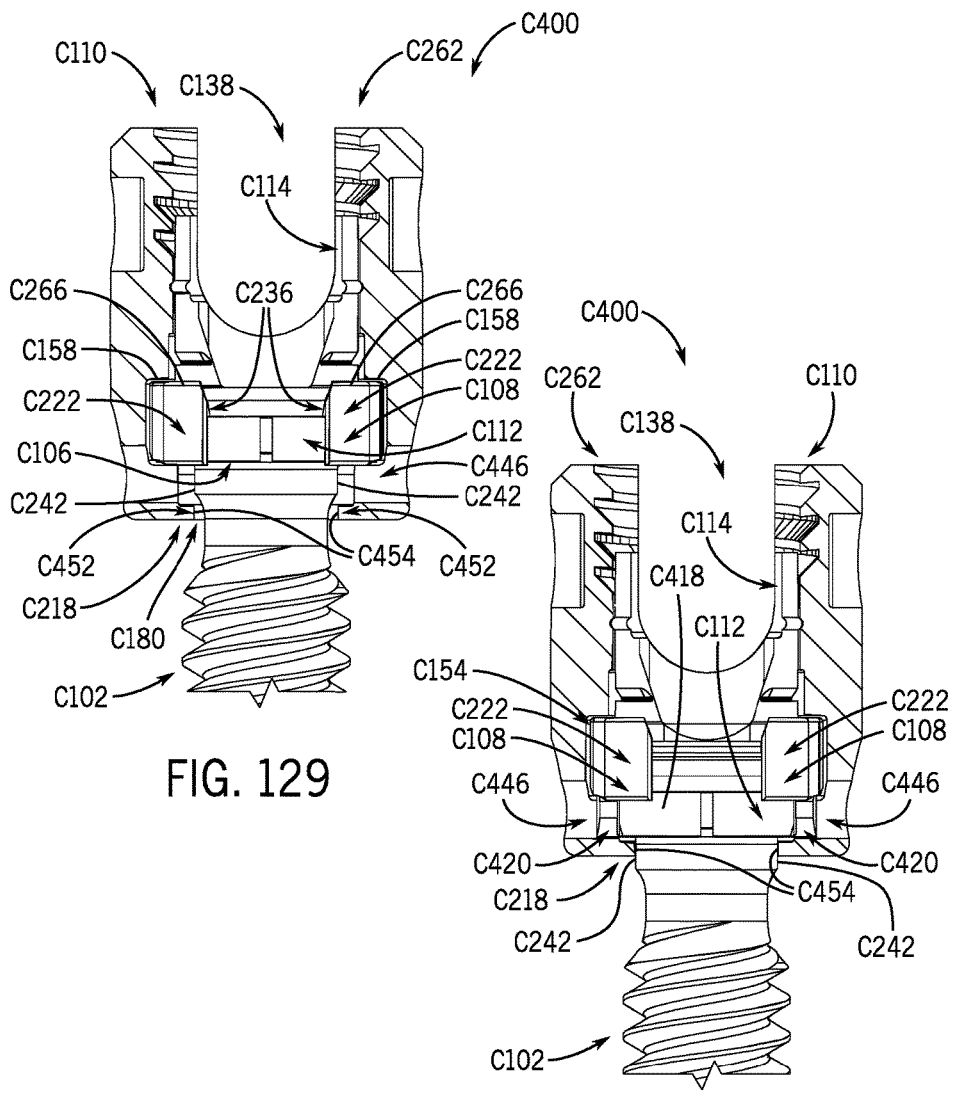

FIG. 129 is a front view of the head assembly coupled with the shank with the receiver viewed in cross-section.

FIG. 130 is a front view of the shank and retainer being proximately displaced relative to the head assembly.

Figure 131:
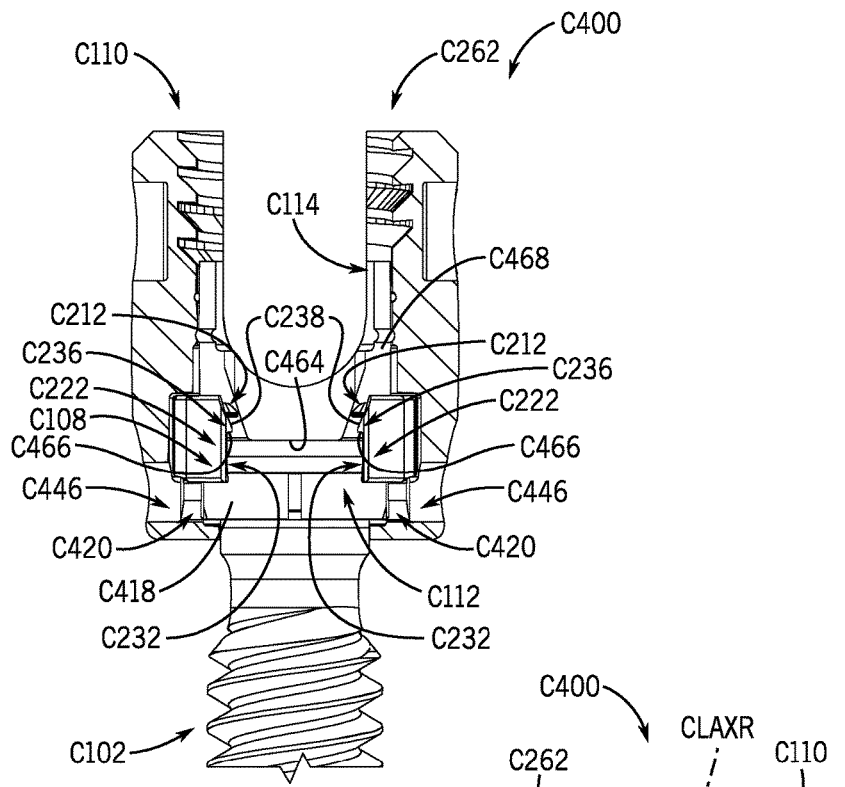

FIG. 131 is a front view of the insert being distally displaced relative to the receiver.

Figure 132:
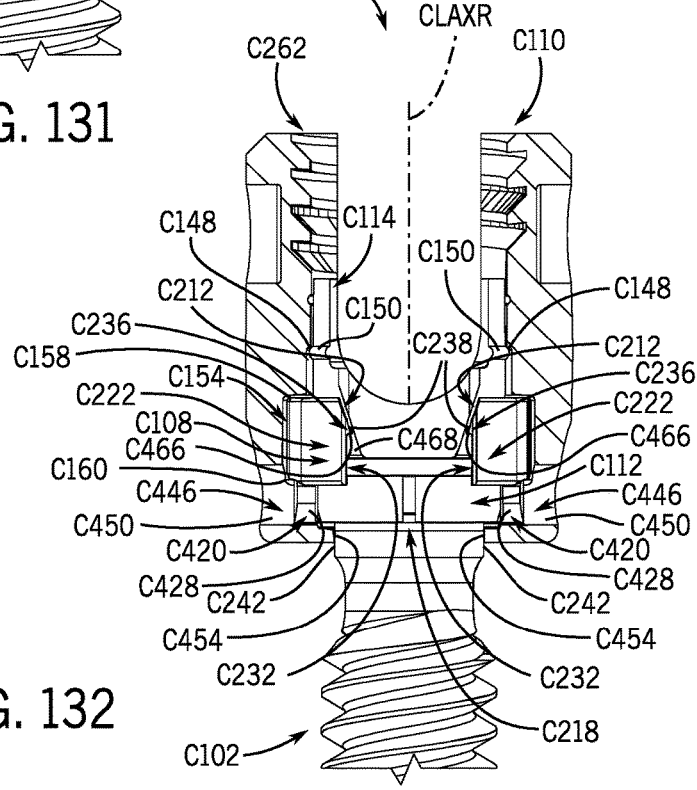

FIG. 132 is a front view of the positioner coupling with the insert within the head assembly.

Figures 133, 134:
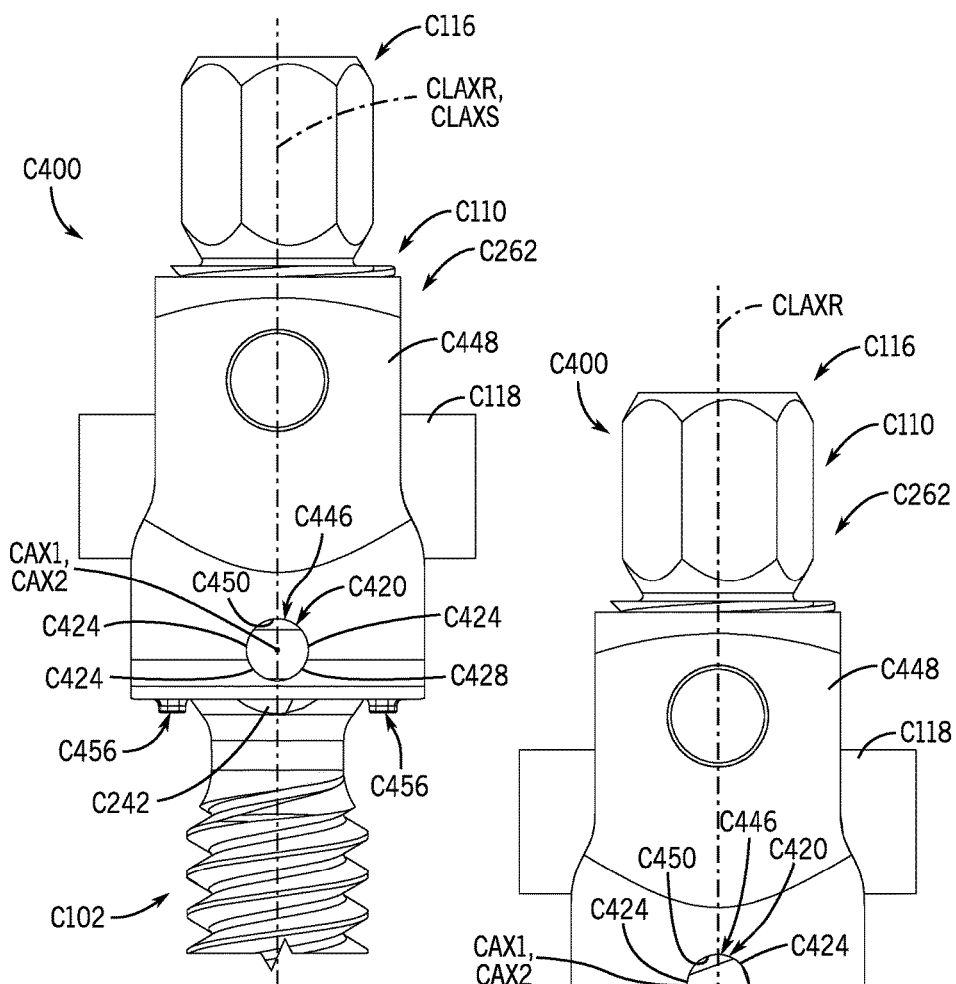

FIG. 133 is a side view of the bone anchor with the shank with a longitudinal access of the shank coaxial with a longitudinal axis of the receiver.

FIG. 134 is a side view of the bone anchor with a longitudinal axis of the shank angled relative to a longitudinal axis of the receiver.

Figure 135:
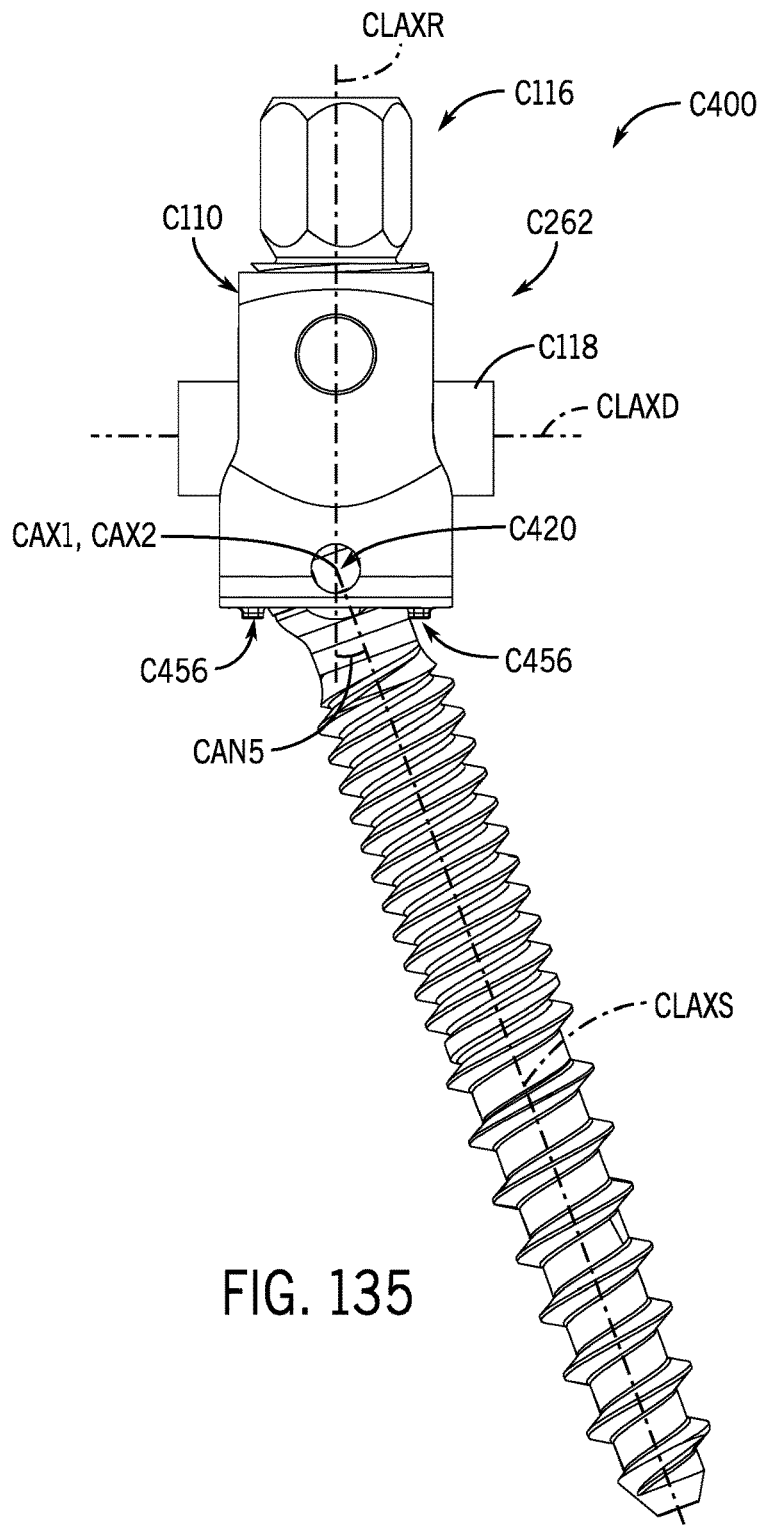

FIG. 135 is another side view of the bone anchor with the longitudinal axis of the shank angled relative to the longitudinal axis of the receiver.

Figure 136:
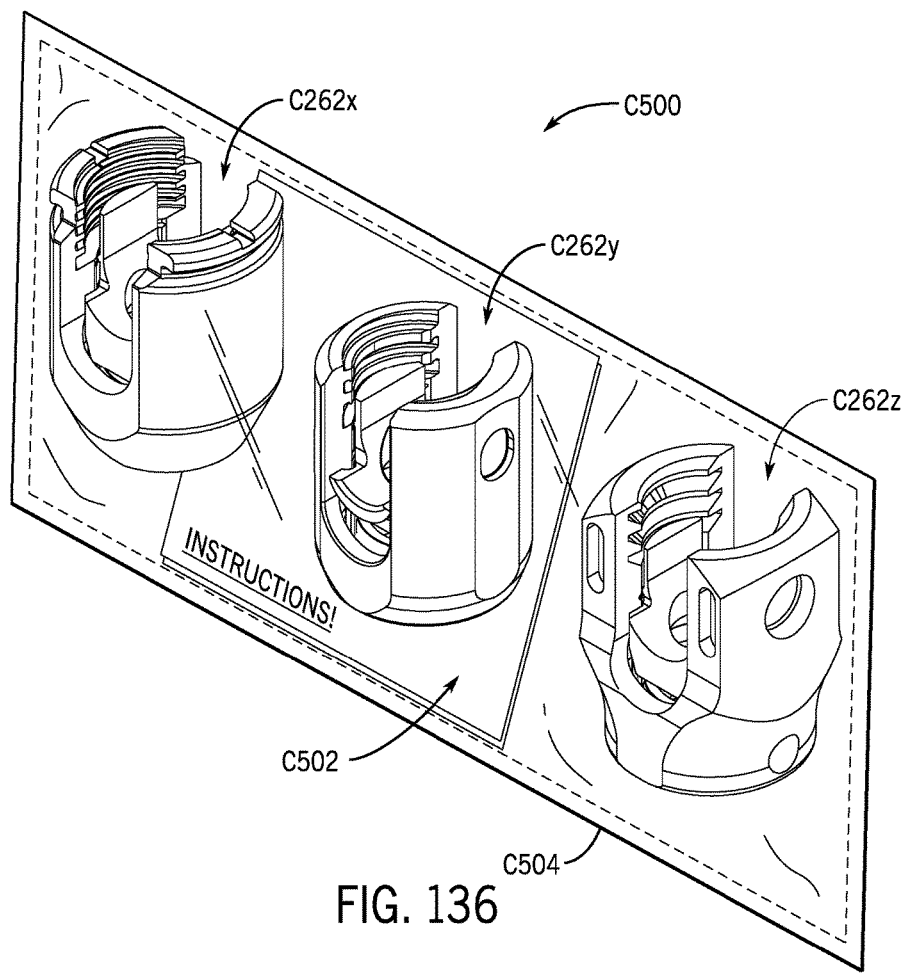

FIG. 136 is a kit including multiple head assemblies.

Figures 137, 138:
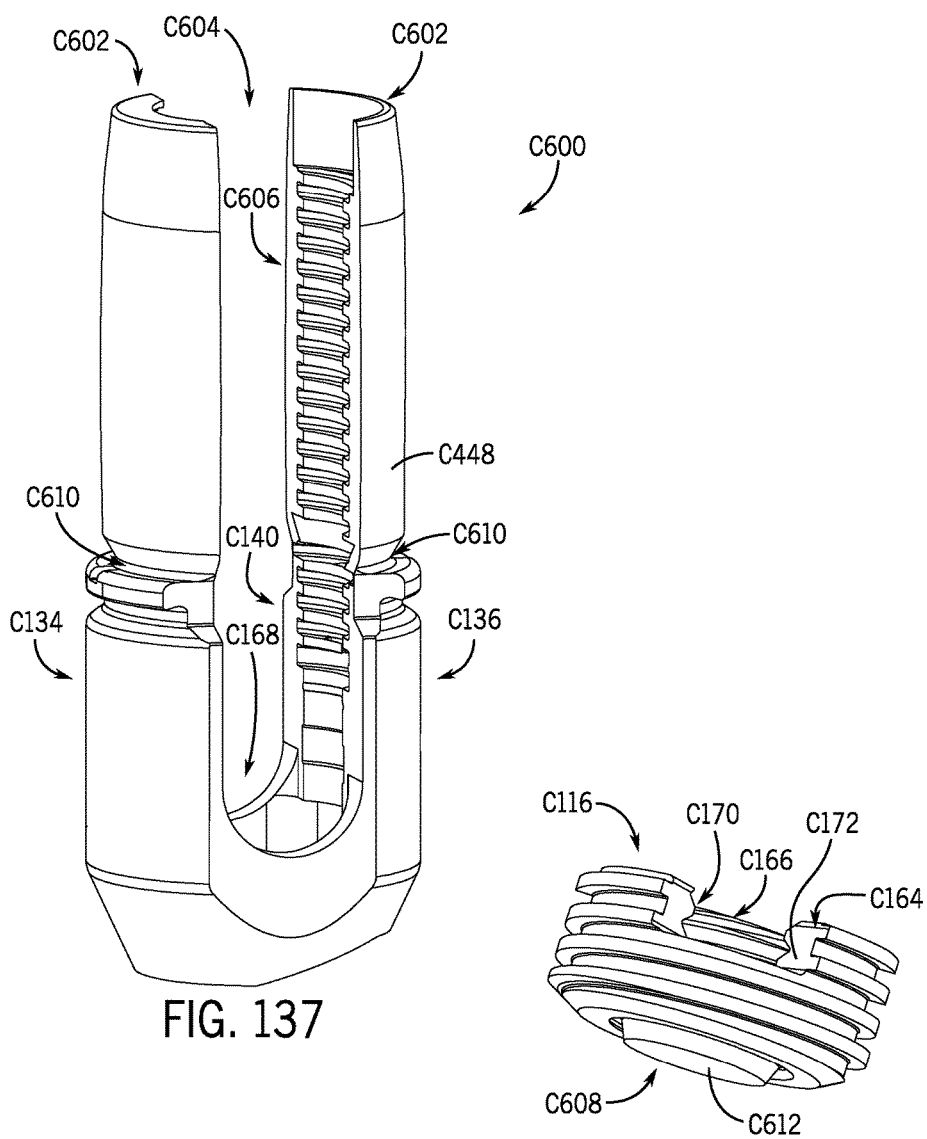

FIG. 137 is an isometric view of another embodiment of a receiver having break-off reduction tabs.

FIG. 138 is an isometric view of a closure structure with a flat bottom set screw.

FIG. 139 is an isometric view of another embodiment of a head assembly of a bone anchor.

FIG. 140A is an isometric view of the positioner.

FIG. 140B is an isometric view of the positioner and the retainer.

Figure 141:
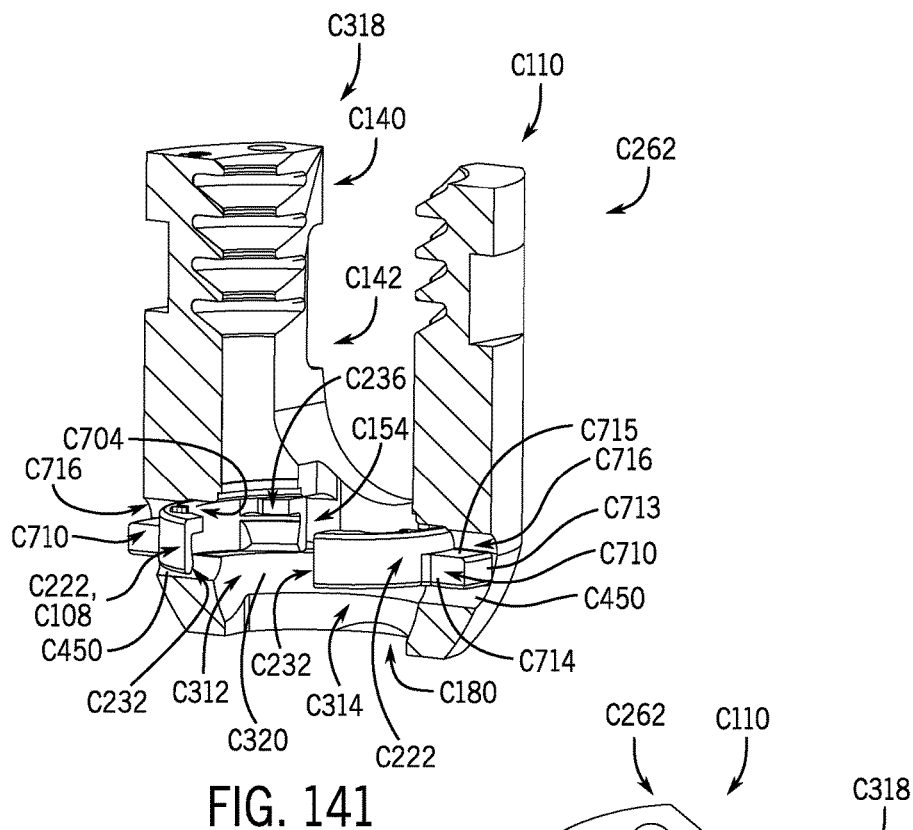

FIG. 141 is an isometric cross-sectional view of the receiver with the positioner members positioned within the receiver.

Figure 142:
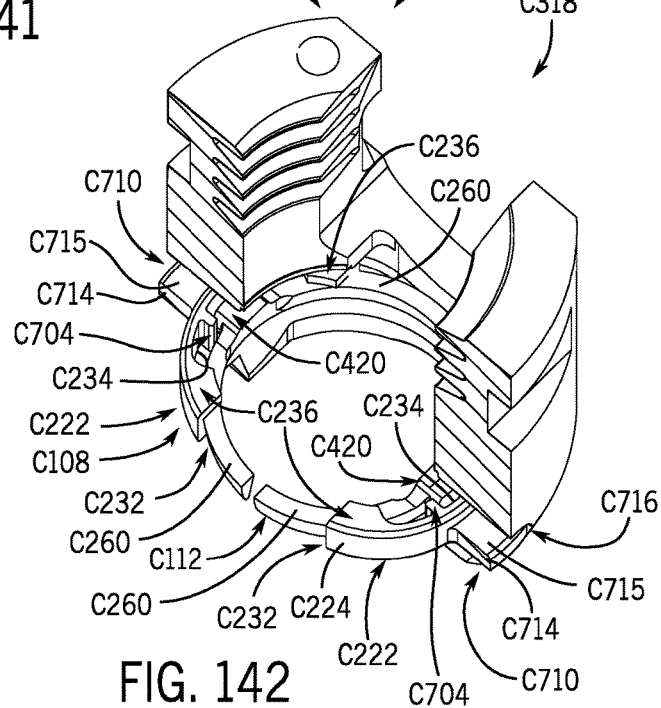

FIG. 142 is an isometric cross-sectional view of the receiver with the positioner members and the retainer positioned with in the receiver.

Figure 143:
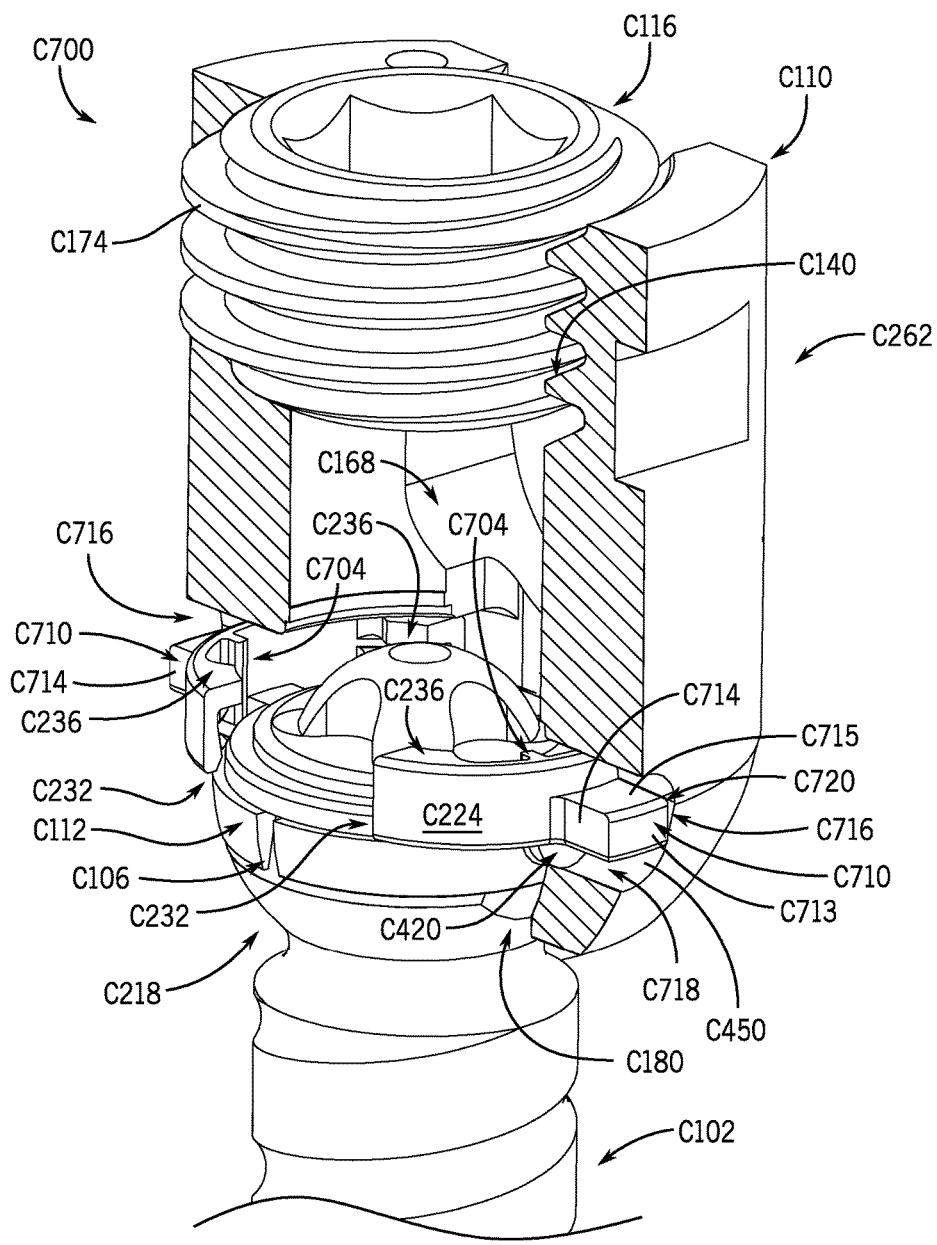

FIG. 143 is an isometric view of the bone anchor with the receiver viewed in cross-section and the rod hidden from view.

DETAILED DESCRIPTION

As required, detailed embodiments of the present disclosure are disclosed herein; however, it is to be understood that the disclosed embodiments are merely exemplary of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Figures 1, 2:
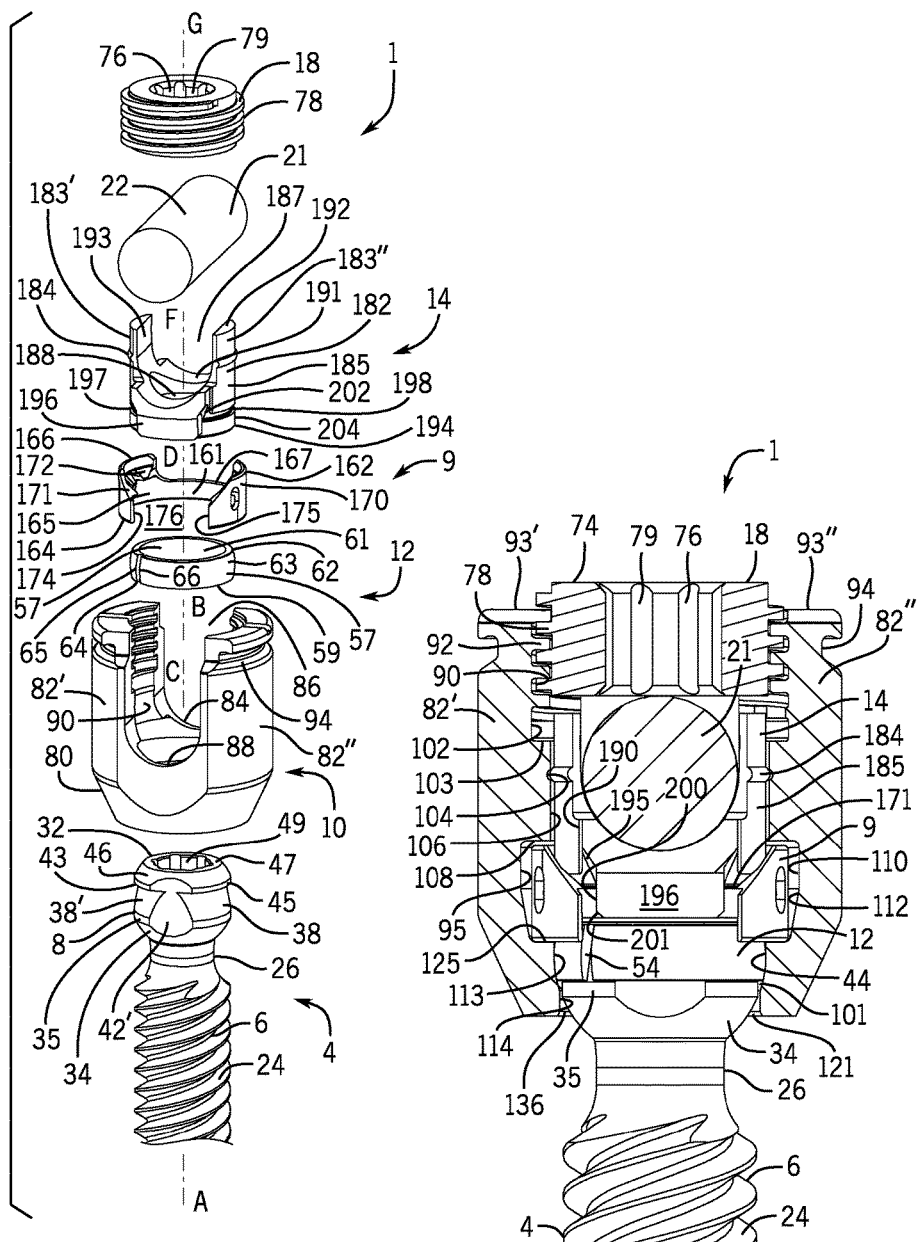
FIG. 1 is a fragmentary exploded perspective view of an embodiment of a multiplanar bone screw assembly according to the present disclosure including a first embodiment of a shank, a receiver, a pivoting retainer, a positioner, a pressure insert and a closure, shown in conjunction with a rod.
FIG. 2 is an enlarged fragmentary side elevation view of the bone screw assembly of FIG. 1 with portions of the receiver and closure cut away to show cooperation of the parts at a stage whereat the bone screw assembly is fully locked by a closure.

With reference to FIGS. 1-2 the reference number 1 generally represents an embodiment of a multi-planar, multi-axial, or polyaxial bone screw apparatus or assembly according to the present disclosure. While the illustrated anchor 1 is generally a polyaxial bone screw, it is foreseen that the disclosure could be utilized with other types of spinal implants that utilize pressure inserts, such as polyaxial bone hooks or clamps, for example. The illustrated assembly 1 includes: a shank 4, that further includes a body 6 integral with an upwardly extending upper portion or capture structure 8; a positioner 9; a receiver 10; a pivoting retainer structure 12; a compression or pressure insert 14; and a closure 18. The assembly 1 may also be included to be adapted for use with an elongated rod or connecting member 21. The receiver 10, the positioner 9, the pivoting retainer 12, and compression insert 14 are preferably initially pre-assembled and may be further assembled with the shank 4 either prior or subsequent to implantation of the shank body 6 into a vertebra (not shown), as will be described in greater detail below.

FIG. 2 shows the closure structure 18 of the disclosure capturing the longitudinal member, for example, a spinal fixation rod or longitudinal connecting member 21 which in turn engages the compression insert 14 that presses against the shank upper portion or capture portion 8 and the positioner 9 into fixed frictional contact with the pivoting retainer 12, so as to capture, and fix the longitudinal connecting member 21 within the receiver 10 and thus fix the member 21 relative to the vertebra (not shown). The illustrated rod 21 is hard, stiff, non-elastic and cylindrical, having an outer cylindrical surface 22. It is foreseen that in other embodiments of the disclosure, the rod 21 may be elastic, deformable and/or of a different cross-sectional geometry. The receiver 10 and the shank 4 cooperate in such a manner that the receiver 10 and the shank 4 can be secured at any of a plurality of angles, angulation, articulations, or angular alignments relative to one another and within a selected range of angles to from side to side and from front to rear, to enable flexible or articulated engagement of the receiver 10 with the shank 4 until both are locked or fixed relative to each other near the end of an implantation procedure, as seen in FIG. 2, for optimal surgical relationship with the spinal column (not shown).

The shank 4 is elongate, with the shank body 6 having a helically wound bone implantable thread 24 (single or multi start thread forms, which can have various types of thread patterns and cross sections) extending from near a neck 26 located adjacent to the upper portion or capture structure 8, to a tip (not shown) of the body 6 and extending radially outwardly therefrom. During use, the body 6 utilizes the thread 24 for gripping and advancement as it is implanted into the vertebra (not shown) leading with the tip (not shown) and driven down into the vertebra with a suitable installation or driving tool (not shown), so as to be implanted into the vertebra to up near the neck 26. The shank 4 has a longitudinal axis of rotation generally identified by the reference letter A in FIG. 1.

The neck 26 extends axially upward from the shank body 6. The neck 26 may be of the same or is typically of a slightly reduced radius as compared to an adjacent upper end or top 32 of the body 6 where the thread 24 terminates. Further extending axially and outwardly from the neck 26 is the shank upper portion 8 that provides a connective or capture apparatus disposed at a distance from the neck 26 and thus at a distance from the vertebra (not shown) when the body 6 is implanted in such vertebra.

The shank upper capture portion 8 is configured for a pivotable connection with respect to the receiver 10 prior to fixing of the shank 4 in a desired position with respect to the receiver 10. The illustrated shank upper portion 8 has an bulbous, convex and partially spherical outer lower surface 34 that extends outwardly and upwardly from a neck 26 terminates at a lower cylindrical surface 35 (FIG. 2). The lower cylindrical surface 35 is illustrated as parallel to axis A. It is also foreseen that the lower cylindrical surface 35 may not be parallel with axis A. The lower cylindrical surface 35 terminates at a frusto-conical interface surface 38. The frusto-conical interface surface 38 is adjacent an upper shelf 43. The upper shelf surface 43 is substantially perpendicular to the axis A. The frusto-conical interface surface 38 is illustrated as having a larger radius near the lower cylindrical surface 35 than at the upper shelf or ledge surface 43. The spherical lower surface 34 has an outer radius that is the same or substantially similar to an outer radius of the shank 4.

It is foreseen that the upper shelf or the ledge surface 43 could further include non-flat geometry, such as bumps or ridges.

In this embodiment the frusto-conical interface surface 38 and upper ledge 43, which is discontinuous, cooperate to capture and fix the resilient open pivoting retainer 12 to the shank upper portion 8, prohibiting compression of the pivoting retainer 12 with respect to axis A once the pivoting retainer 12 is located underneath the ledge 43. A top surface 62 of the pivoting retainer 12 interacts with the upper shelf surface 43 and is positioned beneath a top surface 47 of the shank 4. Extending upwardly from the upper ledge 43 is a cylindrical surface 45. The width or diameter or radius (not shown) of the cylindrical surface 45 is the same, and can be seen in U.S. Provisional Patent Application No. 62/194,955, previously referenced.

Extending upwardly from the upper cylindrical surface 45 is an upper partially spherical or domed surface 46. The radius of the upper spherical surface 46 may be the same as the radius of the lower spherical surface 34. Located near or adjacent to the surface 46 is an annular top surface 47. It is foreseen that the upper spherical surface 46 may be formed by stepped surfaces (not shown) having radiused radii between the upper cylindrical surface 45 and the top surface 47. The illustrated shank top surface 47 is substantially perpendicular to the axis A. The upper spherical surface 46 shown in the present embodiment is substantially smooth and sized and shaped for cooperation and ultimate frictional engagement with the compression insert 14.

Formed in the shank upper portion 8 of the shank 4 are opposite or opposed parallel flat planar surfaces 42 that extend downwardly, parallel to the direction of axis A, and separate the shelf surface 43 into two opposed and spaced apart surfaces. The flat planar surfaces 42 may be machined or molded, such that the width between the flat planar surfaces 42 is less than or substantially equal to the width or radius or diameter (not shown) of the interface surface 38, or separated surfaces 38 and 38'. The opposite and parallel flat planar surfaces 42 create a disconnect, such that the upper shelf or ledge surface 43, the upper spherical surface 46, the upper cylindrical surface 45, the interface surface 38, the lower spherical surface 34, and the lower cylindrical surface 35 are all discontinuous. The upper ledge surface 43 stops at each of the flat planar surfaces 42 and continue there past along the circular path created by the interface surfaces 38 and 38'. It is foreseen that the flat planar surfaces 42 may also include a lower key extension, as seen in U.S. patent application Ser. No. 13/573,516, previously referenced above. The pivoting retainer 12 can be top, bottom, or side loaded onto the shank head 8. Once the shank head 8 passes through the pivoting retainer 12, for example, by top loading, the planar side surfaces 42 mate with the pivoting retainer 12 creating a substantially spherical ball shape structure 44, as will be further described below.

A counter sunk substantially planar base or seating surface (not shown) partially defines an internal drive feature or imprint or structure 49 of the shank 4. As best seen in FIG. 1, the illustrated internal drive feature 49 is an aperture formed in the top surface 47 of the shank head 8 extending downwardly from the top surface 47, and has a hexagonal or hex shape designed to receive the hex tool (not shown) of an Allen wrench type, into the aperture for rotating and driving the bone screw shank 4. It is foreseen that such an internal tool engagement structure may take a variety of tool-engaging forms and may include one or more apertures of various shapes, such as a pair of spaced apart apertures or a multi-lobular or star-shaped aperture, such as those sold under the trademark TORX, or the like, having a non-round shape for positive drive engagement by a complementary shaped drive tool. It is foreseen that the drive tool structure may be made of a somewhat softer metal compared to that of the head. The seat or base (not shown) of the drive feature 49 is disposed perpendicular to the axis A with the drive feature 49 otherwise being coaxial with the axis A. In operation, the driving tool (not shown) is received in the internal drive feature 49, being seated at the base and engaging faces of the drive feature 49 for both driving and rotating the shank body 6 into the vertebra (not shown), either before the shank 4 is attached to the receiver 10 or after the shank 4 is attached to the receiver 10, with the shank body 6 being driven into the vertebra with the driving tool extending into the receiver 10.

The shank 4 may be cannulated, having a small central bore (not shown) extending an entire length of the shank 4 along the axis A. It is foreseen that the central bore may not have to extend in a parallel direction with A, and that the bore may not extend the entire length of the shank 4. The bore is foreseen to provide a passage through the shank 4 interior for a length of guide wire (not shown) inserted into the vertebra prior to the insertion of the shank body 6, the wire providing a guide for precise insertion of the shank body 6 into the vertebra.

It is foreseen that the shank 4 can be expandable and/or fenestrated, and again, have different thread patterns extending along its length. It is foreseen that the length of the shank may be shortened or lengthened further than illustrated.

To provide a biologically active interface with the bone or vertebra, the threaded shank body 6 may be coated, perforated, made porous or otherwise treated. The treatment may include, but is not limited to, a plasma spray coating or other type of coating of a metal or, for example, a calcium phosphate; or a roughening, perforation or indentation in the shank surface, such as by sputtering, sand blasting or acid etching, that allows for bony ingrowth or ongrowth. Certain metal coatings act as a scaffold for bone ingrowth. Bio-ceramic calcium phosphate coatings include, but are not limited to: alpha-tri-calcium phosphate and beta-tri-calcium phosphate ($Ca_3(PO_4)_2$), tetra-calcium phosphate ($Ca_4P_2O_9$), amorphous calcium phosphate and hydroxyapatite ($Ca_{10}(PO_4)_6(OH)_2$). Coating with hydroxyapatite, for example, is desirable as hydroxyapatite is chemically similar to bone with respect to mineral content and has been identified as being bioactive and thus not only supportive of bone ingrowth, but actively taking part in bone bonding.

The illustrated pivoting or pivotal retainer 12 operates to assist in capturing the shank upper portion 8 within the receiver 10. The upper pivotal retainer 12 has a central axis B that operationally aligns with axis A associated with the shank 4 when assembled thereon, as best seen in FIG. 1. The pivotal retainer 12 is ring shaped, having a central bore 57, and may be made from a resilient material, such as a stainless steel, titanium alloy, cobalt chrome, or the like, as well as polymers, or some combination thereof, so that a body 55 of the retainer 12 may be resiliently expanded and retracted.

The upper pivotal retainer 12 includes a substantially cylindrical continuous body 55 except for a slot or slit 54. In this pivoting retainer embodiment, an outer surface 63 of the upper retainer 12 along a radius (not shown) measured from the center of the bore 57 matches with and is equivalent to the radius (not shown) of at least one of the lower spherical surface 34 or the upper spherical surface 46. It is foreseen that the radius of the pivoting retainer outer surface 63 may be slightly smaller or slightly larger than the lower spherical surface 34 or the upper spherical surface 46 or some combination thereof, but generally are all identical.

It is foreseen that the spherical surface 63 may additionally or alternatively include a roughened or textured surface or surface finish, or may be scored, knurled, grit blasted, or the like, for enhancing frictional engagement with the components within the receiver 10. It is noted that the surfaces 63 need not be spherical and may alternatively be planar, tapered, or faceted or include other surface geometries, such as conical.

The upper retainer body 55, having only the very narrow slit 54 to be used for expansion purposes only when the shank upper capture portion 8, is loaded through the receiver lower opening 136, as best seen in FIG. 2. Surfaces of the bore 57 are sized and shaped such that the upper retainer body 55 cannot compress further when mated with the shank upper capture portion 8. The through slit 54 of the resilient upper retainer 12 is defined by first and second end surfaces, 65 and 66 (FIG. 1), respectively, disposed in spaced relation to one another or they may also be touching when the retainer is in a neutral, natural, or nominal starting state or position. Both end surfaces 65 and 66 are disposed substantially perpendicular to a bottom surface 59 and a top surface 62 of the retainer 12. It is foreseen that the slit 54 may be at an angle or curved. It is foreseen that the pivoting retainer 12 may be loaded through a receiver lower opening 136 (FIG. 2), such that the retainer 12 is loaded in a neutral state, such that it does not need or, in fact, cannot be further compressed to fit within a receiver lower opening 136.

The pivoting retainer through bore 57 passes entirely through the pivoting retainer 12. The channel or bore 57 is defined by sloped or ramped or frusto-conical surface (not shown). An interior surface 61 of the bore 57 extends between the top surface 62 and the bottom surface 59 of the pivoting retainer 12 and is frusto-conical. The bore 57 is sized and shaped to closely fit about and snap onto the shank interface surface 38 during assembly. The frusto-conical surface 61 is continuous about the bore 57 of the pivoting retainer 12. When the pivoting retainer 12 is mated to shank upper capture portion 8, a ball component of a ball and socket structure 44 (FIG. 2) is created. A gap 101 (FIG. 2) exists where the bottom surface 59 of the retainer 12 extends further than the cylindrical surface 35 of the shank upper capture structure 8.

It is foreseen that further surfaces such as a lower shelf surface (not shown) and a fourth cylindrical surface (not shown) may be sized and shaped to further step down the spherical shape of the outer surface 63 internally.

It is also foreseen that the outer surface 63 may include projections or notches as needed for tooling to resiliently hold the pivoting retainer 12. It is foreseen that in other embodiments of the disclosure, fewer or greater number of planar or other surfaces with other geometries may extend between the top surface 62 and the inner surfaces defining the bore 57 of the pivoting retainer 12, as will be discussed further below.

The receiver 10 has a generally U-shaped appearance with a partially discontinuous substantially cylindrical inner and outer profile. The receiver 10 has a cylindrical axis C (FIG. 1) that may align with axis A of the shank 4, and axis B of the pivoting retainer 12, such orientation being desirable, but not required during assembly of the receiver 10 with the shank 4 and pivoting retainer 12. After the receiver 10 is pivotally attached to the shank 4 at a desired predisposed plane or axis, either before or after the shank 4 is implanted in a vertebra, the axis C is typically disposed at an obtuse angle with respect to the axis A.

The receiver 10 includes a substantially cylindrical base 80 integral with a pair of opposed upstanding arms 82' and 82" forming a cradle and defining a channel 84 between the arms 82' and 82" with an upper opening, generally 86, and a U-shaped lower seat 88, the channel 84 having a width for operably snugly receiving the rod 21 between the arms 82' and 82", best seen in FIG. 2. Each of the arms 82' and 82" has an interior surface, generally 90, that includes various inner cylindrical profiles, an upper of which is a partial or discontinuous helically wound guide and advancement structure 92 located adjacent top surfaces 93' and 93" respectively of the arms 82' and 82". It is foreseen that the receiver may further include extensions (not shown) attached to the arms 82' and 82" and having break off junctures to the arms 82' and 82". The breakoff extensions can also have internal threads similar to structures 92.

The illustrated guide and advancement structure 92 is a partial helically wound interlocking square thread flange form configured to mate under rotation with a similar structure on the closure structure 18, as described more fully below. However, it is foreseen that the guide and advancement structure 92 could alternatively be a square-shaped thread, a buttress thread, a flange form thread or other thread-like or non-thread-like helically wound and non-helically wound discontinuous advancement structure for operably guiding, under complete or partial rotation, and advancing the closure structure 18 downward between the arms 82' and 82", as well as, eventual torquing when the closure structure 18 abuts against the rod 21. It is also foreseen that the structures 92 may be guide and advancement structures that resist or prevent outward splaying of the arms 82' and 82" when the closure is strongly torqued therebetween. It is also foreseen that the closure 18 may have a breakoff head in certain embodiments.

An opposed pair of tool receiving and engaging apertures or indentations 94 are formed on outer surfaces 96 of the illustrated arms 82' and 82". Some or all of the apertures 94 may be used for holding the receiver 10 during the implantation of the shank body 6 into a vertebra when the shank is pre-assembled with the receiver 10, and during assembly of the bone anchor assembly 1 with the rod 21 and the closure structure 18. It is foreseen that tool receiving grooves or apertures 94 may be configured in a variety of shapes and sizes and be disposed at other locations on the receiver arms 82' and 82", such as near the top of the receiver arms in the form of horizontal radiused grooves.

The interior surface 90 of the receiver arms 82' and 82", located just below the guide and advancement structure 92 is a discontinuous cylindrical surface 102. The cylindrical surface 102 has a diameter equal to or slightly less than a root diameter of the guide and advancement structure 92. The channel 84 separates portions of the surfaces 102 of the arms 82' and 82", such that the surface 102 is not continuous about the interior surface 90 of the receiver 10. Moving downwardly, in a direction toward the base 80, adjacent the cylindrical surface 102 is a discontinuous insert attachment structure or groove or slot or spherical surface 104 that extends outwardly from the axis C and runs perpendicular to the axis C. It is foreseen there may be a subsequent second insert attachment groove (not shown) located below the first insert attachment groove 104. Adjacent to and located below the insert groove surface 104 is a second discontinuous cylindrical surface 106 having a diameter or width or radius equal to or less than the diameter or width or radius of the surface 102. A discontinuous annular surface 108 that provides an abutment surface or stop for capturing the positioner 9 in the receiver 10 is located below and adjacent to the second cylindrical surface 106. The abutment surface 108 is disposed substantially perpendicular to the axis C. Another cylindrical surface 110 is located below and adjacent to the surface 108. The cylindrical surface 110 is oriented substantially parallel to the axis C and is sized and shaped to capture the positioner 9 as will be described in greater detail below. The surface 110 surrounds the U-shaped channel seat 8 and is discontinuous. The cylindrical surface 110 has a diameter greater than the diameter of the cylindrical surface 102 and the second cylindrical surface 106. A discontinuous sloped surface 112 is located below and adjacent to the cylindrical surface 110, sloping downwardly and inwardly toward the central axis C. A fourth partially cylindrical surface 114 is located below and adjacent to the surface 112. A bevel or sloped surface 121 is below the cylindrical surface 112. The bevel slopes away from axis C and downwardly.

The cylindrical surface 110, the stop or abutment surface 108, and a lower abutment surface 125 partially define a circumferential recess or expansion chamber 95 that is sized and shaped to house the positioner 9 and pivoting retainer 12 in combination as they expand around the shank upper portion 8 as the shank upper capture portion 8 moves upwardly toward the channel 84 during assembly. Additionally, the expansion chamber 95 forms a restriction to prevent the pivoting retainer 12 and the positioner 9 from moving upwardly with the shank portion 8, the stop surface 108 preventing the pivoting retainer 12 and the positioner 9 from passing from the expansion chamber 95 into an upper cavity 91 of the receiver 10 whether the pivoting retainer 12 is in an expanded position or in a neutral or original operative position, as shown in FIG. 2.

The lower opening 136 has a diameter or width or radius (not shown) measured from the upper edge of a curved surface 121. The illustrated surface 121 has a diameter that is substantially the same as the diameter of the surface 106, allowing for slidable down loading of the compression insert 14 while requiring compression or squeezing of the positioner 9 during uploading of the pivoting retainer 12 and the positioner 9 through the lower opening 136, and in some embodiments the pivoting retainer may also be compressed to be uploaded. The pivoting retainer 12 and positioner in combination operate to capture the shank upper portion 8 within the receiver 10.

The positioner 9 operates to control, capture and hold the pivoting retainer 12 within the receiver 10 expansion chamber 95 and is described in U.S. Provisional Patent Application Nos. 62/137,713; 62/137,707; 62/078,173; 62/066,813; 62/066,806; and 62/078,154, each of which were previously referenced above.

The positioner 9 has a central axis D (FIG. 1) that is operationally aligned with axis C associated with the receiver 10, and may be aligned with axis A associated with the shank 4 and axis B of the pivoting retainer 12. The positioner 9 may be made from a resilient material, such as a stainless steel, titanium alloy, or the like, as well as polymers, so that the positioner may be expanded and contracted during various steps of assembly, as will be described in greater detail below.

The illustrated positioner 9 is of an at least partially annular or ring-like shape and has a central channel, opening, or hollow through bore, generally 161, that passes entirely through the positioner 9 from a top surface 162 to a bottom surface 164 thereof.

It is foreseen that the top surface portion 162 and also the rest of the cylindrical outer surface 170 thereof may additionally or alternatively include a roughened or textured surface or surface finish, or may be scored, knurled, grit blasted, or the like, for enhancing frictional engagement with the surfaces 125 and 108 of the receiver 10 and a top surface 62 of the pivoting retainer 12. The additional surfacing may be necessary for the bottom surface of the positioner 9 to prevent or limit rotational movement of the pivotal retainer 12 with respect to the positioner 9 and also the receiver 10.

The friction fit compression or pressure insert 14 is sized and shaped to be received and either uploaded into the receiver 10 through the lower opening 136 or downloaded through the channel 84. The illustrated compression insert 14 has a central axis F (FIG. 1) that is operationally aligned with the central axis C of the receiver 10. In operation, the insert 14 advantageously frictionally engages the bone screw shank upper portion 8, allowing for un-locked, but non-floppy placement of the angle of the shank 4 with respect to the receiver 10 during surgery prior to locking of the shank with respect to the receiver near the end of the procedure with a rod or connecting member 21 and a closure 18. The insert 14 is thus preferably made from a resilient material, such as a stainless steel or titanium alloy, so that portions of the insert may be expanded about and then contracted, snapped or popped onto the shank upper portion 8. Furthermore, in operation, the insert 14 is suspended within the receiver 10, being frictionally held in place by a receiver thread run off groove 103 and prohibited from moving upward even with the insertion of the positioner 9, pivoting retainer 12, and the shank upper capture portion 8, as is described in U.S. Provisional Patent Application No. 62/078,154, previously referenced above.

The illustrated insert 14 includes a lower body 182 with a pair of spaced upstanding arms 183' and 183". The arms 183' and 183" have a radially outer surface 185 on each side which are substantially smooth and vertically or axially opposed, but radially spaced from the axis F. The outer surface 185 includes receiver attachment projection structures 184 on each arm 183' and 183". Each receiver attachment projection structure 184 extends circumferentially about the outer surface and may include a beveled or sloped surface (not shown) on either or both sides of the projection 184. The projection 184 has a maximum diameter or width or radius similar to that of the lower opening 136 of the receiver 10 or the channel 84 measured about the center of the projection 184, so as to be able to be top or bottom loaded. The arms 183' and 183" form a central U-shaped channel 187 therebetween, and there is a central axially aligned and centered bore 188 formed through the insert 14. The through bore 188 runs from an annular planar top surface 192 to an annular planar and discontinuous bottom surface 194 thereof. The bore 188 is defined by an inner cylindrical surface 196 that is at least partially defined by the U-shaped channel 187 and a spherical shank gripping surface portion (not shown) extending between the cylindrical surface 196 and the bottom surface 194. The compression insert 14 through bore 188 is sized and shaped to receive a driving tool (not shown) therethrough that engages the shank drive feature 49 when the shank body 6 is driven into bone with the receiver 10 attached or without.

It is foreseen that the shank gripping surface portion (not shown) may additionally or alternatively include a roughened or textured surface or surface finish, or may be scored, grit blasted, knurled, or the like (not shown), for enhancing frictional engagement with the shank upper portion 8.

When the shank 4 is locked into position by a rod or other connecting member 21 being pressed downwardly on the insert U-shaped channel 187 by the closure top 18, the insert shank gripping portion 198 applies locking pressure to the shank surface 46, and thus securely fixes the shank upper portion 8 to the insert 14, as seen in FIG. 2.

The illustrated compression insert 14 also includes a first outer and upper cylindrical surface 202 adjacent to the outer surfaces 185 of the arms 183' and 183". The surface 202 may be continuous with and including the outer surfaces 185 of the insert arms 183' and 183", although this is not necessarily required. The insert 14 may also include a second outer lower and discontinuous cylindrical surface 204 adjacent to the bottom surface 194. A discontinuous annular transitional surface (not shown) may extend between and connect the upper and lower cylindrical surfaces 202 and 204. The cylindrical surfaces 202 and 204, projection 184, and outer surface 185 are sized and shaped to be received within the receiver interior surfaces 90 when loaded.

Ledges 196 radially project from opposite sides of the cylindrical surfaces 202, 204 and outer surface 185 just proximal to a circumferentially extending groove 197 and separating groove ends 198. Proximal-facing saddle surfaces 191 are defined in a semi-cylindrical curved fashion through the insert 14 and across the proximal-facing portions of the ledges 196. In some embodiments, the curved saddle surfaces 191 have a diameter that are essentially equal to the diameter of the implant rod 21, such that the implant rod surface 22 can extend across a saddle surfaces 191. The curved saddle surfaces 191 transition into upwardly extending planar sidewall surfaces 193 that face radially inward. Ledges 196' and 196" are defined by opposed side surfaces 190, 195. Ledge 196', as illustrated is further defined by opposed side surfaces 200 and 201. Ledge 196" has a bottom surface (not shown) that engages the valley surface 167 of the positioner 9. Adjacent the saddle surfaces 191 is a planar side surface 190 terminating at a inwardly sloping side surface 195. Adjacent the side surface 195 is a second planar side surface 200 terminating at a second inwardly sloping side surface 201.

It is foreseen that the insert 14 may not include arms 183' and 183". It is also foreseen that the arms 183' and 183" may not be spaced from the closure top 18 in some embodiments and may be sized and shaped to contact the closure top 18 in other embodiments in order to provide locking of the polyaxial mechanism of the assembly with pivoting retainer 12, but without fixing of the rod or other longitudinal connecting member 21 with respect to the closure top 18.

Preferably, the receiver 10, the positioner 9, and the compression or pressure insert 14 are assembled at a factory setting that includes tooling for holding and alignment of the component pieces and pinching or compressing of the retainer 12, as well as, the positioner 9. As described herein with respect to the assembly 1, similarly, the shank 4, may be assembled with the receiver 10, positioner 9, pivoting retainer 12, and compression or pressure insert 14 at the factory or it may be desirable to "pop" the shank 4 into the receiver subassembly 10 at a later time, either before or after implantation of the shank 4 in the vertebra.

It is foreseen that pre-assembly of the receiver 10, pivoting retainer 12, positioner 9, and compression insert 14 may be chosen by the manufacturer. In some cases, the compression insert 14 is loaded firstly into the receiver 10 with the insert top surface 192 facing the receiver bottom surface 134. At this point, the insert 14 is captured and frictionally held in place by the mating of the receiver projection attachment structures 184 within the thread run off groove 103. This prevents the insert 14 from any unwanted downward movement or further upward movement towards the guide and advancement structure 92 of the receiver 10 and provides adequate clearance for the later step of pushing the bone screw head shank upper portion 8 through the pivoting retainer 12 and positioner 9 combination. Although the grooves 103 would prohibit the insert 14 from moving out the upper opening 86 of the receiver 10 and moving downward, it is foreseen that a tool or tools (not shown) may be used to push up, pull or otherwise lift the insert into position.

The resilient open pivoting retainer 12 is prepared for insertion into the receiver 10 by squeezing or pressing the retainer end surfaces 65 and 66 toward one another. The compressed retainer 12 is inserted into the receiver 10 by either bottom or top loading. The retainer 12 is typically moved upwardly into the receiver 10 and enters the expansion chamber 95 and allowed to expand to a neutral uncompressed state within the chamber 95.

The open positioner 9 is prepared for insertion into the receiver 10 by squeezing or pressing or folding or compressing positioner end surfaces 174 and 175 toward one another. The positioner 9 is typically moved into the receiver 10 and allowed to expand to a neutral uncompressed state within the expansion chamber 95 engaging the abutment surface 125. Peaks 167 of the positioner 9 may engage the stop surface 108.

The retainer ring 12 resides within the distal confines of the positioner 9, such that the top surface 62 of the retainer ring 12 is in abutting planar contact with a planar distal face 169 of at least one radially inward projecting flange 171 of the positioner 9. The illustrated embodiment there are two sets of flanges 171 on each side of the positioner 9. It is foreseen that more flanges may be added to the positioner 9. Also, the spherical outer surface 63 of the retainer ring 12 abuts against the distally narrowing interior conical circumferential surface 165 of the positioner 9, thereby locking the retainer ring 12 within the distal circumferential confines of the positioner 9. Thus, the structural interaction of the positioner 9 and the retainer ring 12 maintains the two components 9, 12 in a substantially concentric relationship.

At this time, the compression insert 14, the positioner 9, and the pivoting retainer 12 are captured within the receiver 10. The receiver 10, compression insert 14 and the positioner 9 and pivoting retainer 12 combination are now pre-assembled and ready for shipment or assembly with the shank 4 either at the factory, by surgery staff prior to implantation, or directly after implanting the shank 4 by the surgeon. The pivoting retainer 12 and the positioner 9 in combination may rotate until a sloping surface 163 of the positioner 9 engages the second sloped side surface 201 of the compression insert 14.

Next, the top surface 47 of the shank 4 is partially inserted into the expansion chamber 95, and the upper capture portion 8 of the shank 4 abuts against the pivoting retainer 12, held down by the positioner 9. The pivoting retainer 12 and positioner 9 in combination are lifted up by the shank 4. The proximal driving of the shank 4 has caused the top surface 162 of the positioner 9 to abut against the proximal planar step face 108 (FIG. 2) of the interior cavity 91 of the receiver member 10, thereby arresting proximal displacement of the positioner 8 and retainer 12 combination within the confines of the expansion chamber 95 of the receiver member 10. Also, the proximal (upward, as seen in FIG. 2) driving of the shank 4 has caused the upper spherical surface 46 of the shank upper portion 8 to abut against the interior surface 61 of the retainer ring 12 and the projecting flange 171 of the positioner 9, thereby causing the retainer ring 12 and the positioner 9 to radially expand as the shank upper portion 8 proximally displaces into the confines of the cavity 91 of the receiver member 10. The sloping surface 163 of the positioner 9 slides outwardly across the second sloped surface 201 of the insert 14 while expanding radially outward. The retainer 12 and positioner 9 have reached a maximum expansion about the shank capture portion 8 at the point where the upper cylindrical surface 45 engages the projecting flange 171 of the positioner 9, just prior to capture the shank upper capture portion 8 within the receiver 10.

As the shank upper portion continues to move proximally, the retainer ring 12 captures the shank head 8 after expanding in the expansion chamber 95 and then returning to a neutral state, all while being forced downward by the positioner 9. Thus, the retainer ring 12 is positioned to be received on the conically tapered interface surface 38 of the shank upper portion 8. Also, since the positioner 9 is held in a radially expanded condition on account of its radially inward projecting flange 171 contacting the upper cylindrical surface 45 of the shank upper portion 8, the interior of the positioner 9 is spaced apart from the exterior of the retainer ring 12, thereby freeing the retainer ring 12 from its locked retention within the positioner 9. The retainer ring 12 fully seats in the conically tapered interface surface 38 of the shank upper portion 8, and distal or opposite displacement of the shank upper portion 8 seats the retainer ring 12 in a spherical inner surface 113 (FIG. 2) of the retainer 10. The seating of the retainer ring 12 in the conically tapered notch or interface surface 38 captures and prevents the shank upper portion 8 from exiting the lower opening 136 in the receiver member 10, as the combined diameter of the shank head portion 8 and the retainer ring 12 nested thereon exceeds the diameter of the lower opening 136 in the receiver member 10. The shank upper capture portion 8 at this point cannot be pulled out of the receiver 10. The pivoting retainer 12 is stabilized on the shank head upper capture portion 8 with respect to pivotal, rotational, and elevational alignments.

It is foreseen that the retainer 12 may snap on, pop on, twist on, rotate on, screw on, or other actions so as to capture the shank upper portion 8.

The insert 14 remains in the fixed position, aligned and prevented from rotating and moving vertically. Once the shank upper portion 8 is captured, the compression insert 14 is pressed downwardly by a tool, such as a screw driver (not shown), toward the shank upper portion 8. As a result, the second sloped surface 201 of the insert 14 forces against a distally narrowing conical or sloped proximal surface 172 of the radially inward projecting flange 171 of the positioner 9 to wedge the flange 171 radially outward and allowing the distal portion of the lower cylindrical surface 204 of the insert 14 to slide past the flange 171 until the flange 171 encounters and is received in the circumferentially extending groove 197 of the insert 14, thereby securing the insert 14 and the positioner 9 together. Thus, a tight, non-floppy, substantially spherical ball and socket joint 44 is now created between the insert 14 and the shank upper portion 8 and the pivoting retainer 12 combination. This second fixed position of the insert 14 creates an interference friction fit connection. The friction fit between the compression insert 14 and the shank upper portion 8 and pivoting retainer 12 combination is not totally locked or fixed, but at the same time is not loose or floppy either, advantageously allowing the user to articulate the shank 4, in this case, with the pivoting retainer 12, with respect to the receiver 10, but with some resistance, so that when the shank 4 is placed in a desired orientation with respect to the receiver 10, the assembly 1 remains substantially frictionally set in such desired orientation unless purposefully manipulated into another position.

It is foreseen that a friction fit between the receiver 10 and the shank 4 may not be wanted by the surgeon. In this case, the projection structure 184 is positioned within the insert attachment apertures 104, so as to allow the insert 14 to move about the gap or aperture 104, and thus creating a floppy fit between the receiver 10 and the shank 4. A floppy fit will allow the user to move the receiver 10 about the shank 4 freely, but will not stay in any one position chosen. To make the floppy fit stay in a desired orientation, it would require the installation of a rod 21 and a closure 18.

The bone screw shank 4 (or an entire assembly 1 made up of the assembled shank 4 with or without, the pivoting retainer 12, positioner 9, receiver 10, and compression insert 14) is screwed into a bone or vertebra, by rotation of the shank 4 using a suitable driving tool or tool assembly (not shown) that operably drives and rotates the shank body 6 by engagement thereof at the internal drive 49. It is foreseen that the shank 4, the other bone screw assembly parts, the rod 21 (also having a central lumen in some embodiments) and the closure top 18 (also with a central bore drive) can be inserted in a percutaneous or minimally invasive surgical manner, utilizing guide wires (not shown) with or without minimally invasive guide tools.

When the shank 4 is driven into the vertebra without the remainder of the assembly 1, the shank 4 may either be driven to a desired final location or may be driven to a location slightly above the final location or "proud" to provide for ease in assembly with the pre-assembled receiver 10, compression insert 14, positioner 9, and pivoting retainer 12. The pre-assembled receiver 10, insert 14, positioner 9, and pivoting retainer 12 are placed above the shank upper portion 8 until the shank upper portion 8 is received within the opening 136 of the receiver 10.

With reference to FIG. 2, the rod 21 is eventually positioned in an open or percutaneous manner in cooperation with the at least two bone screw assemblies 1. The closure structure 18 is then inserted into and advanced between the arms 82 of each of the receivers 10.

The illustrated closure structure 18 is substantially cylindrical and includes an outer helically wound guide and advancement structure 78 in the form of a square flange thread form that operably joins with the guide and advancement structure 92 disposed on the arms 82 of the receiver 10. The illustrated closure structure 18 also includes a top surface 74 with an internal drive 76 in the form of an aperture that may be a star-shaped internal drive such as that sold under the trademark TORX, or may be, for example, a hex drive, or other non-round internal drives such as slotted, tri-wing, spanner, two or more apertures of various shapes, and the like. A driving tool (not shown) sized and shaped for engagement with the internal drive 76 is used for both rotatable engagement and, if needed, disengagement of the closure 18 from the receiver arms 82. The closure structure 18 may include a break-off head (similar structures seen in FIGS. 4, 6, 9, 13, 15, and 18) designed to allow such a head to break from a base of the closure at a preselected torque, for example, at 70 to 140 inch pounds. Such a closure structure would use the internal drive 76 for closure removal.

The closure structure 18 is rotated, using a hex tool (not shown) until a selected pressure is reached at which point the rod 21 engages the U-shaped channel 187 of the compression insert 14, further pressing the insert spherical surface (not shown) against the shank spherical surface 46.

As the closure structure 18 rotates and moves downwardly into the respective receiver 10, the point 75 and bottom surface rim 77 engage and penetrate the rod surface 22, and the closure structure 18 presses downwardly against and biases the rod or connecting member 21 into engagement with the insert 14 that thereby urges the shank upper portion 8 toward the lower opening 136 of the retainer 10 and into locking engagement therewith, with the pivoting retainer 12 frictionally abutting the surface 113 of the receiver 10.

The closure top 18 may include a cannulation through bore 79 extending along a central axis G thereof and through top and bottom surfaces thereof. Such a through bore 79 provides a passage through the closure 18 interior for a length of wire (not shown) inserted therein to provide a guide for insertion of the closure top 18 into the receiver arms 82, for example implantation of the assembly 1 during minimally invasive techniques. It is foreseen that any of a variety of different closure structures for use in conjunction with the present disclosure with suitable mating structure on the upstanding arms 82 can be utilized. For example, a multi-start threaded closures (not shown) are foreseen to be utilized in this disclosure.

It is foreseen that different sizes of rods may be utilized with the same components of the bone screw assembly 1. The only difference is the amount of rotation of the closure 18 required to fix the different sizes of the rods 21 within a receiver. It is foreseen that inner cores or tensionable cords (FIG. 5) and sleeves (FIG. 5) utilized in soft or dynamic stabilization procedures may also be used in this disclosure, such as those seen in U.S. patent application Ser. No. 14/731,064, previously referenced above.

If removal of the rod 21 from any of the bone screw assemblies 1 is necessary, or if it is desired to release the rod 21 at a particular location, disassembly may be accomplished by using a driving tool (not shown) that mates with an internal drive 76 of the closure structure 18 to rotate and remove such closure structure 18 from the cooperating receiver 10. Disassembly is then accomplished in reverse order to the procedure described previously herein for assembly. It is also foreseen that the implant may be a permanent fixture and may not be disassembled, only removed as a whole assembled unit, if necessary.

With reference to FIGS. 3-4, the reference number 1001 generally represents an embodiment of a multi-planar, multi-axial, or polyaxial bone screw apparatus or assembly according to the present disclosure. While the illustrated anchor 1001 is generally a polyaxial bone screw, it is foreseen that the disclosure could be utilized with other types of spinal implants that utilize pressure inserts, such as polyaxial bone hooks or clamps, for example. The illustrated assembly 1001 includes: a shank 1004, that further includes a body 1006 integral with an upwardly extending upper portion or capture structure 1008; a positioner 1009; a receiver 1010; a pivoting retainer structure 1012; a compression or pressure insert 1014; a closure 1018; and a rod or connecting member 1021. The rod 1021 and the positioner 1009 are substantially similar to their counterparts in assembly 1, as discussed above the positioner may be initially assembled with the retainer 1012 and insert 1014 and further assembled with the shank 1004 either prior or subsequent to implantation of the shank body 1006 into a vertebra (not shown), as discussed above.

The receiver 1010 and the shank 1004 cooperate in such a manner that the receiver 1010 and the shank 1004 can be secured at any of a plurality of angles, articulations or angular alignments relative to one another and within a selected range of angles from side to side and/or from front to rear, to enable flexible or articulated engagement of the receiver 1010 with the shank 1004 until both are locked or fixed relative to each other near the end of an implantation procedure, as seen in FIG. 4.

The shank 1004 is elongate, with the shank body 1006 having a helically wound bone implantable thread 1024 (single or multi start thread forms, which can have different types of thread patterns) extending from near a neck 1026 located adjacent to the upper portion or capture structure 1008, to a tip (not shown) of the body 6 and extending radially outwardly therefrom. During use, the body 1006 utilizing the thread 1024 for gripping and advancement is implanted into the vertebra (not shown) leading with the tip (not shown) and driven down into the vertebra with an installation or driving tool (not shown), so as to be implanted in the vertebra to near the neck 1026, as more fully described in the paragraphs above. The shank 1004 has a longitudinal axis of rotation generally identified by the reference letter H in FIG. 3.

The neck 1026 extends axially upward from the shank body 1006. The neck 1026 may be of the same or is typically of a slightly reduced radius as compared to an adjacent upper end or top 1032 of the body 1006 where the thread 1024 terminates. Further extending axially and outwardly from the neck 1026 is the shank upper portion 1008 that provides a connective or capture apparatus disposed at a distance from the upper end 1032 and thus at a distance from the vertebra when the body 1006 is implanted in such vertebra.

The shank upper capture portion 1008 is configured for a pivotable connection relative to the shank 1004 and the upper pivoting retainer 1012 with respect to the receiver 1010 prior to fixing of the shank 1004 in a desired position with respect to the receiver 1010. The shank upper portion 1008 has an outer bulbous, convex and partially spherical lower surface 1034 that extends outwardly and upwardly from the neck 1026 and terminates at a lower cylindrical surface 1035. The lower cylindrical surface 1035 is parallel to axis H and has a diameter or width or radius (not shown) measured from the top most edge from one side to the other. It is foreseen that the lower cylindrical surface 1035 may not have to be parallel with axis H. The lower cylindrical surface 1035 terminates at a substantially planar ledge or shelf surface 1036 that is annular and disposed perpendicular to the shank axis H. The spherical lower surface 1034 has an outer radius that is the same or substantially similar to an outer radius of the pivoting retainer 1012, as will be described in greater detail below. The spherical lower surface 1034, as well as the upper pivotal retainer 1012 outer surface, cooperate to form a ball component 1044 of a ball and socket joint formed by the shank 1004 and attached upper retainer 1012 within an interior 1090 of the receiver 1010 defining an inner cavity or space 1091. Extending upwardly from the ledge 1036 is a cylindrical interface surface 1038, the surface 1038 having a radius or diameter or width that is smaller than the radius of the lower spherical surface 1034 and the diameter of the lower cylindrical surface 1035.

In the illustrated embodiment of FIG. 3, there is a secondary step surface 1037 that is adjacent to the lower ledge 1036 surface. The secondary step surface 1037 terminates at a secondary ledge surface 1039. It is foreseen that the secondary ledge 1039 and step surface 1037 can be located adjacent an upper ledge or shelf 1043 rather than the lower ledge 1036 as shown. Extending outwardly from the cylindrical interface surface 1038 is the annular shelf surface or upper ledge 1043 that faces downwardly toward the ledge 1036 and is also substantially perpendicular to the axis H. It is envisioned that either the lower ledge 1036 or the upper shelf surface 1043 may be curved or sloped, as will be discussed in greater detail below. The lower ledge 1036, cylindrical interface surface 1038 and upper ledge 1043 cooperate to capture and fix the resilient open upper retainer 1012 to the shank upper portion 1008, prohibiting compression of the upper retainer 12 with respect to axis H once the upper retainer 12 is located between the ledges 1036 and 1043. Extending upwardly from the upper ledge 1043 is a cylindrical surface 1045 having a width or diameter or radius (not shown), measured from the top most edge from one side to the other. The width or diameter or radius is smaller than the width or diameter or radius (not shown) of the lower cylindrical surface 1035, but larger than the radius of the cylindrical interface surface 1038. The cylindrical surface 1045 width or diameter or radius (not shown) is configured for sliding cooperation and ultimate frictional mating with an interior 1057 of the upper retainer 1012, so as to assist in initiating the expansion of the upper retainer 1012.

Extending upwardly from the upper cylindrical surface 1045 is an upper partially spherical or domed surface 1046. The radius of the upper spherical surface 1046 is preferably the same than the radius of the lower spherical surface 1034. Located near or adjacent to the surface 1045 is an annular top surface 1047. It is foreseen that a bevel (not shown) may extend about the spherical surface 1046 and may be located between the spherical surface 1046 and the annular planar top surface 1047.

The spherical surface 1046 has the outer radius configured for sliding cooperation and ultimate frictional mating with a concave surface 1142 of the compression insert 1014, having a substantially similar radius, and also a flat or, in some embodiments, curved surface, and will be discussed more fully in the paragraphs below.

The shank top surface 1047 is substantially perpendicular to the axis H. The upper spherical surface 1046 shown in the present embodiment is substantially smooth with the exception of a stepped or graduated upper surface portion 1040 located adjacent to the top surface 1047 and sized and shaped for cooperation and ultimate frictional engagement with the compression insert 1014. In the illustrated embodiment of assembly 1001, the surface portion 1040 includes at least three graduated cylindrical surfaces 1041 disposed substantially parallel to the axis H and adjacent perpendicular step surfaces that are disposed generally perpendicular to the axis H. It is foreseen that the surface portion 1040 may include greater or fewer number of stepped surfaces and that the stepped surfaces be further structure rather than carved into the shank spherical surface 1034. It is also foreseen that similar stepped surfaces could be carved in and winding helically about on the spherical surface 1034 near the neck 1026 as envisioned in U.S. patent application Ser. No. 14/164,882, previously referenced above. It is foreseen that the surface portion 1040 and also the rest of the spherical surface 1046 may additionally or alternatively include a roughened or textured surface or surface finish, or may be scored, knurled, grit blasted, or the like, for enhancing frictional engagement with the pivoting retainer 1012 and/or the compression insert 1014.

Formed in a shank upper portion 1008 of the shank head 1004 are opposite or opposed parallel flat planar surfaces 1042 that extend downwardly in the direction of axis H and separate the shelf surface 1043 into two opposed and spaced apart surfaces. In the illustrated embodiment of the shank in FIG. 3, the flat planar surfaces 1042 may be shaped, machined or molded, such that the width between the flat planar surfaces 1042 is less than or substantially equal to the width or radius or diameter (not shown) of the interface surface 1038 or now separated surfaces 1038. The opposite and parallel flat planar surfaces 1042 create a disconnect, such that the upper shelf and ledge surface 1043, the upper spherical surface 1046, the upper cylindrical surface 1045, the interface surface 1038, the secondary step surface 1037, the lower spherical surface 1034, the lower cylindrical surface 1035, and the lower ledge surface 1036 are all discontinuous. Each of the upper ledge surface 1043 and the lower ledge surface 1036 stop at each of the flat planar surfaces 1042 and continue after along the circular path created by the substantially spherical surfaces. It is foreseen that the flat planar surfaces 1042 may also include a lower key extension, as seen in U.S. patent application Ser. No. 13/573,516, previously referenced above. The upper pivoting retainer 1012 can be top, bottom, or side loaded onto the shank head. Once the shank head 1008 passes through the upper retainer 1012, for example, by top loading, the planar side surfaces 1042 mate with the pivoting retainer 1012 creating a spherical ball shape structure 1044, as will be further described below. In this way, the pivoting retainer 1012 is prevented from rotating along the axis H with respect to the shank.

A counter sunk substantially planar base or seating surface (not shown) partially defines an internal drive feature or imprint or structure 1049. As best seen in FIG. 3, the illustrated internal drive feature 1049 is an aperture formed in the top surface 1047 extending downwardly from the top surface 1047 and has a hexagonal or hex shape designed to receive the hex tool (not shown) of an Allen wrench type, into the aperture for rotating and driving the bone screw shank 1004. It is foreseen that such an internal tool engagement structure may take a variety of tool-engaging forms and may include one or more apertures of various shapes, such as a pair of spaced apart apertures or a multi-lobular or star-shaped aperture, such as those sold under the trademark TORX, or the like, having a non-round shape for positive drive engagement by a complementary shaped drive tool. It is foreseen that the drive tool structure may be made of a somewhat softer metal compared to that of the head. In operation, the driving tool is received in the internal drive feature 1049, being seated at the base (not shown) and engaging the six faces of the drive feature 1049 for both driving and rotating the shank body 1006 into the vertebra, either before the shank 1004 is attached to the receiver 1010 or after the shank 1004 is attached to the receiver 1010, with the shank body 1006 being driven into the vertebra with the driving tool extending into the receiver 1010.

The shank 1004 may be cannulated, having a small central bore (not shown) extending an entire length of the shank 1004 along the axis H. It is foreseen that the central bore may not have to extend in a parallel direction with H, that the bore may not extend the entire length of the shank 1004. The bore may provide a passage through the shank 1004 interior for a length of wire (not shown) inserted into the vertebra prior to the insertion of the shank body 1006, the wire providing a guide for precise insertion of the shank body 1006 into the vertebra.

It is foreseen that the shank 1004 can be expandable and/or fenestrated, and again, have different thread patterns extending along its length. It is foreseen that the length of the shank may be shortened or lengthened further than illustrated.

To provide a biologically active interface with the bone or vertebra (not shown), the threaded shank body 1006 may be coated, perforated, made porous or otherwise treated. The treatment may include, but is not limited to, a plasma spray coating or other type of coating of a metal or, for example, a calcium phosphate; or a roughening, perforation or indentation in the shank surface, such as by sputtering, sand blasting or acid etching, that allows for bony ingrowth or ongrowth. Certain metal coatings act as a scaffold for bone ingrowth. Bio-ceramic calcium phosphate coatings include, but are not limited to: alpha-tri-calcium phosphate and beta-tri-calcium phosphate ($Ca_3(PO_4)_2$), tetra-calcium phosphate ($Ca_4P_2O_9$), amorphous calcium phosphate and hydroxyapatite ($Ca_{10}(PO_4)_6(OH)_2$). Coating with hydroxyapatite, for example, is desirable as hydroxyapatite is chemically similar to bone with respect to mineral content and has been identified as being bioactive and thus not only supportive of bone ingrowth, but actively taking part in bone bonding.

The upper pivotal retainer 1012 operates to assist in capturing the shank upper portion 1008 within the receiver 1010, and is similar to the pivotal retainer 12. The upper pivotal retainer 1012 has a central axis I that operationally aligns with axis H associated with the shank 1004 when assembled thereon. The upper pivotal retainer 1012 is ring shaped, having a central bore 1057, and may be made from a resilient material, such as a stainless steel, titanium alloy, cobalt chrome, or the like, as well as polymers, or some combination thereof, so that a retainer body 1055 may be resiliently expanded.

The upper pivotal retainer 1012 includes an outer surface 1063 defined by the substantially cylindrical continuous body 1055 and is continuous, except for a slot or slit 1054. It is foreseen that the spherical surface 1063 may additionally or alternatively include a roughened or textured surface or surface finish, or may be scored, knurled, grit blasted, or the like, for enhancing frictional engagement with the positioner 1009. It is noted that the surfaces 1063 need not be spherical and may be planar, tapered, or faceted or include other surface geometries, such as conical.

The upper retainer body 1055, having only the very narrow slit 1054 to be used for expansion purposes only when the shank upper capture portion 1008, is loaded in combination with the shank upper capture portion 1008 through the receiver lower opening 1136. The bore 1057 surfaces are sized and shaped such that the upper retainer body 1055 cannot compress further when mated with the shank upper capture portion 1008. The through slit 1054 of the resilient upper retainer 1012 is defined by first and second end surfaces, 1065 and 1066, respectively, disposed in spaced relation to one another or they may also be touching when the retainer is in a neutral, natural, or nominal starting state or position. Both end surfaces 1065 and 1066 are disposed substantially perpendicular to a bottom surface 1059 and a top surface 1062. It is foreseen that the slit 1054 may be at an angle or curved. A width between the surfaces 1065 and 1066 is very narrow in the nominal state to provide stability and more surface contact area for the upper retainer 1012 during operation. When the upper retainer 1012 and shank upper capture portion 1008 are in combination, the upper retainer 1012 is in a neutral state, such that it does not need or, in fact, cannot be further compressed.

Referring now to FIG. 20, the upper retainer 1012 hollow through bore 1057 passes entirely through the upper retainer 1012. Surfaces that define the channel or bore 1057 include: an upper cylindrical surface 1058 adjacent to the retainer top surface 1062, a sloped surface 1060 adjacent the upper cylindrical surface 1058, and a cylindrical surface 1061 adjacent the sloped surface 1060. The bore 1057 is sized and shaped to closely fit about and snap onto the shank interface surfaces 1038 during assembly. The upper cylindrical surface 1058 is continuous about the bore 1057 of the upper retainer 1012. When mated the top surface 1062 of the pivoting retainer 1012 does not extend above the top of the shank top surface 1047. The sloped surface 1060 does not mate with the secondary ledge 1039 and secondary step surface 1037, but does engage an edge 1071 at the point where the secondary ledge 1039 and secondary step surface 1037 meet. The sloped surface 1060 has another advantage as being able to avoid the stepped portion 1040 when the shank 1004 is uploaded. When the pivoting retainer 1012 is mated to shank upper capture portion 1008, the ball structure 1044 that is substantially spherical is created. Again, the pivoting retainer 1012 is stabilized on the shank head upper capture portion 1008 with respect to pivotal, rotational, and elevational alignments.

It is foreseen that further surfaces such as a lower shelf surface (not shown) and a fourth cylindrical surface (not shown) may be sized and shaped to further step down the spherical shape of the outer surface 1063 internally. It is foreseen that in other embodiments of the disclosure, fewer or greater number of planar or other surfaces with other geometries may extend between the top surface 1062 and the inner surfaces defining the bore 1057 of the pivoting retainer 1012.

The gap functions only in expansion to allow the upper retainer 1012 to expand about the shank upper portion 1008 and return to the natural state when fully mated. This results in a stronger retainer 1012 that provides more surface contact with the shank upper portion 1008 upon locking, resulting in a sturdier connection with less likelihood of failure than a retainer ring having a greater gap or one that is compressible on the shank. Furthermore, because the retainer body 1055 is only expanded and not further compressed, the upper retainer 1012 does not undergo the mechanical stress that typically is placed on spring ring type retainers that are both compressed and expanded during insertion of the shank upper capture portion 1008.

The receiver 1010 is similar to the receiver 10 described above. The first difference being that the guide and advancement structure 1092 is a partial helically wound interlocking reverse angle buttress thread form configured to mate under rotation with a similar structure on the closure structure 1018, as described more fully below.

An opposed pair of tool receiving and engaging apertures or indentations 1094 are formed on outer surfaces 96 of the illustrated arms 1082' and 1082". Two pairs of tool receiving and engaging apertures 1097 may be formed in front and rear surfaces 1078' and 1078" of the arms 1082' and 1082". Furthermore, it is foreseen that two pairs of tool receiving and engaging apertures (not shown) may be formed near the top surfaces 1093' and 1093" of the arms 1082' and 1082", as is seen in FIG. 2. Some or all of the apertures 1094 and 1097 may be used for holding the receiver 1010 during the implantation of the shank body 1006 into a vertebra when the shank is pre-assembled with the receiver 1010, and during assembly of the bone anchor assembly 1001 with the rod 1021 and the closure structure 1018.

In lieu of a run off groove 103, the receiver 1010 includes a shipping groove 1103 that serves the same purpose to frictionally hold the insert 1014 in position prior to displacing the insert 1014 distally toward the receiver lower opening 1136, so as to engage the second set of grooves or insert attachment apertures 1104.

The illustrated insert 1014 is substantially similar to the insert 14 described above and includes a lower body 1182 with a pair of spaced upstanding arms 1183' and 1183". The arms 1183' and 1183" are specifically designed to be longer than the arms 183' and 183", so that the arms 1183' and 1183" are meant to engage the closure 1018, and therefore be modified to be located above the greatest diameter of the rod 1021, as is best illustrated in FIG. 4. This design creates an independent lock such that shank and receiver are locking independent or prior to the locking of the rod by a separate inner set screw.

The closure structure or nested fastener 1018 can be any of a variety of different types of closure structures for use in conjunction with the present disclosure with suitable mating structure on the upstanding arms 1083' and 1083" of the head or receiver 1010, one such closure is described in U.S. patent application Ser. No. 11/140,343, the entirety of which is incorporated by reference herein.

The illustrated fastener 1018 includes an outer fastener 1204 and an uploaded inner set screw 1206. The fastener 1204 includes a base 1208 integral or otherwise attached to a break-off head 1210. The base 1208 cooperates with the receiver head 1010 of the bone screw assembly 1001, as illustrated in FIG. 4, to close a head U-shaped channel 1084 and to clamp the spinal fixation rod 1021 within the bone screw head 1010. The break-off installation head 1210 includes an outer surface 1220 and a drive structure 1221 sized and shaped for engagement with a tool (not shown) for installing the fastener 1204 to the bone screw head or receiver 1010 and thereafter separating the break-off head 1210 from a respective base 1208 when installation torque exceeds selected levels.

The base 1208 of the fastener 1204 is substantially cylindrical, having an axis of rotation J and an external surface 1250 having a guide and advancement structure 1252 disposed thereon. The guide and advancement structure 1252 is matingly attachable to a guide and advancement structure 1092 of the bone screw head 1010. As with the guide and advancement structure 1092, the guide and advancement structure 1252 can be of any type, including V-type threads, buttress threads, reverse angle threads, or square threads. Preferably the guide and advancement structure 1252 is a helically wound reverse angled buttress thread form that interlocks with the reciprocal reverse angled thread form as part of the guide and advancement structure 1092 on the interior 1090 of the bone screw head 1010. The guide and advancement structures 1092 and 1252 are preferably of a type that do not exert radially outward forces on the arms 1083' and 1083" and thereby avoid tendencies toward splaying of the arms 1083' and 1083" of the bone screw head 1010 when the fastener 1204 is tightly torqued into the head 1010.

The fastener 1204 includes an internal, centrally located through-bore 1254. At the base 1208, the bore 1254 is substantially defined by a guide and advancement structure, shown in FIG. 4 as an internal V-shaped thread 1256. The thread 1256 is sized and shaped to receive the threaded set screw 1206 therein as will be discussed in more detail below. Although a traditional V-shaped thread 1256 is shown, it is foreseen that other types of helical guide and advancement structures may be used. Near a substantially annular planar top surface 1258 of the base 1208, an abutment shoulder 1260, extends uniformly radially inwardly. The abutment shoulder 1260 is spaced from the V-shaped thread 1256 and is sized and shaped to be a stop for the set screw 1206, prohibiting the set screw 1206 from advancing out of the top 1258 of the base 1208. It is foreseen that alternatively, the set screw 1206 may be equipped with an outwardly extending abutment feature near a base thereof, with complimentary alterations made in the base 1208, such that the set screw 1206 would be prohibited from advancing out of the top 1258 of the base 1208 due to abutment of such outwardly extending feature against a surface of the base 1208. An inner cylindrical wall 1262 separates the abutment shoulder 1260 from the thread 1256. The cylindrical wall 1262 has a diameter slightly greater than a root or major diameter of the internal thread 1256.

The set screw 1206 has a substantially planar top 1276 and a bottom 1277. The set screw 1206 is substantially cylindrical in shape, and includes an outer cylindrical surface 1278 with a V-shaped thread 1280 extending from the top 1276 to the bottom 1277 thereof. The surface 1278 and thread 1280 are sized and shaped to be received by and mated with the inner thread 1256 of the fastener base 1208 in a nested relationship.

The fastener break-off head 1210 is integral or otherwise attached to the fastener 1204 at a neck or weakened region 1266. The neck 1266 is formed of a material having a selected fail strength and is dimensioned in thickness to control the torque at which the break-off head 1210 separates from the fastener 1204. The preselected separation torque of the neck 1266 is designed to provide secure clamping of the rod 1021 by the fastener 1204 before the head 1010 separates. For example, 120 inch pounds of force may be a selected break-off torque. Separation of the break-off head 1210 leaves only the more compact base 1208 of the fastener 1204 installed in the bone screw head or receiver 1010, so that the installed fastener 1204 has a low profile.

It is foreseen that the base 1208 of the fastener 1204 and the inner set screw 1206 may include structure to provide clamping engagement between the base 1208 and the insert 1014 and the bottom surface 1277 and the rod 1021.

The assembly and disassembly of the bone screw assembly 1001 is substantially similar to the assembly and disassembly of bone anchor assembly 1 described above.

Figures 5, 6:
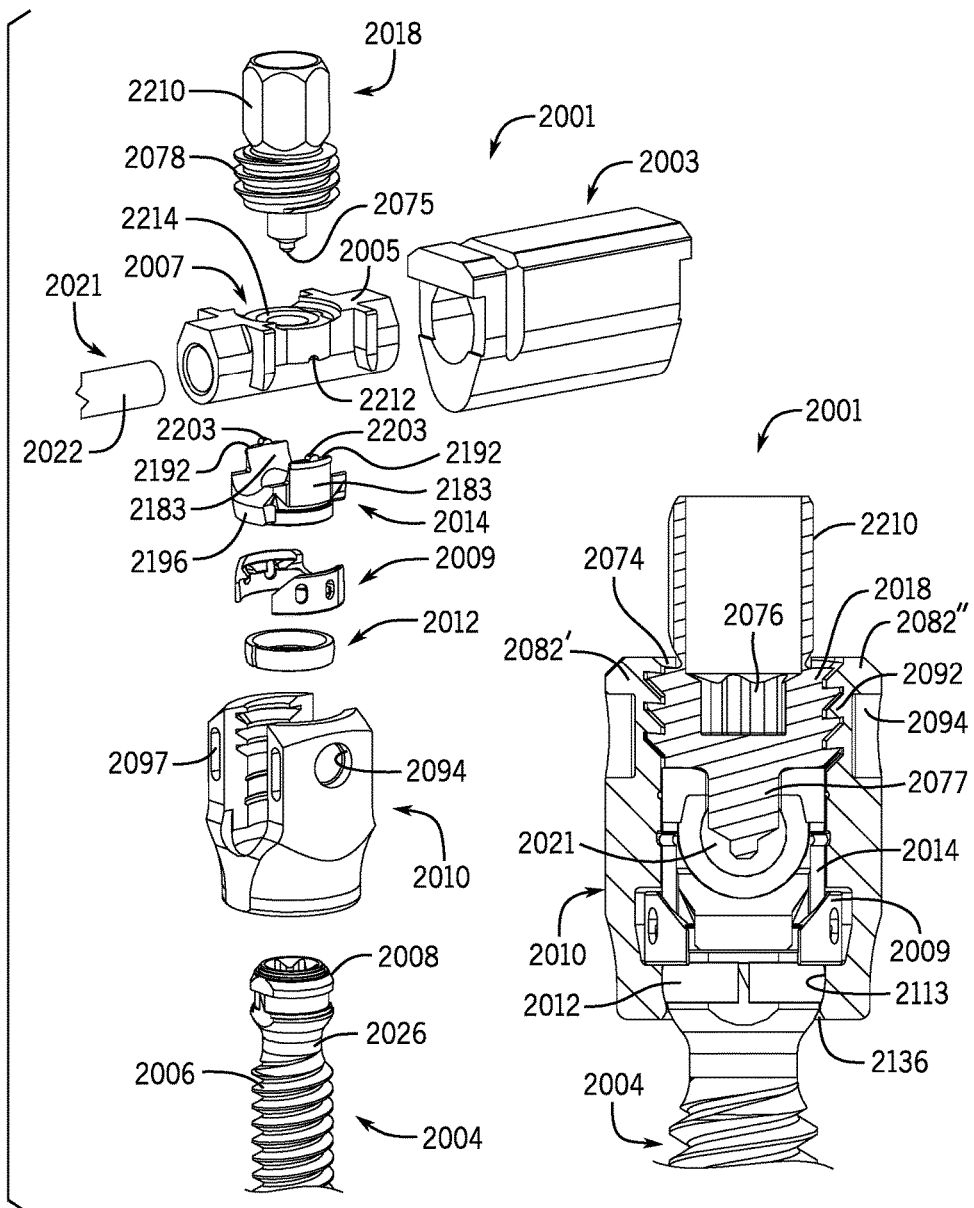
FIG. 5 is a fragmentary exploded perspective view of a third embodiment of a multiplanar bone screw assembly according to the present disclosure including the second embodiment of the shank, the receiver, the second embodiment of the pivoting retainer, a positioner, a third embodiment of a pressure insert, a sleeve, a spacer, and a closure shown in an third embodiment of a cord gripping configuration, all shown in conjunction with a tensionable cord.
FIG. 6 is an enlarged fragmentary side elevation view of the bone screw assembly of FIG. 5 with portions of the receiver and closure cut away to show cooperation of the parts at a stage whereat the multiplanar bone screw assembly is fully locked by the gripping closure.

With reference to FIGS. 5-6 the reference number 2001 generally represents an embodiment of a soft or tensioned or dynamic stabilization multi-planar, multi-axial, or polyaxial bone screw apparatus or assembly according to the present disclosure. While the illustrated anchor 2001 is generally a polyaxial bone screw, it is foreseen that the disclosure could be utilized with other types of spinal implants that utilize pressure inserts, such as polyaxial bone hooks or clamps, for example.

Referring now to FIGS. 5-6, the illustrated assembly 2001 includes: a spacer 2003, a shank 2004, that further includes a body 2006 integral with an upwardly extending upper portion or capture structure 2008; a sleeve 2005 that further includes a transfer structure or transfer 2007, a positioner 2009; a receiver 2010; a pivoting retainer structure 2012; a compression or pressure insert 2014; a closure 2018; and a cord or inner core 2021. The receiver 2010, the positioner 209, the pivoting retainer 2012, and compression insert 2014 are initially assembled and may be further assembled with the shank 2004 either prior or subsequent to implantation of the shank body 2006 into a vertebra (not shown), as was described above. The shank 2004, the positioner 2009, the receiver 2010, and pivoting retainer 2012 are substantially similar to the shank 1004, the positioner 1009, the receiver 1010, pivoting retainer 1012, as previously disclosed above. The compression insert 2014 is substantially similar to the insert 14 with the exception being that at the top of each arm 2183 is a pressure transfer surface 2192 each of which has an upward extending and centrally located nub 2203. The nubs 2203 align with and snugly fit into indentations or indents 2212 of the transfer 2007. The sleeve 2005 with the transfer 2007 comprised of a different material than the sleeve 2005, the spacer 2003, and the inner core 2021 are substantially similar to those as described in U.S. patent application Ser. Nos. 14/731,064 and 12/148,465, previously referred to above.

The illustrated closure structure 2018 is substantially cylindrical and includes an outer helically wound guide and advancement structure 2078 in the form of a reverse angled buttress thread form that operably joins with a guide and advancement structure 2092 disposed on the arms 2082' and 2082" of the receiver 2010. The illustrated closure structure 2018 also includes a top surface 2074 with an internal drive 2076 in the form of an aperture that may be star-shaped internal drive such as that sold under the trademark TORX, or may be, for example, a hex drive, or other non-round internal drives such as slotted, tri-wing, spanner, two or more apertures of various shapes, and the like. A driving tool (not shown) sized and shaped for engagement with the internal drive 2076 is used for both rotatable engagement and, if needed, disengagement of the closure 2018 from the receiver arms 2082' and 2082". The closure structure includes a break-off head 2210 designed to allow such a head to break from a base of the closure at a preselected torque, for example, at 70 to 140 inch pounds.

The closure structure 2018 is rotated, using a hex tool (not shown) until a selected pressure is reached at which point the cord 2021 is engaged and prohibited from lateral, longitudinal, or rotational movement.

As the closure structure 2018 rotates and moves downwardly through an aperture 2214 in the sleeve 2005 and into the respective receiver 2010, a point 2075 and bottom protrusion surface 2077 engage and penetrate a cord outer surface 2022, and the closure structure 2018 presses downwardly against a top surface 2216 of the transfer 2007 and biases the transfer 2007 into engagement with the insert 2014 that thereby urges the shank upper portion 2008 toward the lower opening 2136 of the retainer 2010 and into locking engagement therewith, with the pivoting retainer 2012 frictionally abutting a surface 2113 of the receiver 2010.

It is foreseen that any of a variety of different closure structures for use in conjunction with the present disclosure with suitable mating structure on the upstanding arms 2082' and 2082" can be utilized, such as the slip and grip closures described in U.S. Prov. Pat. App. 61/336,911, previously referred to above. For example, multi-start threaded closures (not shown) are foreseen to be utilized in this disclosure.

Assembly and disassembly of the shank 2004, pivoting retainer 2012, positioner 2009, receiver 2010, and the insert 2014 is substantially similar to assembly and disassembly of similar parts of the bone anchor assembly 1001 described above.

With reference to FIGS. 7-9, the reference number 3001 generally represents an embodiment of a multi-planar, multi-axial, or polyaxial bone screw apparatus or assembly with an extended or favored angle, according to the present disclosure. While the illustrated anchor assembly 3001 is generally a polyaxial bone screw, it is foreseen that the disclosure could be utilized with other types of spinal implants that utilize pressure inserts, such as polyaxial bone hooks or clamps, for example. The illustrated assembly 3001 includes: a shank 3004, that further includes a body 3006 integral with an upwardly extending upper portion or capture structure 3008; a positioner 3009; a receiver 3010; a pivoting retainer structure 3012; a compression or pressure insert 3014; a closure 3018; and a rod or connecting member 3021. The shank 3004, the retainer 3012, the positioner 3009, the insert 3014, including the extended arms 3183' and 3183", and the rod 3021 are substantially similar to their similarly numbered counterparts in assembly 1, as discussed above. The positioner 3009 may be initially assembled with the retainer 3012 and insert 3014 and further assembled with the shank 3004 either prior or subsequent to implantation of the shank body 3006 into a vertebra (not shown), as discussed above.

The receiver 3010 and the shank 3004 cooperate in such a manner that the receiver 3010 and the shank 3004 can be secured at any of a plurality of angles, articulations or angular alignments with one preferential angle relative to one another and within a selected range of angles from side to side and from front to rear, to enable flexible or articulated engagement of the receiver 3010 with the shank 3004 until both are locked or fixed relative to each other near the end of an implantation procedure, as seen in FIG. 9.

Referring now to FIG. 8, the receiver 3010 is substantially similar to the receiver 10 as discussed above with the exception being that a bottom surface 3134 of the receiver 3010 includes a sloped or ramped surface 3135 that is radial about the lower opening 3136, such that an inner spherical surface 3113 is graduated on one side, as better seen in FIG. 9.

Referring now to FIG. 9, the sloped surface 3135 allows the shank 3004 to angulated more in the direction of the slope of ramped surface 3135 as shown. The closure structure or nested fastener 3018 can be any of a variety of different types of closure structures for use in conjunction with the present disclosure with suitable mating structure on the upstanding arms 3083' and 3083" of the head or receiver 3010.

The illustrated closure structure 3018 includes an outer fastener 3204 and an inner set screw 3206. The set screw 3206 includes a base 3208 integral with or otherwise attached to a break-off head 3210. The outer fastener 3024 cooperates with the head 3010 of the bone screw assembly 3001, as illustrated in FIG. 9, to close the head U-shaped channel 3084 and to clamp the spinal fixation rod 3021 within the bone screw head 3010. The break-off installation head 3210 includes an outer hexagonal faceted surfaces 3220 of the break-off head 3210 enables positive, non-slip engagement of the head 3210 by an installation and torquing tool (not shown). The outer fastener 3204 includes a castle drive structure 3221 with slots 3222 sized and shaped for engagement with a suitable tool (not shown) for installing the outer fastener 3204 to the bone screw head or receiver 3010. Thereafter, the break-off head 3210 is separated from the respective base 3208 of the set screw 3206 when installation torque exceeds selected levels.

The outer fastener 3204 is substantially cylindrical, having an axis of rotation K and an external surface 3250 having a discontinuous guide and advancement structure 3252 disposed thereon. The guide and advancement structure 3252 is matingly attachable to the guide and advancement structure 3092 of the bone screw head 3010. As with the guide and advancement structure 3092, the guide and advancement structure 3252 can be of any type, including V-type threads, buttress threads, reverse angle threads, or square threads. Preferably the guide and advancement structure 3252 is a helically wound square thread form that interlocks with the reciprocal square thread form as part of the guide and advancement structure 3092 on the interior 3090 of the bone screw head 3010. The guide and advancement structures 3092 and 3252 are preferably of a type that do not exert radially outward forces on the arms 3083' and 3083" and thereby avoid tendencies toward splaying of the arms 3083' and 3083" of the bone screw head 3010, when the fastener 3204 is tightly torqued into the head 3010.

The fastener 3204 includes an internal, centrally located through-bore 3254. The bore 3254 is substantially defined by a guide and advancement structure, shown in FIG. 9 as an internal V-shaped thread 3256. The thread 3256 is sized and shaped to receive the threaded set screw 3206 therein as will be discussed in more detail below. Although a traditional V-shaped thread 3256 is shown, it is foreseen that other types of helical guide and advancement structures may be used.

The set screw 3206 has a substantially planar top 3276 and a bottom 3277. The base 3208 of the set screw 3206 is substantially cylindrical in shape, and includes an outer cylindrical surface 3278 with a V-shaped thread 3280 extending from the top 3276 to the bottom 3277 thereof. The surface 3278 and thread 3280 are sized and shaped to be received by and mated with the inner thread 3256 of the fastener base 3208 in a nested relationship.

The fastener break-off head 3210 is integral or otherwise attached to the set screw base 3208 at a neck or weakened region 3266. The neck 3266 is dimensioned in thickness to control the torque at which the break-off head 3210 separates from the set screw base 3208. The preselected separation torque of the neck 3266 is designed to provide secure clamping of the rod 3021 by the set screw base 3208 before the head 3010 separates. For example, 120 inch pounds of force may be a selected break-off torque. Separation of the break-off head 3210 leaves only the more compact base 3208 of the set screw 3206 and the fastener 3204 installed in the bone screw head or receiver 3010, so that the installed fastener 3204 and inner set screw 3206 have a low profile.

It is foreseen that the outer fastener 3204 and the inner set screw 3206 may include structure to provide clamping engagement between the outer fastener 3024 and the insert 3014 and between the bottom surface 3277 of the inner set screw 3206 and the rod 3021.

Assembly and disassembly of the bone screw assembly 3001 is substantially similar to assembly and disassembly of bone anchor assembly 1001 described above.

With reference to FIGS. 10-11, the reference number 4001 generally represents an embodiment of a mono-planar, uni-planar, or single planar bone screw apparatus or assembly according to the present disclosure. While the illustrated anchor 4001 is generally a mono-planar bone screw, it is foreseen that the disclosure could be utilized with other types of spinal implants that utilize pressure inserts, such as bone anchors, hooks, or clamps, for example such screws as disclosed in U.S. patent application Ser. Nos. 14/061,393, and 13/573,516, previously referenced above. The illustrated assembly 4001 includes: a shank 4004 that further includes a body 4006 integral with an upwardly extending upper portion or capture structure 4008; first and second positioners 4009; a receiver 4010; a pivoting retainer structure 4012; a compression or pressure insert 4014; a closure 4018; and a rod or connecting member 4021. The shank 4004, the closure 4018, and the rod 3021 are substantially similar to their similarly numbered counterparts in assembly 3001, as discussed above. The positioners 4009 may be initially assembled with the retainer 4012 and insert 4014 and further assembled with the shank 4004 either prior or subsequent to implantation of the shank body 4006 into a vertebra (not shown), as discussed above.

The illustrated receiver 4010 and the shank 4004 cooperate in such a manner that the receiver 4010 and the shank 4004 can be secured at any of a plurality of angles with respect to a single plane orientation to enable flexible or articulated engagement along the plane of the receiver 4010 with the shank 4004 until both are locked or fixed relative to each other near the end of an implantation procedure, as seen in FIG. 11.

Referring now to FIG. 10, the receiver 4010 is substantially similar to the receiver 10 in form and function with the exception that a bore 4141 is defined by opposed radiused surfaces (not shown) and opposed planar surfaces (not shown), the retainer surfaces (not shown) being sized and shaped for engagement with the flat planar surfaces 4042', 4042" of the shank 4004. The bottom surface (not shown) of receiver 4010 includes opposite protrusions, bumps, or nubs (not shown), may be placed either aligned with the radiused surfaces, so as to limit mono-planar motion and maintain the shank 4004 within the receiver 4010, and not allow the shank 4004 to potentially position itself out of the receiver 4010. Such nubs act as stops minimizing the axial articulation about the plane of motion. It is foreseen that further nubs (not shown) could also be aligned with the opposed planar surfaces. The illustrated receiver 4010 does not include a beveled surface opening out to the lower opening 4136 of the receiver 4010.

Lastly, the receiver surfaces 4114, 4113, and abutment surface 4125 are discontinuous. These surfaces are broken by four grooves (not shown), each groove being sized and shaped such that they allow the arch structures to fit into the grooves, while allowing for articulation about the single plane of the retainer 4012.

The pivotal retainer 4012 operates to assist in capturing the shank upper portion 4008 within the receiver 4010. The upper pivotal retainer 4012 has a central axis M that operationally aligns with an axis A' associated with the shank 4004 when assembled thereon, as best seen in FIG. 10. The pivotal retainer 4012 is generally ring shaped, having a central bore 4057, and is made from a resilient material, such as a stainless steel, titanium alloy, cobalt chrome, or the like, as well as polymers, so that a retainer body 4055 may be resiliently expanded.

The pivotal retainer 4012 includes a substantially cylindrical continuous body 4055 except for a pair of opposed, opposite, arch shaped structures 4056' and 4056". In the illustrated pivoting retainer 4012 embodiment, the arch structures 4056' and 4056" extend upwardly and outwardly from the body 4055, illustrated at about a ten degree angle, but may be otherwise angled. The arch structures are defined by curved top surfaces 4137, angled side surfaces 4138', 4138" and 4139',4139", and a reverse U-shaped saddle surface 4140.

The upper retainer body 4055, having only the arch structures 4056',4056" to be used for expansion purposes only when the shank upper capture portion 4008, is loaded in through the receiver lower opening 4136. The pivoting retainer 4012 is rotated in and loaded either through the receiver opening 4086 or through the receiver lower opening 4136, such that the pivoting retainer 4012 is loaded in a neutral state, such that it does not need or, in fact, cannot be further compressed to fit within a receiver lower opening 136, and then rotated ninety degrees while within the receiver expansion chamber 4095. The retainer 12 is situated within the grooves (not shown) of the interior 4090 of the receiver 4010, such that the arch structures do not engage the cylindrical surface 4110 of the expansion chamber 4095.

The bore 4057 surfaces are sized and shaped such that the upper retainer body 4055 cannot compress further when mated with the shank upper capture portion 4008. Surfaces that define the channel, slot, or bore 4057 include: an upper cylindrical surface 4058 adjacent to the retainer top surface 4062, a discontinuous shelf surface (not shown) adjacent the upper cylindrical surface 4058, a discontinuous cylindrical surface (not shown) adjacent the shelf surface (not shown). The bore 4057 is sized and shaped to closely fit about and snap onto the shank interface surface 4038 during assembly. The upper cylindrical surface 4058 is continuous about the bore 4057 of the upper retainer 4012, but for, the inner curved surfaces 4064' and 4064" that make up the interior of the arch structures 4056', 4056". The inner surfaces 4064' and 4064" have a circular portion 4070' adjacent the top surface 4137 communicating with the cylindrical surface 4058. The arch structures 4056', 4056" with the circular portions 4070' and 4070" are sized and shaped to substantially so as to not engage the opposed planar surfaces 4042', 4042" of the shank head upper capture portion 4008. When mated the top surface 4062 of the pivoting retainer 12 does not extend above the top of the shank top surface 4047, but the top surface 4137 is foreseen to extend above the top surface 4047 of the shank 4004. When the pivoting retainer 4012 is mated to shank upper capture portion 4008, a ball structure 4044 that is substantially spherical is created. The pivoting retainer 4012 is stabilized on the shank head upper capture portion 4008 with respect to pivotal, rotational, and elevational alignments.

It is foreseen that further surfaces such as a lower shelf surface (not shown) and a fourth cylindrical surface (not shown) may be sized and shaped to further step down the spherical shape of the outer surface 63 internally.

It is also foreseen that the arch structures 4056' and 4056" may include projections or notches as needed for tooling to resiliently hold the pivoting retainer 4012. It is foreseen that in other embodiments of the disclosure, fewer or greater number of planar or other surfaces with other geometries may extend between the top surface 4062 and the inner surfaces defining the bore 4057 of the pivoting retainer 4012.

Referring now to the positioner 4009, which unlike the previous disclosed positioners 9, 1009, 2009, 3009, are split into two components, first and second positioners 4009. It is foreseen that the positioners 4009 may be hinged or connected so as to create a single positioner (not shown). It is also foreseen that the positioners 4009 may include more than two positioners (not shown). Each positioner 4009 includes the top surface 4162, a lower radially inward projecting flange 4163, an interior cylindrical surface 4165, an outer surface 4170, a radially inward projecting upper flanges 4171 having a distally narrowing conical proximal surface 4172 adjacent to a radially inward facing planar edge surface 4173, a planar distal face surface 4169 of the projecting flanges, parallel side surfaces 4179, and a distal bottom surface 4164. The planar distal face 4169 transitions into an interior chambered circumferential surface 4177, which transitions into the lower radially inward projecting flange 4163.

The positioner 4009 also includes cutout regions 4179 that defines the chamber surface 4177 at which it transitions to the interior cylindrical surface 4165 and a proximal bottom surface 4180. The second positioner 4009" is meant to be positioned across from one another within the receiver.

As discussed below, the positioners 4009 keep the retainer ring 4012 properly oriented to be able to receive the shank upper portion 4008 during insertion of the shank upper portion 4008 into the head or receiver 4010. Also, the radially inward projecting flanges 4171 of the positioners 4009 are received in a horizontal groove or slot 4197 in the insert 4014 to prevent the positioners 4009 and the insert 4014 from proximally displacing away from each other along the axis M. Also, on account of the sloped surfaces 4172 of the radially inward projecting flanges 4171, portions of the insert 4014 abut against circumferential terminations of the radially inward projecting flanges 4171 to prevent rotational or pivotal displacement of the insert 4014 and the positioners 4009 relative to each other. A discussion of the features of the insert 210 is now provided.

The insert 4014 is substantially similar to the receiver 14 in form and function with the exception that both ledges 4196 of the insert 4014 do not include surfaces 200 and 2001. The ledges 4196 terminate with the sloped side surface 4197 and have a bottom surface 4207. The next difference is that the arms 4183' and 4183" are longer than the arms 183' and 183" so as to engage the closure 4018, as is discussed above. The arms 4183" and 4183" include a second receiver projection attachment structure 4184".

The positioner 4009 is loaded, such that it is located in-between the arch structures 4056' and the cylindrical wall 4110 of the expansion chamber 4095. The next positioner 4009 is loaded directly across from the first positioner 4009, as can be seen in FIG. 11. It is foreseen that the positioners 4009 will be tilted to fit within the expansion chamber 4095. Once both positioners 4009 are loaded in the expansion chamber, the retainer 4012 is uploaded such that the top surface 4062 of the retainer 4012 engages the distal face surfaces 4169 of the positioners 4009 capture the retainer and hold the retainer in position. The insert is then loaded such that the second receiver projection attachment structure 4184" is received within the insert receiving aperture 4103, as explained above. The shank 4004 is then uploaded and captured by the retainer 4012, as explained above.

Other than the differences mentioned, the assembly and disassembly of the bone screw assembly 4001 is substantially similar to the assembly and disassembly of bone anchor assembly 1 described above.

Figures 12, 13:
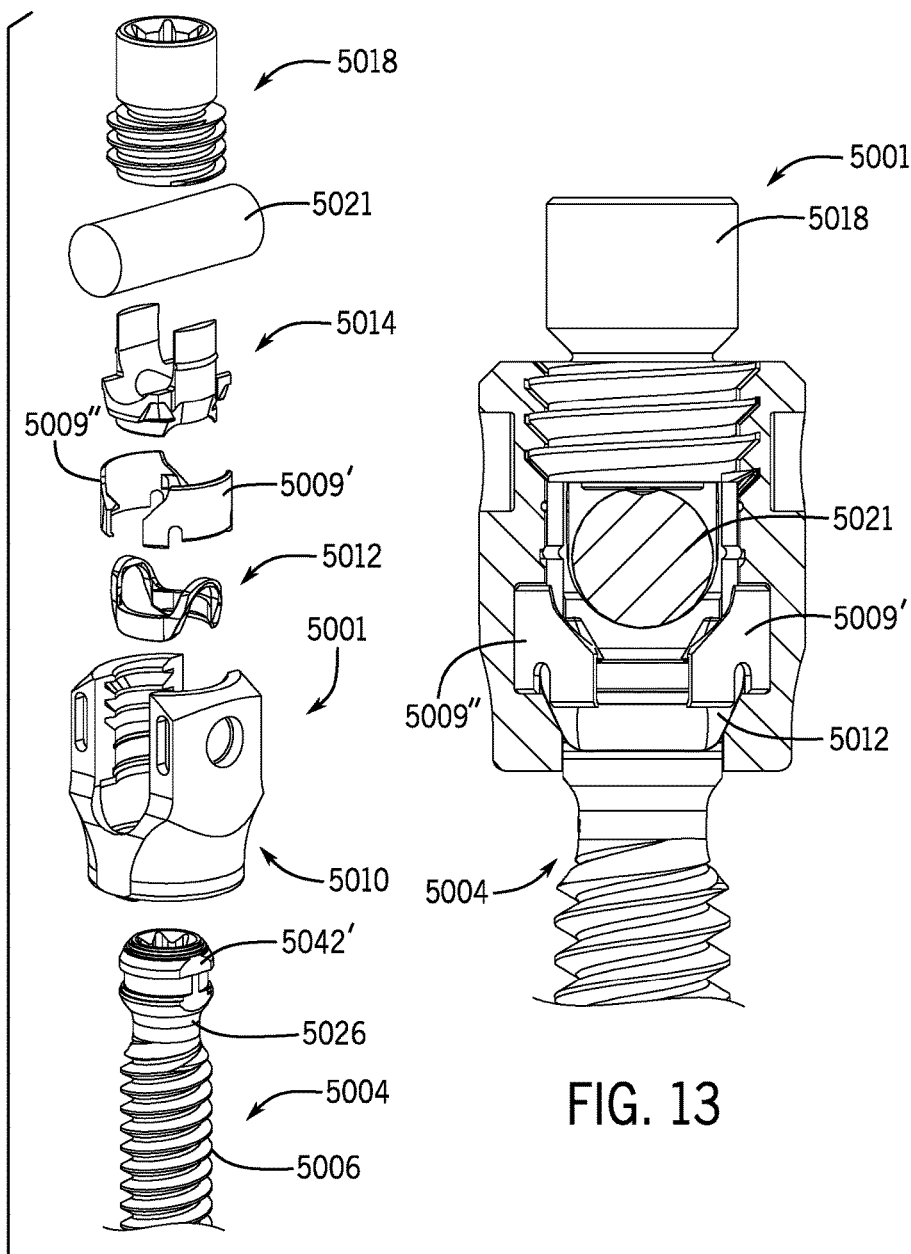
FIG. 12 is a fragmentary exploded perspective view of a second embodiment of a monoplanar bone screw assembly according to the present disclosure including the second embodiment of the shank, the second embodiment of the receiver, the second embodiment of a pivoting retainer, a second embodiment of a positioner, a second embodiment of a pressure insert and a closure shown in a second embodiment of an independent lock configuration, all shown in conjunction with a rod.
FIG. 13 is an enlarged fragmentary side elevation view of the bone screw assembly of FIG. 12 with portions of the receiver and closure cut away to show cooperation of the parts at a stage whereat the monoplanar bone screw assembly is fully locked by the closure.

With reference to FIGS. 12-13, the reference number 5001 generally represents an embodiment of a mono-planar, uni-planar, or single planar bone screw apparatus or assembly according to the present disclosure. While the illustrated anchor 5001 is generally a mono-planar bone screw, it is foreseen that the disclosure could be utilized with other types of spinal implants that utilize pressure inserts, such as bone anchors, hooks, or clamps, for example. The illustrated assembly 5001 includes: a shank 5004, that further includes a body 5006 integral with an upwardly extending upper portion or capture structure 5008; positioners 5009; a receiver 5010; a pivoting retainer structure 5012; a compression or pressure insert 5014; a closure 5018; and a rod or connecting member 5021. The shank 5004, the closure 5018, and the rod 5021 are substantially similar to their counterparts in assembly 1001, as discussed above. The positioners 5009 and the pivoting retainer 5012 are substantially similar to their counterparts in assembly 4001, as discussed above.

The receiver 5010 and the shank 5004 cooperate in such a manner that the receiver 5010 and the shank 5004 can be secured at any of a plurality of angles with respect to a single plane orientation to enable flexible or articulated engagement along the plane of the receiver 5010 with the shank 5004 until both are locked or fixed relative to each other near the end of an implantation procedure, as seen in FIG. 13.

The positioners 5009 may be initially assembled with the retainer 5012 and insert 5014 and further assembled with the shank 5004 either prior or subsequent to implantation of the shank body 5006 into a vertebra (not shown), as discussed above.

The insert 5014 is substantially similar to the counterparts in assembly 4001, as discussed above, with the exception being the second receiver projection attachment structure is removed.

The retainer 5010 is substantially similar to the receiver 1001 in form and function with the exception that a bore 5141 is defined by opposed radiused surfaces (not shown) and opposed planar surfaces (not shown), the surfaces (not shown) are sized and shaped for receiving the flat planar surfaces 5042', 5042" of the shank 5004. It is foreseen that the bottom surface of receiver 4010 includes opposite protrusions, bumps, or nubs (not shown) may be placed either aligned with the radiused surfaces, so as to maintain the shank 5004 within the receiver 5010, and not allow the shank 5004 to potentially position itself out of the receiver 5010. It is foreseen that further nubs (not shown) could also be aligned with the opposed planar surfaces. The receiver 5010 does not include a beveled surface opening out to the lower opening 5136 of the receiver 5010, so as to better direction the mono-planar motion of the bone screw assembly 5001.

Lastly, the receiver surfaces 5114, 5113, and abutment surface 5125 are discontinuous. These surfaces are broken by four grooves (not shown), each groove being sized and shaped such that they allow the arch structures 5056', 5056" to fit into the grooves, while allowing for articulation about the single plane of the retainer 5012.

Other than the differences mentioned, the assembly and disassembly of the bone screw assembly 5001 is substantially similar to the assembly and disassembly of bone anchor assembly 4001 described above.

Figures 14, 15:
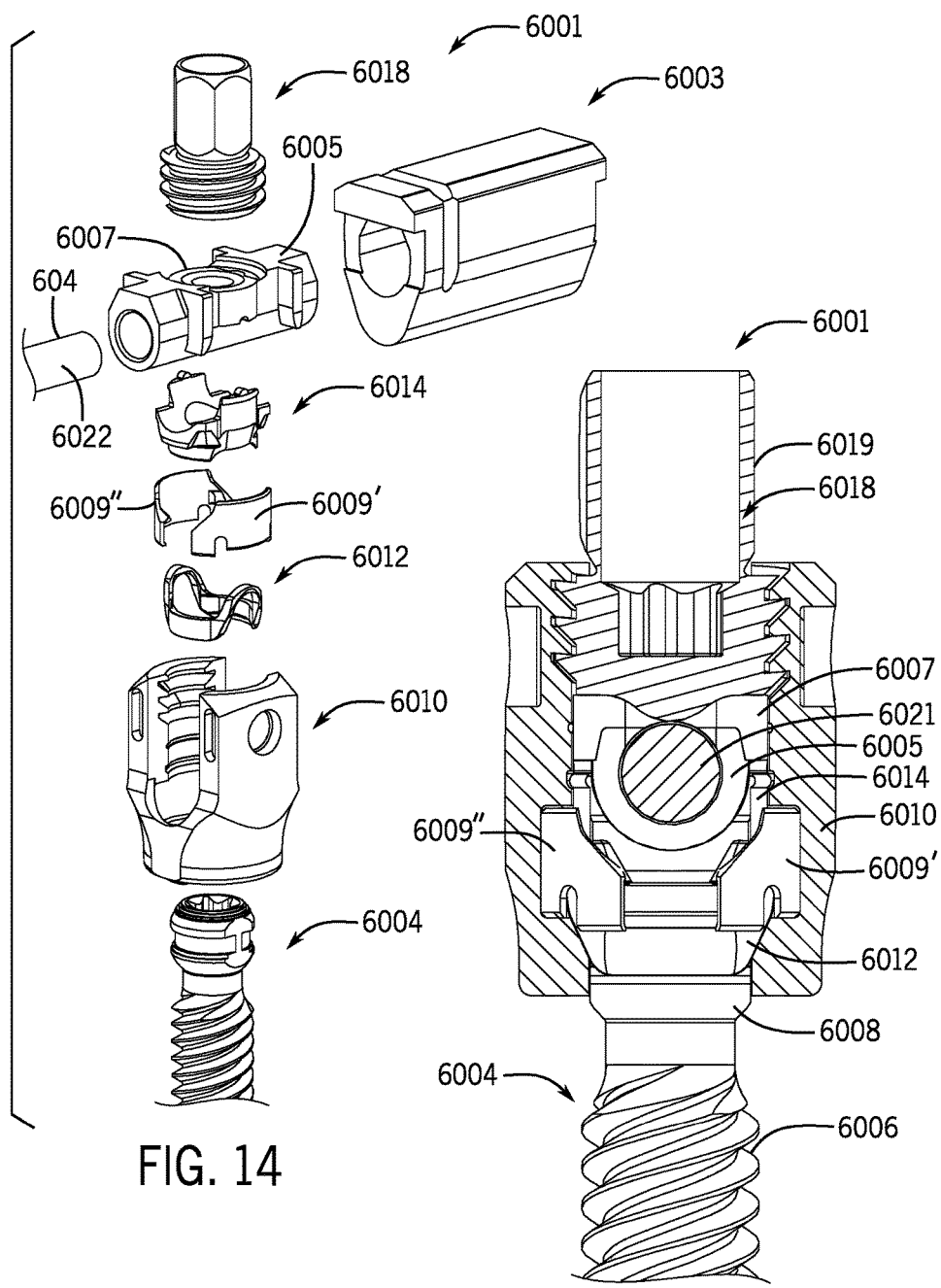
FIG. 14 is a fragmentary exploded perspective view of a third embodiment of a monoplaner bone screw assembly according to the present disclosure including the second embodiment of the shank, the second embodiment of the receiver, the second embodiment of the pivoting retainer, the second embodiment of the positioner, the third embodiment of a pressure insert, the sleeve, the spacer, and a closure shown in an fifth embodiment of a cord slipping configuration, all shown in conjunction with a tensionable cord.
FIG. 15 is an enlarged fragmentary side elevation view of the bone screw assembly of FIG. 14 with portions of the receiver and closure cut away to show cooperation of the parts at a stage whereat the monoplanar bone screw assembly is fully locked by the slipping closure.

With reference to FIGS. 14-15 the reference number 6001 generally represents an embodiment of a soft or tensioned or dynamic stabilization mono-planar, uni-planar, single plane bone screw apparatus or assembly according to the present disclosure. While the illustrated anchor assembly 6001 is generally a mono-planar bone screw, it is foreseen that the disclosure could be utilized with other types of spinal implants that utilize pressure inserts, such as mono-planar bone hooks or clamps, for example.

The illustrated assembly 6001 includes: a spacer 6003, a shank 6004, that further includes a body 6006 integral with an upwardly extending upper portion or capture structure 6008; a sleeve 6005 that further includes a transfer 6007, first and second positioners 6009; a receiver 6010; a pivoting retainer structure 6012; a compression or pressure insert 6014; a closure 6018; and a cord or inner core 6021. The receiver 6010, the positioners 6009, the pivoting retainer 6012, and compression insert 6014 are initially assembled and may be further assembled with the shank 6004 either prior or subsequent to implantation of the shank body 6006 into a vertebra (not shown), as was described above.

The shank 6004, the positioners 6009, the receiver 6010, pivoting retainer 6012, the sleeve 6005 and transfer 6007, the spacer 6003, and the core 6021 are substantially similar to the shank 1004, the positioners 4009, the receiver 5010, pivoting retainer 4012, the sleeve 2005 and transfer 2007, the spacer 2003, and the core 2021, as previously disclosed above.

The compression insert 6014 is substantially similar to the insert 5015 with the exception being that at the top of each arm 6183 is a pressure transfer surface 6192 each of which has an upward extending and centrally located nub 6203. The nubs 6203 align with and snugly fit into the indents 6212 of the transfer 6007. The sleeve 6005 has the transfer 6007 comprised of a different material than the sleeve 6005, the spacer 6003, and the inner core 6021 as described above.

The illustrated closure structure 6018 is substantially similar to the closure structure 2018 described above with the exception being that the penetrating point 2075 is a radial semi-spherical form 6075 that moves downwardly through an aperture 6014 in the sleeve 6005 and into the respective receiver 6010, the bump 6075 engages the core surface 6022, but allows for slidability with respect to the core 6021 and the closure structure 6018, which in turn allows for slidability of the core 6021 with respect to the receiver 6010.

The assembly and disassembly of the mono-planar bone anchor assembly 6001 is substantially similar to the assembly and disassembly of the similar part of bone anchor assembly 2001 described above.

With reference to FIGS. 16-18, the reference number 7001 generally represents an embodiment of a bi-planar or sagittal angle mono-planar bone screw apparatus or assembly according to the present disclosure. While the illustrated anchor 7001 is generally a mono-planar bone screw with an insert 7014 having a saddle 7300, it is foreseen that the disclosure could be utilized with other types of spinal implants that utilize pressure inserts, such as bone anchors, hooks, or clamps, for example, or those seen in U.S. patent application Ser. No. 14/181,998, the entirety of which is incorporated by reference. It is also foreseen that the sagittal angle insert 6014 could be used in a multi-planar bone screw design.

The illustrated assembly 7001 includes: a shank 7004, that further includes a body 7006 integral with an upwardly extending upper portion or capture structure 7008; positioners 7009; a receiver 7010; a pivoting retainer structure 7012; a compression or pressure insert 7014 having a saddle 7300; a closure 7018; and a rod or connecting member 7021. The shank 7004, the receiver 7010, the retainer 7012, and the rod 7021 are substantially similar to their counterparts in assembly 5001, as discussed above. The closure is substantially similar to the counterparts in assembly 6018, as discussed above.

The positioners 7009 are substantially similar to the positioners 5009, with the exception of the U-shaped or saddle surface 7181. The saddle surface 7181 gives the saddle 7300 room to maneuver along a sagittal plane.

The receiver 7010 and the shank 7004 cooperate in such a manner that the receiver 7010 and the shank 7004 can be secured at any of a plurality of angles with respect to a single plane orientation to enable flexible or articulated engagement along the plane of the receiver 7010 with the shank 7004, as well as, the insert saddle 7300 allowing a plurality of angles for the rod 7021 along a sagittal plane until both are locked or fixed relative to each other near the end of an implantation procedure, as seen in FIG. 18. The saddle 7300 also blocks further rotation of the insert 7014.

In the illustrated embodiment, the sagittal plane is traverse to the plane that the shank can angulate. It is foreseen that these planes may be the same or offset and not exactly 90 degrees apart.

The positioners 7009 may be initially assembled with the retainer 7012 and insert 7014 and further assembled with the shank 7004 either prior or subsequent to implantation of the shank body 7006 into a vertebra (not shown), as discussed above.

The compression insert 7014 is best seen in FIGS. 16-17. The friction fit compression insert 7014 is sized and shaped to be received by and loaded into the receiver 7010. The illustrated compression insert 7014 has a central axis N operationally aligned with the central axis C' of the receiver 7010. In operation, the insert 7014 advantageously frictionally engages the bone screw shank upper portion 7008, allowing for un-locked, but non-floppy placement of the angle of the shank 7004 with respect to the receiver 7010 during surgery prior to locking of the shank with respect to the receiver near the end of the procedure with a rod or connecting member 7021 and a closure 7008. The insert 7014 is thus preferably made from a resilient material, such as a stainless steel or titanium alloy, so that portions of the insert may be expanded about and then contracted, snapped or popped onto the shank upper portion 7008. Furthermore, in operation, the insert 7014 is suspended within the receiver 7010, being frictionally held in place by the receiver insert attachment grooves 7103 and prohibited from moving upward even with the insertion of the shank upper capture portion 7008.

The illustrated insert 7014 includes a lower body 7182 with a pair of spaced upstanding arms 7183' and 7183". The arms 7183' and 7183" have a radially outer surface 7185 on each side which are substantially smooth and vertically or axially opposed, but radially spaced from a axis N. The outer surface 7185 includes receiver attachment projection structures 7184 on each arm 7183' and 7183" located proximally. Each receiver attachment projection structure 7184 extends circumferentially about the outer surface and includes a radial surface 7186 at an end thereof. The projection 7184 has a maximum diameter or width or radius (not shown) of measured about the center of the projection 7184. The arms 7183' and 7183" form a central U-shaped channel 7187 therebetween, and there is a central axially aligned and centered bore 7188. The through bore 7188 runs from an annular planar top surface 7192 to an annular planar and discontinuous bottom surface 7194 thereof. The bore 7188 is defined by an inner cylindrical surface 7196 that is at least partially defined by the U-shaped channel 7187 and a shank gripping surface portion (not shown) extending from the bottom surface 7194. It is foreseen that the shank gripping surface may further include flexible panels.

The compression insert 7014 through bore 7188 is sized and shaped to receive the driving tool (not shown) there through that engages the shank drive feature 7049 when the shank body 7006 is driven into bone with the receiver 10 attached or without.

It is foreseen that the shank gripping surface portion 7198 may additionally or alternatively include a roughened or textured surface or surface finish, or may be scored, grit blasted, knurled, or the like (not shown), for enhancing frictional engagement with the shank upper portion 7008.

When the shank 7004 is locked into position by a rod or other connecting member 7021 being pressed downwardly on the insert U-shaped channel 7187 by the closure top 7018, the insert shank gripping portion 7198 that is initially slidable along the shank surface 7046 such that the stepped surfaces 7040 digs or penetrates into the surface and thus securely fixes the shank upper portion 7008 to the insert 7014.

On either interior side of the arms 183' and 183" are flat surfaces 7190' and 7190". It is foreseen that the insert 7014 may not include arms 7183' and 7183". It is also foreseen that the arms 7183' and 7183" may be spaced from the closure top 7018 in some embodiments and may be sized and shaped to contact the closure top 7018 in other embodiments in order to provide locking of the mono-planar angle of the assembly with pivoting retainer 7012, but without fixing of the rod or other longitudinal connecting member 7021 with respect to the closure top 7018.

The insert 7014 is of discrete or unitary, substantially solid construction and includes a curved groove 7302 adjacent to the interior surface 7190, the groove is a pathway for which the saddle 7300 can traverse.

The saddle 7300 includes a curved bottom surface 7304 adjacent to opposed curved side transition surfaces 7306 that are each in turn adjacent to opposed substantially planar side surfaces 7308 that are disposed substantially perpendicular to the bottom surface 7304. It is foreseen that the side surfaces 7308 are not limited to be perpendicular to the bottom surface. Each of the side surfaces 7308 terminate at a substantially planar narrow top rim surface 7310. The saddle 7300 further includes a curved cradle or saddle surface 7312 sized and shaped for closely receiving the rod 7021. The cradle surface 7312 also extends between the top surfaces 7310. A through bore 7314 extends completely through the insert from the top saddle or cradle surface 7312 to the bottom curved surface 7304. Disposed centrally along each of the surfaces 7308 is an outwardly extending projection 7316 that in the illustrated embodiment is in the form of a rounded knob or partial sphere, the illustrated knob 7316 includes another radiused transition surface or flange 7318 that is adjacent both to the substantially spherical surface 7316 and to the respective planar side surface 7308. It is noted that in other embodiments of the disclosure, the projections 7316 may include more or fewer radiused surfaces and may also include one or more surfaces having other geometry. The projection knobs 7316 are opposed from one another, each being spaced from the bottom surface 7304 and also from the top rims 7310.

In operation, when the insert 7014 is located within the receiver cavity 7091, with the saddle 7300 positioned within the insert channel 7187 in the saddle surface 7191. The knobs 7316 are sized and shaped and positioned with respect to the bottom surface 7304, so that in operation, the knobs 7304 extend into the grooves 7320 and slide freely therewithin as the saddle bottom surface 3204 slides along the U-shaped surface 7191. Furthermore, the insert transition surfaces 7306 are sized and shaped such that the surfaces 7306 are received by and slide freely with respect to the saddle surface 7191. In operation, the insert cylindrical outer surfaces 7185 are closely received between the receiver arm interior surfaces 7090, keeping the insert 7014 and saddle 7300 in a desired alignment with the receiver 7010 and, thus, keeping the rod 7021 cradled by the insert U-shaped surface 7312 in a desired alignment with not only the receiver, but the entire bone screw assembly 7001, including the shank 7006 that is integral to the receiver 7010, thus always keeping the rod 7021 in a bi-planar pivotable relationship prior to locking in two planes only, along the run of the rod 7021, which is typically and desirably the sagittal plane, and along the plane defined by the shank 7004 with respect to the receiver 7010. Thus, the bone screw assembly 7001 has a shank 7006 that angulates in the sagittal plane and the plane defined by the shank, this provides for improved strength over polyaxial screws and uni-planar screws.

Bone screws 7004, inserts 7014, and saddles 7300 of embodiments of the disclosure may be made from a variety of materials including metal and metal alloys, including but not limited to stainless steel, titanium, titanium alloys and cobalt chrome; or other suitable materials, including plastic polymers. It may be desirable, for example, to form the insert 7014 from a harder material, such as cobalt chrome and the integral, saddle 7300 from a less hard material, such as a titanium alloy.

As indicated above, the insert saddle or cradle 7300 is in the form of a curved seat sized and shaped to closely, snugly engage the rod 7021 or other longitudinal connecting member. It is foreseen that an alternative embodiment may be configured to include planar holding surfaces that closely hold a square or rectangular bar as well as hold a cylindrical rod-shaped, cord, or sleeved tensioned cord longitudinal connecting members.

Other than the differences mentioned, the assembly and disassembly of the bone screw assembly 7001 is substantially similar to the assembly and disassembly of bone anchor assembly 5001 described above.

Referring now to FIG. 20, the reference number 8004 generally represents a polyaxial bone screw shank according to the present disclosure. The shank 8004 is substantially similar to the shank 7004, with the exception that the shank 8004 does not include a stepped upper portion, as previously shown as 7040. The retainer 1012 is still compatible with such a shank 8004 as seen in FIG. 20.

Referring now to FIGS. 21-22, the shank 9004 and retainer 9012 are substantially similar to shank 4 and retainer 12, with the exception of the interface between the pivoting retainer 9012 and the shank 9004 where they are mated. An upper spherical surface 9046 is substantially spherically and does not further include stepped surfacing for interfacing with an insert (not shown). The differences in the shank 9004 and pivoting retainer 9012 will be discussed below.

The lower cylindrical surface 9035 terminates at a curved interface surface 9038. The curved interface surface 9038 is adjacent a downwardly facing upper shelf 9043. The upper shelf surface 9043 is also substantially perpendicular to the axis T. The curved interface surface 9038 is defined as being wider near the lower cylindrical surface 9035 than at the upper shelf or ledge surface 9043, much like the frusto-conical interface surface 38 described above. The curved or curvate interface surface 9038 is not inclined at one specific angle like the frusto-conical interface surface 38, but curves inwardly toward axis T from the lower cylindrical surface 9035 to the upper shelf surface 9043. It is foreseen that the curve of the curved surface may be outwardly sloped or curved inwardly at a steeper or more gradual incline or stepped or other geometric shapes. The spherical lower surface 9034 has an outer radius that is the same or substantially similar to an outer radius of the shank 4004 and shank 4, as discussed above.

Referring now to FIG. 22, in this embodiment the curved interface surface 9038 and upper ledge 9043 cooperate to capture and fix the resilient open pivoting retainer 9012 to the shank upper portion 9008, prohibiting compression of the pivoting retainer 9012 with respect to axis T once the pivoting retainer 9012 is located underneath the ledge 9043. A top surface 9062 of the pivoting retainer 9012 interacts with the upper shelf surface 9043 and is located beneath a top surface 9047 of the shank 9004. Extending upwardly from the upper ledge 9043 is a cylindrical surface 9045. The width or diameter or radius (not shown) of the cylindrical surface may be the same as previously described of shank 4.

The illustrated pivoting retainer 9012 includes a through bore 9057 passes entirely through the pivoting retainer 9012. The channel or bore 9057 is defined by an inwardly curved surface 9061. The interior curved surface 9061 is adjacent the top surface 9062 and the bottom surface 9059 of the pivoting retainer 9012. When the pivoting retainer 9012 is mated to shank upper capture portion 9008, a partially spherical ball component of a ball and socket structure is created (not shown). A gap (not shown) exists where the top surface 9062 extends further than the cylindrical surface 9045 of the shank upper capture structure 9008.

It is foreseen that the curve of the curved interior surface 9061 may be outwardly sloped or curved inwardly at a steeper or more gradual incline or stepped or other geometric shapes to mate with similar structure of the shank 6004.

Figure 23:
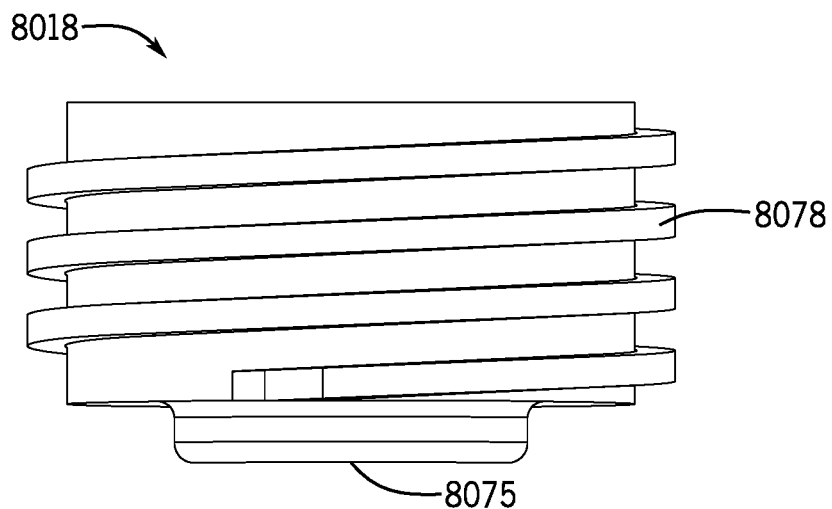
FIG. 23 is a greatly enlarged side elevation of a seventh embodiment of a closure.
Figure 24:
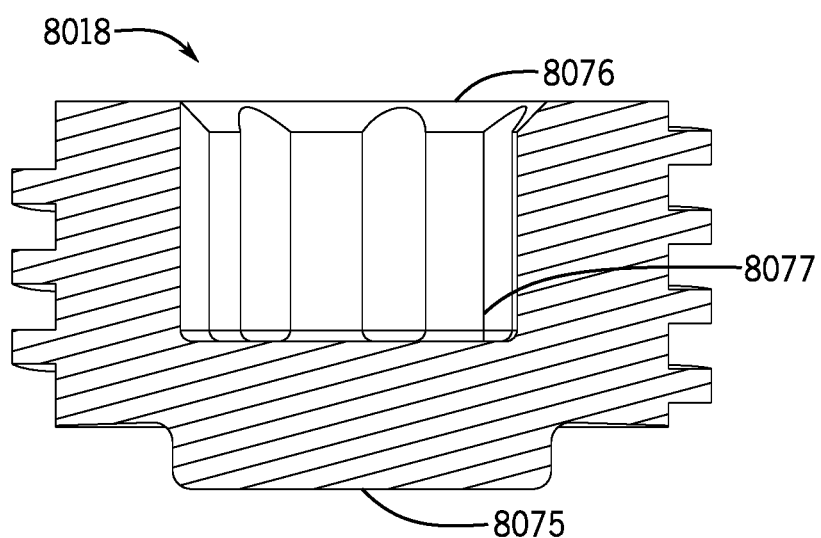
FIG. 24 is a transverse cross section of the closure of FIG. 23.

It is foreseen that any of a variety of different closure structures for use in conjunction with the present disclosure with suitable mating structure on the upstanding arms. Referring now to FIGS. 23-24, the illustrated closure 8018 includes a bottom surface 8077 for the drive structure 8076, and may further include a point or bump or plateau 8075 for engagement and penetration into the surface of the rod in certain embodiments of the disclosure.

As required, detailed embodiments of the present disclosure are disclosed herein; however, it is to be understood that the disclosed embodiments are merely exemplary of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Figure 25:
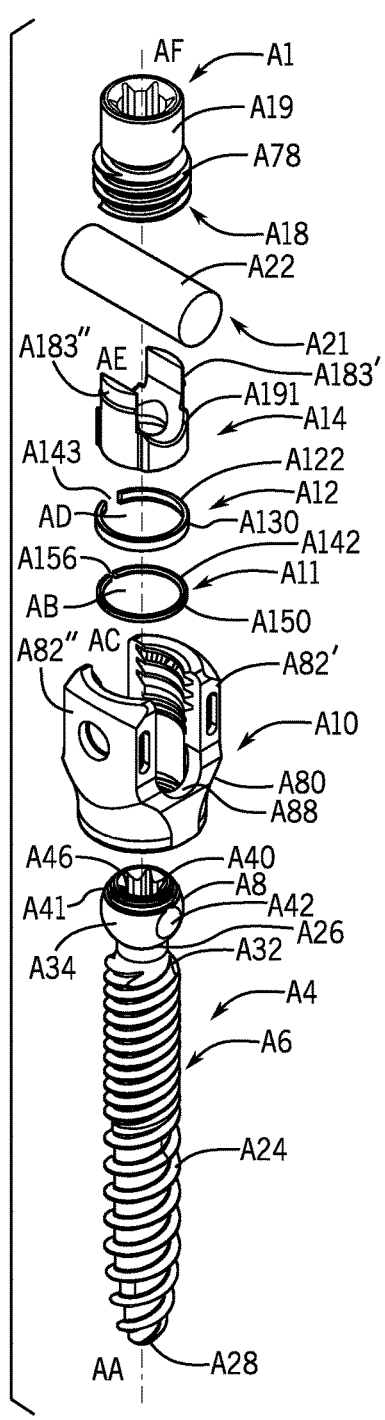
FIG. 25 is an exploded perspective view of an embodiment of a multiplanar bone screw assembly according to the present disclosure including a shank, a multiplanar receiver, a non-pivoting retainer, a multi-purpose positioner, a pressure insert and a closure, shown in conjunction with a rod.

With reference to FIG. 25, the reference number A1 generally represents an embodiment of a multi-planar, multi-axial, or polyaxial bone screw apparatus or assembly according to the present disclosure. While the illustrated anchor A1 is generally a polyaxial bone screw, it is foreseen that the disclosure could be utilized with other types of spinal implants, such as polyaxial bone hooks or clamps, for example. The illustrated assembly A1 includes: a shank A4, that further includes a body A6 integral with an upwardly extending upper portion or capture structure A8; a multi-purpose positioner A12; a receiver A10; a non-pivoting retainer structure A11; a compression or pressure insert A14; and a closure A18. The assembly A1 may also include or be adapted for use with an elongated rod or connecting member A21. The receiver A10, the positioner A12, the non-pivoting retainer A11, and compression insert A14 are preferably initially pre-assembled and may be further assembled with the shank A4 either prior or subsequent to implantation of the shank body A6 into a vertebra (not shown), as will be described in greater detail below.

Figure 26:
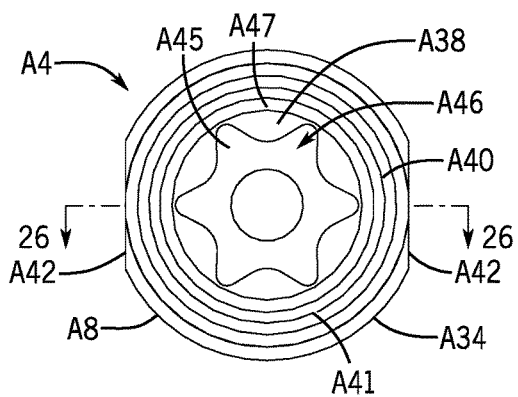
FIG. 26 is an enlarged top plan view of the shank of the assembly.

FIGS. 25-26 further shows a closure structure A18 of the disclosure for capturing a portion of a longitudinal member, for example, a spinal fixation rod or longitudinal connecting member A21 which in turn engages the compression insert A14 that presses against the shank upper portion or capture portion A8 into fixed frictional contact with the non-pivoting retainer A11, so as to capture and fix the longitudinal connecting member A21 within the receiver A10 and thus fix the member A21 relative to the vertebra (not shown). By non-pivoting it is meant that the retainer does not polyaxially rotate with the shank A4, but it may or may not move about its axis, so as to rotate with respect to the receiver, at least until it is held by the positioner.

The illustrated rod portion A21 is preferably hard, stiff, non-elastic and cylindrical, having an outer cylindrical surface A22. It is foreseen that in other embodiments of the disclosure, the rod A21 may be elastic, deformable and/or of a different cross-sectional geometry. The receiver A10 and the shank A4 cooperate in such a manner that the receiver A10 and the shank A4 can be secured at any of a plurality of angles, articulations or angular alignments relative to one another and within a selected range of angles, but not limited to, from side to side and from front to back or rear, to enable flexible or articulated engagement of the receiver A10 with the shank A4 until both are locked or fixed relative to each other near the end of an implantation procedure.

Figure 27:
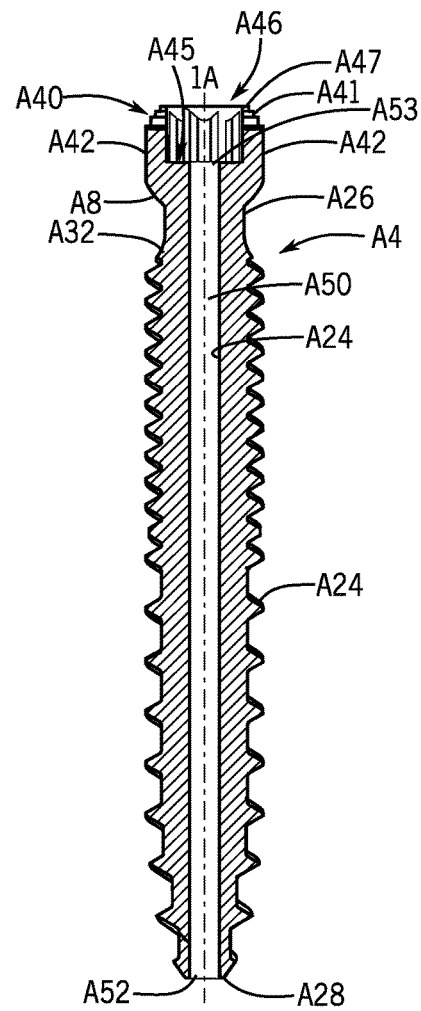
FIG. 27 is an enlarged cross sectional view of the shank, taken along line 3-3 of FIG. 26.
Figure 28:
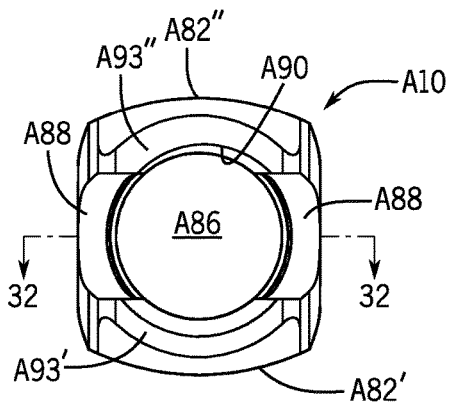
FIG. 28 is an enlarged top plan view of the receiver of the assembly.
Figure 29:
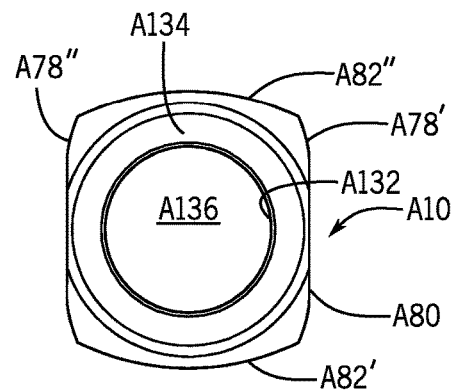
FIG. 29 is a bottom plan view of the receiver.
Figure 30:
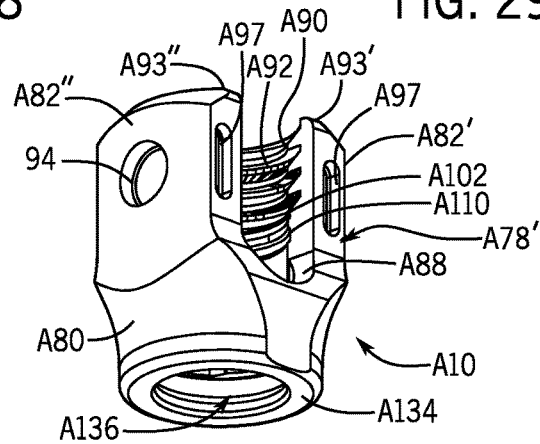
FIG. 30 is a further enlarged perspective view of the receiver.
Figure 31:
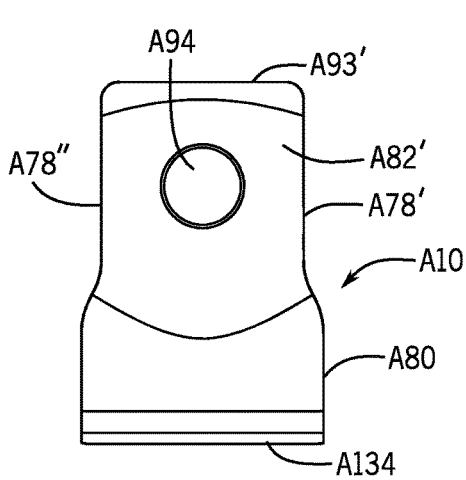
FIG. 31 is a side elevational view of the receiver.

With particular reference to FIGS. 25-27, the shank A4 is elongate, with the shank body A6 having a helically wound bone implantable thread A24 (single or multi start thread pitches, which can have different types of thread patterns) extending from near a neck A26 located adjacent to the upper portion or capture structure A8, to a tip A28 of the body A6 and extending radially outwardly therefrom. During use, the body A6 utilizing the thread A24 for gripping and advancement is implanted into the vertebra leading with the tip and driven down into the vertebra with an installation or driving tool (not shown), so as to be implanted in the vertebra to near the neck A26, as more fully described in the paragraphs below. The shank A4 has an elongate axis of rotation generally identified by the reference letter A in FIGS. 25 and 27.

The neck A26 extends axially upward from the shank body A6. The neck A26 may be of the same or is typically of a slightly reduced radius as compared to an adjacent upper end or top A32 of the body A6 where the thread A24 terminates. Further, extending axially and outwardly from the neck A26 is the shank upper portion A8 that provides a connective or capture apparatus disposed at a distance from the upper end A32 and thus at a distance from the vertebra (not shown) when the body A6 is implanted in such vertebra.

The shank upper capture portion A8 is configured for a pivotable connection relative to the shank A4 and the receiver A10 prior to fixing of the shank A4 in a desired position with respect to the receiver A10. The shank upper portion A8 has an outer bulbous, convex and partially spherical surface A34 that extends outwardly and upwardly from the neck A26 and terminates at the upper end A32. The spherical surface A34 is configured for sliding cooperation and ultimate frictional mating with a lower concave surface A198 of the compression insert A14 having a substantially similar radius.

A shank top surface A47 is substantially perpendicular to the axis AA. The spherical surface A34 shown in the present embodiment is substantially smooth with the exception of a stepped or graduated upper surface portion A40 located adjacent to the top surface A47 and sized and shaped for cooperation and ultimate frictional engagement with the compression insert A14. In the illustrated embodiment of assembly A1, the surface portion A40 includes at least three graduated cylindrical surfaces A41 axially disposed substantially parallel to the axis AA and adjacent perpendicular step surfaces that are disposed generally perpendicular to the axis AA. It is foreseen that the surface portion A40 may include greater or fewer number of stepped surfaces and that the stepped surfaces be further structure rather than carved into the shank spherical surface A34. It is also foreseen that similar stepped surfaces could be carved in and winding helically about on the spherical surface A34 near the neck A26, as envisioned in U.S. patent application Ser. No. 14/164,882, which is incorporated by reference herein.

When the shank A4 is locked into position by a rod or other connecting member A21 being pressed downwardly on an insert U-shaped channel A187 by the closure top A18, the insert shank gripping surface A198 is initially slidable along the shank surface A34 such that the stepped surfaces A40 digs or penetrates into the shank gripping surface A198 and thus securely fixes the shank upper portion A8 to the insert A14. It is foreseen that the insert can be made of a material that is softer or harder than that of the shank.

It is foreseen that the shank upper portion A8 may have a smooth spherical surface A34 without having the stepped or graduated upper surface portion A40. It is foreseen that the surface portion A40 and also the rest of the spherical surface A34 may additionally or alternatively include a roughened or textured surface or surface finish, or may be scored, knurled, grit blasted, or the like, for enhancing frictional engagement with the non-pivoting retainer A11 and/or the compression insert A14.

Formed in a shank upper portion A8 of the shank head A4 are opposite or opposed parallel flat planar surfaces A42 that extend downwardly parallel to the axis AA. In the illustrated embodiment of the shank, the flat planar surfaces A42, may be machined or molded, such that the width between the flat planar surfaces A42 is determined by how much of the spherical surface A34 is removed or machined. It is foreseen that the flat planar surfaces A42 may also include a lower key extension, as seen in U.S. patent application Ser. No. 13/573,516, the entirety of which is incorporated by reference herein.

A counter sunk substantially planar base or seating surface A45 partially defines an internal drive feature or imprint or structure A46. As best seen in FIG. 25, the illustrated internal drive feature A46 is an aperture formed in the top surface A47 extending downwardly from the top surface A47 and has a hexagonal or hex shape designed to receive the hex tool (not shown) of an Allen wrench type, into the aperture for rotating and driving the bone screw shank A4. It is foreseen that such an internal tool engagement structure may take a variety of tool-engaging forms and may include one or more apertures of various shapes, such as a pair of spaced apart apertures or a multi-lobular or star-shaped aperture, such as those sold under the trademark TORX, or the like, having a non-round shape for positive drive engagement by a complementary shaped drive tool (not shown). It is foreseen that the drive tool structure may be made of a somewhat softer or harder metal compared to that of the head. The seat or base of the drive feature A49 is disposed perpendicular to the axis AA with the drive feature A46 otherwise being coaxial with the axis AA. In operation, the driving tool is received in the internal drive feature A46, being seated at the base and engaging the faces of the drive feature A46 for both driving and rotating the shank body A6 into the vertebra, either before the shank A4 is attached to the receiver A10 or after the shank A4 is attached to the receiver A10, with the shank body A6 being driven into the vertebra with the driving tool extending into the receiver A10.

The illustrated shank A4 is cannulated, having a small central bore A50 extending an entire length of the shank A4 along the axis AA. It is foreseen that the central bore may not have to extend in a parallel direction with axis AA, nor that the bore may extend the entire length of the shank A4. The bore A50 is defined by an inner cylindrical wall A51 of the shank A4 and has a circular opening A52 at the shank tip A28 and an upper opening A53 communicating with the external drive A46 at the surface A45. The illustrated bore A50 is coaxial with the threaded body A6 and the upper portion A8. It is foreseen that the shank does not further include a cannulation bore. It is foreseen that the bore A50 provides a passage through the shank A4 interior such that a length of guide wire (not shown) may be inserted into the vertebra prior to the insertion of the shank body A6, the wire providing a guide for precise insertion of the shank body A6 into the vertebra.

It is foreseen that the shank A4 can be expandable and/or fenestrated, and again, have different thread pitches and patterns extending along its length. It is foreseen that the length of the shank may be shortened or lengthened further. It is foreseen that the stepped surface A40 may be smooth. It is foreseen that the shank includes a spherical head with a capture structure with or without shaved or flat sides cooperating with a pivoting retaining, with or without a positioner.

To provide a biologically active interface with the bone or vertebra, the threaded shank body A6 may be coated, perforated, made porous or otherwise treated. The treatment may include, but is not limited to, a plasma spray coating or other type of coating of a metal or, for example, a calcium phosphate; or a roughening, perforation or indentation in the shank surface, such as by sputtering, sand blasting or acid etching, that allows for bony ingrowth or ongrowth. Certain metal coatings act as a scaffold for bone ingrowth. Bioceramic calcium phosphate coatings include, but are not limited to: alpha-tri-calcium phosphate and beta-tri-calcium phosphate $(Ca_3(PO_4)_2)$, tetra-calcium phosphate $(Ca_4P_2O_9)$, amorphous calcium phosphate and hydroxyapatite $(Ca_{10}(PO_4)_6(OH)_2)$. Coating with hydroxyapatite, for example, is desirable as hydroxyapatite is chemically similar to bone with respect to mineral content and has been identified as being bioactive and thus not only supportive of bone ingrowth, but actively taking part in bone bonding.

Figure 32:
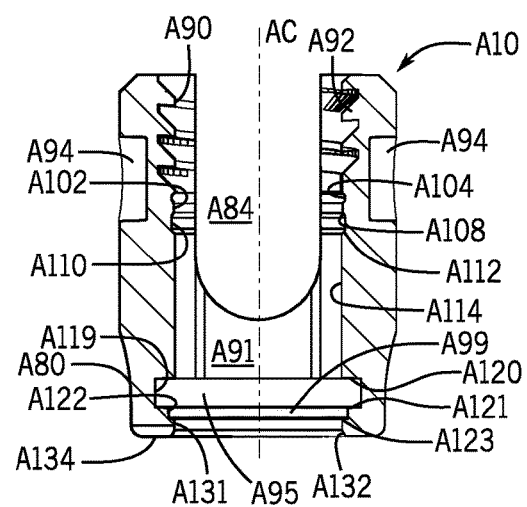
FIG. 32 is a cross sectional view of the receiver, taken along line 8-8 of FIG. 28.

With particular reference to FIGS. 25 and 28-32, the receiver A10 has a generally U-shaped appearance with a partially discontinuous substantially cylindrical inner and outer profile. The receiver A10 has a cylindrical axis AC that is shown in FIGS. 25 and 32 that may align with axis AA of the shank A4, such orientation being desirable, but not required during assembly of the receiver A10 with the shank A4. After the receiver A10 is pivotally attached to the shank A4 at a desired predisposed plane or axis, either before or after the shank A4 is implanted in a vertebra, the axis AC is typically disposed at an obtuse angle with respect to the axis AA.

Figure 56:
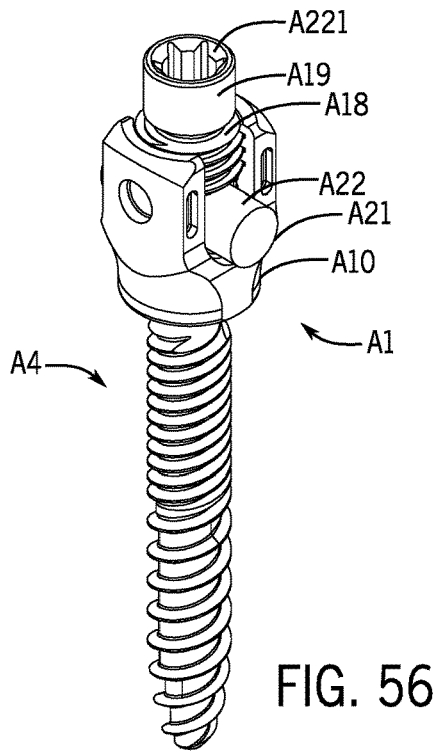
FIG. 56 is a perspective view of the entire assembly of FIG. 25.

The receiver A10 includes a substantially cylindrical base A80 integral with a pair of opposed upstanding arms A82' and A82" forming a cradle and defining a channel A84 between the arms A82' and A82" with an upper opening, generally A86, and a U-shaped lower seat A88, the channel A84 having a width for operably receiving the rod A21 between the arms A82' and A82", best seen in FIGS. 56-57. Each of the arms A82' and A82" has an interior surface, generally A90, that includes various inner cylindrical profiles, an upper of which is a partial helically wound guide and advancement structure A92 located adjacent top surfaces A93' and A93" of each of the arms A82' and A82". It is foreseen that the receiver may further include extensions (not shown) attached to the arms A82' and A82" having break off junctures to the arms. The breakoff extensions can also have internal threads.

The guide and advancement structure A92 is a partial helically wound reverse angle thread form configured to mate under rotation with a similar structure on the closure structure A18 with a breakoff head A19, as described more fully below. However, it is foreseen that the guide and advancement structure A92 could alternatively be a square-shaped thread, a buttress thread, an interlocking flange form or other thread-like or non-thread-like helically wound and non-helically wound discontinuous advancement structure for operably guiding, under complete or partial rotation, and advancing the closure structure A18 downward between the arms A82' and A82", as well as eventual torquing when the closure structure A18 abuts against the rod A21. It is also foreseen that the closure need not have a breakoff head A19 in certain embodiments.

An opposed pair of tool receiving and engaging apertures or indentations A94 are formed on outer surfaces A96 of the illustrated arms A82' and A82". Furthermore, two pairs of tool receiving and engaging apertures A97 may be formed in front and rear surfaces A78' and A78" of the arms A82' and A82". Some or all of the apertures A94 and A97 may be used for holding the receiver A10 during the implantation of the shank body A6 into a vertebra when the shank is pre-assembled with the receiver A10, and during assembly of the bone anchor assembly A1 with the rod A21 and the closure structure A18. It is foreseen that tool receiving grooves or apertures A94 and A97 may be configured in a variety of shapes and sizes and be disposed at other locations on the receiver arms A82' and A82", such as near the top of the receiver arms in the form of horizontal radiused grooves.

Referring to FIG. 32 and returning to the interior surface A90 of the receiver arms A82' and A82", moving downwardly, in a direction toward the base A80, adjacent the guide and advancement structure A92 is a discontinuous insert attachment structure or groove or slot or spherical surface A104 that extends outwardly from the axis AC and runs perpendicular to the axis AC. Adjacent to and located below the insert attachment groove surface A104 is a discontinuous cylindrical surface A102 having a diameter or width or radius equal to or less than the diameter or width or radius of the root of the guide and advancement structure A92. A discontinuous annular surface A108 that provides an abutment surface or stop for capturing the compression insert A14 in the receiver A10 at a second friction fit position is located below and adjacent to the second cylindrical surface A102. The abutment surface A108 is disposed substantially perpendicular to the axis AC. Another cylindrical surface A110 is located below and adjacent to the surface A108. The cylindrical surface A110 is oriented substantially parallel to the axis AC and is sized and shaped to capture the compression insert A14, as will be described in greater detail below. The surface A110 surrounds a U-shaped channel seat A68 and is, by definition, discontinuous. The cylindrical surface A110 has a diameter greater than the diameter of the cylindrical surface A102. A discontinuous sloped surface A112 is located below and adjacent to the cylindrical surface A110, sloping downwardly and inwardly toward the central axis AC. A third partially cylindrical surface A114 is located below and adjacent to the surface A112. An upper shelf surface A120 is located below the fourth partially cylindrical surface A114. The upper shelf surface A120 is disposed substantially perpendicular to the axis AC and forms a stop for the positioner A12, prohibiting the positioner A12 (when in an uncompressed configuration) from moving upwardly into a space or cavity A91 partially defined by the cylindrical surface A114 that holds the compression insert A14. A fourth cylindrical surface A119 is below the upper shelf surface A120. The cylindrical surface A119 is continuous about the interior A90 of the receiver A10 and is at least substantially parallel with axis AC. In the illustrated embodiment, the cylindrical surface A119 has a diameter that is greater than the radii of the first cylindrical surface A102, the cylindrical surface A110, and the cylindrical surface A114 described above. A stop surface A121 is located below the cylindrical surface A119. The stop surface A121 runs perpendicular to the axis AC. A cylindrical surface A122 is located below and adjacent the stop surface A121. The cylindrical surface A122 has a diameter that is less than the cylindrical surface A119.

A lower stop surface A123 is disposed in the cavity adjacent cylindrical surface A122. A cylindrical surface A124 is located below and adjacent to the surface A123. The stop surface A123 is oriented substantially perpendicular to the axis AC and is sized and shaped to receive a neutral state or starting, nominal, uncompressed state of the non-pivoting retainer A11, as will be described in greater detail below. The cylindrical surface A119, the upper stop surface A120, and the lower abutment surface A121 partially define a circumferential recess or expansion chamber A95 that is sized and shaped to house the positioner A12 and to receive the non-pivoting retainer A11 as it expands around the shank upper portion A8, as the shank upper capture portion A8 moves upwardly toward the channel A84 during assembly. Additionally, the expansion chamber A95 forms a restriction to prevent the positioner A12 from moving upwardly with the shank portion A8, the stop surface A120 preventing the positioner A12, and ultimately the non-pivoting retainer A11 from passing from the expansion chamber A95 into the cavity A91, whether the non-pivoting retainer A11 is in an expanded state or in a neutral, nominal, or original operative state.

The cylindrical surface A123 is joined or connected to a surface A131 by one or more beveled, curved or conical surfaces. The surface A131 allows for sliding and gradual movement and/or contraction of the non-pivoting retainer A11, the positioner A12, the insert A14, and the shank A4 into the space defined by the surfaces A122 and A123 and the ultimate final seating of the non-pivoting retainer A11 on a lower annular seating surface A123 located below and adjacent to the cylindrical surface A121. The surfaces A122 and A123 provide a seating or non-expansion chamber A99 for the non-pivoting retainer A11, wherein the non-pivoting retainer A11 slightly expands out to the surface A122 when in a locked position, as is shown, for example, in FIGS. 52-55. The surface A131 communicates with an exterior base surface A134 of the base A80, defining the lower opening, generally A136, of the receiver A10. The lower opening A136 is circularly shaped having a diameter or width or radius (not shown) measured from one side of the cavity to the next. It is foreseen that other geometries, such as opposed flat sides are also envisioned for the bottom or lower opening A136. The illustrated surface A131 has a diameter that is substantially the same as the diameter of the surface A114, potentially allowing for slidable uploading of the compression insert A14 while requiring compression or squeezing of the non-pivoting retainer A11 and positioner A12 during loading of the non-pivoting retainer A11 and the positioner A12, for example, through the lower opening A136. The upper opening A86 potentially allowing for slidable downloading of the compression insert A14, while also requiring compression or squeezing of the non-pivoting retainer A11 and positioner A12 during loading of the non-pivoting retainer A11 and the positioner A12, for example, as seen in FIGS. 42-45.

The positioner A12 operates to control, capture and hold the non-pivoting retainer A11 within the receiver A10 expansion chamber A95 until the shank A4 is fully captured as is described in U.S. Provisional Patent Application Nos. 62/137,713; 62/137,707; 62/078,173; 62/066,813; 62/066,806; 62/078,154, and 62/200,491, each of which were previously incorporated by reference above.

Figure 33:
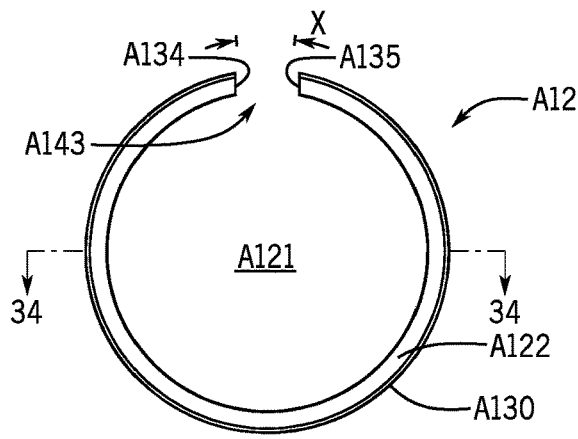
FIG. 33 is a further enlarged top plan view of the positioner of the assembly.
Figure 34:
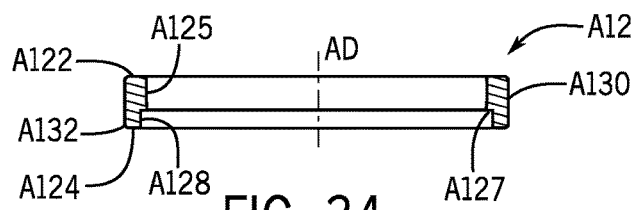
FIG. 34 is a cross sectional view of the positioner, taken along line 10-10 of FIG. 33.

With particular reference to FIGS. 25 and 33-34, the positioner A9 has a central axis AD that is operationally aligned with axis AC associated with the receiver A10 and axis AB of the non-pivoting retainer A11, and may be aligned with axis AA associated with the shank A4. The positioner A12 may be made from a resilient material, such as a stainless steel, titanium alloy, cobalt chrome, or the like, as well as polymers, or some combination thereof, so that the positioner A12 may be expanded and contracted during various steps of assembly, as will be described in greater detail below.

Figure 44:
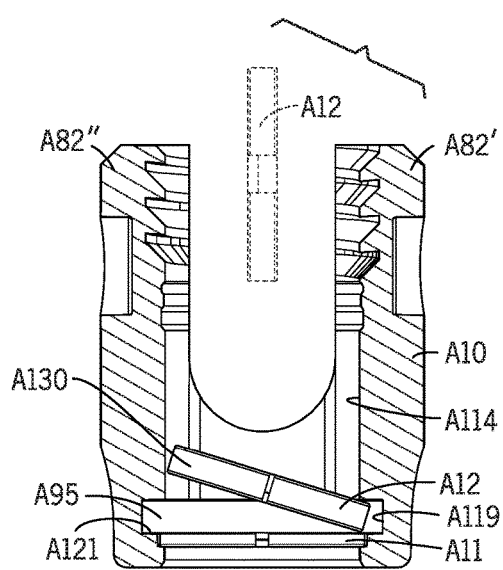
FIG. 44 is a view similar to FIG. 42 showing the receiver, positioner, and non-pivoting retainer with portions of the receiver cut away to show cooperation of the parts at a stage whereat the positioner is being loaded in the receiver.

The positioner A12 has a central channel or hollow through bore, generally A121, that passes entirely through the structure A12 from a top surface A139 to a bottom surface A124 thereof. As illustrated in FIG. 34, surfaces that define the channel or bore A121 include a discontinuous inner curvate concave surface A125 adjacent the top surface A139, a discontinuous shelf surface A127 adjacent the surface A125, and a lower cylindrical surface A128, each surface coaxial with the axis AC when the positioner A12 is in a neutral non-compressed, non-expanded orientation or state. The curvate surface A125 having a curvature similar to that of the spherical outer surface A34 of the shank A4, so as to mate better with the convex surface of the shank A4. The positioner A12 further includes an outer cylindrical surface A130 located adjacent the top surface A139 and an outer beveled or frusto-conical surface A140 adjacent the bottom surface A124. The surface A130 is oriented parallel to the axis AC. The resilient positioner A12 further includes first and second end surfaces, A137 and A138 disposed in spaced relation to one another when the retainer is in a neutral non-compressed state. Both end surfaces A137 and A138 are disposed substantially perpendicular to the top surface A139 and the bottom surface A124. A gap A143 having nominal width X between the surfaces A137 and A138 is determined by a desired amount of compressibility of the open positioner A12 when loaded into the receiver A10. The space A143 shown in FIG. 33 provides adequate space between the surfaces A137 and A138 for the positioner A12 to be pinched, with the surfaces A137 and A138 compressed toward one another to a closely spaced or even touching configuration, if necessary, to an extent that the compressed positioner A12 is up or bottom loadable through the receiver opening A136 or down loadable, as shown in FIG. 44. After passing through the opening A86 and along a portion of the inner surface A114, the positioner A12 expands or springs back to an original uncompressed, rounded or collar-like configuration, see, e.g., FIG. 45. The embodiment shown in FIGS. 33-35 illustrates the surfaces A137 and A138 as substantially parallel, however, it is foreseen that it may be desirable to orient the surfaces A137 and A138 obliquely or at a slight angle depending upon the amount of compression desired during loading of the positioner A12 into the receiver A10.

It is foreseen that the positioner A12 may be hinged or connected so as to create a single positioner (not shown) without a gap. It is also foreseen that the positioner A12 may include more than one positioner (not shown), so as to be configured as a multi-part positioner. It is foreseen that the positioner A12 can further include interior opposed flanges (not shown), so as to assist in capturing the retainer A11.

It is foreseen that the top surface A139 and also the inner surfaces A127 and A128 may additionally or alternatively include a roughened or textured surface or surface finish, or may be scored, knurled, grit blasted, or the like, for enhancing frictional engagement with the non-pivoting retainer top surface A142 and the outer surface A150 of the non-pivoting retainer A11. The additional surfacing may be necessary for the bottom surface A124 of the positioner A12 to prevent or limit rotational movement of the non-pivotal retainer A11 with respect to the positioner A12 and also the receiver A10.

Figure 35:
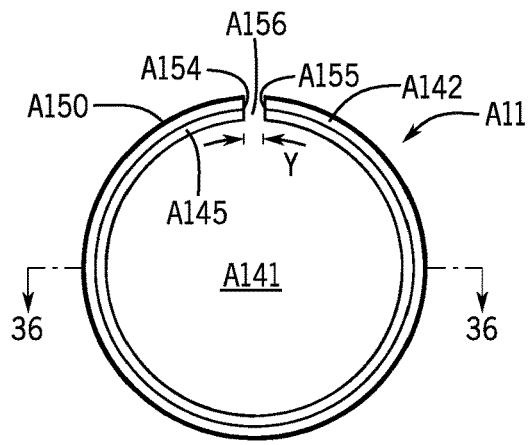
FIG. 35 is a top plan view of the non-pivoting retainer of the assembly.
Figure 36:
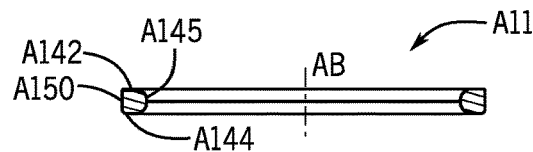
FIG. 36 is a cross sectional view of the non-pivoting retainer, taken along line 12-12 of FIG. 35.
Figures 37, 38:
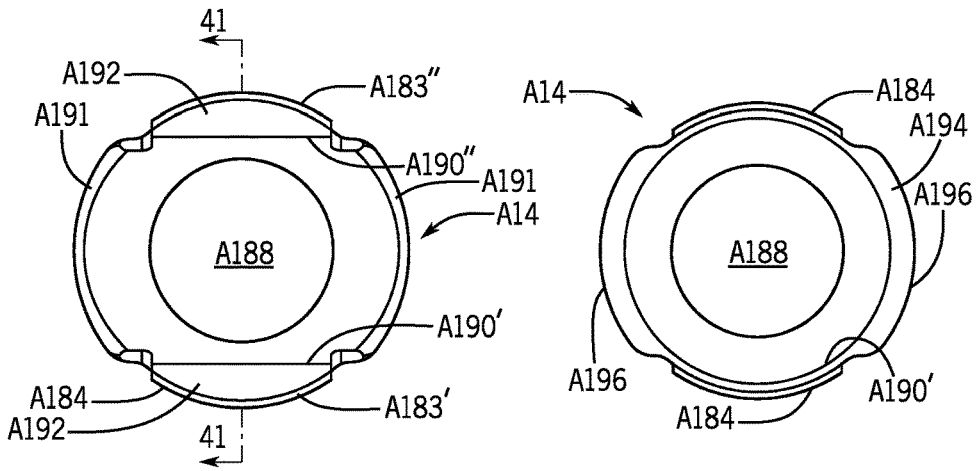
FIG. 37 is a top plan view of the pressure insert of the bone screw assembly.
FIG. 38 is a bottom plan view of the insert.
Figure 39:
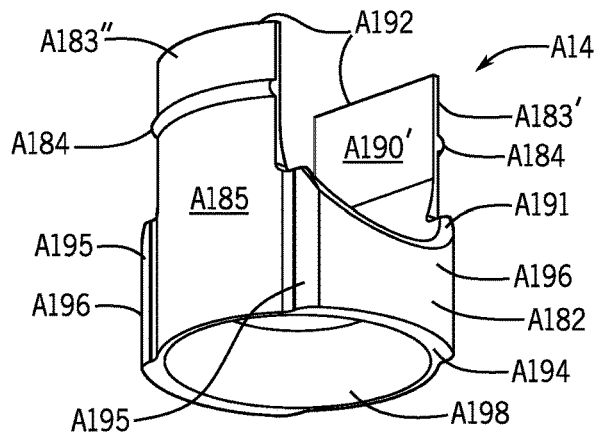
FIG. 39 is an enlarged perspective view of the insert.
Figures 40, 41:
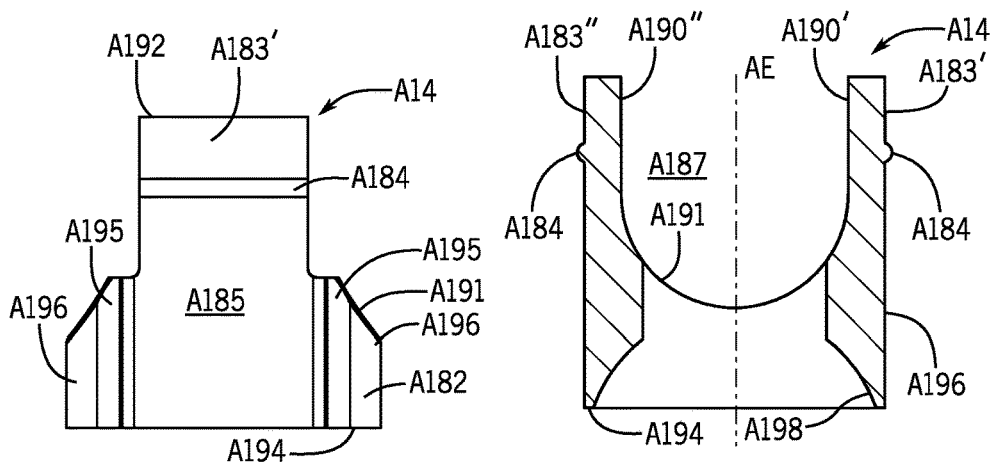
FIG. 40 is a side elevation view of the insert.
FIG. 41 is a cross sectional view of the receiver, taken along line 17-17 of FIG. 37.

With reference to FIGS. 25 and 35-36, the non-pivoting retainer A11 operates to capture the shank upper portion A8 within the receiver A10. The non-pivoting retainer A11 has a central axis AB that is operationally aligned with the axis AC associated with the receiver A10, and may be aligned with axis AA associated with the shank A4, and can be seen in FIG. 25. The non-pivoting retainer A11 may be made from a resilient material, such as a stainless steel or titanium alloy, cobalt chrome, or the like, or a polymer, or some combination thereof, so that the non-pivoting retainer A11 may be expanded during various steps of assembly, as will be described in greater detail below. It is foreseen that the non-pivoting retainer A11 may be made of a softer metal compared to that of the positioner A12, so that the positioner A12 is able to overpower or be structurally stronger than the non-pivoting retainer A11 in assembly. It is foreseen that the non-pivoting retainer A11 may be used for compression as well and held in rotational alignment by the receiver A14 or in some embodiments by a spring ring, a centering spring, a wave spring, additional inserts, or other structures, such as a multi-purpose positioner A12.

The non-pivoting retainer A11 is annular or ring-like in shape and has a central channel or opening or hollow through bore A141, that passes entirely through the non-pivoting retainer A11 from a top surface A142 to a bottom surface A144 thereof. The non-pivoting retainer A11 is configured to not pivot with the shank A4, but situated to ultimately stay within the confides of the locking chamber A99. Surfaces that define the channel or bore A141 include a discontinuous inner curvate surface A145 adjacent the top surface A142 and the bottom surface A144. The non-pivoting retainer A11 further includes an outer cylindrical surface A150 located adjacent a top surface A142. The outer surface A150 is oriented parallel to the axis AB. It is foreseen that the corners (not shown) located about either the top surface A142 or bottom surface A144 could be rounded or beveled as needed. It is also foreseen that two or more evenly spaced notches or bumps (not shown) may be formed in the top surface A142, outer surface A150, or bottom surface A144 to more evenly distribute stress across the entire non-pivoting retainer A11 during contraction and expansion thereof. The resilient non-pivoting retainer A11 further includes first and second end surfaces, A154 and A155 disposed in opposed spaced relation to one another when the retainer A11 is in a neutral non-compressed state. Both end surfaces A154 and A155 are disposed substantially perpendicular to the top surface A142 and the bottom surface A144 and parallel with axis AB. The embodiment shown in FIG. 35 shows a slit or gap A156 as substantially parallel; however, it is foreseen that it may be desirable to orient the surfaces A154 and A155 obliquely or at a slight angle depending upon the amount of compression desired during loading of the non-pivoting retainer A11 into the receiver A10.

Figure 42:
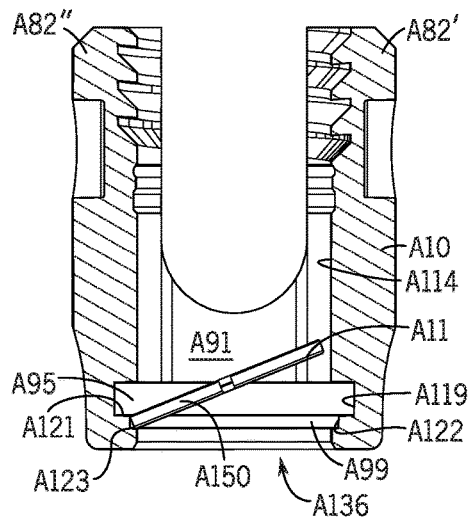
FIG. 42 is an enlarged side elevation view of the receiver and non-pivoting retainer with portions of the receiver cut away to show cooperation of the parts at a stage whereat the non-pivoting retainer is being positioned in the receiver.

The gap A156 of nominal width Y between the surfaces A154 and A155 is determined by a desired amount of compressibility of the open non-pivoting retainer ring A11 when loaded into the receiver A10. The gap A156 provides adequate space between the surfaces A154 and A155 for the non-pivoting retainer A11 to be pinched, with the surfaces A154 and A155 compressed toward one another to a closely spaced or even touching configuration, if necessary, to an extent that the compressed non-pivoting retainer A11 is up loadable through the receiver opening A136 or down loadable, as seen in FIG. 42. After passing through the opening A136 and along a portion of the cavity A91, the non-pivoting retainer A11 expands or springs back to an original uncompressed, rounded or collar-like shape. It is foreseen that the end portions A154 and A155 can be overlappingly compressed together to get the non-pivoting retainer in the receiver A10.

It is foreseen that the top surface portion A142 and also the rest of the cylindrical outer surface A150 may additionally or alternatively include a roughened or textured surface or surface finish, or may be scored, knurled, grit blasted, or the like, for enhancing frictional engagement with the cylindrical inner surface A122 of the receiver A10 and an interior of the positioner A12. The additional surfacing may be necessary to prevent or limit rotational movement of the non-pivotal retainer A11 with respect to the positioner A12.

It is foreseen that the non-pivoting retainer A11 may include further embodiments as seen in U.S. patent application Ser. No. 12/924,802, which is incorporated by reference herein. It is foreseen that the retainer A11 may have a super structure or infra-structure extending up and down therefrom.

With reference to FIGS. 25 and 37-41, the friction fit compression or pressure insert A14 is sized and shaped to be received by and loaded into the receiver A10, for example through the upper opening A86. The illustrated compression insert A14 has a central axis AE operationally aligned with the central axis AC of the receiver A10. In operation, the insert A14 advantageously frictionally engages the bone screw shank upper portion A8, allowing for un-locked, but non-floppy placement of the angle of the shank A4 with respect to the receiver A10 during surgery prior to locking of the shank with respect to the receiver near the end of the procedure with a rod or connecting member A21 and a closure A8. It is foreseen that the insert A14 may be made from a resilient material, such as a stainless steel or titanium alloy, or a polymer, or some combination thereof, so that portions of the insert may be expanded about and then contracted, snapped or popped onto the shank upper portion A8 and into the insert grooves A102, A104. Furthermore, in operation, the insert A14 is suspended within the receiver A10, being frictionally held in place by the receiver insert attachment grooves A104 and prohibited from moving upward or downward until deployed, even with the insertion of the shank upper capture portion A8. As will be explained in greater detail below, after initial assembly and during operation of the assembly A1, preferably neither the non-pivoting retainer A11 nor the inner surfaces A90 of the receiver A10 that define the cavity A91 place any compressive force on the insert A14 to hold the shank upper capture portion A8 therein.

The illustrated insert A14 includes a lower body A182 with a pair of spaced upstanding arms A183' and A183''. The arms A183' and A183'' have a radially outer surface A185 on each side which are substantially smooth and vertically or axially opposed, but radially spaced from an axis AE. The outer surface A185 includes receiver attachment projection structures A184 on each arm A183' and A183''. Each receiver attachment projection structure A184 extends discontinuously circumferentially about the outer surface. It is foreseen that the receiver attachment projection structure A184 may further include a beveled or sloped surface (not shown) on either or both upper and lower sides of the projection A184. The projection A184 has a maximum diameter or width or radius (not shown) measured about the center of the projection A184 that is substantially similar to the diameter of the insert groove A104 of the retainer A10. The arms A183' and A183'' form a central U-shaped channel A187 therebetween, and there is a central axially aligned and centered through bore A188. The through bore A188 runs from an annular planar top surface A192 to an annular planar and discontinuous bottom surface A194 thereof. The bore A188 is defined by an inner cylindrical surface (not shown) that is at least partially defined by the U-shaped channel A187 and a shank gripping surface portion (not shown) extending between the cylindrical surface and the bottom surface A194.

It is foreseen that the insert shank gripping surface A198 may include one or more stepped surfaces (not shown) and that, again, the insert can be made of a softer material or metal compared to that of the shank. The compression insert A14 through bore A188 is sized and shaped to receive the driving tool (not shown) there through that engages the shank drive feature A46 when the shank body A6 is driven into bone with the receiver A10 attached or without.

It is foreseen that the insert shank gripping surface A198 and also the bottom surface A194 may additionally or alternatively include a roughened or textured surface or surface finish, or may be scored, grit blasted, knurled, or the like (not shown), for enhancing frictional engagement with the shank upper portion A8.

It is foreseen that a plurality of slits or slots (not shown) may be formed in the spherical shank gripping surface running through the bottom surface A194.

On either side of the arms A183' and A183" are flat surfaces A190' and A190". At one end the flat surfaces A183' and A183" are adjacent top surfaces A192 and at the opposed end of the surfaces A190' and A190" are saddle surfaces A191.

Ledges or flanges A196 radially project from opposite front and back faces or sides of the outer surface A185. Proximal-facing saddle surfaces A191 are defined in a semi-cylindrical curved fashion through the insert A14 and across the proximal-facing portions of the ledges A196. In some embodiments, the curved saddle surfaces A191 have diameters that are essentially greater than or equal to the diameter of the implant rod A21, such that the implant rod outer surface A22 can extend across a saddle surfaces A191. Ledges A196 are defined by opposed side surfaces A195.

The ledges A196 allow the insert A14 to move vertically during loading into the receiver A10, but prevents the insert A14 from rotating about the axis AC relative to the receiver A10. It is foreseen that the ledges A196 may further include a bottom surface that is located below the lower body bottom surface A194, so that the insert may further engage the positioner A12. Such an insert can be seen in U.S. Provisional Patent Application No. 62/200,501, which the entirety of which was incorporated by reference above.

It is foreseen that the insert A14 may not include arms A183' and A183". It is also foreseen that the arms A183' and A183" may be spaced from the closure top A18 or as illustrated may be sized and shaped to contact the closure top A18 in order to provide independent locking of the polyaxial mechanism of the assembly with non-pivoting retainer A11, but without fixing of the rod or other longitudinal connecting member A21 with respect to the closure top A18. It is foreseen that the insert could be configured to work with soft stabilization sleeves, as is described in U.S. patent application Ser. No. 14/731,064, the entirety of which is incorporated by reference above.

Assembly and disassembly of the bone screw assembly A1 will now be discussed. It is foreseen that pre-assembly of the receiver A10, non-pivoting retainer A11, positioner A12, and compression insert A14 may be chosen by the manufacturer. It should be understood that the order of the assembly of the insert A14, the positioner A12, and the non-pivoting retainer A11 within the receiver A10 may be interchangeable and not in any specific order.

Figure 43:
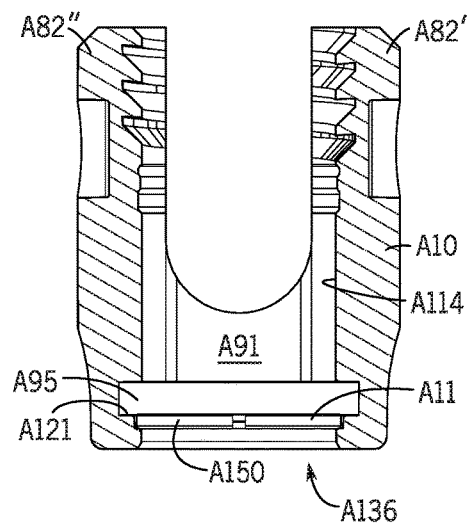
FIG. 43 is a view similar to FIG. 42 with portions of the receiver cut away to show cooperation of the parts at a stage whereat the non-pivoting retainer is loaded and in a nominal state in a seating or locking chamber.

Referring now to FIGS. 42-43, firstly, the resilient open non-pivoting retainer A11 is prepared for insertion into the receiver A10 by squeezing or pressing the retainer end surfaces A154 and A155 toward one another. The compressed retainer A11 is inserted into the receiver A10 by either bottom or top loading. The non-pivoting or bottom retainer A11 is typically moved upwardly into the receiver A10 and enters the expansion chamber A95. The retainer A11 is then allowed to expand to a neutral uncompressed state within the chamber A95. Once returned to the neutral state, the outer surface A150 of the non-pivoting retainer A11 situates or is located in the seating or locking chamber A99. There exists a gap between the outer surface A150 of the non-pivoting retainer A11 and cylindrical surface A122, to allow for some expansion of the retainer A11, when the shank A4 is captured.

Figure 45:
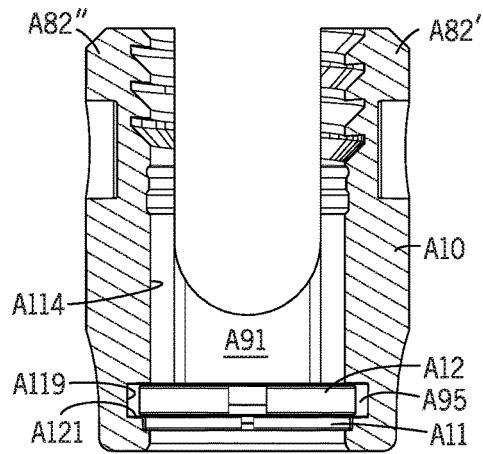
FIG. 45 is a view similar to FIG. 44 of the receiver, positioner, and non-pivoting retainer portions of the receiver cut away to show cooperation of the parts at a stage whereat the positioner is within an expansion chamber above the non-pivoting retainer and the non-pivoting retainer is seated in the locking chamber.

Referring now to FIGS. 44-45, the open positioner A12 is prepared for insertion into the receiver A10 by squeezing or pressing or folding or compressing positioner end surfaces A137 and A138 toward one another. The positioner A12 is typically moved into the receiver A10 and allowed to expand to a neutral uncompressed state within the expansion chamber A95 engaging the abutment surface A121.

The illustrated retainer ring A11 of FIG. 45 resides within the distal confines of the positioner A12, such that the top surface A142 of the non-pivoting retainer ring A11 is in abutting planar contact with the bottom surface A124 of the positioner A12.

Figure 46:
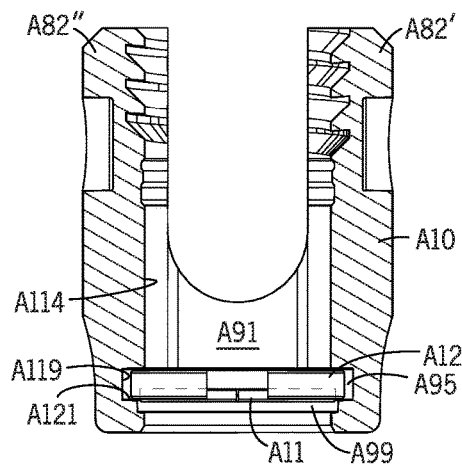
FIG. 46 is a view similar to FIG. 45 of the receiver, positioner, and non-pivoting retainer with portions of the receiver cut away and portions of the non-pivoting retainer in phantom to show cooperation of the parts at a stage whereat the non-pivoting retainer is positioned within the positioner in the expansion chamber.
Figure 47:
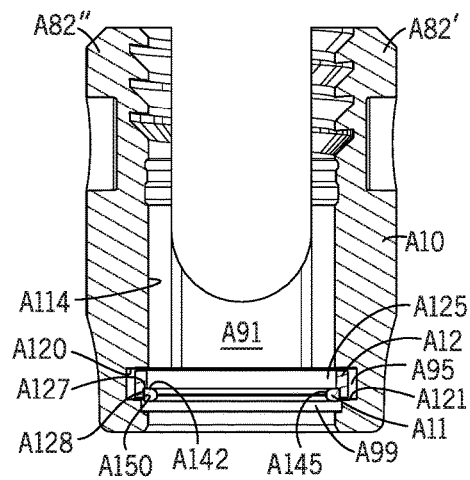
FIG. 47 is a view similar to FIG. 46 showing the positioner and non-pivoting retainer in cross section.

Referring now to FIGS. 46-47, the spherical outer surface A150 of the non-pivoting retainer ring A11 is adjusted such that the top surface A142 of the non-pivoting retainer A11 abuts against the interior circumferential abutment surface A127 of the positioner A12 and the outer surface A150 mates against the cylindrical surface A128 in a friction fit, as the positioner A12 is designed to compress slightly the non-pivoting retainer A11 within the interior confines or surfaces of bore A121, and thereby lock the retainer ring A11. In this combination, the positioner A12 gap A143 is held a little wider and the positioner compresses the non-pivoting retainer gap A156 closed or at least partially closed. Thus, the structural interaction of the positioner A12 and the non-pivoting retainer ring A11 maintains the two components A11, A12 in a substantially concentric relationship and in a dynamic pre-loaded state. The non-pivoting retainer A11 and the positioner A12 are ideally situated such that the gaps A143, A156 are situated parallel with each other, but it is foreseen that this does not have to be the case. In the illustrated example, width X is greater than width Y, but it is foreseen that width X may be equal to or less than width Y, dependent upon the needs of compression.

It is foreseen that the positioner A12 and the retainer A11 in combination may be loaded within the receiver, as opposed to loading them separately as shown.

Figure 48:
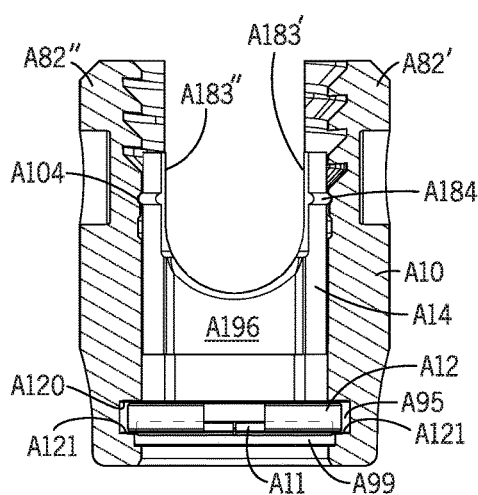
FIG. 48 is a view similar to FIG. 47 showing the receiver, positioner, non-pivoting retainer, and insert with portions of the retainer broken away to illustrate the loading of the insert and the initial shipping position of the receiver, positioner, non-pivoting retainer, and insert.
Figure 49:
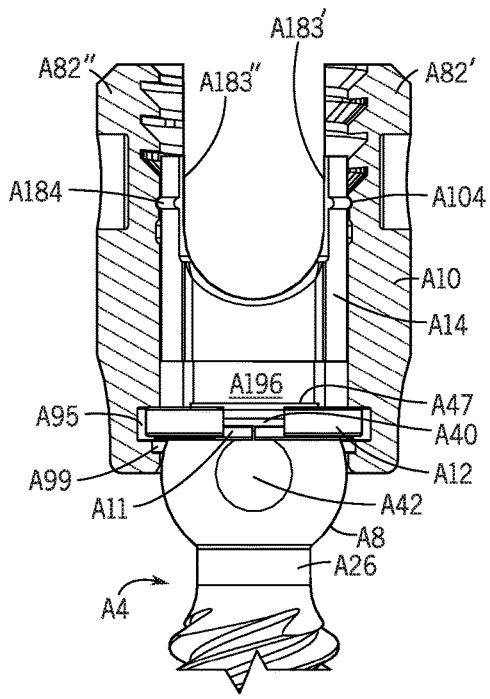
FIG. 49 is a view similar to FIG. 48 showing the receiver, insert, non-pivoting retainer, shank, and positioner with portions of the receiver cut away to show the cooperation of the parts at a stage when the shank is being loaded into the receiver lower opening.

Referring now to FIGS. 48-49, the loading of the insert A14 is shown. In some cases, the compression insert A14 is loaded firstly into the receiver A10 with the insert top surface A192 facing the receiver bottom surface A134 as the insert A14 is loaded through the bottom opening A136. The illustrated insert A14 is loaded, captured, and frictionally held in place by the mating of the receiver attachment structures A184 within the insert attachment groove A104. This prevents the insert A14 from any further unwanted downward movement or any upward movement towards the guide and advancement structure A92 of the receiver A10 and provides adequate clearance for the later step of pushing the bone screw head shank upper portion A8 through the non-pivoting retainer A11 and positioner A12 and keeps the insert A14 away from the lower opening A136 during assembly with the non-pivoting retainer A11, positioner A12, and subsequent assembly with the shank A4. It is foreseen that a tool or tools (not shown) may be used to push down, pull or otherwise drop the insert into this position. It is foreseen that at least the insert arms A183' and A183" will need to be able spring back to their original orientation once compressed through the receiver interior A90. In this position the ledges A196 prevent rotational movement of the insert A14 within the receiver A10.

At this time, the compression insert A14, the positioner A12, and the non-pivoting retainer A11 are captured within the receiver A10. The receiver A10, compression insert A14 and the positioner A12 and non-pivoting retainer A11 combination are now pre-assembled and ready for shipment or assembly with the shank A4 either at the factory, at the spine company, by surgery staff prior to implantation, or directly after implanting the shank A4 by the surgeon. It is foreseen that the non-pivoting retainer A11 and the positioner A9 in combination may rotate or could be restricted from rotating within the receiver A10 and with respect to each other. It is foreseen that the insert ledges A195 could further include a sloping surface (not shown) that would engage a second sloped side surface (not shown) of the positioner A12 to prevent rotation of the positioner A12 and non-pivoting retainer A11 combination.

Figure 50:
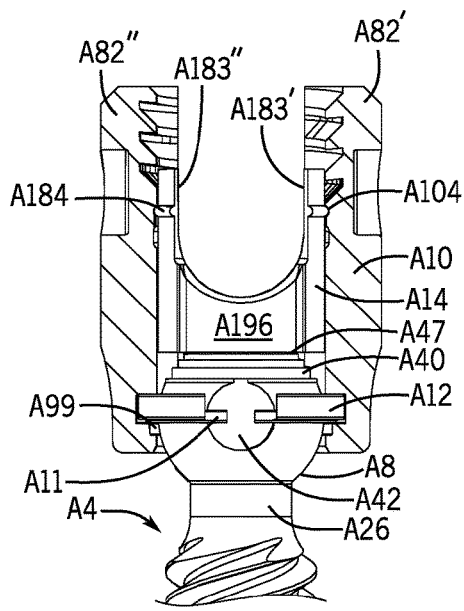
FIG. 50 is a view similar to FIG. 49 showing the cooperation of the parts at a second stage of the positioning of the shank in the receiver, wherein the positioner and non-pivoting retainer in combination have reached a center or fixed point of rotation of the shank and a maximum expansion point.
Figure 51:
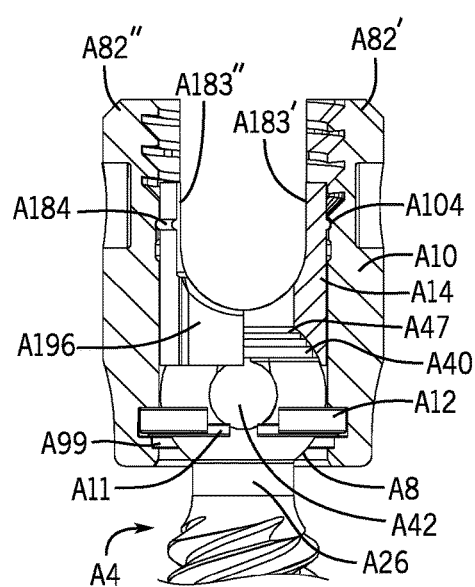
FIG. 51 is a view similar to FIG. 50 of the receiver and insert with a portion of the insert broken away to show a third stage of the positioning of the shank in the receiver, wherein the shank is halted from upward movement by the insert.

Referring now to FIGS. 49-51, next, the top surface A47 of the shank A4 is partially inserted into the expansion chamber A95, and the upper capture portion A8 of the shank A4 abuts against the non-pivoting retainer A11, held down by the positioner A12. The non-pivoting retainer A11 and positioner A12 in combination are lifted up by the shank A4. The proximal driving of the shank A4 causes the top surface A139 of the positioner A12 to abut against the proximal planar step face A120 (FIG. 50) of the interior cavity A91 of the receiver member A10, thereby arresting proximal displacement of the positioner A12 and non-pivoting retainer A11 combination within the confines of the expansion chamber A95 of the receiver member A10. Also, the proximal (upward, as seen in FIG. 50) driving of the shank A4 causes the upper spherical surface A46 of the shank upper portion A8 to abut against the interior surface A145 of the non-pivoting retainer ring A11 and the curvate surface A125 of the positioner A12, thereby causing the retainer ring A11 and the positioner A12 to radially expand as the shank upper portion A8 proximally displaces into the confines of the cavity A91 of the receiver member A10. In FIG. 50, the non-pivoting retainer A11 and positioner A12 have reached a maximum expansion about the shank capture portion A8 at the point where the non-pivoting retainer A11 is situated about the center or equator of the spherical head A8 of the shank A4, just prior to capture the shank upper capture portion A8 within the receiver A10.

In FIG. 51, as the shank upper portion A8 continues to move proximally, the non-pivoting retainer ring A11 captures the shank head A8 after expanding in the expansion chamber A95 and then returning to a neutral state, all of this occurs while the retainer ring is being biased downward by the positioner A12. The top surface A47 of the shank A47 is stopped by the shank gripping surface A198 of the insert A14.

Figure 52:
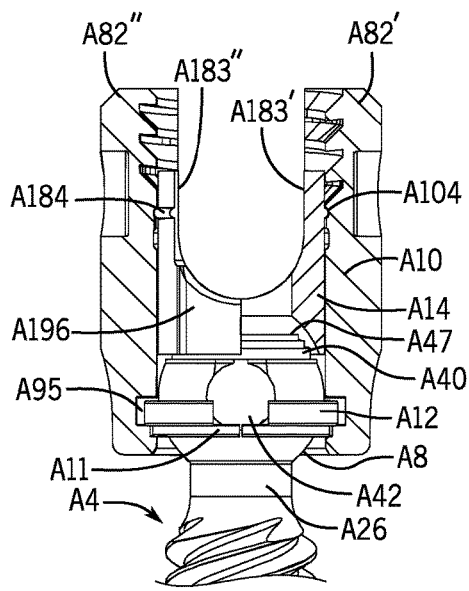
FIG. 52 is a view similar to FIG. 51 showing a fourth stage of the positioning of the shank in the receiver, wherein the shank is halted from downward movement by the non-pivoting retainer and the non-pivoting retainer is positioned within the locking chamber and the positioner has contracted so as to engage the shank in a frictional fit.

Referring to FIG. 52, the shank is moved downward to be captured, the positioner A12 is held in a radially expanded condition on account of the shank having a larger diameter than the nominal non-expanded state of the positioner, such that the positioner inner curvate surface A125 contacts the upper cylindrical surface A34 of the shank upper portion A8 in a friction fit manner, and the interior of the positioner A9 spaces apart from the exterior of the non-pivoting retainer A11, thereby freeing the retainer A11 from its locked retention within the positioner A12. As the retainer A11 is being pulled down out of the positioner A12 to enter the locking chamber A99, the width Y is slowly increased and referentially the non-pivoting retainer A11 slowly expands to its nominal shape or state, which assures the retainer A11 enters and positions itself into the locking chamber A99. At this point the positioner A12, which has now contracted back into nominal shape, also prevents or limits upward movement of the non-pivoting retainer A11 once the retainer is positioned in the locked seating chamber A99. The positioner A12 stays within the confines of the expansion chamber A95. Therefore, distal or opposite displacement of the shank upper portion A8 fully seats the non-pivoting retainer ring A11 in a cylindrical inner surface A122 and the stop surface A123 of the retainer A10. The seating of the non-pivoting retainer ring A11 captures and prevents the shank upper portion A8 from exiting the lower opening A136 in the receiver member A10, as the diameter of the shank head portion A8 and the non-pivoting retainer ring A11 nested thereon exceeds the diameter of the lower opening A136 in the receiver member A10. The shank upper capture portion A8 at this point cannot be pulled out of the receiver A10. The non-pivoting retainer A11 is stabilized, aligned, constrained, and restrained on the shank head upper capture portion 8 with respect to pivotal, rotational, and elevational alignments by means of the multi-purpose positioner. As the positioner A12 cannot enter the locking chamber A99, the positioner A12 does not participate in capturing the shank upper portion. Only the retainer captures the shank and prevents the shank from exiting the lower opening of the receiver A10. It is foreseen that the positioner may include a friction fit with the shank, but even in such a case, it is foreseen that the positioner would not prohibit escape of the shank. It is foreseen that the positioner A12 may contribute to the capturing of the shank.

It is foreseen that a pivoting retainer (not shown) may also be captured in combination with the shank A4, as is described in U.S. Provisional Patent Application No. 62/194,955, the entirety of which was incorporated by reference above. Such a pivoting retainer or separate head may snap on, pop on, twist on, rotate on, screw on, or other actions so as to assist in capturing the shank upper portion A8 within the receiver. The insert A14 remains in the fixed position, aligned and prevented from rotating and moving vertically.

Figure 53:
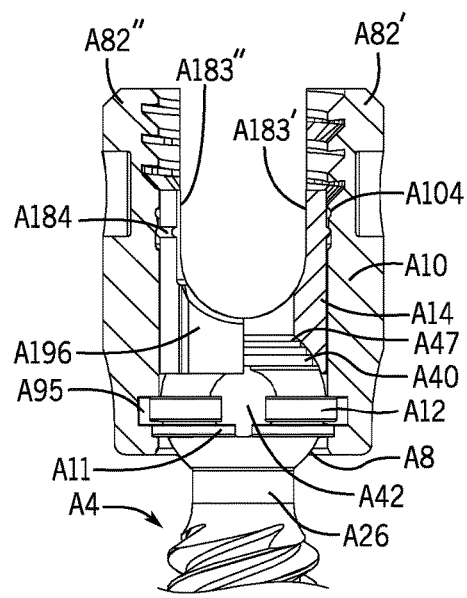
FIG. 53 is a view similar to FIG. 51 showing a second stage of the positioning of the insert in the receiver, wherein the insert engages the shank in a frictional fit.

Referring now to FIG. 53, once the shank upper portion A8 is captured, the compression insert A14 is pressed downwardly by a tool, such as a screw driver (not shown), toward the shank upper portion A8 into a second insert groove A103, defined by the interior surfaces which include the abutment surface A108, the cylindrical surface A110, and the sloped surface A112. The length of the cylindrical surface A110 allows for the receiver projection attachment structure A184 to slide about this surface with some upward and downward movement. This second fixed position of the insert A14 creates an interference friction fit connection. As a result of the downward movement of the insert A14, the shank gripping surface A198 of the insert A14 forces against the top surface A47 and the stepped surface A40 without penetration into the interior of the insert A14. Thus, a tight, non-floppy, substantially spherical ball and socket joint A44 is now created between the insert A14 and the shank upper portion A8. The friction fit between the compression insert A14 and the shank upper portion A8 is not totally locked or fixed, but at the same time is not loose or floppy either, advantageously allowing the user to articulate the shank A4 with respect to the receiver A10 by application of manual or tool associated pressure or force, but with some resistance, so that when the shank A4 is placed in a desired orientation with respect to the receiver A10, the assembly A1 remains substantially frictionally set in such desired orientation unless purposefully manipulated into another position, as can be seen in FIGS. 54-59.

It is foreseen that a friction fit between the receiver A10 and the shank A4 may not be wanted by the surgeon. In this case, the projection structure A184 is positioned within the insert attachment apertures A104, so as to allow the insert A14 to move about the gap or aperture A104 and, thus, creating a floppy fit between the receiver A10 and the shank A4. A floppy fit will allow the user to move the receiver A10 about the shank A4 freely, but results in the receiver A10 frictionally staying in any one position chosen relative to the shank A4 when not being moved. To make the floppy fit lock in a desired orientation, it would require the installation of a rod A21 and a closure A18 and into a final locking of the shank A4 with respect to the receiver A10.

The bone screw shank A4 (or an entire assembly A1 made up of the assembled shank A4 with or without, the non-pivoting retainer A11, positioner A12, receiver A10, and compression insert A14) is screwed into a bone or vertebra, by rotation of the shank A4 using a suitable driving tool or tool assembly (not shown) that operably drives and rotates the shank body A6 by engagement thereof at the internal drive A49. It is foreseen that the shank A4, the other bone screw assembly parts (also having a central lumen in some embodiments), the rod A21 and the closure top A18 (also with a central bore drive) can be inserted in a percutaneous or minimally invasive surgical manner, utilizing guide wires (not shown) with or without minimally invasive guide tools.

When the shank A4 is driven into the vertebra without the remainder of the assembly A1, the shank A4 may either be driven to a desired final location or may be driven to a location slightly above the final location or "proud" to provide for ease in assembly with the pre-assembled receiver A10, compression insert A14, positioner A12, and non-pivoting retainer A11. The pre-assembled receiver A10, insert A14, positioner A12, and non-pivoting retainer A11 are placed above the shank upper portion A8 until the shank upper portion A8 is received within the opening A136 of the receiver A10.

Figure 54:
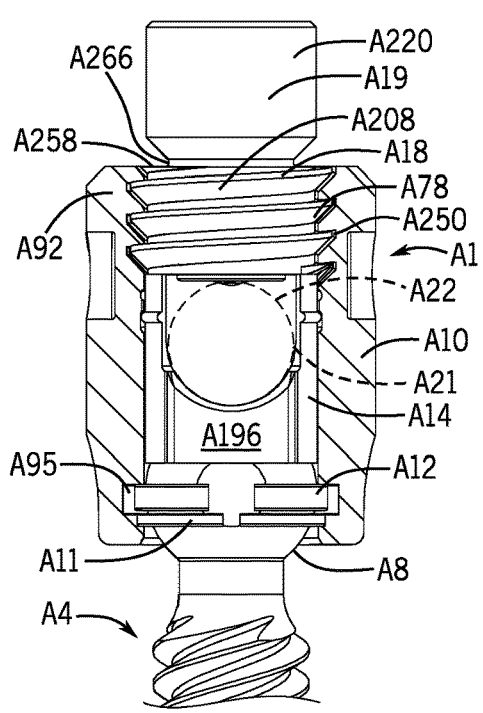
FIG. 54 is a cross sectional view of the receiver, as in FIG. 52, showing a stage of the positioning of the compression insert and shank in the receiver, with a spinal fixation rod of a selected diameter shown in phantom and closure added, with the closure applying downward pressure to the rod.
Figure 55:
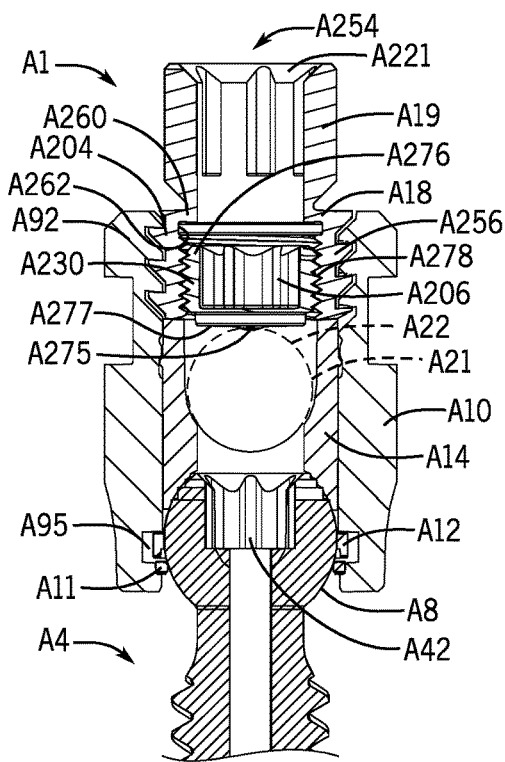
FIG. 55 is a fragmentary cross sectional view of the receiver, closure, and insert showing a third stage of the positioning of the shank in the receiver, wherein the shank is halted from upward movement by the insert.

With reference to FIGS. 54-56, the rod A21 is eventually positioned in an open or percutaneous manner in cooperation with the at least two bone screw assemblies A1. The closure structure A18 is then inserted into and advanced between the arms A82 of each of the receivers A10, as seen in FIG. 54.

The illustrated closure structure or nested fastener A18 can be any of a variety of different types of closure structures for use in conjunction with the present disclosure with suitable mating structure on the upstanding arms A82' and A82" of the head or receiver A10, one such closure is described in U.S. patent application Ser. No. 11/140,343, the entirety of which is incorporated by reference herein.

The illustrated fastener A18 includes an outer fastener A204 and an uploaded inner set screw A206. The fastener A204 includes a base A208 integral or otherwise attached to a break-off head A19. The base A208 cooperates with the receiver head A10 of the bone screw assembly A1 to close a head U-shaped channel A84 and to clamp the spinal fixation rod A21 within the bone screw head A10. The break-off installation head A19 includes an outer surface A220 and a drive structure A121 sized and shaped for engagement with a tool (not shown) for installing the fastener A204 to the bone screw head or receiver A10 and thereafter separating the break-off head A19 from a respective base A208 when installation torque exceeds selected levels.

The base A208 of the fastener A204 is substantially cylindrical, having an axis of rotation F and an external surface A250 having a guide and advancement structure A78 disposed thereon. The guide and advancement structure A78 is matingly attachable to a guide and advancement structure A92 of the bone screw head A1010. As with the guide and advancement structure A92, the guide and advancement structure A78 can be of any type, including V-type threads, buttress threads, reverse angle threads, or square threads. Preferably, the guide and advancement structure A78 is a helically wound reverse angled buttress thread form that interlocks with the reciprocal reverse angled thread form as part of the guide and advancement structure A92 on the interior A90 of the bone screw head A10. The guide and advancement structures A92 and A78 are preferably of a type that do not exert substantial radially outward forces on the arms A82' and A82" and thereby avoid tendencies toward splaying of the arms A82' and A82" of the bone screw head A10 when the fastener A204 is tightly torqued into the head A10.

The fastener A204 includes an internal, centrally located through-bore A254. At the base A208, the bore A254 is substantially defined by a guide and advancement structure, as an internal V-shaped thread A256. The thread A256 is sized and shaped to receive the threaded set screw A206 therein, as will be discussed in more detail below. Although a traditional V-shaped thread A256 is shown, it is foreseen that other types of helical guide and advancement structures may be used. Near a substantially annular planar top surface A258 of the base A208, an abutment shoulder A260, extends uniformly radially inwardly. The abutment shoulder A260 is spaced from the V-shaped thread A256 and is sized and shaped to be a stop for the set screw A206, prohibiting the set screw A206 from advancing out of the top A258 of the base A208. It is foreseen that alternatively, the set screw A206 may be equipped with an outwardly extending abutment feature near a base thereof, with complimentary alterations made in the base A208, such that the set screw A206 would be prohibited from advancing out of the top A258 of the base A208 due to abutment of such outwardly extending feature against a surface of the base A208. An inner cylindrical wall A262 separates the abutment shoulder A1260 from the thread A256. The cylindrical wall A262 has a diameter slightly greater than a root or major diameter of the internal thread A256.

The set screw A206 has a substantially planar top A276 and a bottom A277. The set screw A206 is substantially cylindrical in shape, and includes an outer cylindrical surface A278 with a V-shaped thread A280 extending from the top A276 to the bottom A277 thereof. The surface A278 and thread A280 are sized and shaped to be received by and mated with the inner thread A256 of the fastener base A208 in a nested relationship.

The fastener break-off head A19 is integral or otherwise attached to the fastener A204 at a neck or weakened region A266. The neck A266 is formed of a material having a selected fail strength and is dimensioned in thickness to control the torque at which the break-off head A19 separates from the fastener A204. The preselected separation torque of the neck A266 is designed to provide secure clamping of the rod A21 by the fastener A204 before the head A19 separates. For example, 80 to 120 inch pounds of force may be a selected break-off torque. Separation of the break-off head A19 leaves only the more compact base A208 of the fastener A204 installed in the bone screw head or receiver A10, so that the installed fastener A204 has a low profile.

It is foreseen that the base A208 of the fastener A204 and the inner set screw A206 may include structure (not shown) to provide clamping engagement between the base A208 and the insert A14 and the bottom surface A277 and the rod A21.

As the closure structure A18 rotates and moves downwardly into the respective receiver A10, the outer fastener A204 abuts against the top surfaces A192 of the arms A183',A183" of the insert A14, which are located above a diameter of the rod A21. An inner set screw point A275 and bottom rim surface A277 are also rotated downwardly to engage and penetrate the rod surface A22, and the closure structure inner set screw A206 presses downwardly against and biases the rod or connecting member A21 into engagement with the insert A14 that thereby urges the shank upper portion A8 toward the lower opening A136 of the retainer A10 and into locking engagement therewith, with the non-pivoting retainer A11 frictionally abutting the surface A113 of the receiver A10.

The closure top A18 may include a cannulation through bore A254 extending along a central axis AF thereof and through top and bottom surfaces thereof. Such a through bore A254 provides a passage through the closure A18 interior for a length of wire (not shown) inserted therein to provide a guide for insertion of the closure top A18 into the receiver arms A82',A82", for example implantation of the assembly A1 during minimally invasive techniques. It is foreseen that any of a variety of different closure structures for use in conjunction with the present disclosure with suitable mating structure on the upstanding arms A82',A82" can be utilized. For example, multi-start threaded closures (not shown) are foreseen to be utilized in this disclosure.

As shown in FIGS. 57-59, when the shank A4 is articulated at an angle with respect to the receiver A10 both smooth side surfaces A42 and stepped A40 surface portions of the spherical surface A34 are in frictional engagement with the spherical surface A198 of the compression insert. When the shank A4 is axially aligned with the receiver A10 as shown in FIGS. 54-56, the surface A198 primarily engages the stepped surface portion A40 of the shank upper portion A8.

It is foreseen that the receiver assembly may be a mono-planar or uni-planar subassembly. It is also foreseen that the receiver assembly or subassembly could be a bi-planar subassembly as described in U.S. Provisional Patent Application Nos. 62/200,491, and 62/200,501, both of which were incorporated by reference above.

It is foreseen that different sizes of rods may be utilized with the same components of the bone screw assembly A1. The only difference is the amount of rotation of the closure A18 required to fix the different sizes of the rods A21 within a receiver. It is foreseen that inner cores or tensionable cords (FIG. 28) and sleeves (FIG. 28) utilized in soft or dynamic stabilization procedures may also be used in the current disclosure, such as those seen in U.S. patent application Ser. No. 14/731,064, previously referenced above.

If removal of the rod A21 from any of the bone screw assemblies A1 is necessary, or if it is desired to release the rod A21 at a particular location, disassembly may be accomplished by using a driving tool (not shown) that mates with an internal drive A221 of the closure structure A18 to rotate and remove such closure structure A18 from the cooperating receiver A10. Disassembly is then accomplished in reverse order to the procedure described previously herein for assembly. It is also foreseen that the implant may be a permanent fixture and may not be dissembled, only removed as a whole assembled unit, if necessary.

A bone anchor B10 is disclosed herein having a shank B15 and a head B20 configured to bottom load a proximal end portion B106 of the shank B15 into the head B20 and couple to the shank proximal end portion B106 via a snap-fit, snap-on, or pop-on mechanical arrangement. The head B20 includes a receiver member B204, a retainer ring B206, a positioner B208, and an insert B210. In one embodiment, the retainer ring B206, the positioner B208 and the insert B210 are in a configuration within the confines of the receiver member B204 that is coaxially aligned, nested and stacked.

The positioner B208 is detachably coupled with the retainer ring B206 and, while detachably coupled therewith, the positioner B208: (1) limits the proximal displacement of the retainer ring B206 within the confines of the receiver member B204; (2) maintains the retainer ring B206 coaxially aligned with a distal opening B344 in the receiver member B204 through which the shank proximal end portion B106 enters the receiver member B204 in the course of the shank B15 being coupled with the head B20; and (3) prevents the retainer ring B206 from distally exiting the distal opening B344 in the receiver member B204. Thus, the positioner B208 can be considered to be a structure or member that temporarily maintains the orientation and location of the retainer ring B206 with respect to the x-axis, the y-axis and the z-axis in a three axis coordinate system. Further, once the retainer ring B206 is no longer in need of positioning by the positioner B208 on account of the retainer ring B206 having been coupled about the shank proximal end portion B106, the positioner B208 can then be interlocked with the insert B210 to become a proximal-distal displacement limiter of the insert B210.

The following discussion of the bone anchor B10 takes place in the context of the bone anchor B10 being in the form of a polyaxial bone screw B10 employing a threaded shank B15. In certain embodiments, the bone anchor B10 may be in the form of a favored angle polyaxial screw B10 or uni-planar bone screw B10, among others. Further, in other embodiments, the bone anchor B10 may be in the form of non-screw types of bone anchors including, but not limited to, nails, hooks, clamps, or etc. In such non-screw embodiments, the shank B15 may respectively be a nail, hooks, ligaments, or etc. Accordingly, the context of the following discussion of the bone anchor B10 should not be limited to polyaxial bone screws, but should be considered as also encompassing other types of bone screw embodiments and also non-screw bone anchor embodiments.

a. Overview of Polyaxial Screw Embodiment of the Bone Anchor

Figure 60:
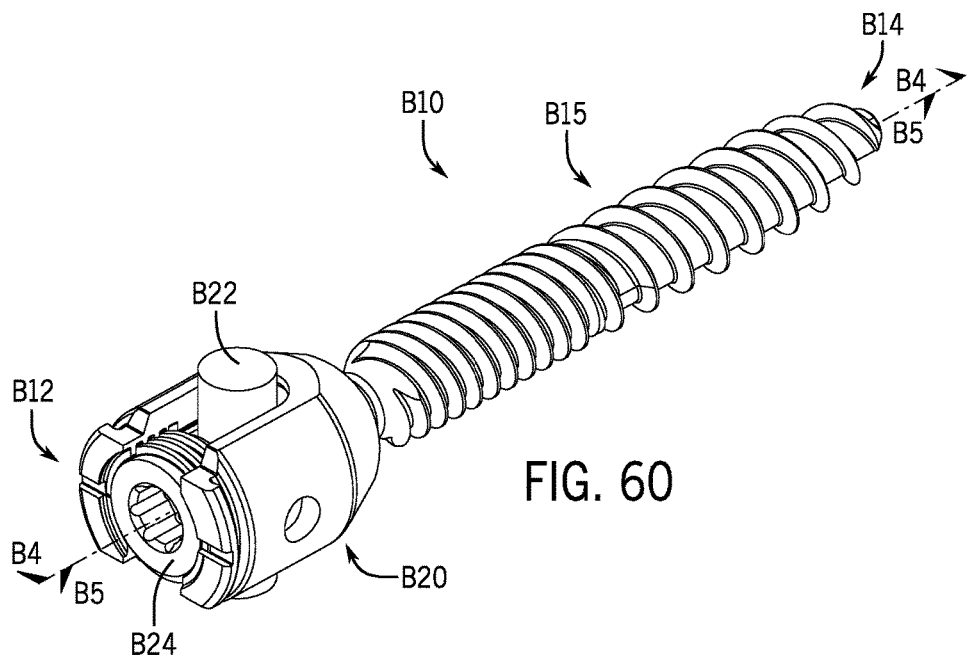
FIG. 60 is an isometric view of the polyaxial screw as viewed from a proximal end of the polyaxial screw.

To begin a detailed discussion of the polyaxial screw B10, reference is made to FIG. 60, which is an isometric view of the polyaxial screw B10 as viewed from a proximal end B12 of the polyaxial screw B10. As shown in FIG. 60, the polyaxial screw B10 includes the proximal end B12, a distal end B14, a shank B15 and a head B20. The head B20 is located at the proximal end B12 of the screw B10, and the shank B15 extends distally from the head B20. While the discussion refers to a polyaxial screw, the discussion is equally applicable and intended to additionally apply to uni-planar and favored angle screws, among others.

Figure 61:
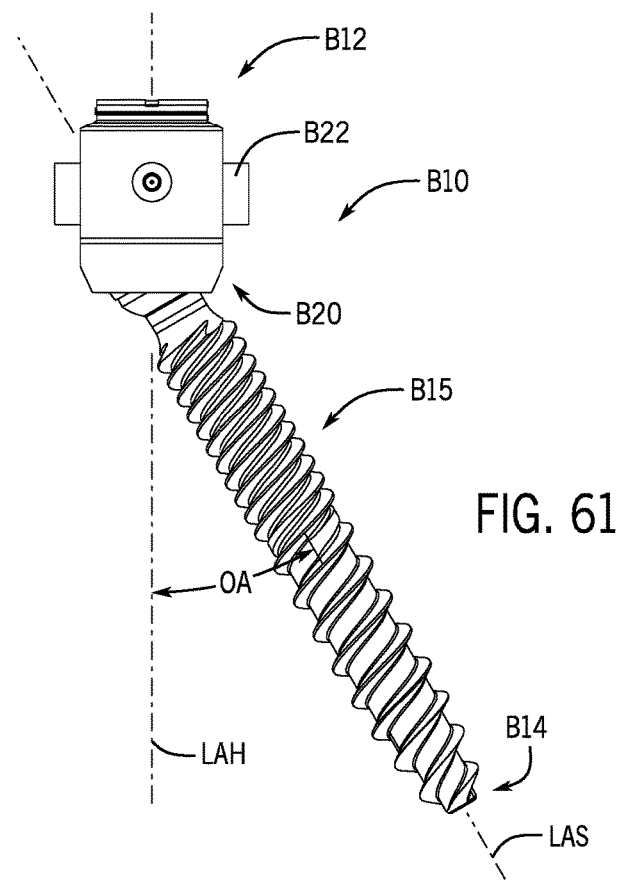
FIG. 61 is a sagittal side view of the polyaxial screw with the longitudinal axes of the head and shank angled relative to each other.

As can be understood from FIG. 3, which is a sagittal side view of the polyaxial screw B10, the shank B15 is pivotally coupled to the head B20. For example, the shank 15 and head 20 may be oriented relative to each other such that the longitudinal axis of the head LAH and the longitudinal axis of the shank LAS are coaxially aligned. As illustrated in FIG. 61, the shank B15 may be pivoted relative to the head B20 such that the longitudinal axis of the shank LAS is angularly offset from the longitudinal axis of the head LAH by an offset angle OA of between approximately 25 degrees and approximately 40 degrees. In one embodiment, the offset angle OA may be approximately 30 degrees. These offset angles OA may be made in any direction relative to the longitudinal axis of the head LAH in a 360 degree circumference extending radially about the longitudinal axis of the head LAH.

In certain embodiments where the screw B10 is a favored angle screw or a uni-planar screw, the offset angles OA may be limited in certain directions or limited to certain directions. For example, a favored angle screw may allow movement of the shank B15 relative to the head B20 that is variable depending on a direction of movement of the shank B15 relative to the head B20. That is, the offset angles OA may be different along the 360 degree circumference extending radially about the longitudinal axis of the head LAH. The offset angle OA may, for example, be about 35 degrees in a first direction along a first axis and may be about 35 degrees in a second direction along a second axis. Uni-planar screws, on the other hand, allow for movement of the shank B15 relative to the head B20 along a common plane and equal amount in opposite directions while restricting movement of the shank B15 relative to the head B20 that is outside of the common plane. Thus, the offset angle OA may be within the common plane, which may, for example, restrict motion in a medial-lateral direction. In certain embodiments, the offset angle OA may, for example, be about 35 degrees in a first direction within the common plane and about 35 degrees in a second (opposite) direction within the common plane. In the case of a uni-planar screw, angular movement outside the common plane will be limited. In certain embodiments, angular movement outside the common plane may be limited to approximately zero degrees to about two degrees.

As can be understood from FIGS. 60-61 and discussed in greater detail below, an implant rod B22 is received in the head B20 and secured within the head B20 via a closure plug B24. The shank B15 may be anchored in a patient's bone tissue and the implant rod B22 is secured in the head B20 via the closure plug B24 to maintain the implant rod B22 in a desired position during the surgical procedure and postoperative.

Figure 62:
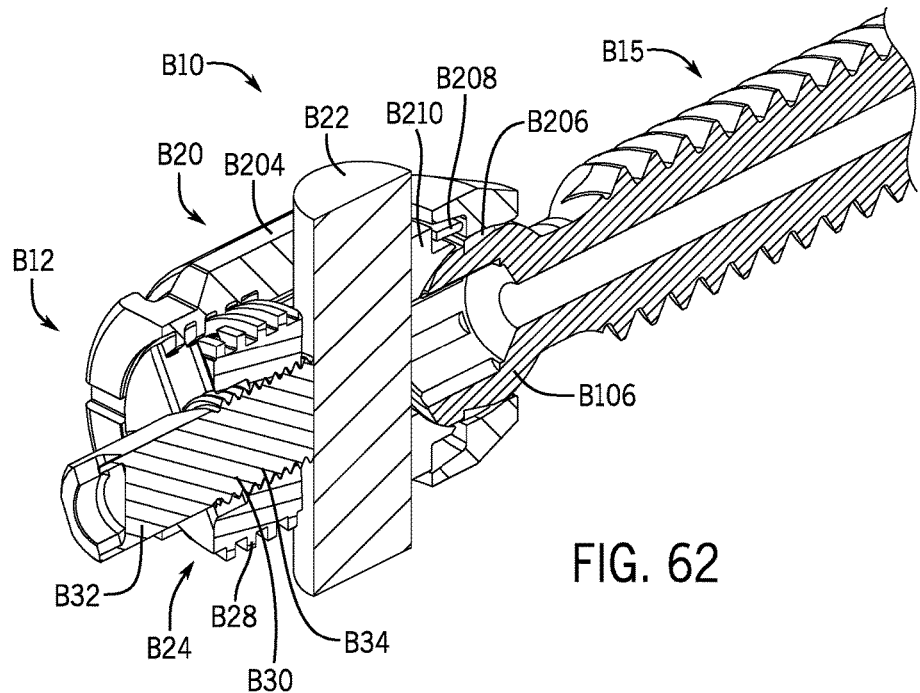
FIG. 62 is an enlarged view of the head region of the polyaxial screw.
Figure 63:
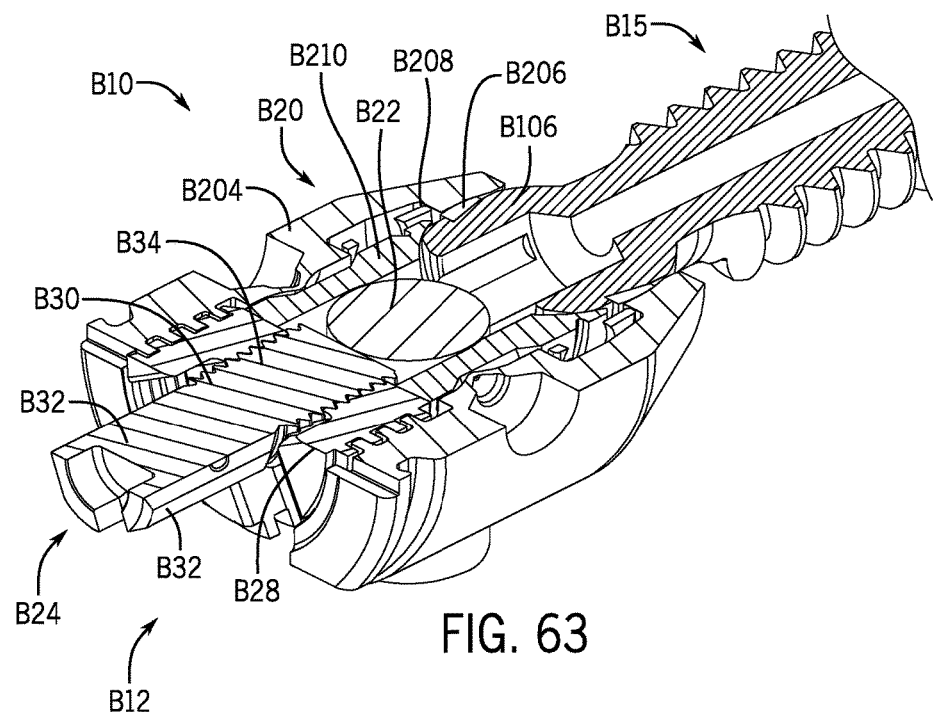
FIG. 63 is an enlarged view of the head region of the polyaxial screw.

As indicated in FIGS. 62 and 63, which are longitudinal cross sections respectively taken along section lines 4-4 and 5-5 in FIG. 60, the head B20 includes multiple components that will be discussed in detail below and allow the head B20 to be snap-fit to a proximal end B26 of the shank B15. As illustrated in FIGS. 62 and 63, the proximal end B26 of the shank B15 is received in the head B20, and the closure plug B24 is coupled with the head B20 via engagement of corresponding threads on the closure plug and receiver B204 to compress the implant rod B22 against the insert B210, which compresses against the proximal end B26 of the shank B15, thereby locking the shank B15 in a fixed orientation relative to the longitudinal axis of the head LAH, whether that fixed orientation is coaxial, or some version of deflected or angled, as representatively depicted in FIG. 61.

As shown in FIGS. 62 and 63, which are enlarged views of the head region of the polyaxial screw B10, the closure plug B24 may be of a Dual-Innie configuration wherein the closure plug B24 includes an outer threaded portion B28 that engages the head B20 and an inner threaded portion or set screw B30 that engages the outer threaded portion B28 and abuts against the implant rod B22. The inner threaded portion B30 may include a proximal twist-off or breakoff portion B32 and a distal portion B34 that remains within the confines of the outer threaded portion B28. The threaded set screw portion may also have an internal drive. The plug B24 may also include a point and rim distal portion.

b. The Shank

Figure 64:
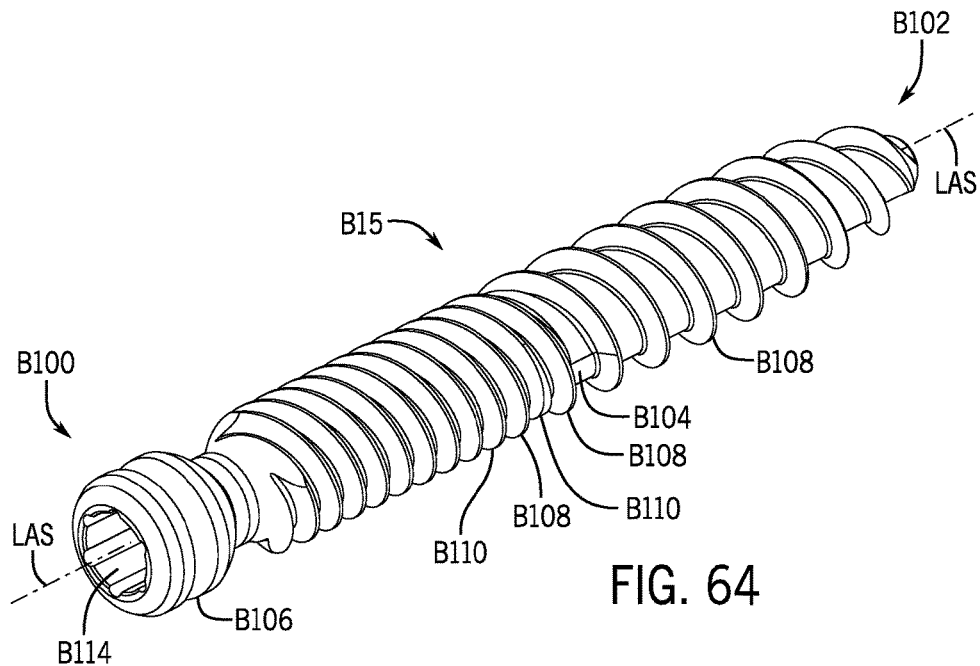
FIG. 64 is an isometric view of the shank as viewed from the proximal end of the shank.

As indicated in FIG. 64, which is an isometric view of the shank B15 as viewed from the proximal end B100 of the shank B15, the shank B15 may be in the form of a bone screw having a threaded shaft B104 and a proximal end portion B106 at the shank proximal end B100 and from which the threaded shaft B104 extends. The threaded shaft B104 includes a first thread B108 and a second thread B110. The first thread B108 helically extends the full length of the threaded shaft B104, and the second thread B110 extends along the proximal half of the threaded shaft B104 such that the proximal half of the threaded shaft B104 has a dual-thread arrangement and the distal half of the threaded shaft B104 has a single-thread arrangement. As can be understood from FIG. 64, the dual-thread arrangement of the proximal half of the threaded shaft B104 has the first and second threads B108, B110 in a staggered or alternating helical spacing relative to each other such that the second thread B110 helically winds between the helical threads of the first thread B108.

As can be understood from FIGS. 62, 63, and 64, the shank B15 is cannulated such that a guidewire shaft or lumen B112 extends coaxial with the longitudinal axis of the shank LAS the full length of the threaded shaft B104 to daylight at the tapered distal end B102 of the shank B15 and a tool engagement orifice B114 defined in the proximal end portion B106 of the shank B15. The tool engagement orifice B114 is configured for receiving and engaging with a tip of a screw driver, Allen wrench or other type of tool for screwing the shank threaded shaft B104 into and out of bone tissue. While the shank B15 is described herein being in the form of a threaded bone screw having a threaded shaft B104, in other embodiments the shank B15 may be in the form of other types of bone tissue anchors including, for example, non-threaded bone tissue anchors like nails, spikes, clamps, or hooks.

Figure 65:
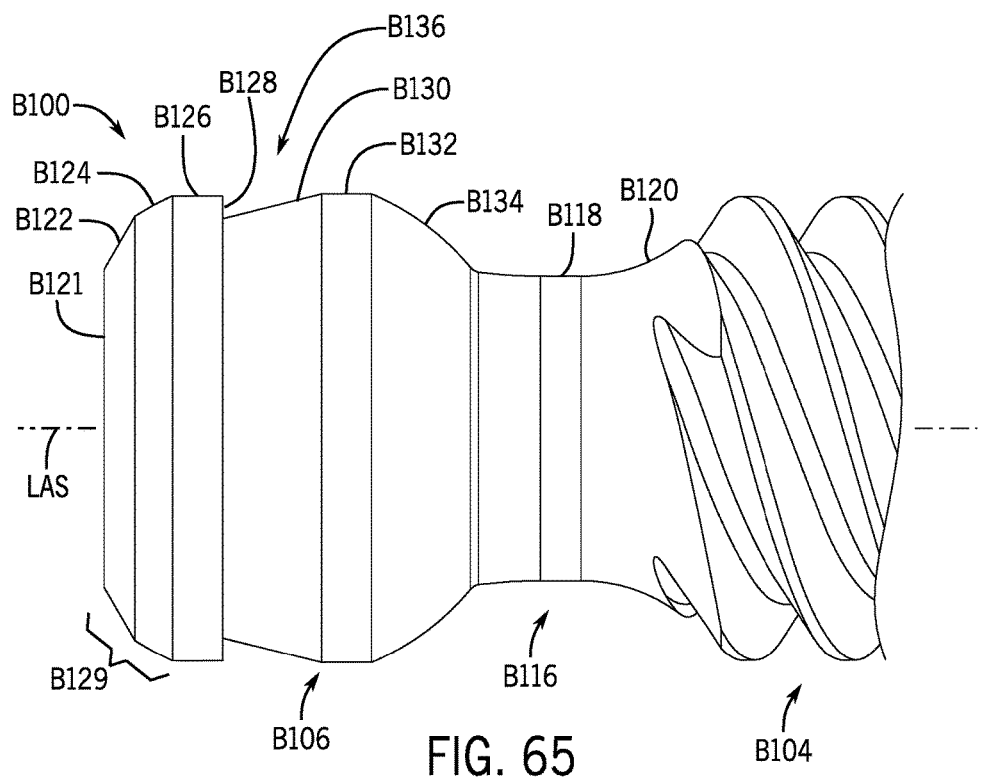
FIG. 65 is an enlarged side view of the distal end of the shank of FIG. 64.

As indicated in FIG. 65, which is an enlarged side view of the proximal end B100 of the shank B15 of FIG. 64, the shank proximal end B100 includes the proximal end portion B106 and a neck portion B116 that transition the shank B15 from its thread shaft B104 to its proximal end portion B106. The neck portion B116 has a diameter that is substantially less than the diameter of the proximal end portion B106 and includes a proximal generally cylindrical segment B118 that accurately transitions into a conical segment B120 that increases in diameter moving distally into the proximal end of the shank threaded shaft B104.

As illustrated in FIGS. 64-65, the shank proximal end portion B106 moving along the shank proximal end portion B106 proximal to distal starts with a proximal face or edge B121 circumferentially bordering the opening of the tool engagement orifice B114. Still moving along the shank proximal end portion B106 proximal to distal, the shank proximal end portion B106 next includes a first distally expanding conical segment B122, a distal spherical segment B124 immediately distal and intersecting the first distally expanding conical segment B122, a first cylindrical segment B126 immediately distal and intersecting the distal spherical segment B124, and a distally oriented lip or step face B128 that radially inwardly extends from the first cylindrical segment B126. The distally oriented lip or step face B128 is perpendicular with the longitudinal axis of the shank LAS, but need not be absolutely perpendicular therewith.

The first distally expanding conical segment B122 forms an acute angle with the longitudinal axis of the shank LAS of approximately 60 degrees (plus or minus approximately 10 degrees) and the distal spherical segment B124 includes a spherical radius of approximately 3.75 mm (plus or minus approximately 0.5 mm). Together, these segments B122, B124 combine to define a tapered proximal shape B129 of the shank proximal end portion B106 that forms a tapered leading interface B129 that facilitates entry of the shank proximal end portion B106 into the head B20, as described below. Also, as discussed below, the adjacent spherical segment B124 facilitates the shank proximal end portion B106 pivoting within the confines of a spherical recess defined in a distal region of the insert B210.

Still referring to FIGS. 64-65 and continuing the journey along the shank proximal end portion B106 proximal to distal, the shank proximal end portion B106 next includes a third distally expanding conical segment B130, a second cylindrical segment B132 immediately distal and intersecting the third distally expanding conical segment B130, and a distally reducing arcuate or spherical segment B134 that transitions between the second cylindrical segment B132 and the proximal generally cylindrical segment B118 of the neck portion B116. The second cylindrical segment B132 has a diameter at least as large as the diameter of the first cylindrical segment B126. In certain embodiments the second cylindrical segment B132 is somewhat larger than the first cylindrical segment B126.

The third distally expanding conical segment B130 forms an acute angle with the longitudinal axis of the shank LAS of approximately 14 degrees (plus or minus approximately 5 degrees). The acute angle of the third distally expanding conical segment B130 is less than the acute angle of the distal spherical segment B124. The third distally expanding conical segment B130 and the distally oriented lip or step face B128 combine to form a stepped and conically tapered notch B136 that receives a retainer ring of the snap-fit components of the head B20, as described in detail below.

The shank B15 may be machined or otherwise formed from any of the following biocompatible materials including, but not limited to, titanium, stainless steel, or cobalt chrome, among others.

c. The Head Assembly

Figure 66:
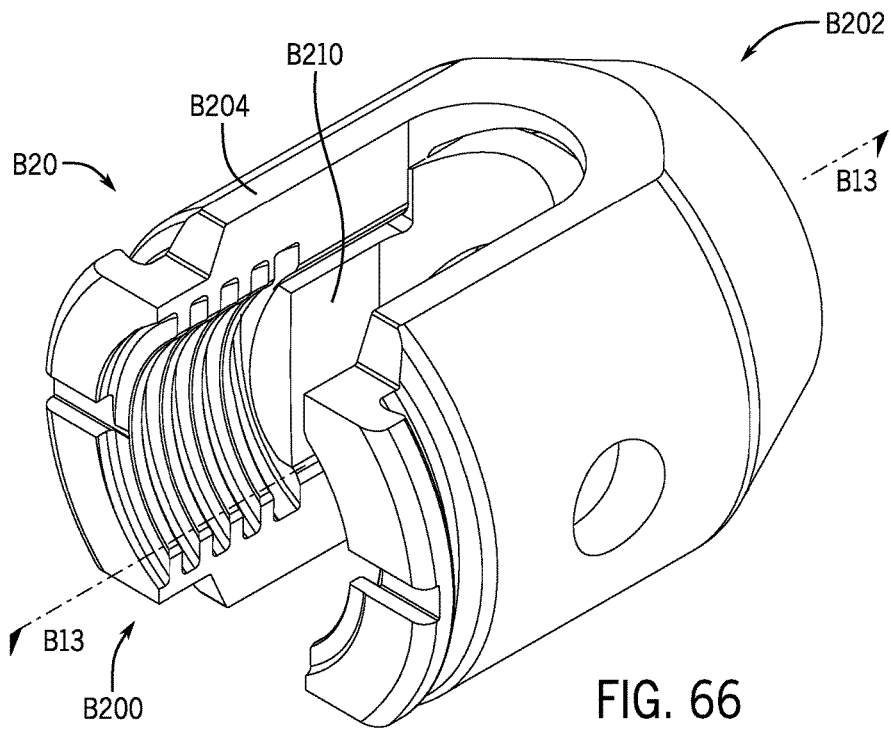
FIG. 66 is an isometric view of the head of the polyaxial screw of FIG. 60 as viewed from a proximal end of the head.
Figure 67:
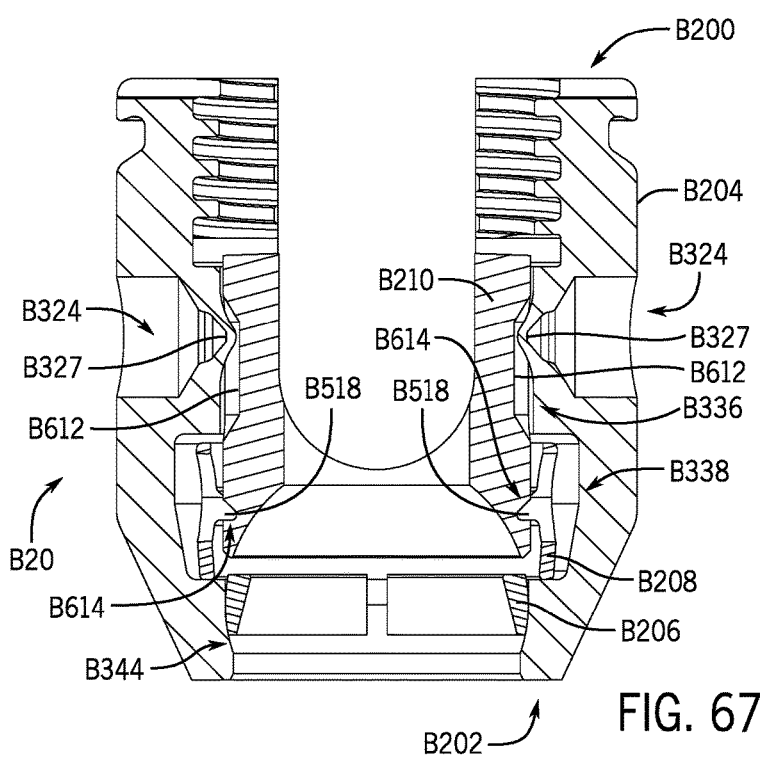
FIG. 67 is a longitudinal cross section of the head as taken along section line 13-13 in FIG. 66.
Figure 68:
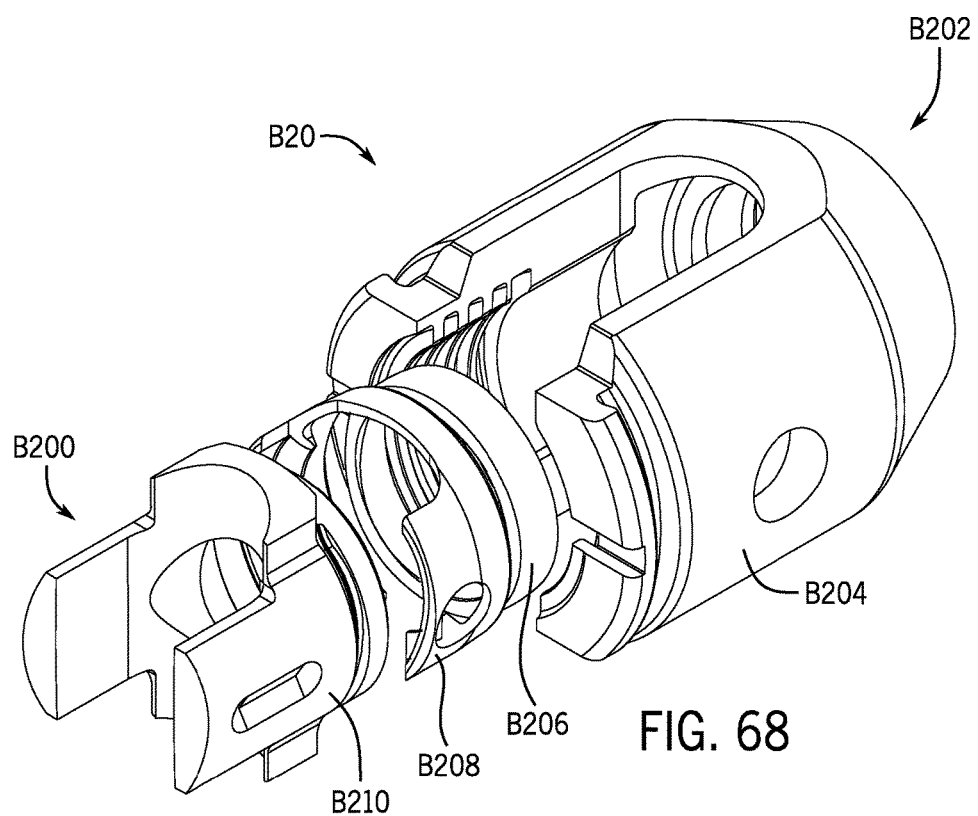
FIG. 68 is the same view as FIG. 66, except the head is depicted in an exploded condition to illustrate its various components.

To begin a discussion of the head B20 of the polyaxial screw B10, reference is made to FIGS. 66 and 67. FIG. 66 is an isometric view of the head B20 of the polyaxial screw B10 of FIG. 60 as viewed from a proximal end B200 of the head B20. FIG. 67 is a longitudinal cross section of the head B20 as taken along section line 13-13 in FIG. 66. FIG. 68 is the same view as FIG. 66, except the head B20 is depicted in an exploded condition to illustrate its various components.

As shown in FIGS. 66 and 67, the head B20 is an assembly and includes the proximal end B200, the distal end B202, a receiver member B204, a retainer ring B206, a positioner B208, and an insert B210. The retainer ring B206, positioner B208 and insert B210 reside within the receiver member B204. As explained in detail below, the retainer ring B206 and the positioner B208 cooperate to form a snap-fit retaining assembly that snap-fit engages the shank proximal end portion B106 when the shank proximal end portion B106 is inserted in the head distal end B202. The positioner B208 keeps the retainer ring B206 properly oriented to cause the retainer ring B206 to be received in the conically tapered notch B136 of the shank proximal end portion B106, as can be understood from FIGS. 62-63, 64 and 67. The retainer ring B206 residing in the conically tapered notch 136 retains the shank proximal end portion B106 within the head B20. A distal inner surface of the receiver member B204 prevents the retainer ring B206 from distally exiting the receiver member B204, and the positioner B208 prevents the retainer ring B206 from proximally exiting the receiver member B204. Features of the insert B210 receive features of the positioner B208 and the receiver member B204 to lock these three components together and to keep the positioner B208 and insert B210 from exiting the receiver member B204. The insert B210 is secured against the shank proximal end portion B106 by a closure plug B24 distally forcing the implant rod B22 against the insert B210, which abuts the shank proximal end portion B106 and the retainer ring B206, as can be understood from FIGS. 62 and 63.

Any of the components of the head B20, namely, the receiver member B204, retainer ring B206, positioner B208 and insert B210, may be machined or otherwise formed from any of the following biocompatible materials including, but not limited to, titanium, stainless steel, Polyether ether ketone ("PEEK"), or cobalt chrome, among others. In a one embodiment, the receiver member B204 is formed of titanium, the retainer ring B206 is formed of titanium, the positioner B208 is formed of titanium, and the insert B210 is formed of titanium. Additionally, the components described in the present application may accomplish different and/or additional functions than those expressly described herein.

Each of the components of the head B20 will now be discussed in turn, followed by a summary of their assembly, interaction and operation.

1. The Receiver Member of the Head Assembly

Figure 69:
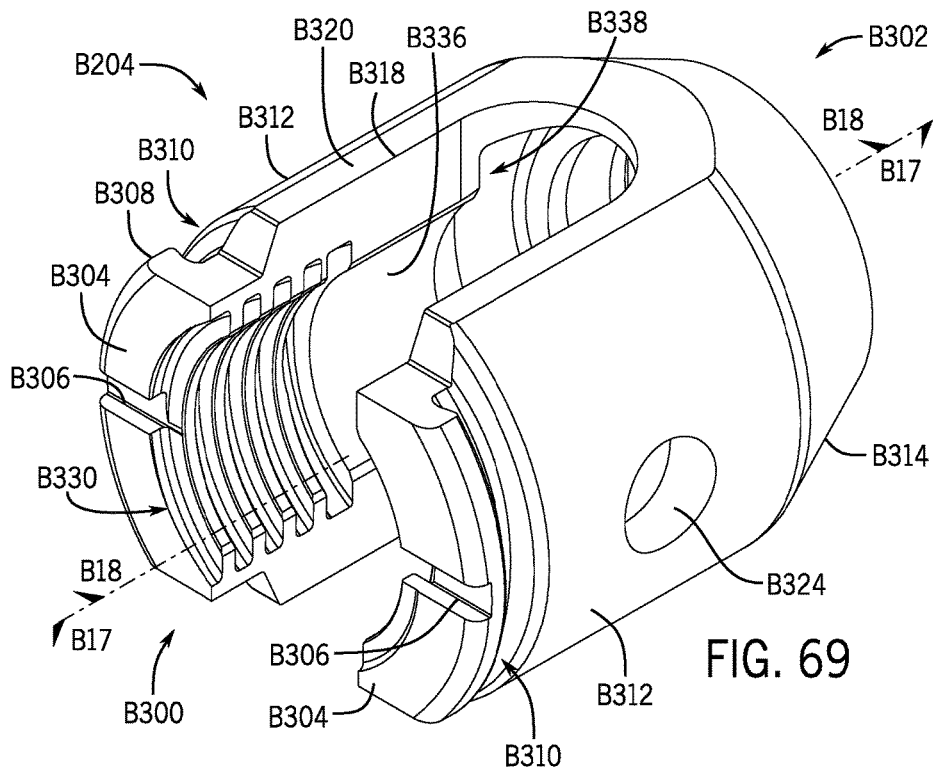
FIG. 69 is an isometric view of the receiver as viewed from the proximal end of the receiver member 204.
Figure 70:
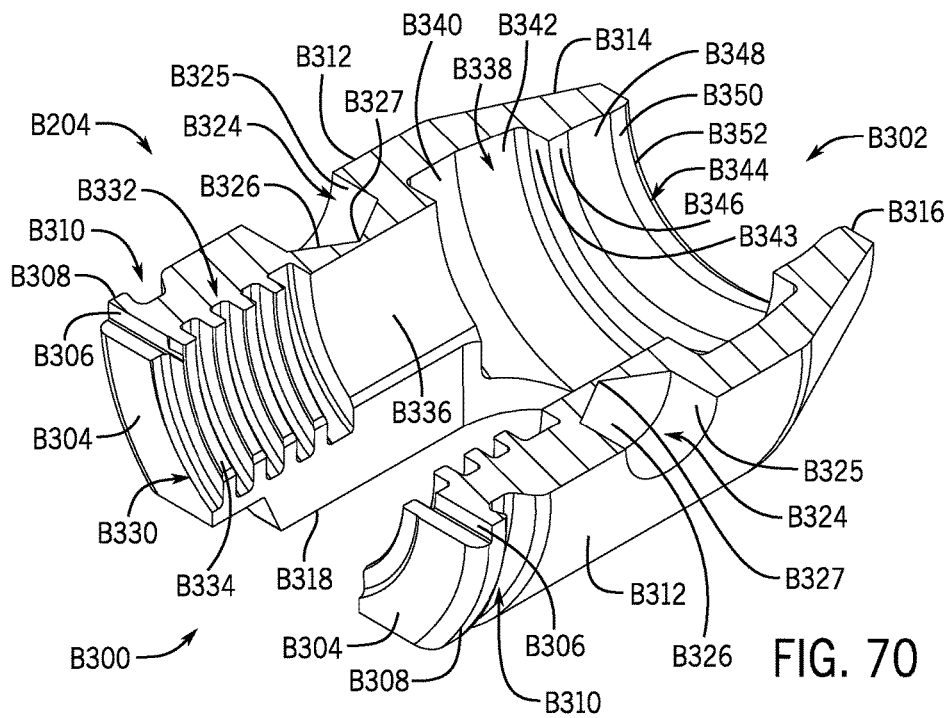
FIG. 70 is a longitudinal cross section of the receiver as taken along section line 17-17 in FIG. 69.
Figure 71:
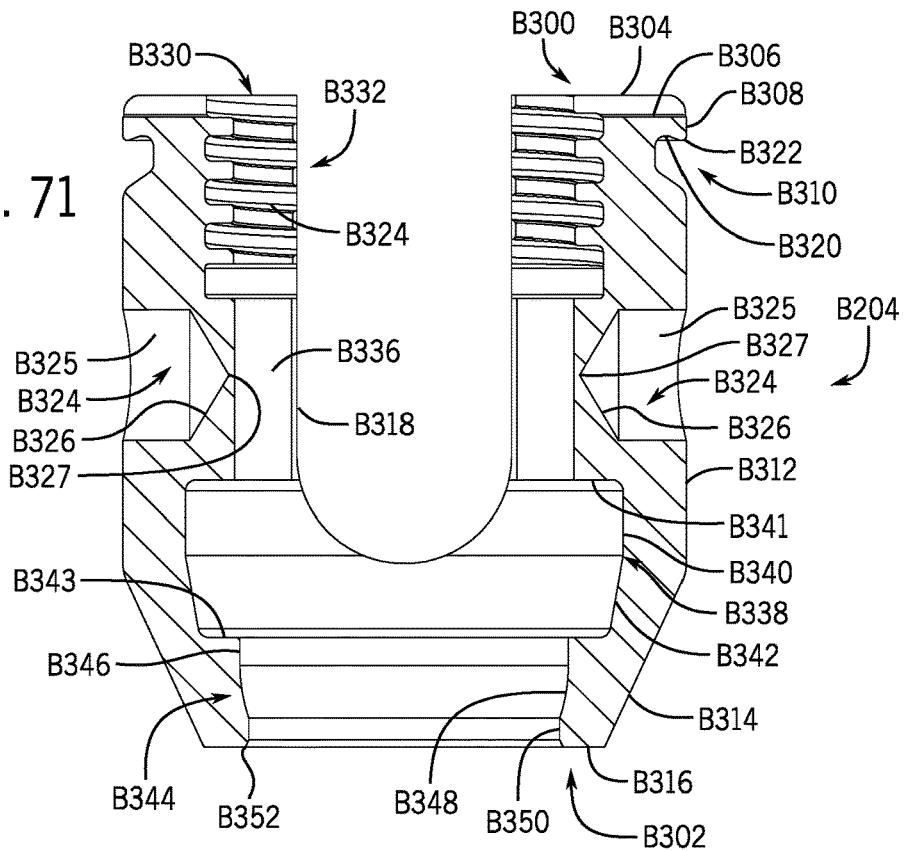
FIG. 71 is a longitudinal cross section of the receiver.

To begin a discussion of the receiver member B204 of the head B20 of the polyaxial screw B10 of FIG. 60, reference is made to FIGS. 69-71. FIG. 69 is an isometric view of the receiver member B204 as respectively viewed from the proximal end B300 and distal end B302 of the receiver member B204. FIG. 70 is a longitudinal cross section of the receiver member B204 as taken along section line 17-17 in FIG. 69. FIG. 71 is a longitudinal cross section of the receiver member B204.

As can be understood from FIGS. 69, 70, and 71 and traversing the receiver member B204 proximal to distal along its exterior, the receiver member B204 includes a top-notch equipped proximally oriented face B304 having a pair of aligned notches B306 defined in the proximal face B304. The notches 306 extend in a direction that intersects the longitudinal axis of the head LAH and is perpendicular with said axis LAH, as can be understood from FIGS. 61-63.

As indicated in FIGS. 69-71 and continuing to move proximal to distal along the exterior or the receiver member B204, the receiver member B204 also includes a circumferential radially extending rim B308, a circumferentially extending side groove or recess B310, a generally cylindrical intermediate outer surface B312, and a distal conical outer surface B314. As shown in FIGS. 69-71, the receiver distally terminates as a distally oriented face B316.

As shown in FIGS. 69-71 sidewall slots B318 extend distally through opposite sides of the receiver member B204 from the proximal face B304 and through the circumferential radially extending rim B308, the circumferentially extending side groove or recess B310, and the generally cylindrical intermediate outer surface B312. A planar boundary region B320 surrounds each sidewall slot B318. As can be understood from FIGS. 60-63, the implant rod B22 is capable of extending through the header B20 on account of the sidewall slots B318 defined through the sidewalls of the receiver member B204.

As illustrated in FIG. 71, the circumferentially extending side groove or recess B310 extends slightly proximal such that a proximally extending recess B320 undercuts the circumferential radially extending rim B308, thereby defining a distally projecting or overhanging lip B322 of the rim B308. The top notches B306, side groove B310 and overhanging lip B322 of the rim B308 are configured to be engaged by complementary structures of a deliver device or tool, such as, for example an elongated guide tool as commonly found in minimally invasive surgical systems ("MIS") as known in the spinal surgery arts.

As depicted in FIGS. 69-71, a pair of holes B324 are defined in opposite sides of the generally cylindrical intermediate outer surface B312. As best understood from FIGS. 70 and 71, each such hole B324 has an outward cylindrical shape B325 and an inward conical shape B326 that inwardly terminates as a point B327. As can be understood from FIG. 67 and as discussed in greater detail below, the point B327 can be crimped or otherwise pressed inwardly during the manufacture of the head B20 to force the thin sidewall of the receiver immediately adjacent the point B327 into a complementary void defined in the insert B210, thereby securing the insert B210 against exiting proximally from the receiver member B204.

Turning to the interior or the receiver and again moving along the receiver from proximal to distal, as can be understood from FIGS. 69-71, the receiver also includes a proximal opening B330 defined in the proximal face B304 and extending immediately into a threaded region B332 having a series of threads B334. Immediately distal the threaded region B332, the receiver member B204 includes a cylindrical throat B336 and immediately after that is located an expansion chamber B338 having a proximal cylindrical segment B340 and a distal conical segment B342 that tapers distally. Both the segments B340, B342 of the expansion chamber B338 have diameters that substantially exceed the diameter of cylindrical throat B336. A proximal planar step face B341 of the interior chamber B338 radially transitions from the throat B336 to the interior chamber B338, and distal planar step face B343 of the interior chamber B338 radially transitions from the interior chamber B338 to a distal opening B344 of the receiver member B204.

Still referring to FIGS. 69-71 and moving along the receiver from proximal to distal, immediately distal the expansion chamber B338, the receiver member B204 includes the distal opening B344 that daylights in the distal face B316 and includes a proximal cylindrical segment B346, an intermediate spherical segment B348 that tapers distally and is slightly arcuate, a distal cylindrical segment B350 having a diameter that is less than the proximal cylindrical segment B346, and a distal conical segment B352 that distally expands and daylights in the distal face B316. The overall diameters of the cylindrical throat B336 and the distal opening are substantially similar. As discussed below, the intermediate spherical segment B348 has a radius and curvature matching those found on the shank proximal end portion B106.

As can be understood from FIG. 67, when the head B20 is fully assembled, the insert B210 extends through the cylindrical throat B336 and the expansion chamber B338, the positioner B208 resides in the expansion chamber B338, and the retainer ring B206 substantially resides in the distal opening B344. To facilitate the angulation of the shank B15 relative to the head B20 when the shank B15 is coupled to the head B20 via the snap-fit assembly of the head B20, the retainer ring B206 can pivot up into the expansion chamber B338 and occupy a spherical void in a distal end of the insert B210, as discussed in detail below.

2. The Retainer Ring of the Head Assembly

Figure 72:
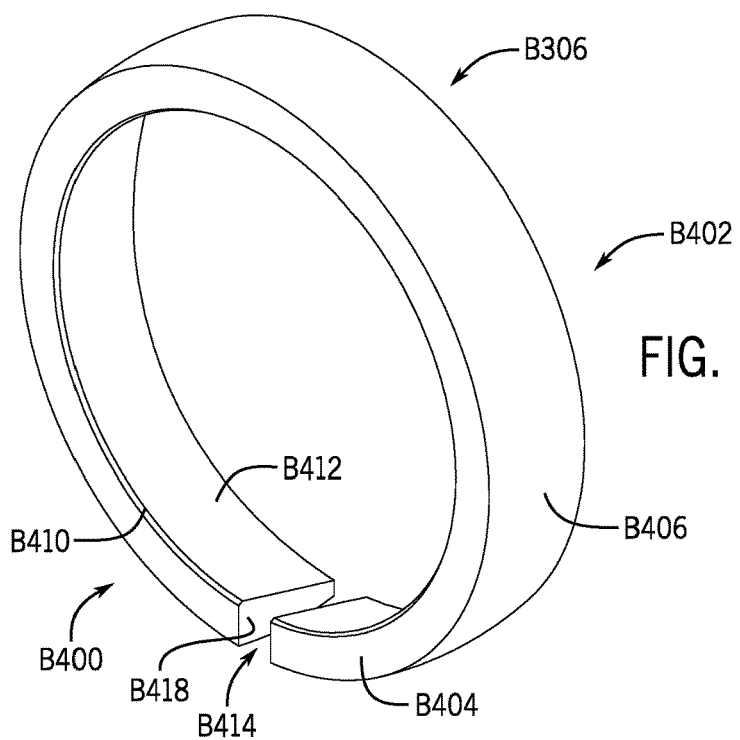
FIG. 72 is an isometric view of the retainer ring as viewed from a proximal end of the retainer ring.
Figure 73:
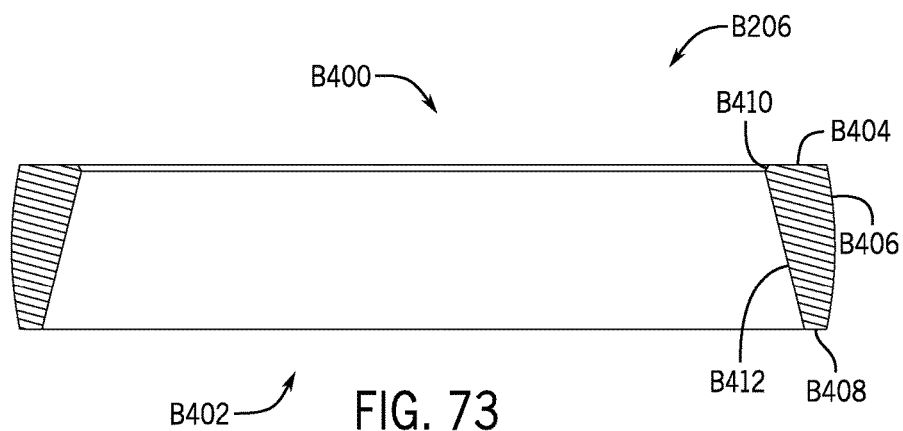
FIG. 73 is a transverse cross section of the retainer ring.

To begin a discussion of the retainer ring B206 of the head B20 of the polyaxial screw B10 of FIG. 60, reference is made to FIGS. 72-73. FIG. 72 is an isometric view of the retainer ring B206 as viewed from a proximal end B400 of the retainer ring B206. FIG. 73 is a transverse cross section of the retainer ring B206

As can be understood from FIGS. 72-73 and traversing the retainer ring B206 proximal to distal along its exterior, the retainer ring B206 includes a planar proximal face B404, a spherical circumferential exterior surface B406, and a planar distal face B408. As shown in FIGS. 72-73, the proximal face B404 and the distal face B408 are parallel to each other, and the spherical shape of the circumferential exterior surface B406 is convex. The circumferential exterior surface B406 extends between and intersects the two faces B404, B408. The width of the proximal face B404 is over twice the width of the distal face B408, as indicated in FIG. 73.

As can be understood from FIGS. 72-73 and traversing the retainer ring B206 proximal to distal along its interior, the retainer ring B206 includes the planar proximal face B404, a chamfer surface B410, a conical circumferential interior surface B412, and the distal face B408. As illustrated in FIG. 73, the chamfer surface B410 extends between and intersects the proximal face B404 and the circumferential interior surface B412, which extends to and intersects the distal face B408. The conical nature of the circumferential interior surface B410 is such that the distance between opposite sides of the circumferential interior surface B410 at the distal end B402 of the retainer ring B206 is greater than the distance between opposite sides of the circumferential interior surface B410 at the proximal end B400 of the retainer ring B206.

As depicted in FIGS. 72-73, the retainer ring B206 also includes a gap B414 that radially extends completely through one side of the retainer ring B206 from the circumferential exterior surface 406 to the circumferential interior surface B410. The gap B414 also vertically extends completely through the one side of the retainer ring B206 from the proximal face B404 to the distal face B408. The gap B414 makes the retainer ring B206 a discontinuous circumference. The gap B414 defines parallel opposed planar ends B416, B418 that extend vertically between the faces B404, B408 and radially between the circumferential surfaces B406, B410. The gap B414 may, however, define rounded ends, or ends that are otherwise not parallel. The parallel opposed planar ends B416, B418 of the gap B414 may be spaced apart between approximately 0.1 mm and approximately 0.5 mm when the retainer ring B206 is in a non-deflected state. As discussed in detail below, gap B414 is aligned with a similar gap in the positioner B208 so as to minimize an insertion force required to insert the shank proximal end portion B106 into the snap-fit assembly of the head B20.

Figure 74:
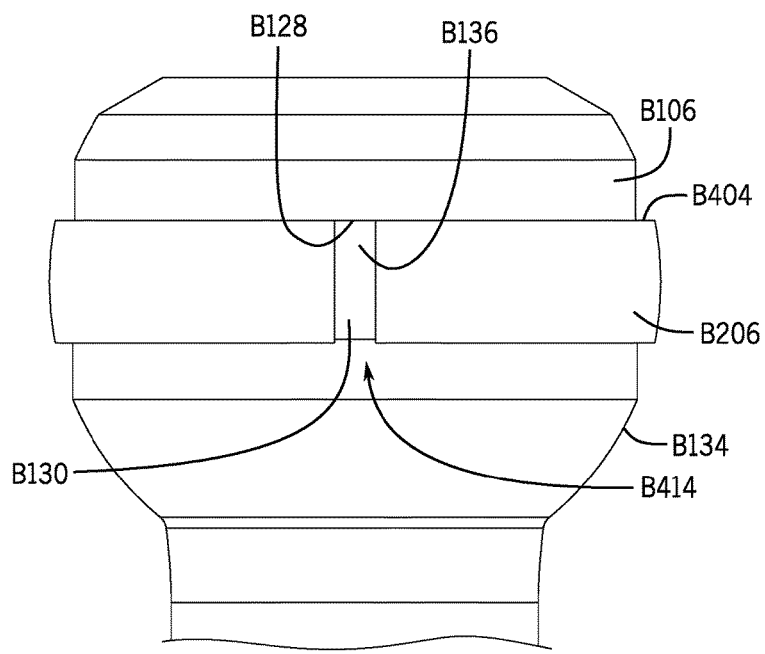
FIG. 74 is an enlarged side view of the shank head portion and the retainer ring received in and engaged with the conically tapered notch of the shank head portion.

FIG. 74 is an enlarged side view of the retainer ring B206 coupled to the shank proximal end portion B106. As shown in FIG. 74, when the shank proximal end portion B106 and retainer ring B206 are coupled together, the retainer ring B206 is received in and engaged with the conically tapered notch B136 of the shank proximal end portion B106. As can be understood from FIG. 75, which is the same view as FIG. 74, except shown as a longitudinal cross section extending along the central longitudinal axis of the shank B15, with the retainer ring B206 received in the conically tapered notch B136 of the shank proximal end portion B106, the planar proximal face B404 of the retainer ring B206 abuts against the distally oriented lip or step face B128 of the shank proximal end portion B106, and the conical circumferential interior surface B412 of the retainer ring B206 abuts against the conical segment B130 of the shank proximal end portion B106.

Figure 75:
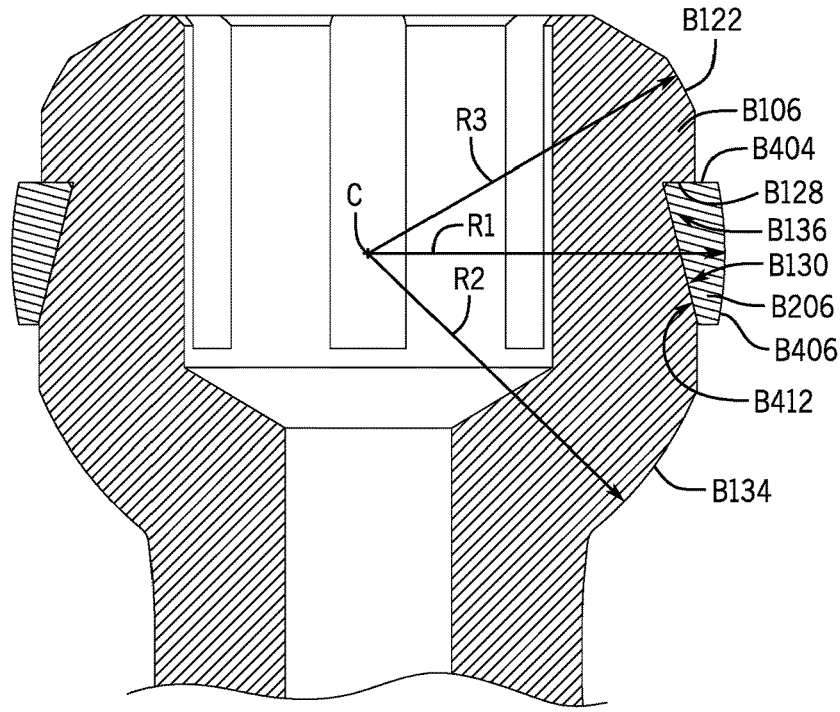
FIG. 75 is the same view as FIG. 74, except shown as a longitudinal cross section extending along the central longitudinal axis of the shank.

As illustrated in FIG. 75, radius arrows R1, R2 and R3 extend from the center point C of the shank proximal end portion B106 to the spherical circumferential exterior surface B406 of the retainer ring B206, the distal spherical exterior surface B134 of the shank proximal end portion B106, and the proximal spherical exterior surface B122 of the shank proximal end portion B106, respectively. These spherical surfaces B406, B134, B122 have equal curvature, and the radii R1, R2 and R3 are also equal. Accordingly, when the retainer ring B206 is engaged with the notch B136 of the shank proximal end portion B106 as depicted in FIGS. 74 and 75, the combined shank proximal end portion B106 and retainer ring B206 each contribute segments of an overall integrated spherical surface having a constant spherical curvature and radius.

While the retainer ring B206 is described as being a single, monolithic structure, the retainer ring B206 may also include multiple, separate structures that combine to form the retainer ring B206 described herein. A mult-piece retainer ring B206 may, for example, snap together or be assembled prior to, during, or subsequent to insertion into the receiver B204.

3. The Positioner of the Head Assembly

Figure 76:
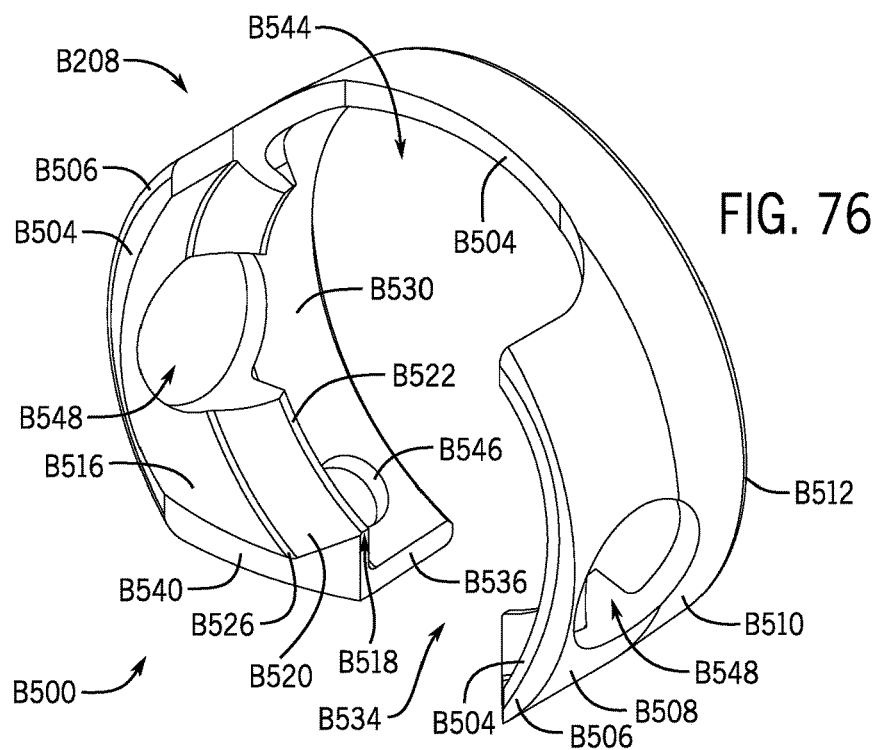
FIG. 76 is an isometric view of the positioner as viewed from a proximal end of the positioner.
Figure 77:
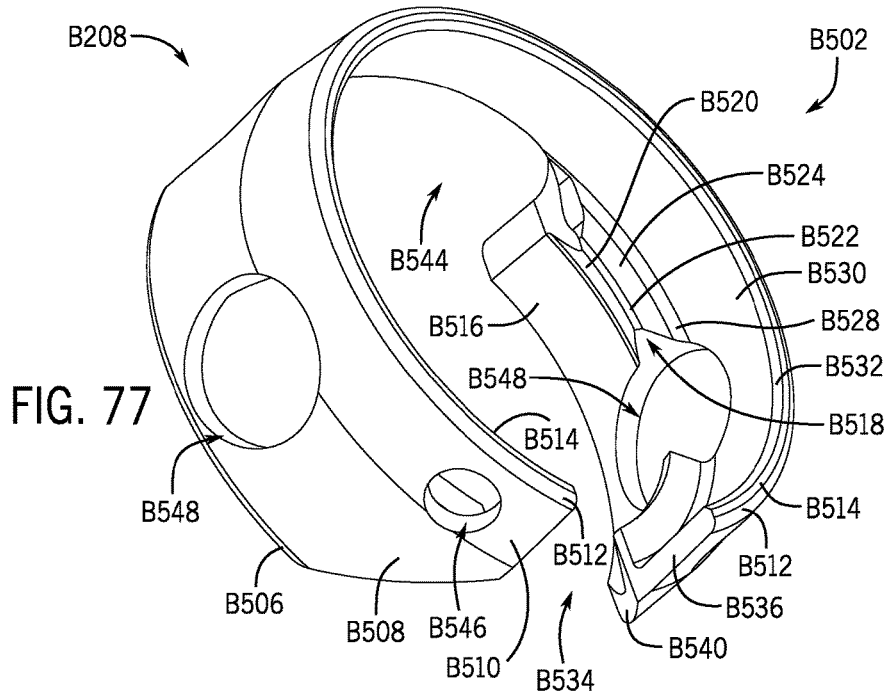
FIG. 77 is an isometric view of the positioner as viewed from a distal end of the positioner.
Figure 78:
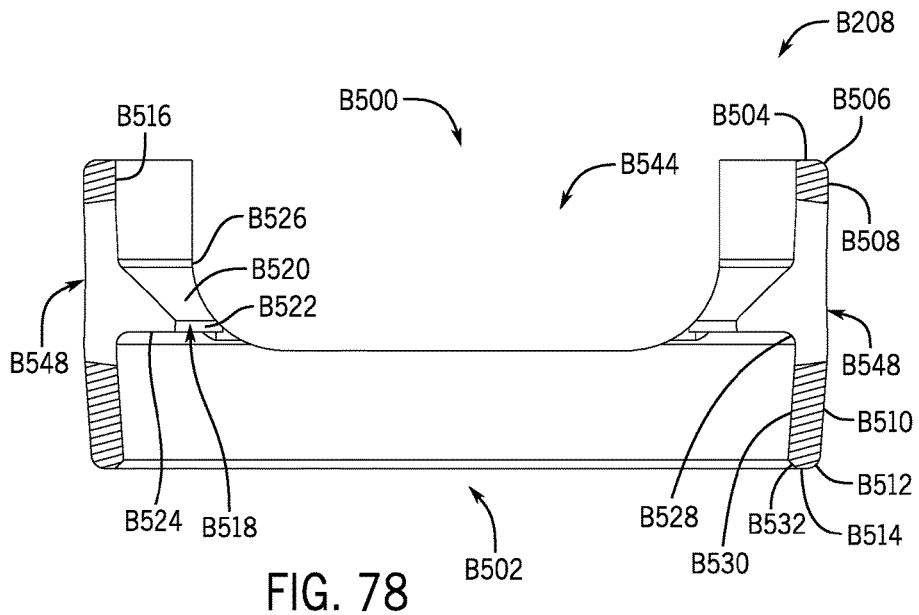
FIG. 78 is a transverse cross section of the positioner.

To begin a discussion of the positioner B208 of the head B20 of the polyaxial screw B10 of FIG. 60, reference is made to FIGS. 76-78. FIG. 76 is an isometric view of the positioner B208 as viewed from a proximal end B500 of the positioner B208. FIG. 77 is an isometric view of the positioner B208 as viewed from a distal end B502 of the positioner B208. FIG. 78 is a transverse cross section of the positioner B208.

As can be understood from FIGS. 76-78 and traversing the positioner B208 proximal to distal along its exterior, the positioner B208 includes a planar proximal face B504 that transitions into a proximal arcuate circumferential corner B506, which transitions into an exterior cylindrical side surface B508. The exterior cylindrical side surface B508 transitions into an exterior conical side surface B510 that transitions into a distal arcuate circumferential corner B512, which transitions into a planar distal face B514.

As can be understood from FIGS. 76-78 and traversing the positioner B208 proximal to distal along its interior, the positioner B208 includes the planar proximal face B504, an interior cylindrical side surface B516, and radially inward projecting flange B518 having a distally narrowing conical proximal surface B520, a radially inward facing planar edge surface B522, and a planar distal face B524. The interior cylindrical side surface B516 transitions into the distally narrowing conical proximal surface B520 via an arcuate circumferential surface B526. The planar distal face B524 transitions via another arcuate circumferential surface B528 into an interior conical circumferential surface B530 that distally narrows, this conical surface B530 then transitioning into a chamfered circumferential surface B532, which transitions into the planar distal face B514.

As depicted in FIGS. 76-77, the positioner B208 also includes a gap B534 that radially extends completely through one side of the positioner B208 from the circumferential exterior surfaces B506, B508, B510, B512 to the circumferential interior surfaces B516, B526, B520, B522, B524, B528, B530, B532. The gap B534 also vertically extends completely through the one side of the positioner B208 from the proximal face B504 to the distal face B514. The gap B534 makes the positioner B208 a discontinuous circumference. The gap B534 defines a combination of parallel opposed planar ends B536, B538 at its distal region and obliquely opposed planar ends B540, B542 at its proximal region that extend over a vertical distance between the faces B504, B514 and radially between the exterior circumferential surfaces B506, B508, B510, B512 and the interior circumferential surfaces B516, B526, B520, B522, B524, B528, B530, B532.

The parallel opposed planar ends B536, B538 of the gap B534 may be spaced apart between approximately 2.25 mm and approximately 2.5 mm when the positioner B208 is in a non-deflected state. As can be understood from FIG. 79, which is a side view of the shank proximal end portion B106, the retainer ring B206, the positioner B208 and the insert B210 all coupled together, the positioner gap B534 is aligned with retainer ring gap B414. Such an alignment of the gaps B414, B534 minimizes an insertion force required to insert the shank proximal end portion B106 into the snap-fit assembly of the head B20.

As illustrated in FIGS. 76-78, the positioner B208 also includes a cutout region B544 that causes the planar proximal face B504 to step distally towards the distal planar face B514 such that the proximal-distal height of the sidewall of the positioner is substantially smaller than elsewhere on the sidewall of the positioner B208. The cutout region B544 is opposite the gap B534 and provides clearance through which the implant rod B22 may pass through the assembled head B20, as can be understood from FIGS. 62-63, 67-68, and 79.

As also shown in FIGS. 76-78, the positioner B208 also includes small circular holes B546 through the sidewall of the positioner on either side of the gap B534 and opposed large circular holes B548 centered ninety degrees from the center lines of the gap B534 and cutout region B544. The small circular holes B546 reduce the weight and rigidity of the positioner B208, and the large holes align with the holes B324 of the receiver member B204 to allow the inward crimping of the points B327 of the holes B324 of the receiver member B204 in the securing of the insert B210 and receiver member B204 together, as indicated in FIG. 67.

As discussed below, the positioner B208 keeps the retainer ring B206 properly oriented to be able to receive the shank proximal end portion B106 during insertion of the shank proximal end portion B106 into the head B20. Also, as can be understood from FIG. 79, the radially inward projecting flange B518 of the positioner B208 is received in a horizontal groove or slot in the insert B210 to prevent the positioner B208 and the insert B210 from proximally displacing away from each other along the distal-proximal axis. Also, on account of the segmented nature of the radially inward projecting flange B518, which is circumferentially discontinuous due to the gap B534 and the cutout region B544 that extend through the radially inward projecting flange B518, portions of the insert B210 abut against circumferential terminations of the radially inward projecting flange B518 to prevent rotational or pivotal displacement of the insert B210 and the positioner B208 relative to each other. A discussion of the features of the insert B210 is now provided.

4. The Insert of the Head Assembly

Figure 80:
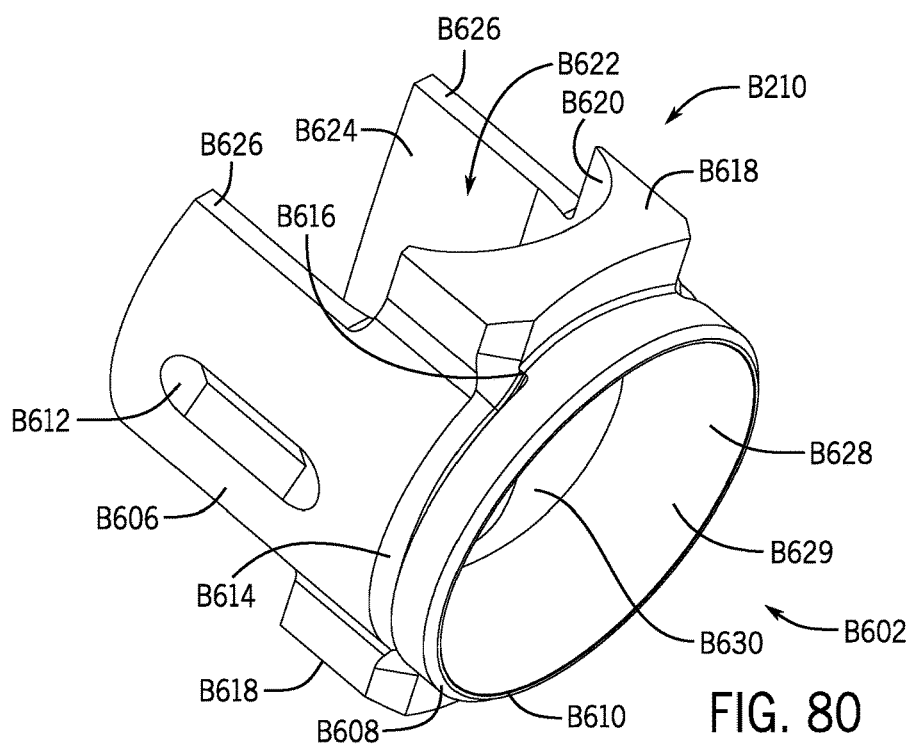
FIG. 80 is an isometric view of the insert as viewed from a distal end of the insert.
Figure 81:
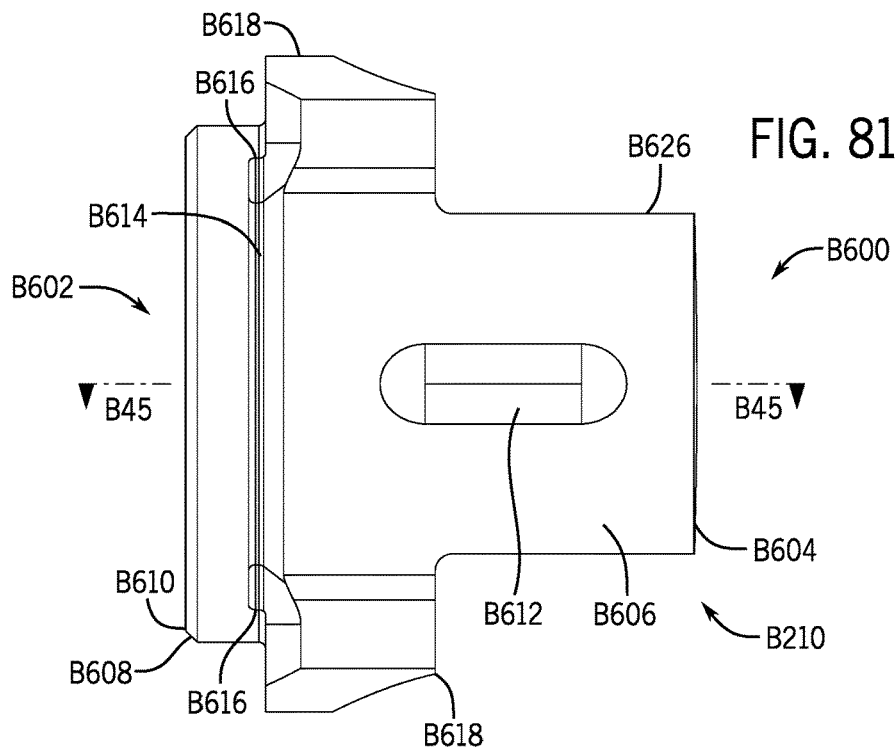
FIG. 81 is a sagittal side view of the insert.
Figure 82:
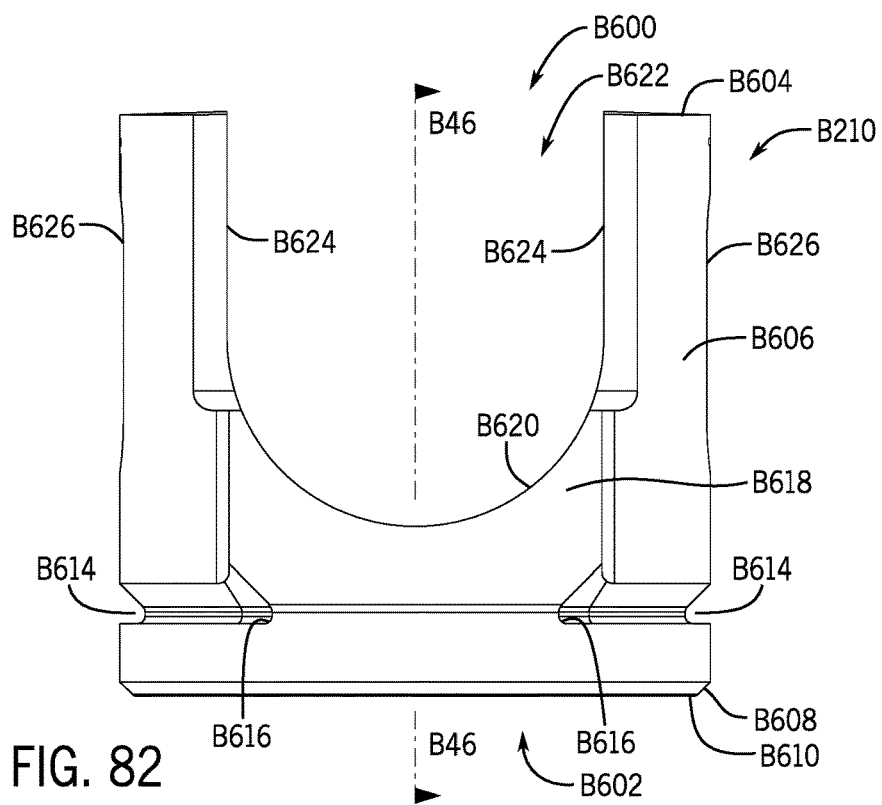
FIG. 82 is a side view of the insert that is ninety degrees from sagittal.

To begin a discussion of the insert B210 of the head B20 of the polyaxial screw B10 of FIG. 60, reference is made to FIGS. 80-83. FIG. 80 is an isometric view of the insert B210 as viewed from a distal end B602 of the insert B210. FIG. 81 is a sagittal side view of the insert B210. FIG. 82 is a side view of the insert B210 that is ninety degrees from sagittal.

Figure 83:
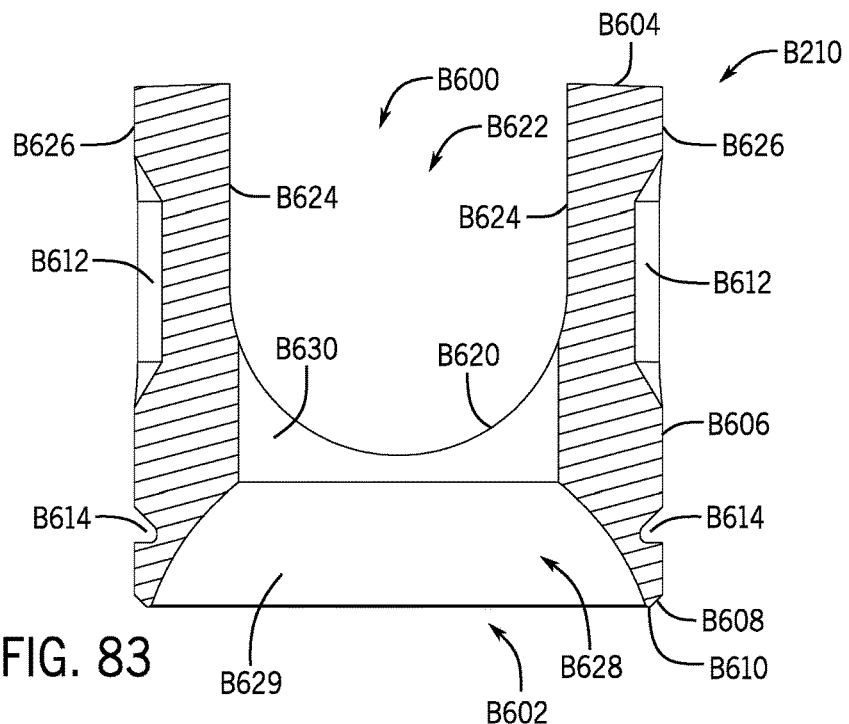
FIG. 83 is longitudinal cross section of the insert as taken along section line 46-46 in FIG. 82.

FIG. 83 is longitudinal cross section of the insert B210 as taken along section line 46-46 in FIG. 82.

As can be understood from FIGS. 80-83 and traversing the insert B210 proximal to distal along its exterior, the insert B210 includes a planar proximal face B604, a cylindrical side surface B606, a distal chamfer surface B608, and a distal edge B610. Longitudinally extending grooves B612 are defined in the cylindrical side surface 606 on opposite sides of the insert B210. As discussed above and as can be understood from FIGS. 63 and 67, each hole B324 of the receiver member B204 has an inward conical shape B326 that inwardly terminates as a point B327. The point B327 can be crimped or otherwise pressed inwardly during the manufacture of the head B20 to force the thin sidewall of the receiver immediately adjacent the point B327 into the void of the immediately adjacent longitudinally extending groove B612 defined in the insert B210, thereby securing the insert B210 against exiting proximally from the receiver member B204.

As can be understood from FIGS. 80-83, circumferentially extending grooves B614 are defined in the cylindrical side surface B606 on opposite sides of the insert B210 near the distal end B602. The grooves B614 are generally the same circumferential length. Each groove B614 extends approximately 50 degrees on either side of the part midline (perpendicular to the rod axis) for a total included angle of approximately 100 degrees. Each groove B614 has a pair of terminal ends B616 at which the groove B614 terminates. As indicated in FIGS. 67 and 79, each of the radially inward projecting flanges B518 of the positioner B208 is received in a respective circumferentially extending groove B614 of the insert B210, which prevents the insert B210 from proximally displacing relative to the positioner B208 or rotating relative to each other.

As illustrated in FIGS. 80-82, ledges B618 radially project from opposite sides of the cylindrical side surface B606 just proximal the circumferentially extending grooves B614 and through areas of the side surface B606 separating the groove ends B616 and through which no groove B614 extends. As shown in FIGS. 80, and 82-83, proximal-facing saddle surfaces B620 are defined in a semi-cylindrical curved fashion through the insert B10 and across the proximal-facing portions of the ledges B618. The curved saddle surfaces B620 have a diameter that are essentially equal to the diameter of the implant rod B22 such that the implant rod B22 can extend across a saddle region B622 defined by the curved saddle surfaces B620 in the insert B210, as depicted in FIGS. 60-63. The curved saddle surfaces B620 transition into distal-proximal extending planar saddle sidewall surfaces B624 that face radially inward, as indicated in FIGS. 80, and 82-83. The saddle region B622 divides the insert into two opposed proximally extending projections B626 over at least the most proximal two thirds of the insert B210.

As shown in FIGS. 80, and 83, a spherical recess B628 having a spherical surface B629 is defined in the distal end B602 of the insert B210. A cylindrical hole B630 is also defined in the insert B210 such that the hole B630 is coaxial with a center longitudinal axis of the insert B210 and extends distal-proximal between the spherical recess B628 and the curved saddle surfaces B624 to place the spherical recess B628 in communication with the saddle region B622.

Figure 79:
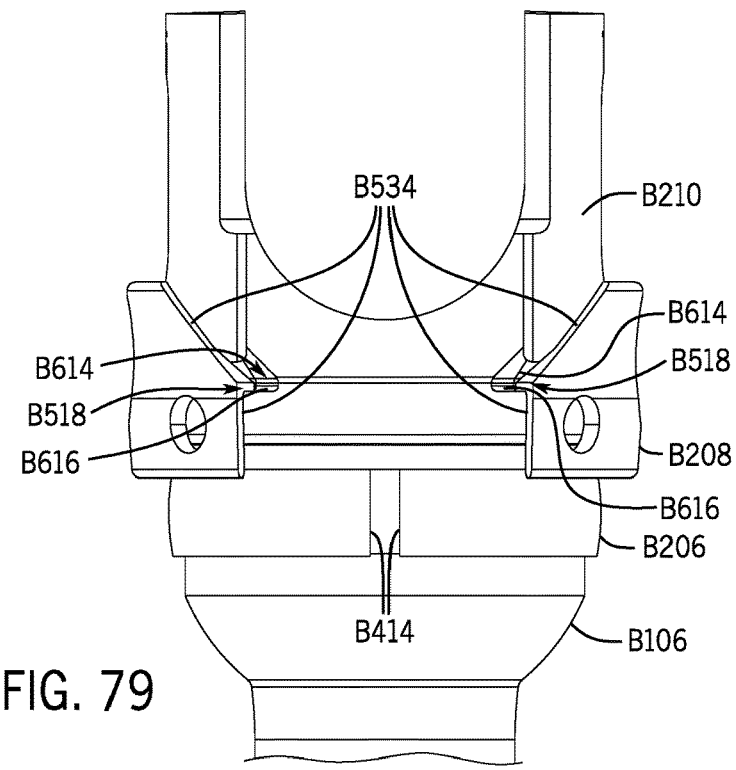
FIG. 79 is a side view of the shank head portion, the retainer ring, the positioner and the insert all coupled together.
Figure 84:
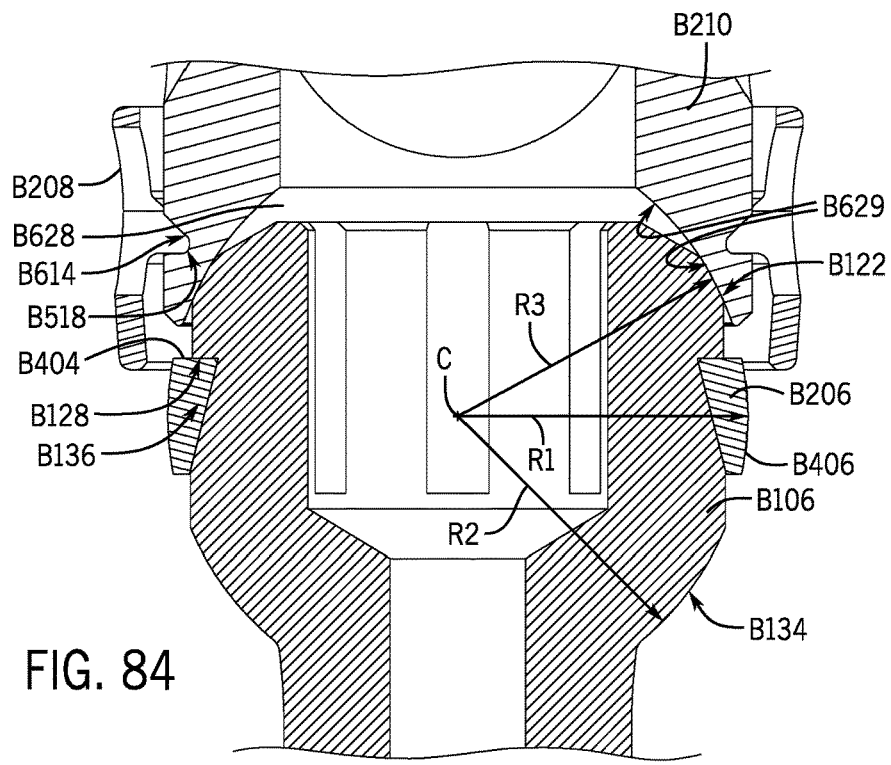
FIG. 84 is the same view as FIG. 79, except shown as a longitudinal cross section extending along the central longitudinal axis of the shank.

FIG. 84 is the same view as FIG. 79, except shown as a longitudinal cross section extending along the central longitudinal axis of the shank B15. FIG. 84 illustrates the shank proximal end portion B106, the retainer ring B206, the positioner B208, and the insert B210 coupled together. As so coupled, the retainer ring B206 is received in the conically tapered notch B136 of the shank proximal end portion B106, and the planar proximal face B404 of the retainer ring B206 abuts against the distally oriented lip or step face B128 of the shank proximal end portion B106. Also, the conical circumferential interior surface B412 of the retainer ring B206 abuts against the conical segment B130 of the shank proximal end portion B106, and each of the radially inward projecting flanges B518 of the positioner B208 is received in a respective circumferentially extending groove B614 of the insert B210.

As depicted in FIG. 84, radius arrows R1, R2 and R3 extend from the center point C of the shank proximal end portion B106 to the spherical circumferential exterior surface B406 of the retainer ring B206, the distal spherical exterior surface B134 of the shank proximal end portion B106, and the spherical interior surface B629 of the spherical recess B628 of the insert B210, respectively. Radius arrow R3 also extends from the center point C of the shank proximal end portion B106 to the proximal spherical exterior surface B122 of the shank proximal end portion B106. These spherical surfaces B406, B134, B122, B629 have equal curvature, and the radii R1, R2 and R3 are also equal. Accordingly, when the retainer ring B206 is engaged with the notch B136 of the shank proximal end portion B106 as depicted in FIGS. 74-75 and 84, the combined shank proximal end portion B106 and retainer ring B206 each contribute segments of an overall integrated spherical surface having a constant spherical curvature and radius, this overall integrated spherical surface being matingly received by the spherical surface B629 of the spherical recess B628 of the insert B210. In certain embodiments, R1, R2, and R3 are each approximately 3.75 mm.

As shown in FIG. 85, which is the same view as FIG. 84, except showing all of the components of the head B20 and the shank proximal end portion B106 secured in the head B20 at a 30 degree angle relative to the longitudinal axis of the head B20 by the compressing forces of the components B28, B32 of the plug B24 and the implant rod B22, the spherical surface B629 of the insert B210 and the spherical surface B348 of the receiver B208 combine to define a spherical receiving chamber B650 at the distal end of the head B20. The spherical combination of the shank proximal end portion B106 and retainer ring B206 is received in the spherical receiving chamber of the head B20. The complimentary and matching spherical surfaces B122, B134 of the shank proximal end portion B106 and the complimentary and matching spherical surface B406 of the retainer ring B206 mate with and are in sliding hemispherical contact with the spherical surfaces B629, B348 of the spherical receiving chamber B650 at the distal end of the head B20.

Since all of these spherical surfaces B122, B134, B406, B348, B629 share the same curvature and radii from the center point C of the shank proximal end portion B106, the shank proximal end portion B106 is able to be pivoted within the spherical receiving chamber B650 at the distal end of the head B20 such that the longitudinal axis of the shank LAS angularly offset from the longitudinal axis of the head LAH by an offset angle OA of between approximately 35 (plus or minus 5 degrees). In one embodiment, the offset angle OA may be approximately 30 degrees. These offset angles OA may be made in any direction relative to the longitudinal axis of the head LAH in a 360 degree circumference extending radially about the longitudinal axis of the head LAH.

d. The Assembly and Interaction of the Components of the Head and Shank

To begin a discussion of the assembly of the head B20 and the interaction of the components of the head B20 and the shank proximal end portion B106, reference is made to FIG. 86, which is an exploded ninety degree of sagittal side elevation view of the head, wherein the receiver is shown as a longitudinal cross section. As shown in FIG. 86, the retainer ring B206, positioner B208 and the insert B210 are arranged in that order to be distally directed down into the interior of the receiver member B204. These head components B206, B208, B210 may be inserted into the interior of the head B20 individually with the retainer ring B206 entering first, followed in order by the positioner B208 and the insert B210. Alternatively, these head components B206, B208, B219 may be assembled together in their stacked and nested arrangement depicted in FIG. 87 and then inserted as a unit into the interior of the head B20. It should be noted that the point B327 of the inward conical shape B326 of the hole B324 in the receiver member B204 has not yet been crimped inwardly.

Figure 87:
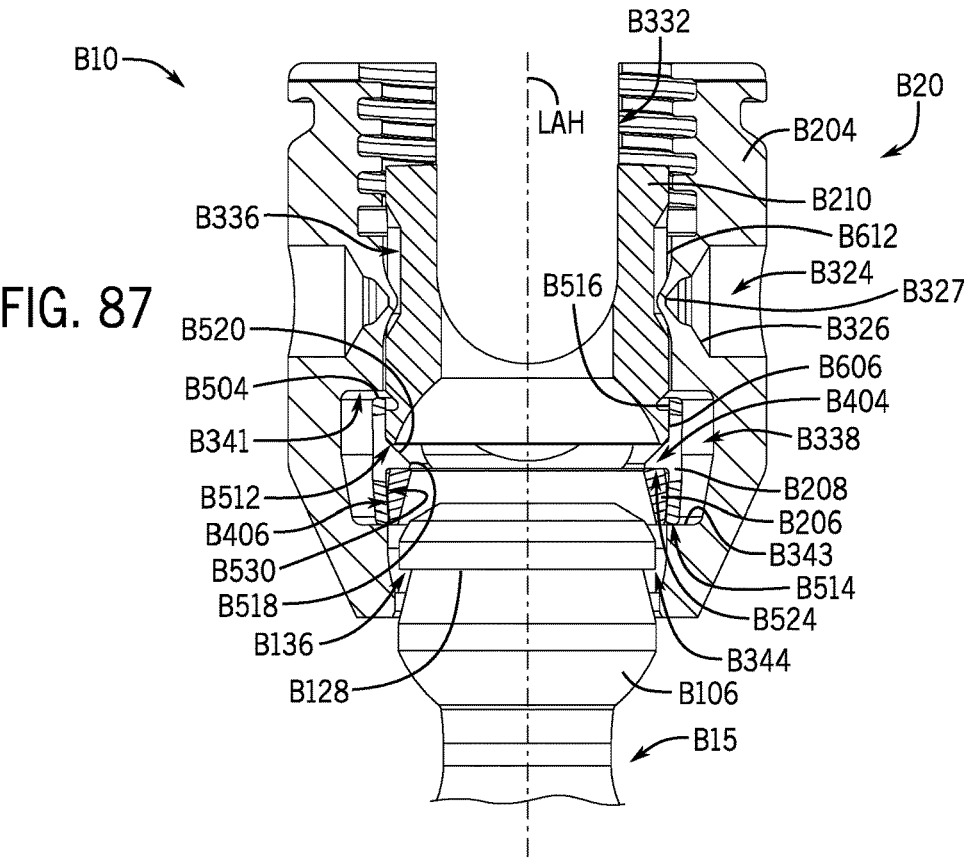
FIG. 87 is a ninety degree of sagittal side elevation view of the head in an assembled condition with the shank proximal end portion being proximally inserted into the distal end of the head, wherein the components of the head are shown longitudinally cross sectioned.

FIG. 87 is the same view as FIG. 86, except the head B20 is fully assembled into a configuration in which it would be shipped and a condition that is preparatory for beginning the coupling process with the shank proximal end portion B106, all of the components of the head B20 being shown longitudinally cross sectioned. As shown in FIG. 87, the retainer ring B206, positioner B208 and insert B210 are positioned in a stacked and nested arrangement such that the retainer ring B206 and positioner B208 reside in the expansion chamber B338 of the receiver member B204 and the insert B210 extends from a proximal region of the expansion chamber B338 of the receiver member B204 through the throat B336 and threaded region B332 of the receiver member B204. The structural interaction of the receiver member B204 and the insert B210 maintains the two components B204, B210 in a coaxial relationship.

As can be understood from FIG. 87, in the shipped condition, the retainer ring B206 resides within the distal confines of the positioner B208 such that the planar proximal face B404 of the retainer ring B206 is in abutting planar contact with the planar distal face B524 of the radially inward projecting flange B518 of the positioner B208. Also, the spherical outer surface B406 of the retainer ring B206 abuts against the distally narrowing interior conical circumferential surface B530 of the positioner B208, thereby locking the retainer ring B206 within the distal circumferential confines of the positioner B208. Thus, the structural interaction of the positioner B208 and the retainer ring B206 maintains the two components B206, B210 in a coaxial relationship.

As shown in FIG. 87, the distal region of the insert B210 resides within the confines of a proximal region of the positioner B208. In doing so, the distal portion of the cylindrical side surface B606 of the insert B210 abuts against the interior cylindrical side surface B516 of the positioner B208. Also, the distal arcuate circumferential corner B512 of the insert B210 rests on the distally narrowing conical proximal surface B520 of the radially inward projecting flange B518 of the positioner B208. Thus, the structural interaction of the positioner B208 and the insert B210 maintains the two components B208, B210 in a coaxial relationship.

Since FIG. 87 represents the head B20 in a shipped condition, the point B327 of the inward conical shape B326 of the hole B324 in the receiver member B204 has been crimped inwardly into the proximal-distal extending groove B612 in the insert B210 to prevent the insert B210 from proximally exiting the receiver member B204 or the rest of the internal components B206, B208, for that matter. The three internal components B206, B208, B210 are fully distally positioned within the confines of the receiver member B204, the three internal components B206, B208, B210 being prevented from exiting the distal opening B344 of the receiver member B204 by the planar distal face B514 of the positioner B208 abutting against a distal planar step face B343 of the interior chamber B338 of the receiver member B204.

The head B106 of FIG. 87 is in a condition that is preparatory for beginning the coupling process with the shank proximal end portion B106, the shank proximal end portion B106 being capable of being proximally displaced into the distal opening B344 of the receiver member B204 of the head B20 in the process of coupling the shank B15 to the head B20, and the three internal components B206, B208, B210 of the head B20 being positioned so as to be able to receive the shank proximal end portion B106 and the ring retainer B206 engage and retain the shank proximal end portion B106 within the confines of the distal region of the receiver member B204.

As can be understood from FIG. 87, the positioner B208 performs a number of functions as will now be described. First, the positioner B208 provides coaxial alignment for the retainer ring B206. Specifically, the positioner B208 maintains the retainer ring B206 in proper alignment within the expansion chamber B338 of the receiver member B204 such that the retainer ring B206 is coaxially aligned with the longitudinal axis of the head LAH and, more specifically, with the center longitudinal axes of the distal opening B344 of the receiver through which the shank proximal end portion B106 passes on its way to coupling with the retainer ring B206.

Second, the positioner B208 provides longitudinal displacement limitations for the retainer ring B206. Specifically, as can be understood from the discussion pertaining to FIG. 87 and as will be further evident for the discussion regarding FIGS. 88 and 89, the positioner B208 limits the extent to which the retainer ring B206 can distally or proximally displace within the confines of the interior chamber B338. For example, when the distal region of the insert B210 is located within the proximal region of the positioner B208 in abutting circumferential contact and the retainer ring B206 is locked in the distal confines of the positioner B208, the diameter of the positioner B208 is sufficiently wide so as to prevent the positioner B208 and the retainer ring B206 attached thereto from distally or proximally exiting the interior chamber B338 of the receiver member B204. For example, as can be understood from FIG. 87, the distal planar face B514 of the positioner B208 abuts the distal planar step face B343 of the interior chamber B338 of the receiver member B204 when the positioner B208 is fully distally displaced within the confines of the receiver member B204. Similarly, the proximal planar face B504 of the positioner B208 abuts the proximal planar step face B341 of the interior chamber B338 of the receiver member B204 when the positioner B208 is fully proximally displaced within the confines of the receiver member B204. Thus, while the positioner B208 and the retainer ring B206 secured thereto are capable of displacing distal-proximal within the interior chamber B338 of the receiver member B204, this displacement is substantially limited and may be approximately 0.2 mm.

As seen in FIG. 87, when the insert B210 is at a proximal-most displacement as limited by the inward crimping of the points B327 in the holes B324, the positioner B208 may be provided with certain rotational freedom because it is not yet coupled with the insert B210. If, however, the insert B210 is positioned distal of the position shown in FIG. 87, the insert B210 would prevent the positioner B208 from rotating because the positioner B208 could not rotate past the outwardly extending ledges B618. To limit rotation of the positioner B208 when the insert B210 is proximally displaced, as shown in FIG. 87, the insert B210 may include a distally projecting alignment member (not shown) that extends distally from the particular ledge B618 that is positioned proximal of the gap B534 in the positioner B208. Thus, as the insert B210 is proximally displaced such that the ledges B618 abut the distal surface B313 of the radially inward projecting flanges B310, the distally projecting alignment member may project distal of the insert B210 to prevent the positioner B208 from rotating past the alignment member. When the insert B210 is subsequently distally advanced, the alignment member, which may include a conical distal end, may urge the positioner B208 back into proper alignment with the insert B210. Accordingly, an insert B210 with a distally projecting alignment member is not symmetric about the axis because one ledge will include and one will not include the distally projecting alignment member. For these reasons, among others, the present disclosure contemplates symmetric and asymmetric inserts B210 of this and other types.

Figure 88:
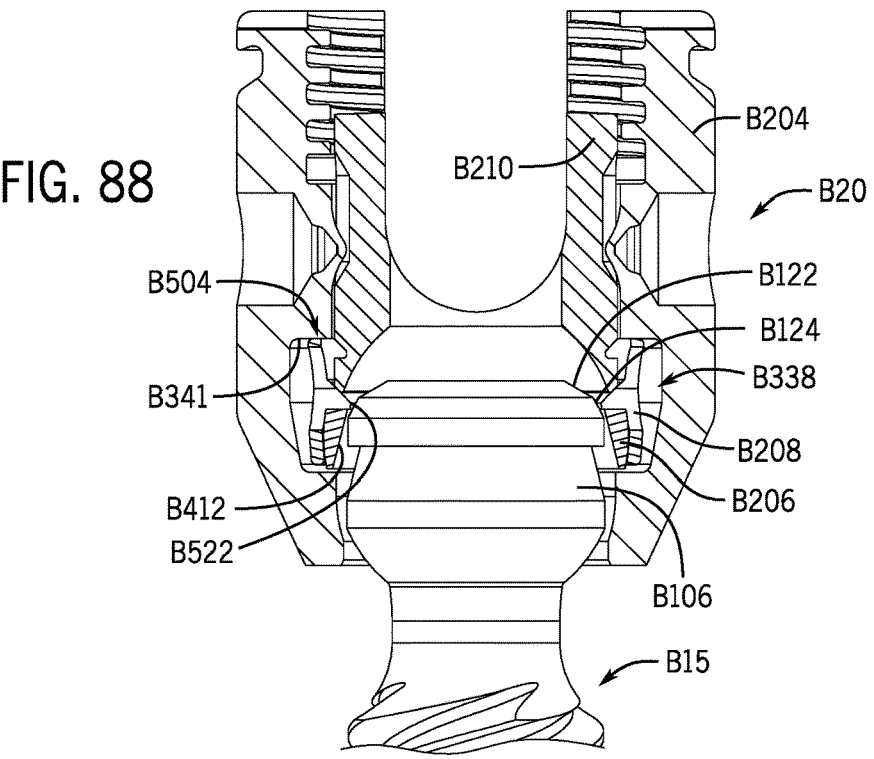
FIG. 88 is the same view as FIG. 87, except the shank proximal end portion has radially expanded the retainer ring and positioner and proximally displaced the retainer ring, positioner and insert.

As can be understood from FIG. 88, which is the same view as FIG. 87, except the shank proximal end portion B106 has been further proximally inserted into the head B20, the proximal driving of the shank proximal end portion B106 has caused the proximal planar face B504 of the positioner B208 to abut against the proximal planar step face B341 of the interior chamber B338 of the receiver member B204, thereby arresting the proximal displacement of the positioner B504 within the confines of the interior chamber B338 of the receiver member B204. Also, the proximal driving of the shank proximal end portion B106 has caused the proximal leading surfaces B122, B124 of the shank proximal end portion B106 to abut against the interior surfaces B412, B522 of the retainer ring B206 and the positioner B208, thereby causing the retainer ring B206 and the positioner B208 to radially expand as the shank proximal end portion B106 proximally displaces into the confines of the interior chamber B338 of the receiver member B204.

Figure 89:
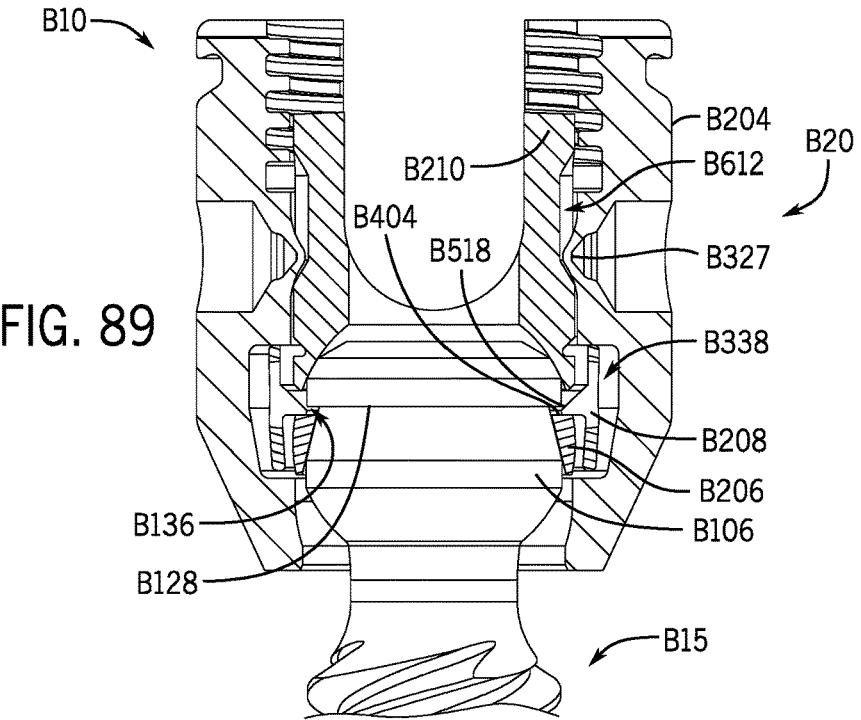
FIG. 89 is the same view as FIG. 88, except the shank proximal end portion has proximally exceeded the extent to which the retainer ring and positioner can proximally displace within the expansion chamber of the receiver, the radially inward projecting flange of the positioner and the retainer ring having cleared the distally oriented lip or step face of the shank proximal end portion such that the retainer ring is now positioned to be received in the conically tapered notch of the shank proximal end portion.

As shown in FIG. 89, which is the same view as FIG. 88, except the shank proximal end portion B106 is fully proximally inserted into the expansion chamber B338 of the receiver member B204, further proximal displacement of the shank proximal end portion B106 is stopped by the shank proximal end portion B106 having driven insert B210 as proximally far as the insert grooves B612 allow on account of the impediment presented by the crimped in hole tips B327. The radially inward projecting flange B518 of the positioner B208 and the planar proximal face B404 of the retainer ring B206 have both distally cleared the distally oriented lip or step face B128 of the shank proximal end portion B106, and the retainer ring B206 has biased radially inward such that the conical inner surface B412 of the retainer ring B206 abuts in planar mating contact with the complementary conical outer surface B130 of the shank proximal end portion B106. Thus, the retainer ring B206 is positioned to be received in the conically tapered notch B136 of the shank proximal end portion B106. Also, since positioner B208 is held in a radially expanded condition on account of its radially inward projecting flange B518 contacting the exterior surface of the shank proximal end portion B106, the interior of the positioner B208 is spaced apart from the exterior of the retainer ring B206, thereby freeing the retainer ring B206 from its locked retention within the positioner B208.

Figure 90:
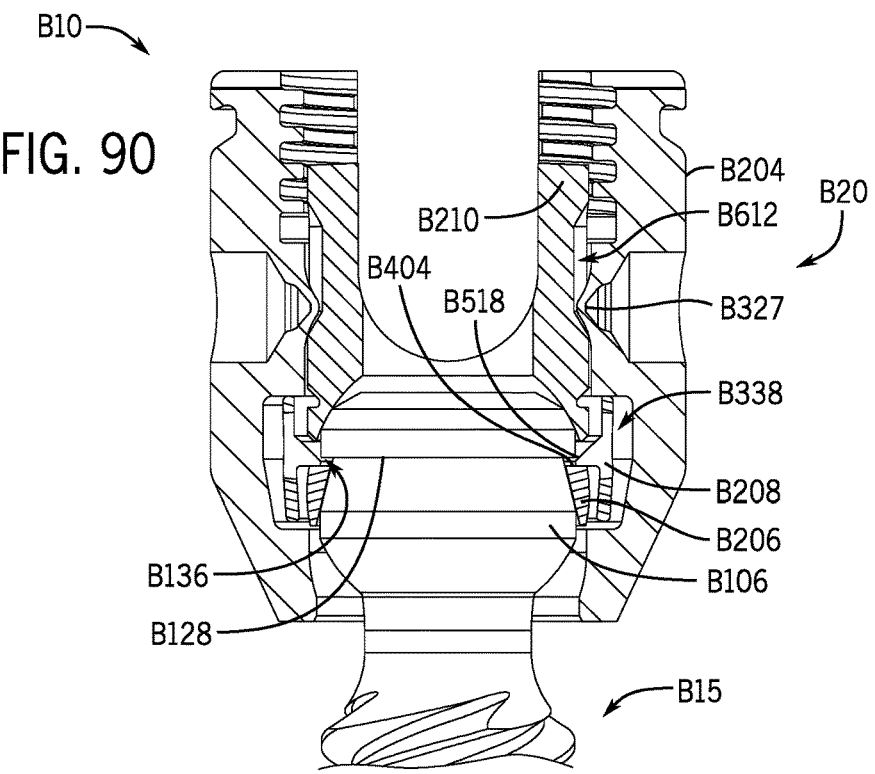
FIG. 90 is the same view as FIG. 89, except the retainer ring has been fully seated in the conically tapered notch of the shank proximal end portion 106.

As can be understood from FIG. 90, which is the same view as FIG. 89, except the retainer ring B206 has been fully seated in the conically tapered notch B136 of the shank proximal end portion B106, distal displacement of the shank proximal end portion B106 seats the retainer ring B206 in the notch B136 and pulls the retainer ring from within the confines of the distal region of the positioner B208. The seating of the retainer ring B206 in the conically tapered notch B135 prevents the shank proximal end portion B106 from exiting the distal opening B344 in the receiver member B204 as the combined diameter of the shank head portion and the retainer ring nested thereon is exceeds the diameter of the distal opening B344 in the receiver member B204.

As indicated in FIG. 90, the distal arcuate circumferential corner B512 of the insert B210 rests on the distally narrowing conical proximal surface B520 of the radially inward projecting flange B518 of the positioner B208. Also, the distal planar face B514 of the positioner B208 abuts the distal planar step face B343 of the interior chamber B338 of the receiver member B204. As a result, the insert B210 remains proximally displaced within the receiver member B204 to nearly a most extreme extent.

Figure 91:
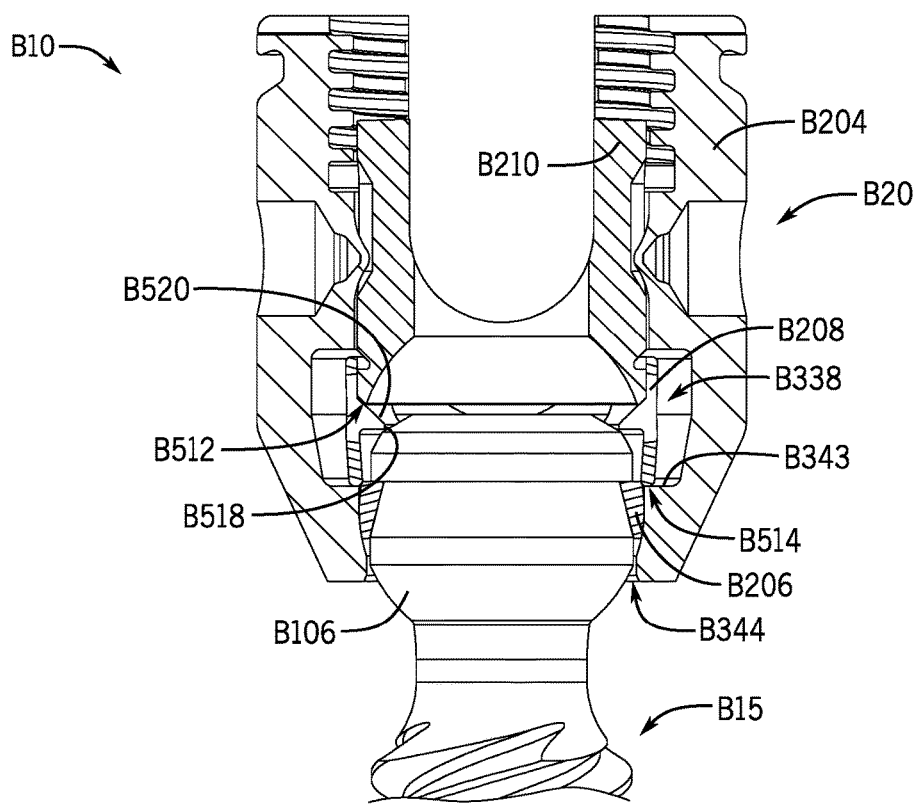
FIG. 91 is the same view as FIG. 90, except the insert and the positioner are interlocked.

As can be understood from FIG. 91, which is the same view as FIG. 90, except the insert B210 and the positioner B208 are interlocked, the insert B210 can be driven distally within the confines of the receiver member B204 and the positioner B208 is prevented from any corresponding distal displacement on account of its abutment with the distal planar step face B343 of the interior chamber of the receiver member B204. As a result, the distal arcuate circumferential corner B512 of the insert B210 forces against the distally narrowing conical proximal surface B520 of the radially inward projecting flange B518 of the positioner B208 to wedge the flange B518 radially outward and allowing the distal portion of the cylindrical side surface B606 of the insert B210 to slide past the flange B518 until the flange B518 encounters and is received in the circumferentially extending groove B614 of the insert B210, thereby securing the insert and the positioner together.

Figure 92:
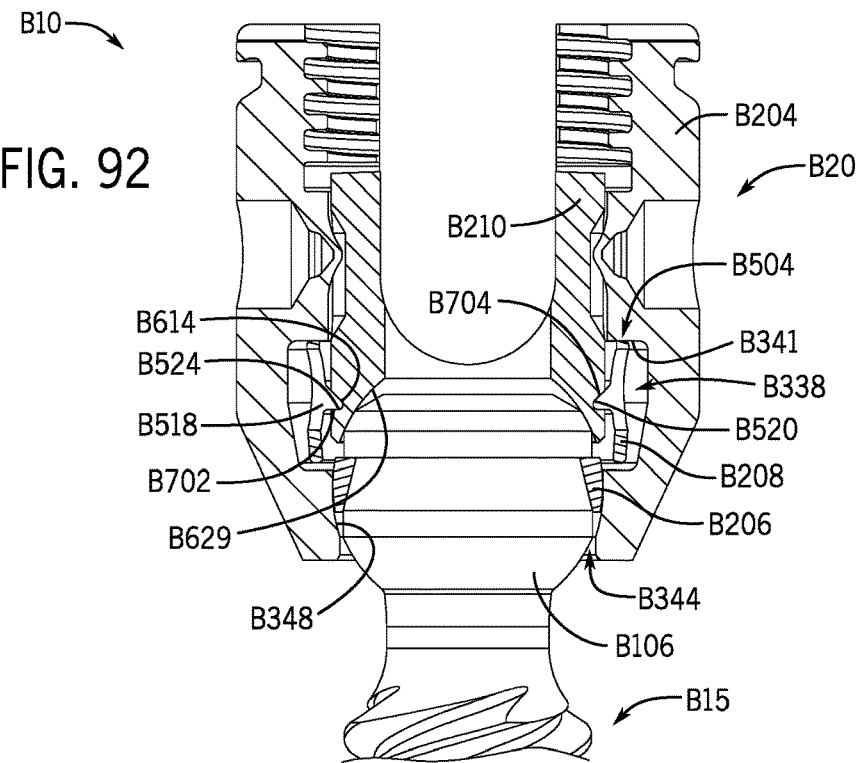
FIG. 92 is the same view as FIG. 91, except the interlocked insert and positioner are proximally displaced with the confines of the receiver.

As illustrated in FIG. 92, which is the same view as FIG. 91, except the interconnected insert B210 and positioner B208 are proximally displaced with the confines of the receiver member B204, the proximal planar face B504 of the positioner B208 abutting against the proximal planar step face B341 of the interior chamber B338 of the receiver member B204 limits the extent to which the insert B210 can proximally displace within the receiver member B204. That is, when the insert B210 is proximally displaced, the planar distal surface B524 of the radially inward projecting flange B518 contacts a planar distal surface B702 of the circumferentially extending groove B614 of the insert B210. And, when the proximal planar face B504 abuts the proximal planar step face B341 of the interior chamber B338, the contacting of the planar surfaces B524, B702 of the positioner B208 and the insert B210 cause a force that is generally normal (i.e., perpendicular) to the planar surfaces B524, B702 such that the positioner B208 is not caused to expand outward into the interior chamber B338, but is, rather, maintained in a locked position with respect to the insert B210. Thus, as can be understood from FIGS. 91 and 92, once the insert B210 and the positioner B208 are secured together, the proximal displacement of the insert B210 is limited by the extent to which the positioner 208 can displace between the distal and proximal extents of the interior chamber 338.

As can be understood from FIGS. 91 and 92, distal displacement, unlike proximal displacement, of the interconnected insert B210 and the positioner B208 is not limited by the positioner B208. As stated above with respect to FIG. 92, proximal displacement is limited by the positioner B208 being positioned within the interior chamber B338 because interaction of the corresponding planar surfaces B524, B702 of the positioner B208 and insert B210 is such that an applied proximal force acts generally normal to the surfaces B524, B702 such that there is no outward expansion of the positioner B208 into the interior chamber B338 which would release the positioner B208 from the insert B210. During distal displacement and referring to FIG. 91, however, a proximal conically beveled inward surface B704 of the circumferentially extending groove B614 of the insert B210 contacts the distally narrowing conical proximal surface B520 of the positioner B208 when the planar distal face B514 of the positioner B208 abuts the distal planar step face B343 of the interior chamber B338. The orientation of the surfaces B704, B520 of the insert B210 and the positioner B208 is such that, during distal displacement, the positioner B208 is caused to radially expand into the interior chamber B338 because a distal force acts generally normal to the surfaces B704, B520 and, thus, drives the surfaces apart. In this way, the positioner B208 does not limit distal displacement of the insert B210. Rather, as the insert B210 is distally displaced and the positioner B208 is radially expanded into the interior chamber B338, the insert B210 is caused to contact the first distally expanding conical segment B122 of the shank proximal end portion B106 of the shank B15, which, in turn, causes the retainer ring B206 to be forced against the intermediate spherical segment B348 of the receiver member B204.

While the embodiments described herein include a positioner B208 and insert B210 that, when used in combination, limits proximal displacement while allow certain distal displacement, the screw B10 could be arranged differently without departing from the teachings of the present disclosure. For example, the screw B10 may be configured to allow certain proximal displacement while limiting certain distal displacement. Also, the screw B10 may be designed such that it restricts both distal and proximal displacement. The embodiments described herein are intended to be exemplary and are not intended to be limiting.

The positioner B208 may be made from a material such that, during expansion, the positioner B208 deforms elastically. That is, the deformation during expansion is reversible and, thus, the shape of the positioner B208 completely returns to its original shape. The positioner B208 may alternatively be made from a material such that, during expansion, the positioner B208 deforms plastically. That is, the deformation is irreversible and once the positioner is expanded beyond a certain point (i.e., yield strength), the positioner B208 will no longer return to its original shape. In certain embodiments, the positioner B208 may be configured to break or fracture during engagement of the shank B15 with the head B20. In certain embodiments, the positioner B208 may be of a single, monolithic construction or the positioner B208 may include multiples constructions or members that are assembled. In the case of a positioner B208 that is assembled, the positioner B208 may be assembled prior to, during, or after being positioned within the receiver member B204. In certain embodiments, the positioner B208 may be formed or coupled with any of the components described herein. For example, in certain embodiments, the positioner B208 may be formed with the insert B210. Additionally or alternatively, the positioner B208 may be configured to perform different tasks involved with securing and supporting the shank B15 within the head B20.

As discussed previously, the screw B10 may be configured as polyaxial, uni-planar, or favored angle, among others, without departing from the teachings of the present disclosure. For example, the internal and/or external geometry and orientation of the components of the embodiments described herein may be modified to restrict shank motion to a specified angle or specified plane to facilitate a favored angle or uni-planar screw. Such modification may be made to the shank B15, insert B210, receiver member B204, positioner B208, or retainer ring B206, among other components, to facilitate the restricted motion.

As illustrated in FIGS. 91 and 92, once the insert B210 and the positioner B208 are secured together, the distal-proximal displacement of the positioner B208 is limited by the extent to which the positioner B208 can displace between the distal and proximal extents of the interior chamber B338. More specifically, a distal-most position of the positioner B208 is illustrated in FIG. 91 and a proximal-most position of the positioner B208 is illustrated in FIG. 92. In certain instances, such distal-proximal displacement of the positioner B208 within the interior chamber B338 may be limited or eliminated by including a biasing member (not shown) positioned between, for example, the planar proximal face B504 of the positioner B208 and the proximal planar step face B341 of the interior chamber B338 to facilitate a "friction-fit" between the various components of the bone anchor. Alternatively, the "friction-fit" may be accomplished by the crimping of the holes B324. More particularly, the holes B324 may be crimped so that the tips B327 contact the longitudinally extending grooves B612 of the insert B210 with sufficient enough force to maintain a position of the insert B210 in a distal-most position. Eliminating the distal-proximal displacement of the positioner B208 by forcing the positioner B208 into, for example, the distal position, causes the retainer ring B206 to exert a greater force on the inner spherical surface B348 of the retainer B204 than would otherwise be exerted if the positioner B206 were in a proximal position. In this way, a biasing member or crimping of the insert B210 that forces the positioner B208 into a distal position increases the amount of resistance between the various components of the bone anchor such that as the head B20 is pivoted relative to the shank B15, there is an increased tendency for the head B20 to remain in its pivoted position. Including a "friction-fit" arrangement in the bone anchor may be beneficial when constructing a spinal fixation system, for example, where numerous anchors and rods are positioned on the patient's spine, where the various anchors must be aligned to position the rods therein. Without any friction-fit between the various components of the bone anchor, the head B20 would have a tendency to "flop" over to a side.

In the case of a bone anchor with a biasing member, the biasing member may be positioned in various positions within the bone anchor. For example, the biasing member may be positioned between the planar distal face B514 of the positioner B208 and the distal planar step face B343 of the interior chamber B338 of the receiver member B204. In certain embodiments, the biasing member may be part of the positioner B208. For example, the positioner B208 may include two halves with a biasing member positioned in between the two halves. In this arrangement, the positioner B208 may exert a force against opposite walls B341, B343 of the interior chamber B338. In certain embodiments, a biasing member may be used in conjunction with the crimping of the holes B324 or by itself.

In addition to facilitating a friction-fit between the various components of the bone anchor, exerting a distal force on the positioner B208 may effectuate closer tolerances between the various components of the system. In this way, boney matter or other biological material may be inhibited from migration into the head B20 of the screw B10.

As can be understood from FIGS. 91 and 92, the respective spherical surfaces B629, B348 of the insert B210 and the receiver member B204 combine to form a spherical chamber of the head B20 that receives the respective spherical surfaces B124, B134, B406 of the shank proximal end portion B106 and the retainer ring B206 such that the shank B15 can pivot relative to the head B20 as described above with respect to FIG. 61.

Figure 93:
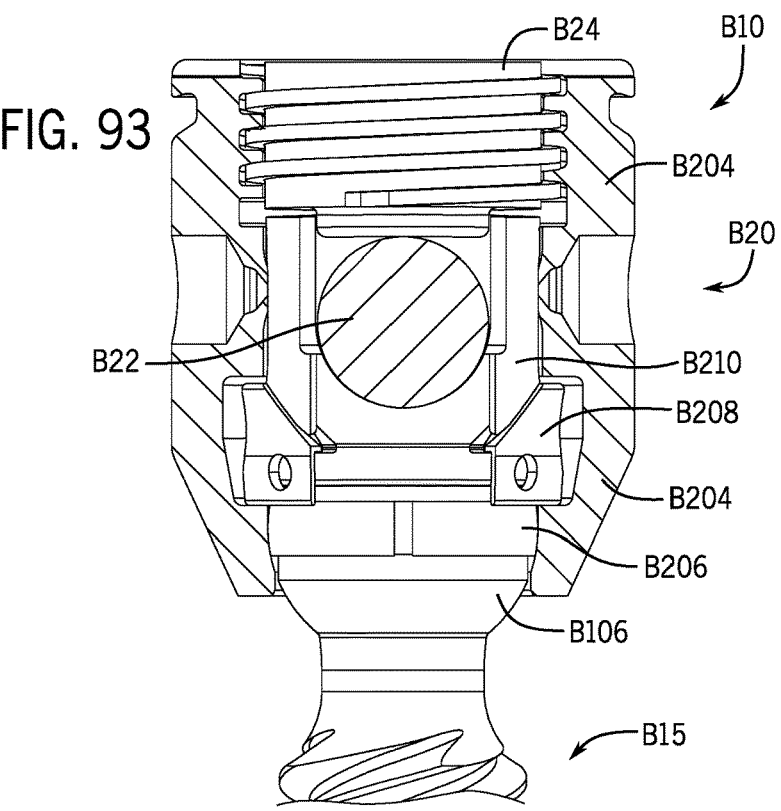
FIG. 93 is the same view as FIG. 92, except the receiver and the implant rod are the only items cross sectioned.

As shown in FIG. 93, which is the same view as FIG. 92, except the receiver member B204 and the implant rod B22 are the only items cross sectioned, a plug B24 can be received in the proximal end of the receiver member B204 via corresponding threads on the receiver member B204 and the plug B24 to compress the implant rod B22 against the insert B210, thereby driving the insert B210 against the shank proximal end portion B106, clamping the spherical surfaces of the shank proximal end portion B106 and the retainer ring B206 mounted thereon between the spherical surfaces of the insert B210 and the receiver member B204. Thus, the implant rod B22 is prevented from displacing within the head B20, and the shank B15 is locked in an orientation relative to the head B20.

Figure 94:
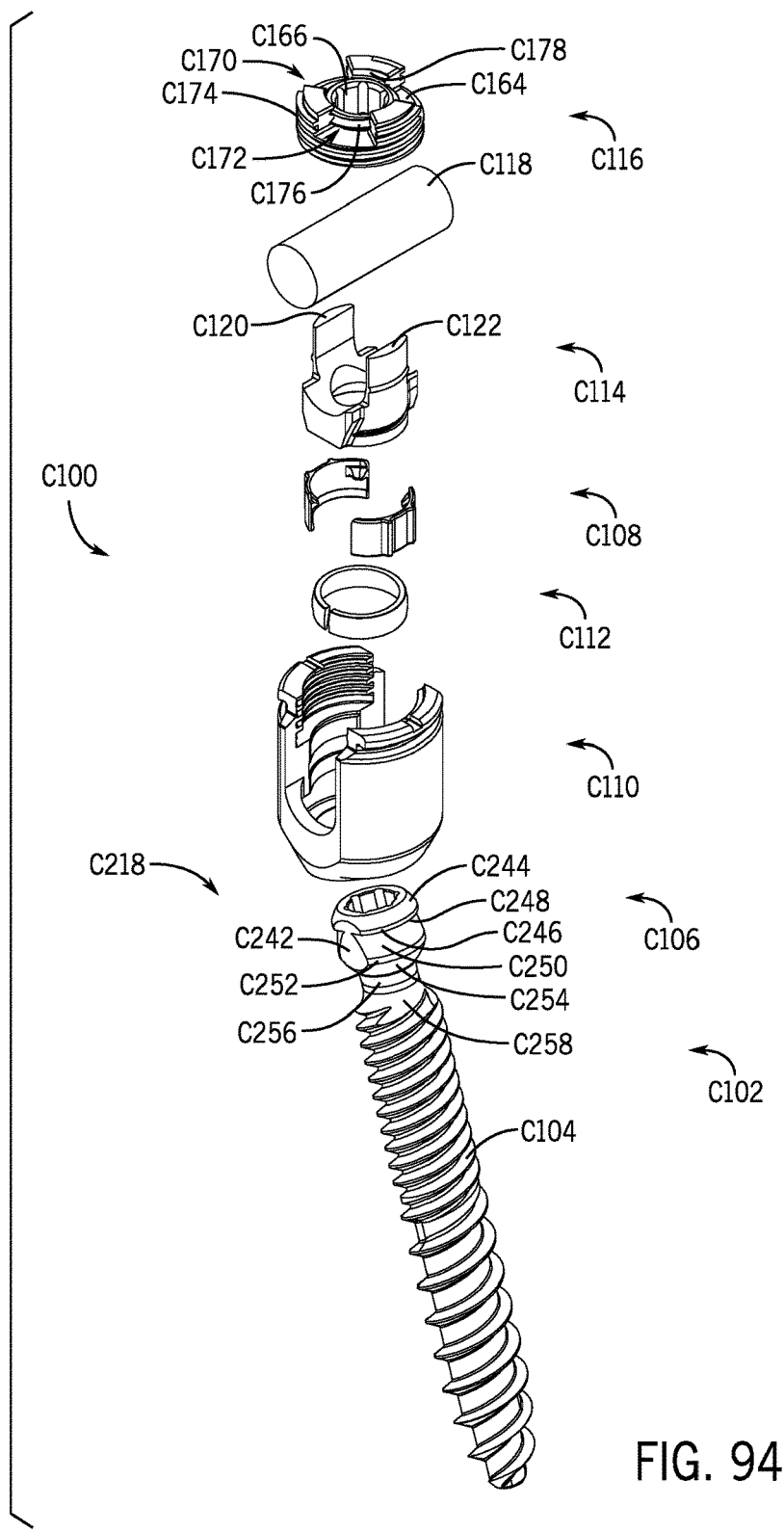
FIG. 94 is an isometric view of another embodiment of a bone anchor as viewed from the proximal end.
Figures 95, 96A:
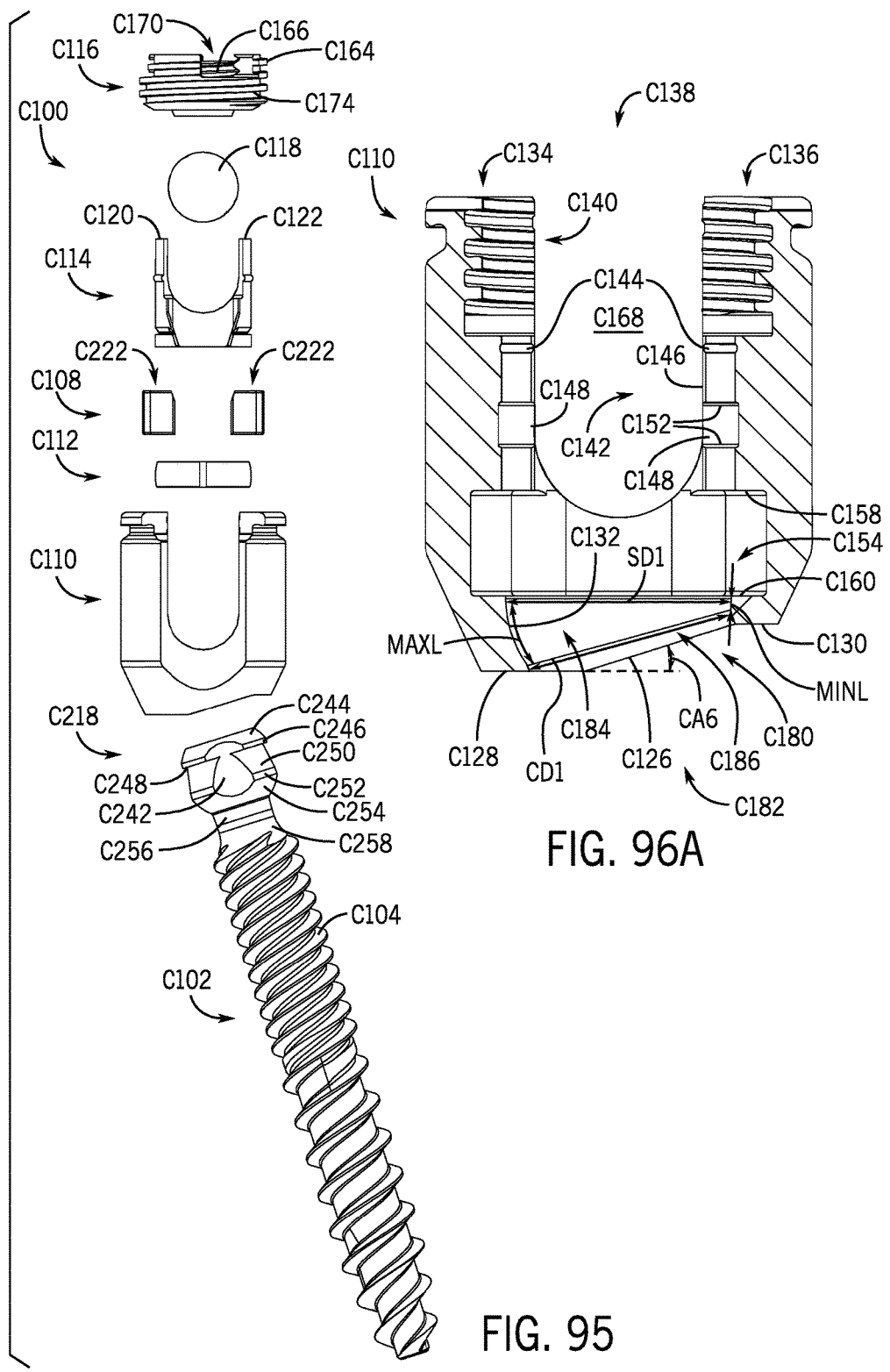
FIG. 95 is a front view of the bone anchor of FIG. 94.
FIG. 96A is a front cross sectional view of the receiver.

With reference to FIGS. 94 and 95, which are, respectively, an isometric exploded view and a front view of another embodiment of a bone screw, the reference number C100 generally represents an embodiment of a multi-planar, multi-axial, or polyaxial bone screw apparatus or assembly with an extended or favored angle, according to the present disclosure. While the illustrated anchor assembly C100 is generally a polyaxial bone screw, it is foreseen that the disclosure could be utilized with other types of spinal implants that utilize pressure inserts, such as polyaxial bone hooks or clamps, for example. The illustrated assembly C100 includes: a shank C102, which further includes a threaded body C104 integral with an upwardly extending upper portion or capture structure C106; a multi-piece positioner C108; a receiver C110; a pivoting retainer structure C112; a compression or pressure insert C114; a closure C116; and a rod or connecting member C118. The shank C102, the retainer C112, the positioner C108, the insert C114, including the extended arms C120 and C122, and the rod C118 are substantially similar to their counterparts in the assembly described in reference to FIGS. 7-9, as discussed above, except that the positioner C108 of the present discussion is multi-part as opposed to a single part. The positioner C108 may be initially assembled with the retainer C112 and insert C114 and further assembled with the shank C102 either prior or subsequent to implantation of the threaded shank body C104 into a vertebra (not shown), as discussed above.

The receiver C110 and the shank C102 cooperate in such a manner that the receiver C110 and the shank C102 can be secured at any of a plurality of angles, articulations or angular alignments with one preferential angle relative to one another and within a selected range of angles from side to side and from front to rear, to enable flexible or articulated engagement of the receiver C110 with the shank C102 until both are locked or fixed relative to each other near the end of an implantation procedure.

Referring now to FIG. 96A, which is a cross-sectional view of the receiver C110, the receiver C110 is substantially similar to the receiver 3010 as discussed above in that a bottom end C124 of the receiver C110 includes a sloped or ramped surface C126 that is radial about the lower opening C128 and positioned between a lower distal surface C128 and an upper distal surface C130 that are parallel to each other, such that an truncated spherical segment C184 C132 is graduated on one side. The sloped surface C132 allows the shank C102 to angulate more in the direction of the slope of ramped surface C132 because there is more bearing surface for the retainer C112 to rotate thereon. The sloped surface C132 angles from horizontal by an angle CA6 that may be about 17.5 degrees. In certain instances, the angle CA6 may be about 15 degrees. In certain instances, the angle CA6 may be about 20 degrees. In certain instances, the angle CA6 may be any degree between about 15 degrees and about 20 degrees.

Still referring to FIG. 96A, a U-shaped channel C168 is formed between the upwardly extending arms C134, C136 of the receiver C110. Further, a proximal end C138 of the receiver C110 includes a threaded region C140 having a female thread pattern that may engage a corresponding male thread pattern of the closure structure C116. The threaded region C140 may, however, be a male thread pattern and the closure structure C116 may be a female thread pattern. The particular thread pattern may be square, reverse angle, or flange, among other possible thread patterns. Distal of the threaded region C140 is a cylindrical throat region C142 having an upper notch C144 and a lower notch C148 each radially projecting into the surface C146 of the throat region C142. The upper notch C144 may receive a protrusion C150, seen in FIG. 97, of the insert C114 in a first orientation, such as a shipping orientation seen in FIG. 105, and may securely support the insert C114 in the first orientation and prevent the insert C114 from distally or proximally displacing during shipping and delivery of the anchor C100 to a medical facility. The lower notch C148 may receive the protrusion C150 after the shank C102 is coupled with the retainer C112 and the pair are distally urged or displaced. At this point, the insert C114 may be distally displaced such that the protrusion C150 transitions from the upper notch C144 to the lower notch C148. As seen in FIG. 96, the lower notch C148 is elongated in a distal-proximal direction such that the protrusion C150 may displace within the lower notch C148, but is caused to remain within the lower notch C148 by the edges or steps C152 at the proximal and distal ends of the notch C148.

Figure 96B:
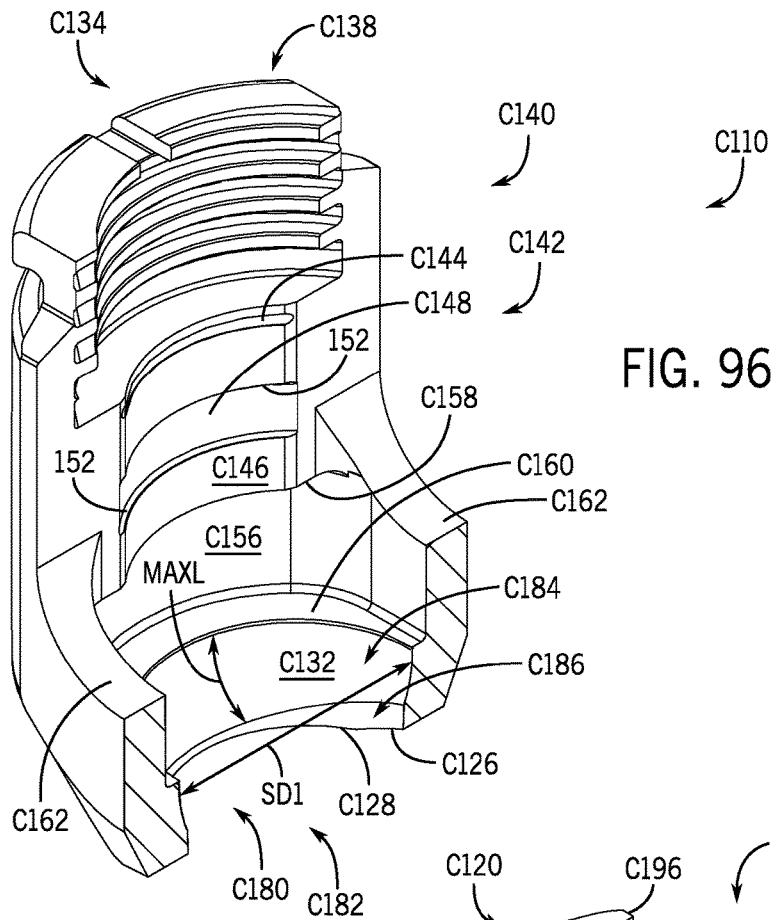
FIG. 96B is an isometric cross sectional view of the receiver.

As seen in FIG. 96A, distal of the cylindrical throat C142 is an expansion chamber C154 having a cylindrical surface C156 that extends between a proximal planar step C158 and a distal planar step C160. As seen in FIGS. 96A and 96B, the expansion chamber C154 extends circumferentially on the extending arms C134, C136 of the receiver C110. That is, the expansion chamber C154 may not extend in a full circumferential manner, but instead only extend into opposing portions of the extending arms C134, C136. Stated another way, the expansion chamber C154 may not extend into the connecting members C162 that extend between the extending arms C134, C136. In this way, the connecting members C162 maintain a wall thickness that is greater than it would be if the expansion chamber C154 extended in a full circumferential manner across the connecting members C162. In other embodiments of the receiver C110, the expansion chamber C162 may extend in a full circumferential manner and may extend through the connecting members C162. In such embodiments, the lessening of the wall thickness of the connecting members C162 may be offset by manufacturing the receiver C110 from a relatively stronger material, adding a flange or other member to couple the proximal ends of the extending arms C134, C136 together, or adding material to the sides of the receiver C110 or connecting members C162.

Each of the expansion chambers C162 may house one of the positioners C108. And, since the positioners C108 are separate from each other, they may not be required to extend and, thus, expand across one or both of the connecting members C162.

Referring back to FIGS. 94-95, the closure structure or nested fastener C116 can be any of a variety of different types of closure structures for use in conjunction with the present disclosure with suitable mating structure on the upstanding arms C134 and C136 of the head or receiver C110. The closure structure C116 as illustrated in the figures includes an outer fastener C164 and an inner set screw C166. The set screw C166 includes an inner feature C168, such as an inner hexagonal faceted surface, for engaging with a tooling head (not shown) to rotationally and distally-proximally displace the set screw C166 relative to the outer fastener C164. The outer fastener C164 cooperates with the receiver C110 of the bone screw assembly C100 to close the head U-shaped channel C168 and to clamp the spinal fixation rod C118 within the bone screw head or receiver C110. The outer fastener C164 includes a structure C170 with slots C172 sized and shaped for engagement with a suitable tool (not shown) for installing the outer fastener C164 to the bone screw head or receiver C110. Thereafter, the inner set screw C166 is displaced until a distal tip of the screw C166 contacts the rod C118.

The outer fastener C164 is substantially cylindrical, having an axis of rotation and an external surface C174 that is threaded and that may be of any type, including V-type threads, buttress threads, reverse angle threads, or square threads. In certain embodiments, the threads of the external surface C174 may be a helically wound square thread form that interlocks with threads on the threaded region C140 of the receiver C110. The threads of the external surface C174 of the closure structure C116 may be of a type that do not exert radially outward forces on the arms C134 and C136 and thereby avoid tendencies toward splaying of the arms C134 and C136 of the bone screw head or receiver C110, when the closure structure C116 is tightly torqued into the head or receiver C110. The outer fastener C164 also includes a through-bore and an inner cylindrical surface C178 having a thread pattern.

The set screw C166 is substantially cylindrical in shape, and includes an outer cylindrical surface C176 with a thread pattern extending from the top to the bottom thereof. The surface C176 and thread pattern are sized and shaped to be received by and mated with the inner threads C178 of the outer fastener C164 in a nested relationship.

It is foreseen that the closure structure C116 may include other features and elements, such as those described previously herein, instead of the outer fastener C164 and the inner set screw C166 shown in FIGS. 94-95. For example, the closure structure C116 may include a fastener with a break-off head, as described previously.

Referring back to FIGS. 96A and 96B, and moving distally from the expansion chamber C154, the receiver C110 includes a truncated spherical segment C184 having the inner spherical surface C132 that is larger on one of the sides than the other. In other words, the inner spherical surface C132 is a spherical segment subtending a maximum angle MAXL of about 36 degrees on one side of the receiver C110 and a minimum angle MINL, opposite the maximum angle MAXL, of about 6 degrees. An arc length associated with the maximum angle MAXL is a function of the radius and the maximum angle MAXL and may, in certain instances, be about 2.4 mm. Similarly, an arc length associated with the minimum angle MINL is a function of the radius and the minimum angle MINL and may, in certain instances, be about 0.37 mm. As will be discussed subsequently, the truncated spherical segment C184 may facilitate the shank C102 pivoting further relative to the receiver C110 in certain directions while being more restricted in other directions. Distal of truncated spherical segment C184 is a cylindrical segment C186 and, then, a distal opening C180 that daylights at a distal end C182 of the receiver C110.

The truncated spherical segment C184 may include a spherical diameter SD1 that is greater than a cylindrical diameter CD1 of the cylindrical segment C186. In this way, once the proximal end C218 of the shank C102 is received within the receiver C110 and is coupled with the retainer C112, a portion of the shank C102 and/or the retainer C112 may be in bearing contact with the spherical surface C132 of the spherical segment C184. And, because the cylindrical diameter CD1 of the cylindrical segment C186 is smaller than the spherical diameter SD1, the proximal end C218 of the shank C102 and the retainer C112 are prevented from exiting the distal opening C180 of the receiver C110. In certain instances, the cylindrical diameter CD1 of the cylindrical segment C186 may be about 0.4 mm less than the spherical diameter SD1 of the truncated spherical segment C184.

Figure 97:
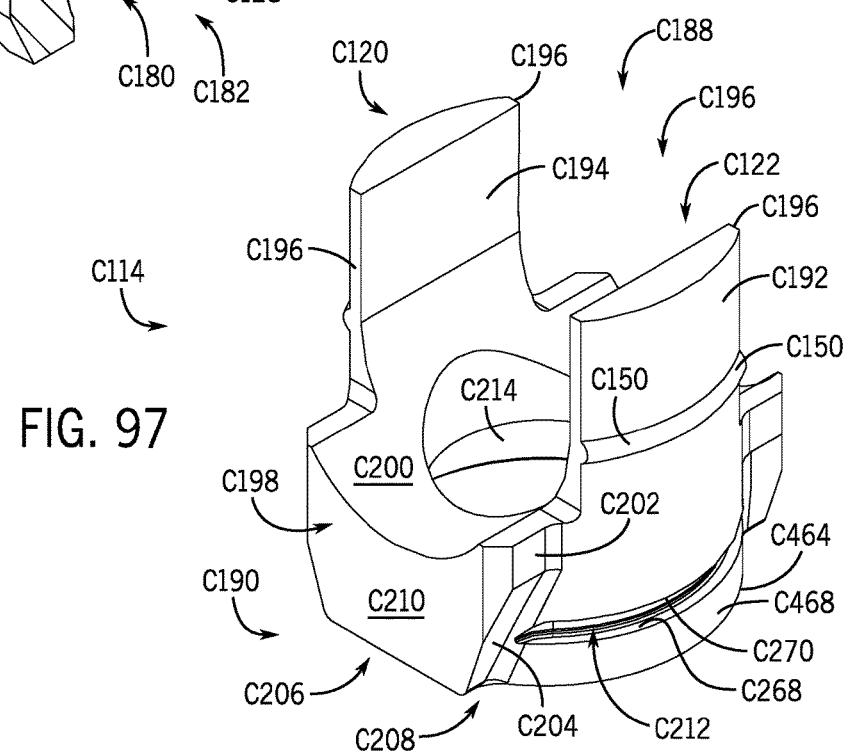
FIG. 97 is an isometric view of the insert.

To begin a discussion of the insert C114, reference is made to FIG. 97, which is an isometric view of the insert C114 from a proximal end C188. As described previously, the insert C114 includes a pair of arms C120, C122 that extend proximally from a body C190 of the insert C114. An external surface C192 of the arms C120, C122 may be cylindrical and sized slightly smaller than an inner diameter of the cylindrical throat segment C142 of the receiver C110. An inner surface C194 of the arms C120, C122 may be planar, and generally parallel to each other, near the proximal end C188, but then may transition into a cylindrical or U-shaped surface near the body C190 of the insert C114. The arms C120, C122 define an opening C196 therebetween for the positioning of the rod C118 (not shown). The external surface C192 of the arms C120, C122 may include the protrusion C150, described previously, which is semi-cylindrical and extends between the planar edges C196 of the arms C120, C122.

The body C190 of the insert C114 may include first and second projections C198 having upper or proximal cylindrical surfaces C200, proximal parallel side surfaces C202, distal angled or converging surfaces C204, and a planar distal surface C206, opposite the cylindrical surface C200, at a distal end C208 of the insert C114. The first and second projections C198 also include planar faces or surfaces C210 that are adjacent the cylindrical surfaces C200, parallel side surfaces C202, distal angled surfaces C204, and the planar distal surface C206.

The external surface C192 of the arms C120, C122, near the distal end C208, include a notch, slot, or recess C212 extending circumferentially between the distal angled surfaces C204 of the first and second protrusions C198. As will be discussed subsequently, the recess C212 may receive a feature, such as a tab, for example, of the positioner C108 to respectively couple the insert C114 and positioner(s) C108 together.

As with previously described embodiments of the insert C114, in FIGS. 80 and 83 for example, the distal end C208 of the body C190 includes a spherical inner surface C214 and a through-bore C216 extending distal-proximal through the insert C114. The spherical inner surface C214 may contact the proximal end C218 of the shank C102 to secure the shank C102 in a desired, locked position.

While the present embodiment of the bone anchor C100 includes an insert C114, it is foreseen that other embodiments of the bone anchor may not include an insert. That is, the rod C118 may directly contact and support the position of the proximal end C218 of the shank C102.

Figure 98:
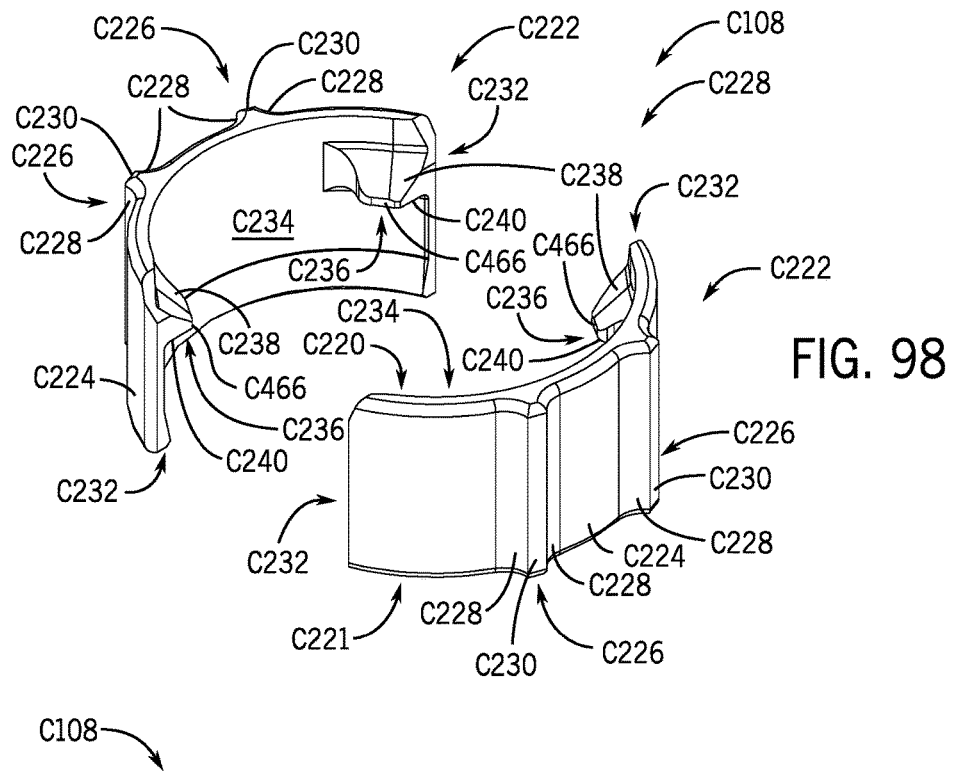
FIG. 98 is an isometric view of the positioner.
Figure 99:
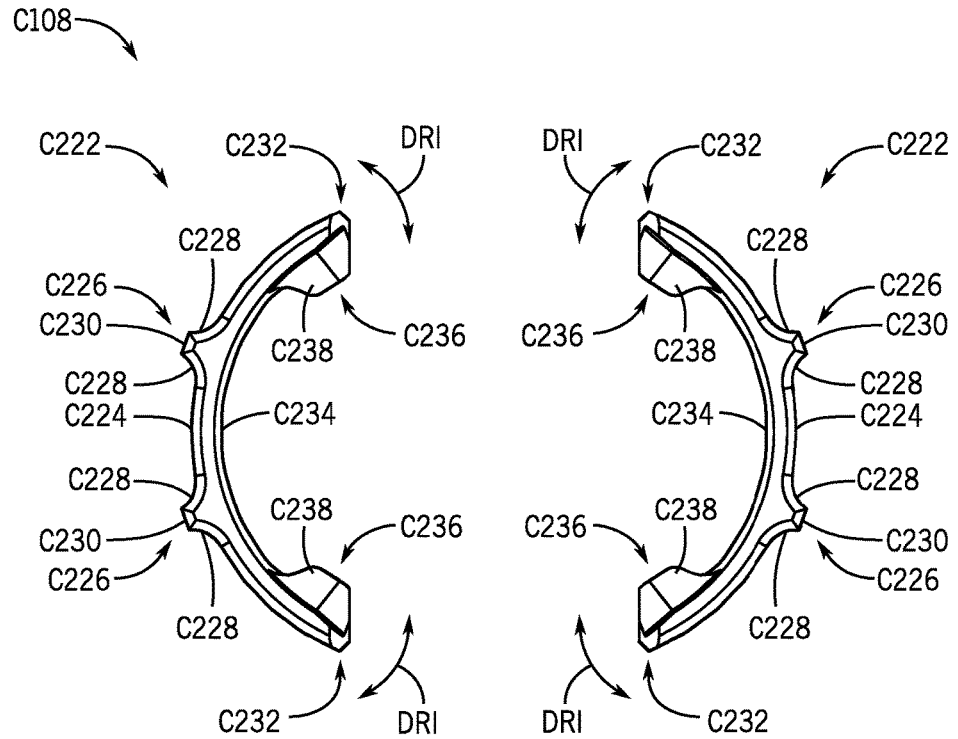
FIG. 99 is a top view of the positioner.

Reference is now made to the multi-piece positioner C108 in FIGS. 98-99, which depict, respectively, an isometric view from a proximal end C220 and a top view of the positioner C108. The multi-piece positioner C108 is similar to previously described embodiments of the positioner, such as the positioner shown in FIGS. 10-11, 16 and 18. And, the positioner C108 of the present discussion is similar to the single piece positioner in FIGS. 76-78, except the positioner C108 of the present discussion is multi-part or multi-piece. Additionally and alternatively, features from the previous embodiments may be incorporated into the embodiment of the present discussion without limitation. Additionally and alternatively, features from the present embodiment may be incorporated into the previously described embodiments of the positioner without limitation.

As seen in FIGS. 98 and 99, the multi-piece positioner C108 includes two positioner members C222 which may be semi-circular members, bands, or tabs that together make up the positioner C108. The positioner members C222 may be sized to fit within the expansion chamber C154 of the receiver C110 and support a position of the retainer C112 within the receiver C110. The positioner members C222 may also couple with the insert C114 and prevent the insert C114 from proximal displacement, once coupled.

Each of the positioner members C222 may include a convex semi-circular outer surface C224 having a pair of ridges, ribs, or protrusions C226 extending from the proximal end C220 to a distal end C221. The ridges C226 include a pair of mirrored curved or sloped surface C228 that terminates in a planar surface C230. While each of the positioner members C222 include two ridges C226, the positioner members C222 may include more or less ridges without departing from the scope of the present disclosure. When the multi-piece positioner C108 is positioned within the expansion chamber C154 the ridges C226 may contact the cylindrical surface C156 of the chamber C154 and act as a spacer such that the semi-circular outer surface C224 is spaced apart or not directly abutting the cylindrical surface C156 of the chamber C154. This way, the positioner members C222 may flex at the radial ends C232 in the direction DR1 shown in FIG. 99 while not being obstructed or restricted by the inner cylindrical surface C156 of the expansion chamber C154.

Each of the positioner members C222 may include a concave semi-circular inner surface C234, opposite the convex semi-circular inner surface C234, extending between the radial ends C232. Near each of the radial ends C232, on the inner surface C234, are tab members C236 having a ramped proximal surface C238 and a planar distal surface C240. The tab members C236 may have many functions. For example, the tab members C236 may support the position of the retainer C112 within the receiver C110 prior to engagement with the shank C102 (i.e., in the shipping orientation) such that the retainer C112 does not proximally displace. As another example, the tab members C236 may engage the recess C212 of the insert C114 and prevent proximal displacement of the insert C114 once the insert C114 is distally advanced within the receiver C110 following coupling of the proximal end C218 of the shank C102 with the retainer C112. Additional and alternative functions are possible and exemplified throughout the figures and the discussion of the various embodiments of the present disclosure. As described herein, the positioner members C22 may, for example, function to hold, align and release the retainer C112.

Referring back to FIGS. 94-95, the pivoting retainer C112 is sized and shaped to couple with the capture structure C106 at the proximal end C218 of the shank C102. The retainer C112 may be any type or configuration of retainer C112 described herein or known in the art. For example, the retainer C112 of FIGS. 94-95 may be the same as the retainers discussed with reference to FIGS. 1-21 and 72-75. For example, the retainer C112 may be sized and shaped to engage with a shank C102 having a universal shank head with a cylindrical, conical, or curvate capture structure C106. As discussed previously, the capture structure C106 at the proximal end C218 of the shank C102 may have different geometries, such as spherical or ball shapes, conical, cylindrical, and curvate shapes, as well as other shapes or geometries.

Referring to the embodiment in FIGS. 94-95, the shank capture structure C106 may include a pair of oppositely oriented flat sides C242 that are spaced apart from each other. Moving proximal to distal, the shank capture structure C106 may also include a proximal spherical segment C244, a proximal cylindrical segment C246, a distally oriented lip or step face C248 which combines to form a stepped and conically tapered notch C250 that receives the retainer C112 thereon. Distal of the conically tapered notch C250 is a distal cylindrical segment C252, and a distal spherical segment C254. Moving distally from the distal spherical segment C254, the shank C102 includes a cylindrical neck segment C256 which transitions to a conical neck segment C258 that increases in diameter moving distally into a proximal end of the threaded portion of the shank body C104.

Figure 100:
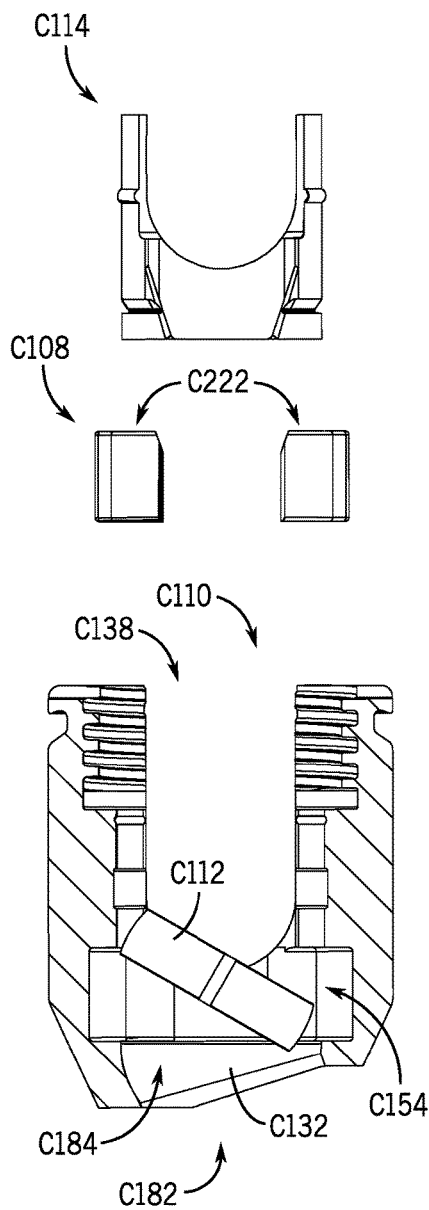
FIG. 100 is an exploded front view of the insert, the positioner, and the retainer positioned within the receiver, which is shown in cross section.
Figure 101:
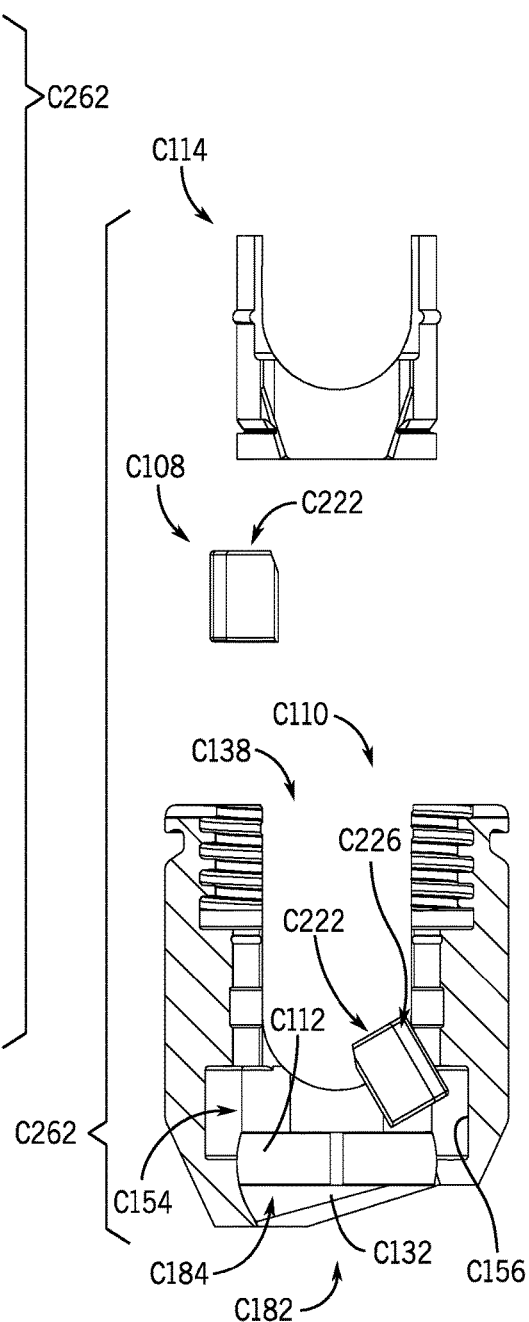
FIG. 101 is the same view as FIG. 100 with one of the positioner members positioned within the receiver.

The discussion of the bone anchor C100 and its assembly will now be discussed with reference made to FIG. 100, which is a front view of the insert C114, the multi-piece positioner C108, and the retainer C112 partially positioned within the receiver C110, which is viewed in the same cross-sectional view of FIG. 96A. As seen in the figure, the components of the bone anchor C100 are initially in an unassembled state. Initially, the retainer C112 may be positioned in the receiver C100 from the top or proximal end C138. The retainer C112 may be seated within a proximal portion of the truncated spherical segment C184, as seen in FIG. 101. In this position, the retainer C112 is partially within the expansion chamber C154 while being supported by the inner spherical surface C132 of the truncated spherical segment C184. Once the retainer C112 is in the position as shown in FIG. 101, each of the positioner members C222 of the multi-piece positioner C108 may be distally advanced within the receiver C110 from the proximal end C138 so as to be positioned within the expansion chamber C154 such that the ridges C226 abut the cylindrical surface C156 of the chamber C154, as seen in FIGS. 101-103. At this point, as seen in FIG. 104, the retainer C112 may be proximally displaced such that a proximal edge C260 of the retainer C112 abuts or is adjacent the tab members C236 of the positioner members C222 of the positioner C108. The insert C114 may then be distally advanced through the proximal end C138 of the receiver C110 until the protrusion C150 is received within the upper notch C144 of the receiver C110, as seen in FIG. 105. This is the shipping state or orientation where the receiver subassembly or head assembly C262 (i.e., the assemblage of the receiver C110, insert C114, positioner C108, and retainer C112 as shown in FIG. 105) of the bone anchor C100 is ready to couple with the proximal end C218 of the shank C102. As discussed herein, the terms receiver subassembly and head assembly may be used interchangeably. Once in the shipping state, the head assembly C262 may be packaged and shipped or otherwise delivered to the surgeon or medical facility. Alternatively, the head assembly C262 may be packaged with other head assemblies C262 of the same or a different configuration. For example, a kit of multiple head assemblies C262, as shown in FIG. 105, may be packaged together and delivered to a medical facility. As another example, a kit of head assemblies C262 may include one or more multi-planar head assemblies, and/or one or more mono-planar head assemblies, and/or one or more favored angle head assemblies. Different combinations of head assemblies are possible and contemplated herein. The kit of head assemblies C262 may optionally include any of a tray, sterile packaging, and any number and configuration of shanks C102 for a given procedure.

Figures 106, 107:
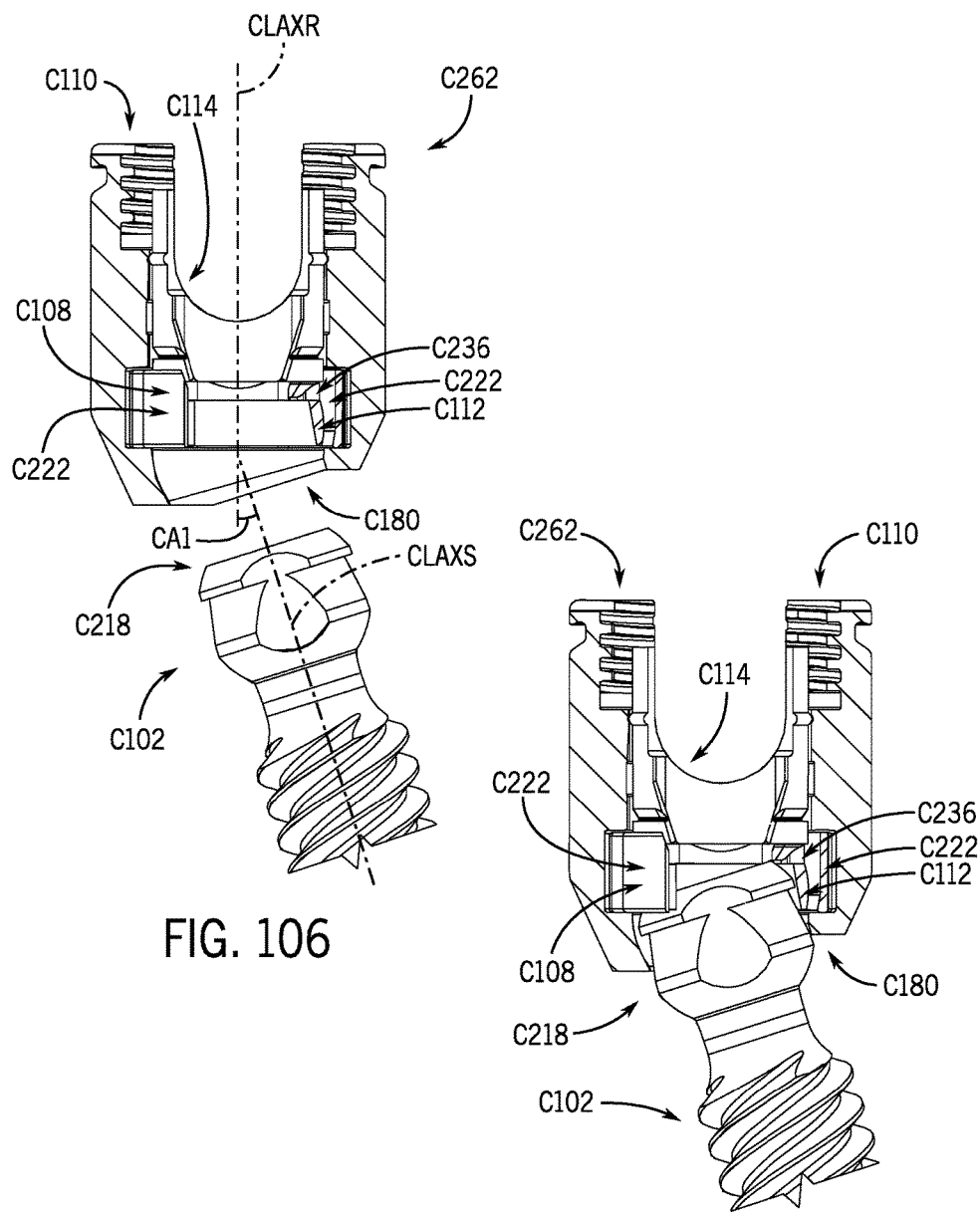
FIG. 106 depicts a shank aligning with the distal opening of the head assembly.
FIG. 107 depicts the shank entering the distal opening of the head assembly.

Coupling of the shank C102 and the head assembly C262 will now be discussed with reference to the following figures. As seen in FIG. 106, which is a front view of the head assembly C262 of FIG. 105 with a shank C102 positioned near the distal opening C180, the shank C102 may be angled relative to a longitudinal axis CLAXR of the receiver C110. More particularly, a longitudinal axis CLAXS of the shank C102 may be angled relative to the longitudinal axis CLAXR of the receiver C110 by an angle CA1 about 43 degrees in order to couple the shank C102 and the head assembly C262. In certain embodiments, angle CA1 may be about 30 degrees. In certain embodiments, angle CA1 may be about 35 degrees. In certain embodiments, angle CA1 may be about 40 degrees. In certain embodiments, angle CA1 may be about 45 degrees. The shank C102 may be angled relative to the receiver C110 because of the particular geometry and orientation of the distal end C182 of the receiver C110.

Figures 108, 109:
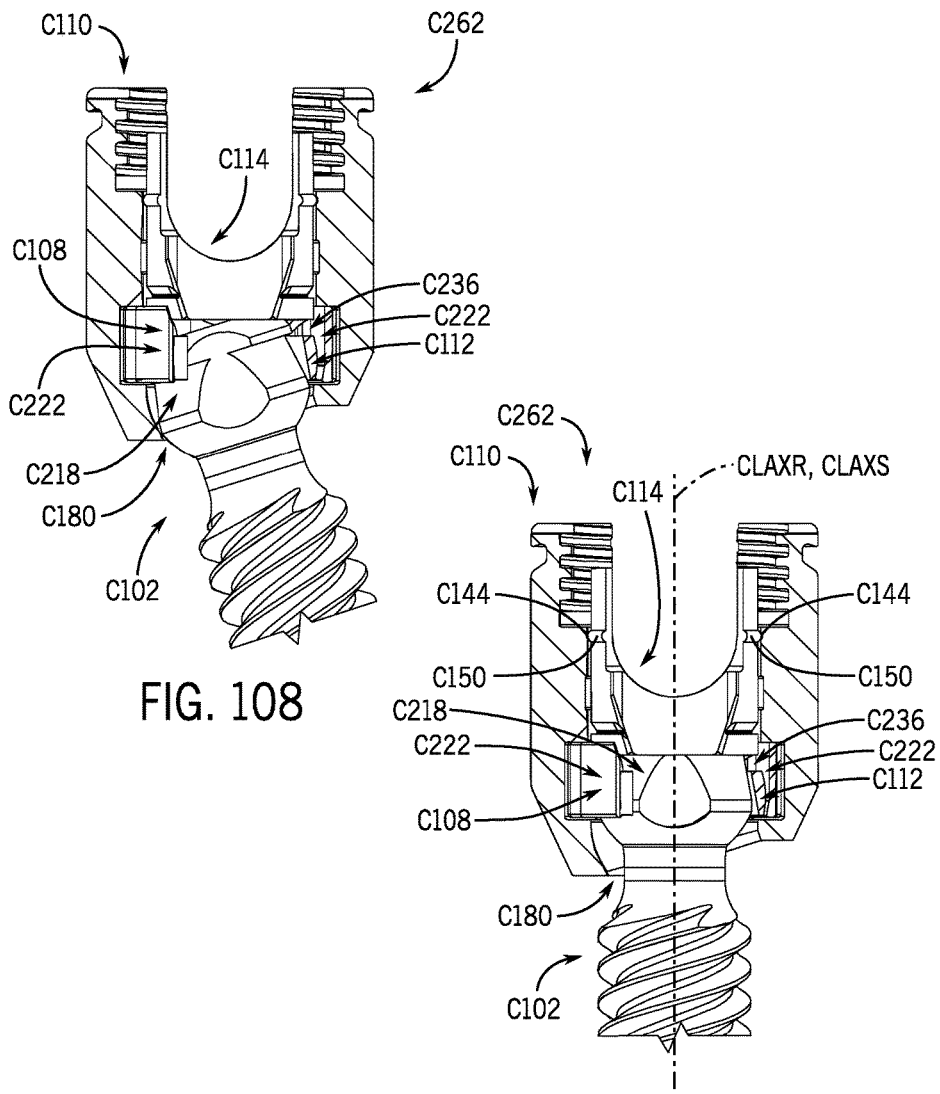
FIG. 108 depicts the shank extending into the distal opening and expanding the retainer and the positioner.
FIG. 109 depicts the shank aligning with and extending into the head assembly in a state of maximum proximal displacement.

Once the shank C102 is oriented relative to the receiver C110 such that the longitudinal axis CLAXS of the shank C102 is angled relative to the longitudinal axis CLAXR of the receiver C110 by the angle CA1, as shown in FIG. 106, the shank C102 may be proximally displaced such that the proximal end C218 of the shank C102 is received within the distal opening C180 of the receiver C110, as shown in FIG. 107. As seen in FIG. 107, the proximal end C218 of the shank C102 may extend into the receiver C110 such that the proximal end C218 is partially positioned within an opening formed by the retainer C112. At this point, the proximal end C218 of the shank C102 may be further proximally displaced, which causes the retainer C112 to further expand into engagement and expansion with the positioner C108. The shank C102 may be further proximally advanced relative to the receiver C110, as seen in FIG. 108, which depicts the retainer C112 in maximum expansion. At this point, the shank C102 may be pivoted relative to the receiver C110 such that the longitudinal axis CLAXS of the shank C102 is generally parallel and coaxial with the longitudinal axis CLAXR of the receiver C110, as seen in FIG. 109. As seen in the figure, the shank C102 may be at its maximum proximal displacement relative to the receiver C110. In this orientation, the shank C102 is prevented from further proximal displacement by the proximal end C218 of the shank C102 contacting the spherical inner surface C214 (not shown in FIG. 109) of the insert C114. And, the insert C114 is prevented from proximal displacement relative to the receiver C110 by the protrusion C150 being positioned within the upper notch C144 of the receiver C110.

Figures 110, 111:
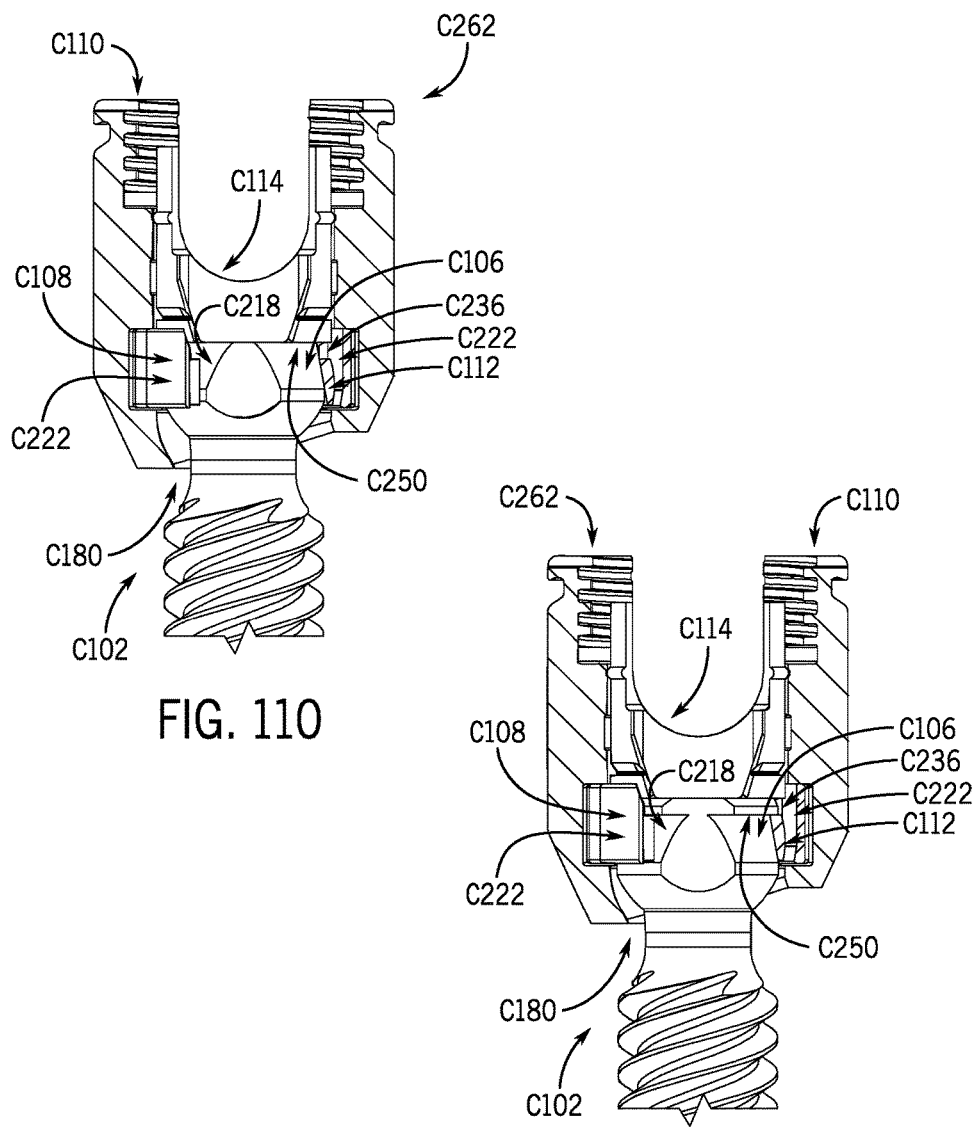
FIG. 110 depicts the retainer snapping on the shank capture structure of the shank.
FIG. 111 depicts distal displacement of the shank and retainer coupled together.
Figure 112:
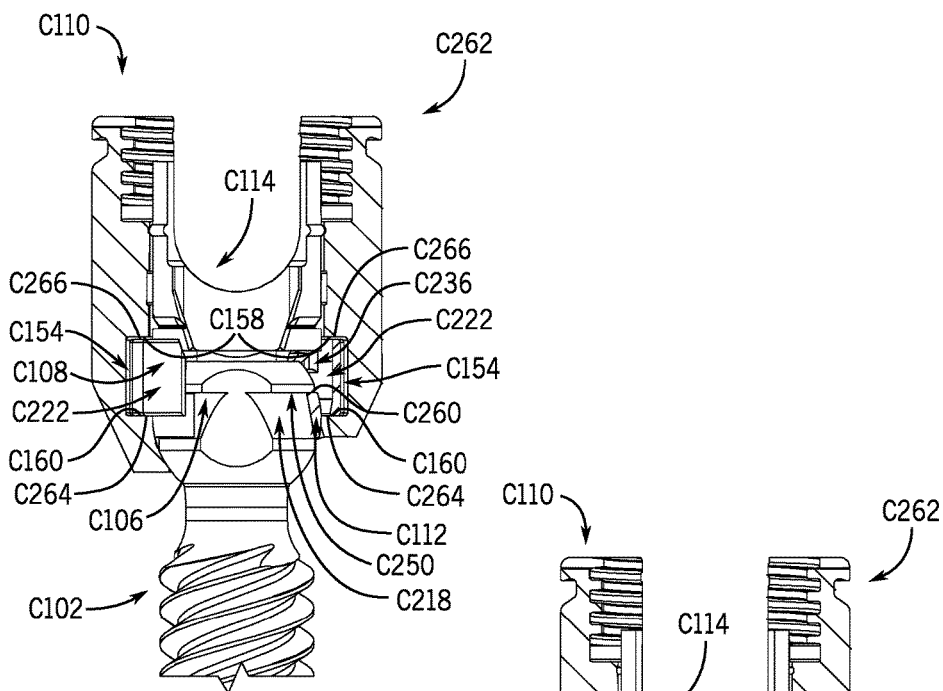
FIG. 112 depicts further distal displacement of the shank and retainer coupled together.

About when the shank C102 is at its proximal-most displacement relative to the receiver C110, the retainer C112 snaps or couples onto the capture structure C106 of the proximal end C218 of the shank C102, as seen in FIG. 110. As the retainer C112 snaps or couples onto the conically tapered notch C250, the retainer C112 and the positioner C108 may contract. Once the retainer C112 is coupled with the capture structure C106 of the shank C102, the shank C102 may be distally displaced relative to the receiver C110, as seen in FIG. 111. Further distal displacement of the shank C102 relative to the receiver C110, as seen in FIG. 112, may cause the proximal edge C260 of the retainer C112 to distally displace away from the tab members C236 of the positioner C108. As seen in the figure, the positioner members C222 of the positioner C108 are positioned in the expansion chambers C154 and are prevented from exiting the chamber C154 because the distal edge C264 may contact the planar distal step C160 of the chamber C154. Similarly, the positioner C108 is prevented from proximal displacement when the shank C102 is proximally displaced relative to the receiver C110 because the proximal edge C266 may contact the proximal planar step C158 of the expansion chamber C154.

Figure 113:
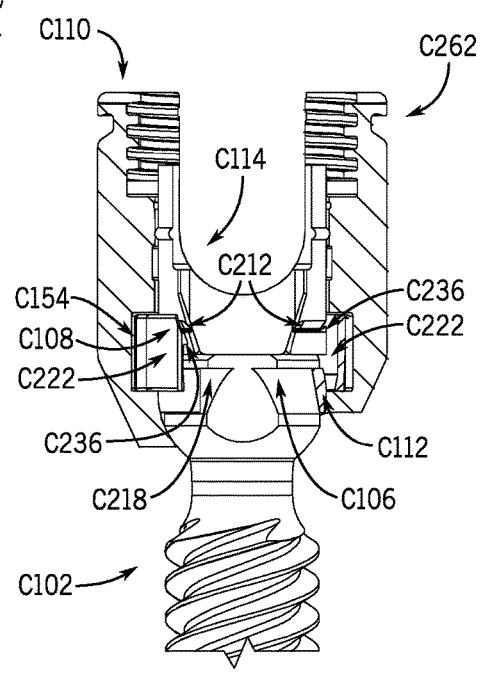
FIG. 113 depicts distal displacement of the inserts relative to the receiver.
Figure 114:
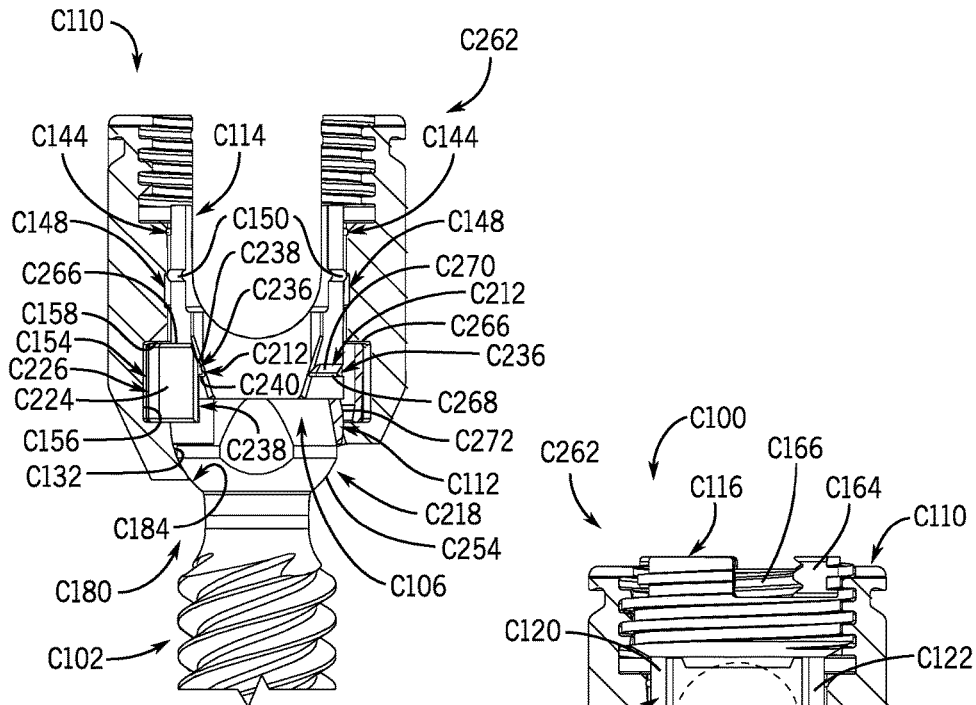
FIG. 114 depicts the positioner coupling with the insert.

Referring to FIGS. 113 and 114, the insert C114 may be distally displaced relative to the receiver C110. FIG. 113 depicts a maximum expansion of the positioner C108 over the insert C114. As seen in FIG. 113, the tab members C236 may be positioned distal of the recess C212 and, as seen in FIG. 114, the tab members C236 may snap into the recess C212 causing the positioner C108 and the insert C114 to operably couple together. Once coupled, the insert C114 is prevented from proximal displacement because the tab member C236 of the positioner C108 is engaged with the recess C212 of the insert C114. More particularly, the planar distal surface C240 of the tab members C236 abuts a corresponding planar distal surface C268 of the insert C114. Thus, when a proximal force is exerted on the insert C114, the force is generally normal to a plane defined by the surfaces C240, C268, which may prevent the disengagement of the insert C114 and the positioner C108. As discussed previously, a proximal force exerted on the positioner C108 (e.g., via a force exerted on the insert C114 when coupled to the positioner C108) may not cause the positioner C108 to proximally displace because each of the positioner members C222 of the positioner C108 is positioned within the expansion chamber C154 and is, thus, restrained from proximal displacement by the proximal planar step C158 abutting the proximal edge C266 of each of the positioner members C222.

Still referring to FIG. 114, when the insert C114 is forced distally, a proximal ramped surface C270, adjacent the distal planar surface C268, of the radially extending recess C212 of the insert C114 abuts the ramped proximal surface C238 of the tab members C236 of the positioner members C222 and may cause the positioner members C222 to expand at the radial ends C232 into the expansion chamber C154. It is noted that the ridges C226 on the outer surface C224 of the positioner members C222 may contact the inner cylindrical surface C156 of the expansion chamber C154, which may provide a space between the outer convex surface C224 of the positioner members C222 and the cylindrical surface C156 so as to provide room for the expansion or flexing of the radial ends C232.

Distal displacement of the insert C114 may be constrained when a distal force is applied because the spherical inner surface C214 (not shown in FIG. 114) of the insert C114 may contact the proximal end C218 of the shank C102, which in turn may cause an outer bearing surface C272 of the retainer C112 and the distal spherical segment C254 of the proximal end C218 of the shank C102 to come into bearing contact with the spherical inner surface C132 of the truncated spherical segment C184 of the receiver C110. Thus, the distal force of the retainer C112 and the proximal end C218 of the shank C102, as applied via a distal force from the insert C114, may be opposed by the inner spherical surface C132 of the truncated spherical segment C184 of the receiver C110. In this way, the shank C102 and retainer C112 may be prevented from distally exiting the distal opening C180 of the receiver C110. That is, when the retainer C112 is coupled to the shank capture structure C106, a diameter of the shank C102 and the retainer C112 may be larger than the cylindrical diameter CD1 (not shown in FIG. 114) of the distal opening C180 of the receiver C110, thus, preventing dislodgement or uncoupling of the head assembly C262 and the shank C102.

Figure 115:
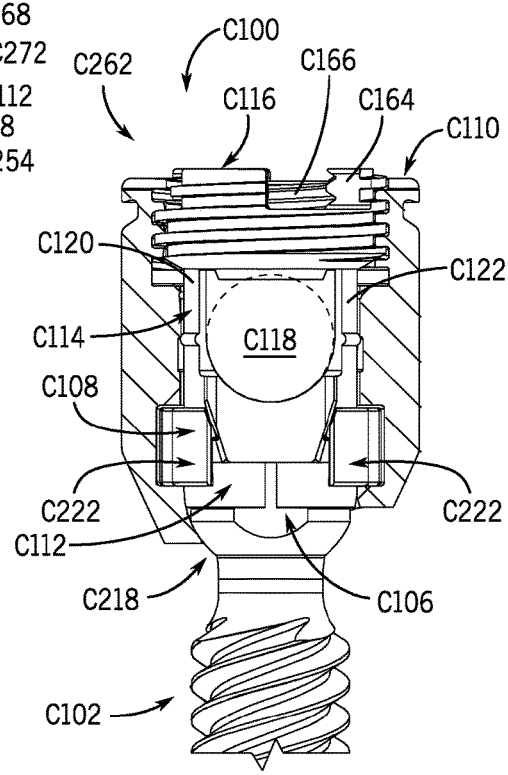
FIG. 115 depicts the closure structure engaging with the receiver and being positioned against the rod.

FIG. 115 depicts the rod C118 being positioned between the extending arms C120, C122 of the insert C114 and the closure structure C116 being secured to the receiver C110. It is noted that the discussion of the distal force applied via the insert C114 may be applied via the closure structure C116 exerting a distal force on the rod C118, which then transfers the force to the insert C114. As seen in FIG. 115, the insert C114 may be distally displaced via distal advancement of the outer fastener C164, which may exert a distal force on the upward arms C120, C122 of the insert C114. Because the outer fastener C164 may be utilized without the inner set screw C166, the insert C114 can be distally displaced prior to use of the inner set screw C166 and the rod C118. Once the insert C114 is distally positioned via the outer fastener C164, the rod C118 may be positioned between the arms C120, C122 of the insert C114 and the inner set screw C166 may be distally advanced to apply a compressive force against the rod C118, which thereby also applies a force against the insert C114.

Once the closure structure C116 is securely fastened to the receiver C110 in a friction-fit arrangement, as determined by the particular structure used, the bone anchor C100 is in a fully assembled state. At this point, the shank C102 may be angled relative to the head assembly C262 in a suitable manner for a particular medical procedure.

Figures 116, 117A:
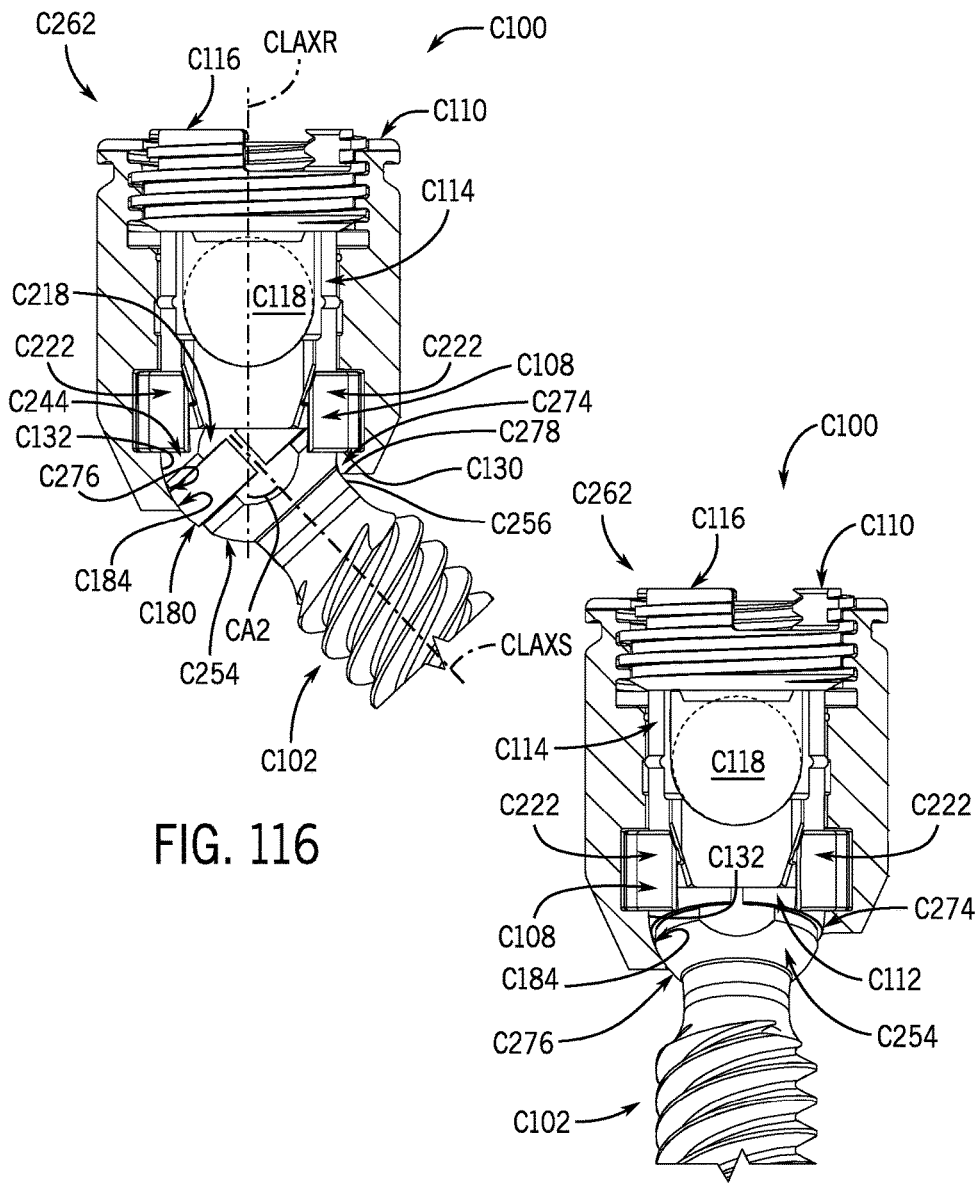
FIG. 116 depicts the bone anchor in a first angled position.
FIG. 117A depicts the bone anchor angling in a second position.
Figure 117B:
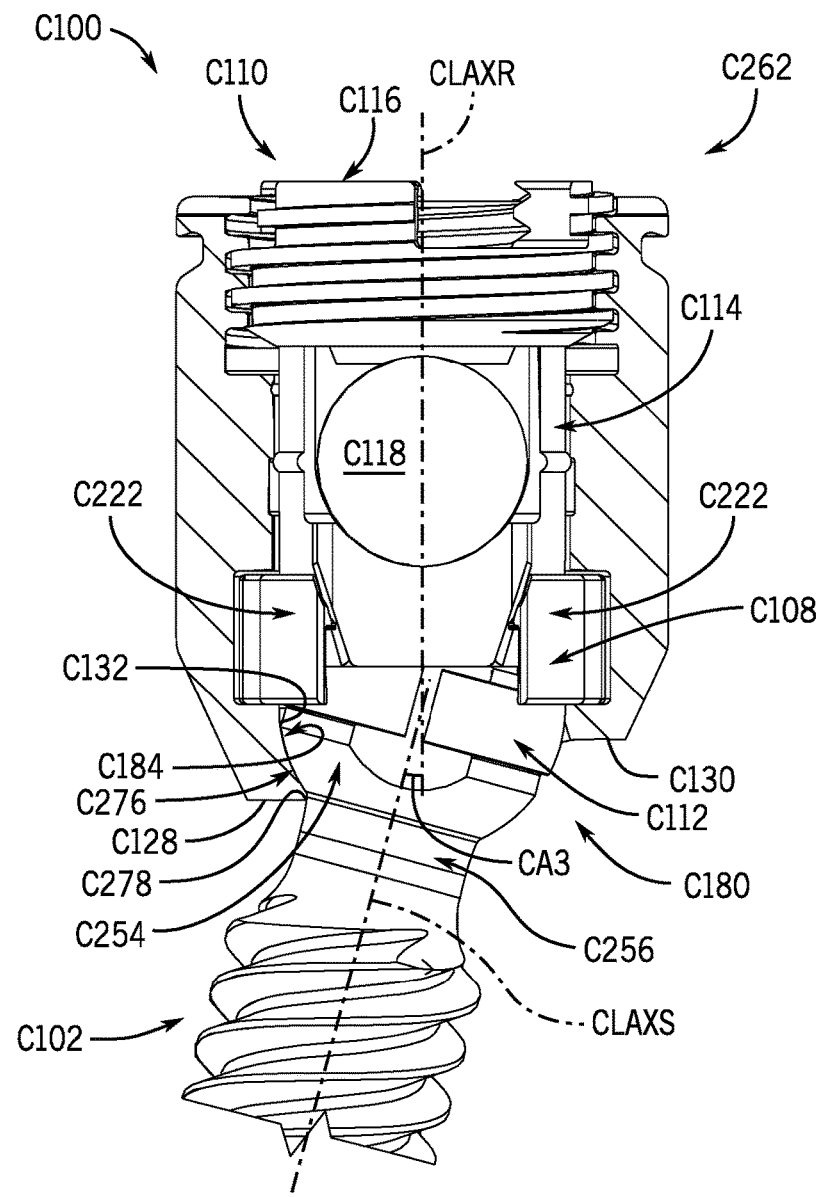
FIG. 117B depicts the bond anchor in a third angled position.

Reference is made to FIGS. 116-117B, which depict the shank C102 in various degrees of angulation relative to the head assembly C262. FIG. 116 depicts the longitudinal axis CLAXS of the shank C102 angled relative to the longitudinal axis CLAXR of the receiver C110 by an angle CA2, which may be about 43 degrees in a certain plane (e.g., transverse plane). In certain embodiments, the angle CA2 may be about 30 degrees. In certain embodiments, the angle CA2 may be about 35 degrees. In certain embodiments, the angle CA2 may be about 40 degrees. In certain embodiments, the angle CA2 may be about 45 degrees. As seen in FIG. 116, the shank C102 may be prevented from rotating beyond the angle CA2 by the proximal end C218 of the shank C102, or more particularly, the cylindrical neck segment C256 of the shank C102 contacting a distal edge C278 defining the distal opening C180 where a smallest portion C274 of the inner spherical surface C132 of the truncated spherical segment C184 meets the upper distal surface C130 of the receiver C110. In this position, the largest portion C276 of the inner spherical surface C132 of the truncated spherical segment C184 may be in bearing contact with the retainer C112 and/or the proximal end C218 of the shank C102 (e.g., proximal spherical segment C244, distal spherical segment C254).

As seen in FIG. 117A, the shank C102 is angled relative to the head assembly C262 by an angle of about 20 degrees in a certain plane (e.g., sagittal plane). In certain embodiments, the shank C102 may be angled relative to the head assembly by an angle of 15 degrees in the sagittal plane. In certain embodiments, the shank C102 may be angled relative to the head assembly by an angle of 25 degrees in the sagittal plane. In certain embodiments, the shank C102 may be angled relative to the head assembly by any angle within a range of about 15 degrees to about 25 degrees in the sagittal plane. As seen in the figure, the plane of rotation of the shank C102 is collinear with an axis of extension of the rod C118. While FIG. 117A does not show the distal edge C278 defining the distal opening C180 limiting the angling of the shank C102 because the receiver C110 is viewed in a cross-section, it can be seen that the smallest portion C274 and the largest portion C276 of the inner spherical surface C132 of the truncated spherical segment C184 may be in bearing contact with the retainer C112 and/or the proximal end C218 of the shank C102 (e.g., proximal spherical segment C244 (not shown in FIG. 117A), distal spherical segment C254). In certain embodiments, the receiver C110 may be in contact with the retainer C112, the proximal spherical segment C244, distal spherical segment C254, or any combination thereof.

As seen in FIG. 117b, the shank C102 is rotated or angled relative to the head assembly C262 oppositely, but within the same plane, as shown in FIG. 116. As seen in the figure, the longitudinal axis CLAXS of the shank C102 angled relative to the longitudinal axis CLAXR of the receiver C110 by an angle CA3, which may be about 14 degrees in a certain plane (e.g., transverse plane). In certain embodiments, the angle CA3 may be about 10 degrees. In certain embodiments, the angle CA3 may be about 12 degrees. In certain embodiments, the angle CA3 may be about 16 degrees. In certain embodiments, the angle CA3 may be about 18 degrees. As seen in FIG. 117B, the shank C102 may be prevented from rotating beyond the angle CA3 by the proximal end C218 of the shank C102, or more particularly, the cylindrical neck segment C256 of the shank C102 contacting the distal edge C278 defining the distal opening C180 where the largest portion C276 of the inner spherical surface C132 of the truncated spherical segment C184 meets the lower distal surface C128 of the receiver C110. In this position, the smallest portion C274 of the inner spherical surface C132 of the truncated spherical segment C184 may be in bearing contact with the retainer C112 and/or the proximal end C218 of the shank C102 (e.g., distal spherical segment C244). As illustrated in the previous figures, the geometry and configuration of the distal end C182 of the receiver C110, in particular, the geometry and configuration of the truncated spherical segment C184, the upper and lower distal surfaces C130, C128, and the ramped surface C126 (not shown in FIG. 117B), may affect the degree to which the shank C102 may rotate or angle relative to the head assembly C262 to facilitate a favored angle type of screw design. Other geometries and configurations are possible and contemplated herein to facilitate a head assembly C262 that may allow a shank C102 to rotate different degrees in the various plane relative to the head assembly C262.

Figures 118, 119:
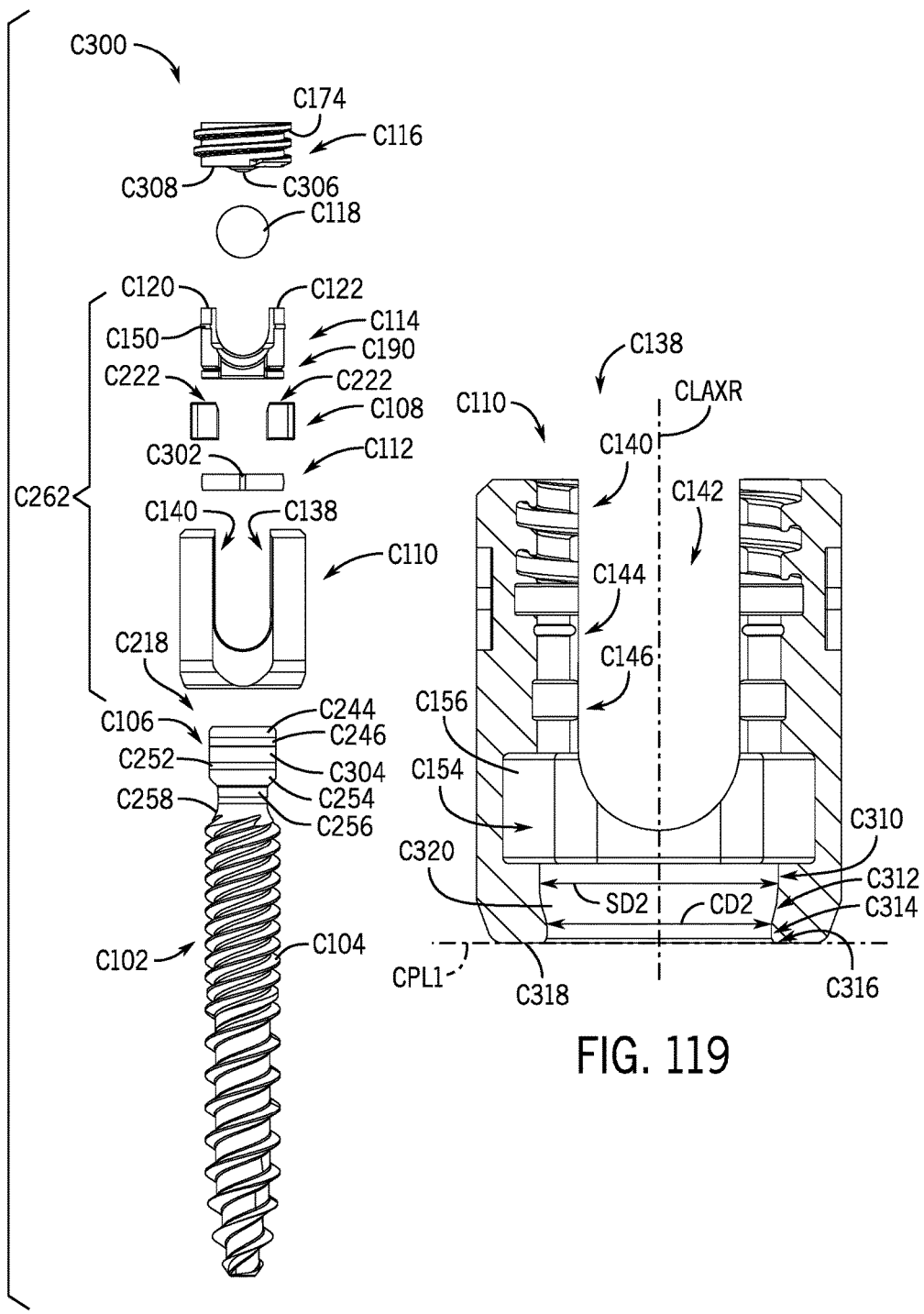

The following discussion will focus on another embodiment of a multi-planar or polyaxial bone anchor C300, as seen in a front exploded view of FIG. 118, that includes similar features and elements to previously described embodiments. In particular, the positioner C108 and the rod C118 are substantially unchanged from the previous embodiment of the muli-planar favored angle bone anchor C100 discussed with reference to FIGS. 94-117B. The retainer C112 and the shank C102 including the shank capture structure C106 are slightly modified in that the retainer C112 is similar to the retainer described in FIG. 22 and the shank C102 includes a capture structure C106 similar to the structure shown in FIG. 21. That is, the retainer C112 includes a curved, convex inner surface C302 and the capture structure C106 of the shank C102 of the present discussion includes a corresponding curvate, concave surface C304. When coupled together, the convex inner surface C302 of the retainer C112 will be matingly received by the concave surface C304 of the capture structure C106 of the shank C102. Otherwise the shank C102 is similar to the previously described embodiment in that it includes a proximal spherical segment C244, a proximal cylindrical segment C246, a distally oriented lip or step face C248 which combines to form the curvate notched surface C304 that receives the retainer C112 thereon. Distal of the curvate notched surface C304 is a distal cylindrical segment C252, and a distal spherical segment C254. Moving distally from the distal spherical segment C254, the shank C102 includes a cylindrical neck segment C256 which transitions to a conical neck segment C258 that increases in diameter moving distally into a proximal end of the threaded portion of the shank body C104. While the retainer C112 and the shank capture C106 are described as being curvate, other geometries and configurations such as those described herein and known to those skilled in the art.

Still referring to FIG. 118, the closure structure C116 is similar to the closure structure described in reference to FIGS. 1 and 2, and the discussion is applicable to the figures of the present discussion. The closure structure C116 may be substantially cylindrical and includes an external surface C174 that is threaded and that may be of any type, including V-type threads, buttress threads, reverse angle threads, or square threads. In certain embodiments, the threads of the external surface C174 may be a helically wound square thread form that interlocks with threads on the threaded region C140 of the receiver C110.

The closure structure C116 may include a break-off head (similar structures seen in FIGS. 4, 6, 9, 13, 15, and 18) designed to allow such a head to break from a base of the closure at a preselected torque, for example, at 70 to 140 inch pounds. Such a closure structure would use the internal drive for closure removal.

The closure structure C116 as seen in FIG. 118 may be rotated, using a hex tool (not shown) until a selected pressure is reached at which point the rod C118 engages the compression insert 14, further pressing the insert spherical surface against the proximal end C218 of the shank C102.

As the closure structure C116 rotates and moves downwardly into the respective receiver C110, a point C306 and bottom surface rim C308 may engage and penetrate the rod surface C118, and the closure structure C116 presses downwardly against and biases the rod or connecting member C118 into engagement with the insert C114 that thereby urges the shank proximal end C218 toward the distal opening C180 of the receiver and into locking engagement therewith, with the pivoting retainer C112 frictionally abutting the inner spherical surface C132 of the receiver C110.

The insert C114 is similar to the previously described embodiment of the insert C114 in FIGS. 94-117B, except the upwardly extending arms C120, C122 may not extend as far from the body C190 of the insert C114. One reason for this is because of the particular closure structure C116 shown in FIG. 118. More particularly, the illustrated closure structure C116 is a single piece structure that may only contact the rod C118 to transmit a distal force to the insert C114. The multi-piece closure structure C116 of FIGS. 94-95 allows for distally displacing the insert C114 with the outer fastener and, then, securing the rod C118 with the inner set screw. In FIG. 118, the closure structure C116 is a single piece and, therefore, the insert C114 may not be distally displaced without the rod C118 in position within the arms C120, C122 of the insert C114. The depiction of a single piece closure structure C116 in FIG. 118 is merely for illustrative purposes. That is, a multi-piece closure structure C116, as shown in FIGS. 94-95, or any of the other closure structures detailed herein and known in the art may be substituted without limitation.

Reference is made to FIG. 119, which is a front cross-sectional view of the receiver C110. The proximal end C138 of the receiver C110 is similar to the receiver C110 shown in FIGS. 96A and 96B in that it includes a threaded region C140 for receiving the threads C174 of the closure structure C116. The cylindrical throat segment C142 includes an upper notch C144 and a lower notch C146 for receiving the protrusion C150 of the insert C140, as previously described. The expansion chamber C154 is also similar to the previously described embodiment of the receiver C110 in FIGS. 96A and 96B in that it includes a cylindrical surface C156 on opposing sides of the receiver C110. The present embodiment differs from the previously described embodiment in FIGS. 96A-96B in that distal of the expansion chamber C154 is an upper distal cylindrical segment C310, a spherical segment C312, a lower distal cylindrical segment C314, and a beveled edge C316. The beveled edge C316 transitions to a distal planar surface C318 defining a plane CPL1 that is generally normal or perpendicular to the longitudinal axis CLAXR of the receiver C110. The spherical segment C312 includes a spherical inner surface C320 having a spherical diameter SD2 that is greater than a cylindrical diameter CD2 of the lower distal cylindrical segment C314. In certain embodiments, the difference between the spherical diameter SD2 and the cylindrical diameter CD2 may be about 0.4 mm. In certain embodiments, the difference between the spherical diameter SD2 and the cylindrical diameter CD2 may be within a range of about 0.25 mm to about 0.6 mm. The difference in the diameters SD2, CD2 allows the proximal end C218 of the shank C102 to be retained within the receiver C110 without uncoupling.

Because the spherical inner surface C320 is symmetric and the distal planar surface C318 is of an unchanging elevation around its perimeter, the receiver C110 may allow multi-planar or poly-axial movement of a shank (not shown) positioned within the receiver C110, where movement of the shank is similar in all planes.

Assembly of the bone anchor C300 into the shipping state is accomplished in the same or a similar manner as discussed with reference to the previous embodiment of the bone anchor C100, except the shank C102 may not need to be angled relative to the head assembly C262 upon coupling the shank C102 with the head assembly C262. That is, the longitudinal axis CLAXS of the shank C102 may be coaxially aligned with the longitudinal axis CLAXR of the receiver C110. Reference is made to FIG. 120, which depicts the bone anchor C300 with the head assembly C262 coupled with the shank C102 according the method described in the previous embodiment of the bone anchor C100. That is, the closure structure C116 is distally displaced relative to the receiver C110 such that the tip C306 is in contact with the rod C118, which is, in turn, in contact with the U-shaped proximal cylindrical surface C200 of the body C190 of the insert C114. It is noted that the closure structure C116 is not in contact with the insert C114 in this particular embodiment of the closure structure C116. With a multi-part closure structure, such as described in the previous embodiment, it may be possible for the closure structure C116 to contact the insert C114.

As seen in FIG. 120, the positioner members C222 are positioned within the expansion chamber C154 and the tab members C236 are positioned within the recess C212 such that proximal displacement of the insert C114 is restricted. The protrusion C150 of the insert C114 is positioned within the lower notch C148 of the receiver C110, as seen in the figures. The inner spherical surface C214 (not seen in FIG. 120) may be in contact with the proximal end C218 of the shank C102 (e.g., proximal spherical segment C244) and the outer bearing surface C272 of the retainer C112 may be in bearing contact with the inner spherical surface C320 of the spherical segment C312 of the receiver C110. As seen in the figure, the shank C102 and retainer C112 combination is prevented from distally displacing out of the distal opening C180 because a diameter of the retainer C112 on the shank C102 is wider than the cylindrical diameter CD2, as shown in FIG. 119, of the distal opening C180.

Accordingly, as seen in FIG. 121, the multi-planar bone anchor C300 may rotate or angle in a plurality of directions and planes, where the degree of rotation is constant in all planes and directions. For example, as seen in FIG. 121, the longitudinal axis CLAXS of the shank C102 is angled relative to the longitudinal axis CLAXR of the receiver C110 by an angle CA4, which may be about 30 degrees in a transverse plane (i.e., assuming the rod C118 is extending along a sagittal plane). In certain embodiments, the angle CA4 may be about 20 degrees. In certain embodiments, the angle CA4 may be about 25 degrees. In certain embodiments, the angle CA4 may be about 35 degrees. In certain embodiments, the angle CA4 may be about 40 degrees.

Figure 122:
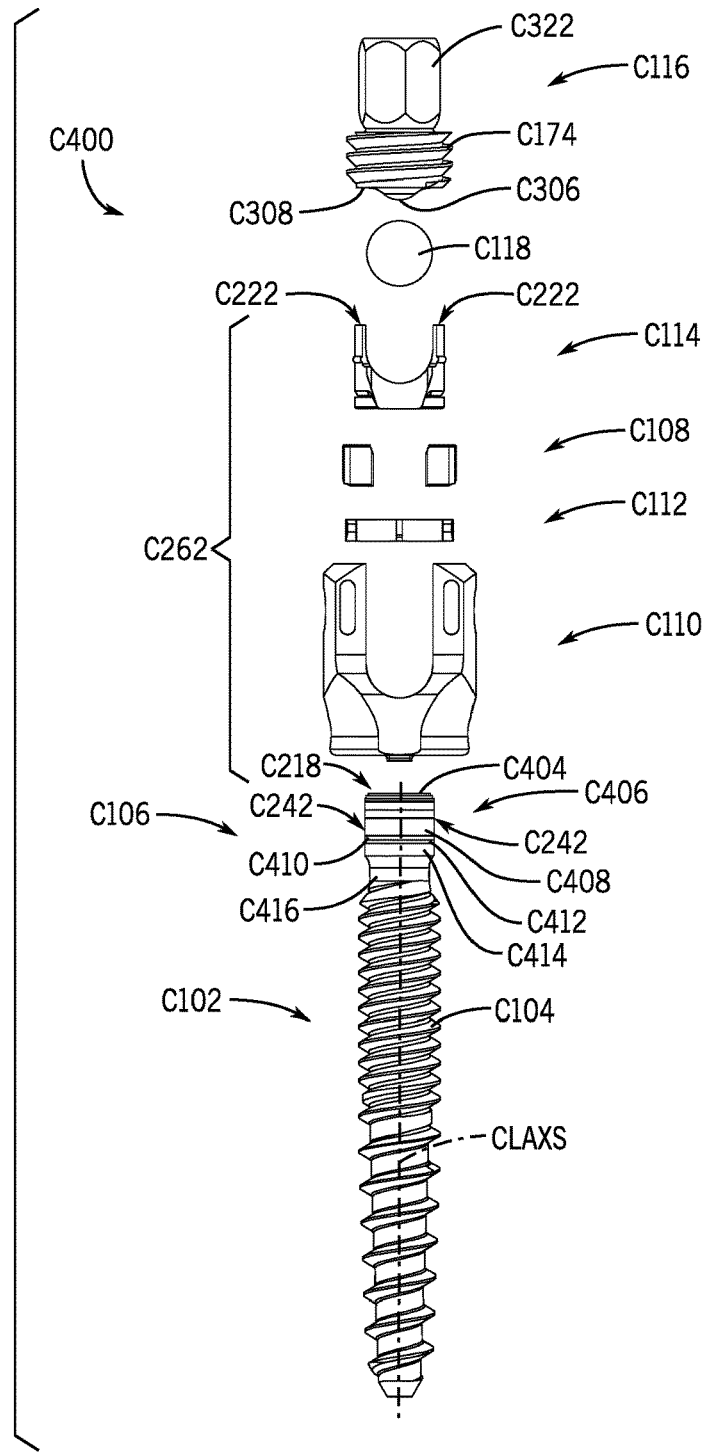

Reference is made to FIG. 122, which depicts another embodiment of a bone anchor C400 with a head assembly C262 that may be interchangeable with any of the universal shanks C102 discussed herein. The head assembly C262 of the bone anchor C400 of FIG. 122 may be a mono-planar or uni-planar assembly that limits movement or angling of the shank C102 to a single plane (e.g., sagittal plane). The retainer C112 and the receiver C110 may be configured to allow angling of the shank C102 in a single plane, as will be discussed subsequently.

As seen in FIG. 122, the insert C114 and the rod C118 are substantially the same as the previously described embodiment of the bone anchor C300 discussed in reference to FIGS. 118-121.

The shank C102 is similar to the shank of previously described embodiments described in reference to FIGS. 3, 5, 12, 14, and 16, among others. In particular, the shank C102 includes a top surface C404 that is substantially perpendicular to the longitudinal axis CLAXS of the shank C102. The proximal end C218 is substantially smooth with the exception of a stepped or graduated upper surface portion C406 located adjacent to the top surface C404 and sized and shaped for cooperation and ultimate frictional engagement with the compression insert C114. In the illustrated embodiment of assembly C400, the upper surface portion C406 includes at least three graduated cylindrical surfaces disposed substantially parallel to the longitudinal axis CLAXS of the shank C102 and adjacent perpendicular step surfaces that are disposed generally perpendicular to the longitudinal axis CLAXS. It is foreseen that the upper surface portion C406 may include greater or fewer number of stepped surfaces and that the stepped surfaces be further structure rather than carved into the proximal end C218 of the shank C102.

The shank C102 may include a cylindrical capture segment C408 for receiving the retainer C112 thereon. Distal of the cylindrical capture segment C408 is a distal step C410 having a planar proximal surface and a planar lateral surface. Distal of the distal step C410 is a distal cylindrical segment C412, followed distally by a distal spherical segment C414 and cylindrical neck section C416.

As seen in FIG. 122, the closure structure C116 is similar to the closure structure described in reference to FIGS. 16-18. It is noted that any of the closure structures C116 described herein may be used with any of the embodiments of the bone anchor. The closure structure C116 in FIG. 122 includes an external surface C174 with a thread feature that may be threadably engaged with the threaded section C140 of the receiver C110. The closure structure C116 also includes a distal tip C306, distal planar surface C308, and a gripping portion C322, which may be a break-away head, as described in previous embodiments.

Figure 123:
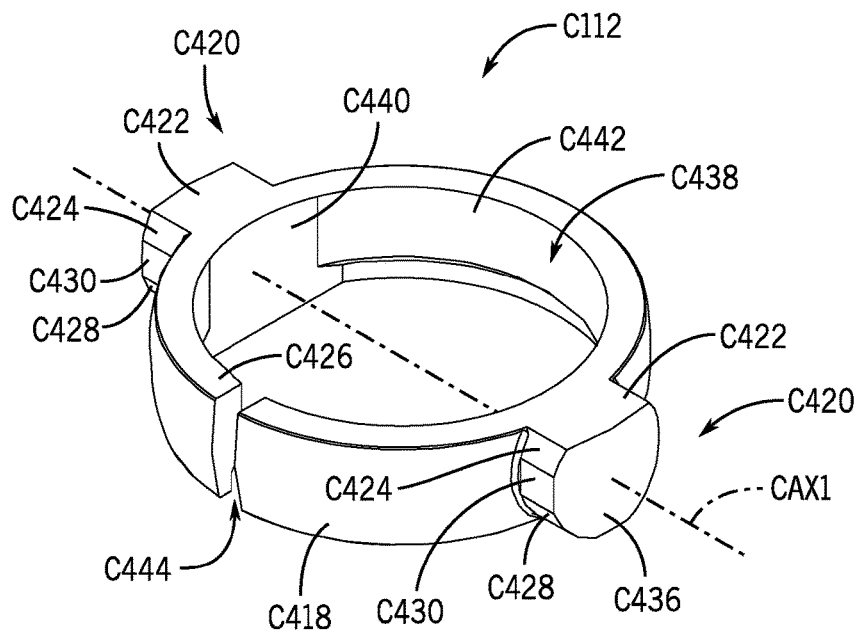
Figure 124A:
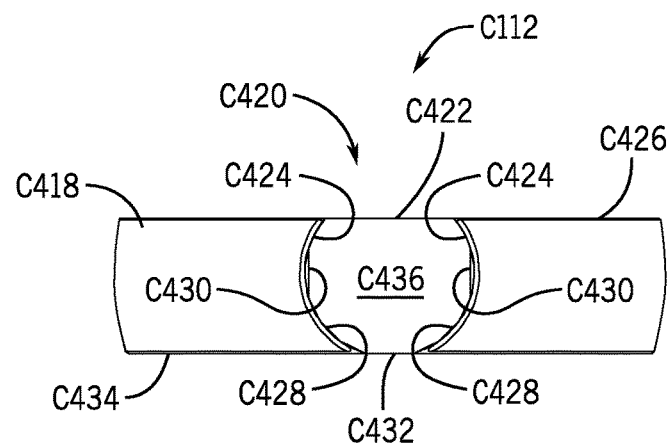

Reference is made to FIG. 123, which is an isometric view of the retainer C112. As seen in the figure, the retainer C112 includes a discontinuous circular band having a spherical external surface C418 having a pair of oppositely oriented pegs, rod ends, or axles C420 extending out from the external surface C418 and defining an axis CAX1 through the pegs C420. As seen in FIG. 124A, which is a side view of the retainer C112, each of the pegs C420 includes a planar proximal surface C422 that is generally parallel with a proximal surface C426 of the retainer C112. The retainer C112 further includes a pair of proximal cylindrical surfaces C424 and a pair of distal cylindrical surfaces C428 that are truncated by a pair of planar medial surfaces C430. The pair of distal cylindrical surfaces C428 are also truncated on a distal side by a planar distal surface C432 that is generally parallel or in plane with a planar distal surface C434 of the retainer C112. The faces C436 of the pegs C420 may be planar.

Opposite the external surface C418 is an inner surface C438 with planar surfaces C440 opposite the pegs C420 and cylindrical surfaces C442 extending between the planar surfaces C440. The cylindrical surface C442 includes an in-cut step C444 near the proximal surface C434 that is sized and shaped to receive a portion of the shank capture structure C106. The planar surfaces C440 of the inner surface C438 of the retainer C112, when coupled with the proximal end C218 of the shank C102, may abut the flat sides C242 of the shank C102.

Figure 124B:
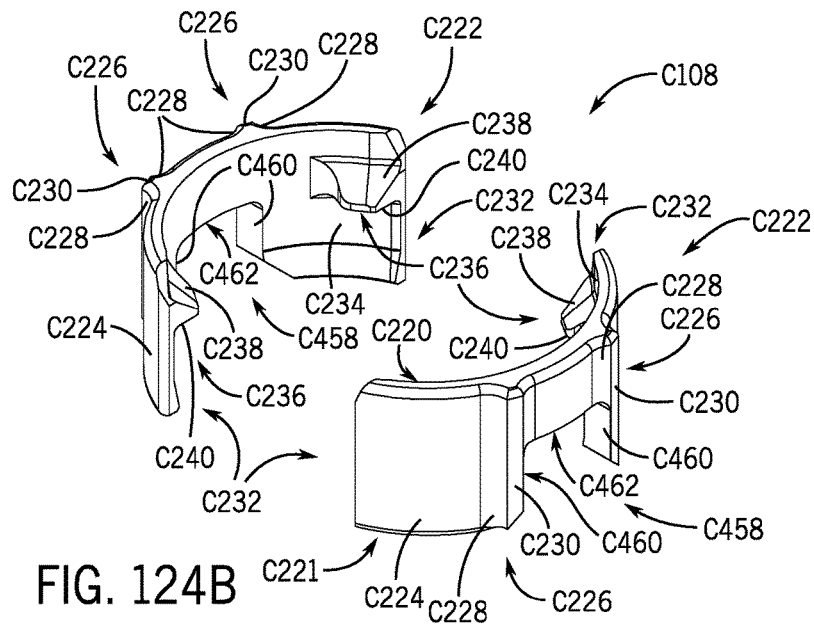
Figure 124C:
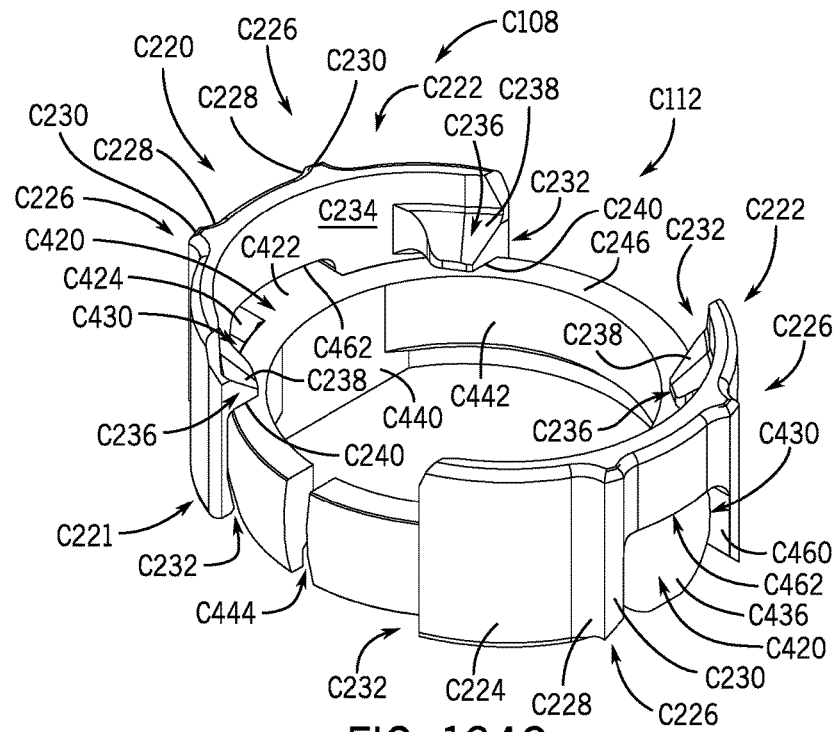

Reference is made to FIGS. 124B and 124C, which are, respectively, an isometric view of the positioner C108 and an isometric view of the positioner C108 adjacent the retainer C112. As seen in FIG. 124b, the positioner C108 is similar to the previously described embodiments of the positioner C108 except that each of the positioner members C222 includes an opening C458 extending from the inner surface C234 to the external surface C224 and extending between the ridges C226. The opening C458 extends to the distal end C221 so as to define a pair of planar lateral side surfaces C460 and a planar proximal side surface C462. As seen in FIG. 124C, when the retainer C112 is engaged with the positioner C108 during, for example, assembly of the head assembly C262, the planar proximal side surface C462 of each of the positioner members C222 may abut or be positioned adjacent the planar proximal surface C422 of the pegs C420 of the retainer C112, and the planar lateral side surfaces C460 of the positioner members C222 may abut or be positioned adjacent the pair of planar medial surfaces C430 of the pegs C420 of the retainer C112. Additionally, the proximal surface C426 of the retainer C112 may abut or be positioned adjacent the planar distal surfaces C240 of the tab members C236 of the positioner members C222. In this way, the tab members C236 and the planar proximal side surfaces C462 of the positioner members C222 may restrict or prevent proximal displacement of the retainer C112, once the positioner C108 is secured in the expansion chamber C154 of the receiver C110.

Reference is made to FIG. 125-126, which are, respectively, cross-sectional front and isometric views of the receiver C110. The receiver C110 may be similar to the embodiment described in reference to FIGS. 118-121 in that the receiver C110 includes a threaded section C140, a cylindrical throat section C142 having an upper notch C144 and a lower notch C146. Distal of the throat section C142 is the expansion chamber C154 for housing the positioner members C222 (not shown). Distal of the expansion chamber C154, and partially extending into the cylindrical surface C156 and the distal planar step C160 of the expansion chamber C154 are a pair of bores C446 extending from the inner spherical surface C320 of the spherical segment C312 to an outer surface C448 of the receiver C110. The pair of bores C446 are coaxial to each other and sized and shaped to fit or support the pegs C420 of the retainer C112 therein. The bores C446 include a cylindrical surface C450 including a diameter that is slightly larger than a diameter of the pegs C420 extending between the proximal cylindrical surface C424 and an oppositely oriented one of the distal cylindrical surfaces C428, of the retainer C112 as seen in FIGS. 123 and 124A, so as to allow pegs C420 of the retainer C112 to rotate within the bores C446.

Extending between the bores C446 is the spherical segment C312 having the spherical bearing surface C320 for supporting and contacting at least one of the outer surface C418 of the retainer C112 and the distal spherical segment C414 of the shank C102. Distal of the spherical segment C312 is a distal cylindrical segment C314 having a pair of inwardly projecting guide members C452 having an inward oriented planar face C454 that may be adjacent, abut, or contact the flat sides C242 of the proximal end C218 of the shank C102. The inwardly projecting guide members C452 are positioned distally of the bores C446. In this way, the shank C102 may be oriented to be received within the receiver C110 in one of two orientations (i.e., each orientation being 180 degrees from each other). In each orientation, the flat sides C242 of the shank C102 may be positioned to be adjacent or abut the planar faces C454 of the inwardly projecting guide members C452. When the proximal end C218 of the shank C102 is coupled with the retainer C112 and the pair are positioned within the receiver C110, the spherical external surface C418 of the retainer C112 and/or a portion of the proximal end C218 of the shank C102 may be in bearing contact with the inner spherical surface C320 of the spherical segment C312 of the receiver C110. The inwardly projecting guide members C452 and the pegs C420 may restrict the shank C102 from angling relative to the head assembly C262 outside of a single plane. In this particular embodiment, the shank C102 may rotate about the axis CAX1 extending through the pegs C420 and in a plane that is generally parallel with a plane defined by the flat sides C242 of the shank C102. And since a longitudinal axis of the rod C118 may lie within the same plane as the movement of the shank C102, the bone anchor C400 may be considered a sagittal mono-planar or uni-planar bone anchor C400. It is noted, that an axis CAX2 extending through the bores C446 is generally coaxial with the axis CAX1 extending through the pegs C420, when the retainer C112 is positioned within the receiver C110 such that the spherical external surface C418 of the retainer C112 is in bearing contact with the inner spherical surface C320 of the spherical segment C312 of the receiver C110.

Referring still to FIGS. 125-126, the distal planar surface C318 of the receiver C110 includes a pair of distal projection C456 that are oriented orthogonally from the inwardly projecting guide members C452. The pair of distal projections C456 may contact a portion of the proximal end C218 of the shank C102 when the shank C102 is at its maximum angle and, thus, prevent further angling of the shank C102 relative to the head assembly C262.

It is noted that the shanks C102 in the previously described embodiments of the bone anchor may be the same universal shank, and may be configured to be received within any of the head assemblies C262 described herein. For example, the same shank C102 (e.g., in FIGS. 94-95, in FIG. 118, in FIG. 122) may be used with a suitable retainer C112 to operably couple with the head assembly C262 of any of FIG. 105, 120, or 122. In this way, a medical professional may choose to couple a universal shank C102 with a particular head assembly C262 that is a multi-planar favored angle head assembly C262 as shown in FIG. 105, a multi-planar head assembly C262 as shown in FIG. 120, or a mono-planar head assembly C262 as shown in FIG. 122.

The following discussion will focus on assembling the various components of the bone anchor C400. The previous discussion of assembling the bone anchor is applicable and may be similar to the steps described subsequently. To begin, reference is made to FIG. 127, which is a front view of the insert C114, the positioner C108, and the retainer C112 positioned within the receiver C110, which is viewed in cross-section. As seen in the figure, the retainer C112 may be distally delivered into the receiver C110 from the proximal end C138 of the receiver C110 and positioned such that the pegs C420 of the retainer C112 are supported by the cylindrical surface C450 of the bores C446 and the spherical external surface C418 of the retainer C112 is supported by the spherical surface C320 of the spherical segment C312 of the receiver C110.

Next, the positioner members C222 of the positioner C108 may be positioned within the receiver C110 via the proximal end C318 and positioned in the expansion chamber C154 such that the ridges C226 abut or lie adjacent the inner cylindrical surface C156 of the expansion chamber C154. The retainer C112 may be proximally displaced such that it is supported by the positioner members C222 in the manner as shown and described in reference to FIG. 124C and also shown in FIG. 128. It is noted that the retainer C112 may be narrow enough to fit within the expansion chamber C154 when the pegs C420 of the retainer C112 are positioned within the openings C458 of the positioner members C222.

Next, the insert C114 may be distally displaced relative to the receiver C110 until the protrusion C150 of the insert is received within the upper notch C144 of the receiver C110. This is the shipping orientation or shipping state of the head assembly C262. At this point, among other points of assembly, the head assembly C262 may be packaged individually or in combination with other head assemblies or shanks C102 and delivered to a medical facility.

As seen in FIG. 129, the proximal end C218 of the shank C102 may be aligned with and received through the distal opening C180 of the receiver C110. As discussed previously, the flat sides C242 of the proximal end C218 of the shank C102 may be oriented parallel to and opposed to the planar faces C454 of the inwardly projecting guide members C452. Once in this orientation, the shank C102 may be proximally displaced relative to the receiver C110 such that the retainer C112 is coupled to or snapped onto the capture structure C106 of the proximal end C218 of the shank C102, as seen in FIG. 129. In this orientation, the retainer C112 is supported in position by the tab members C236 of the positioner members C222 and the positioner members C222 are prevented from proximal displacement by the proximal planar step C158 of the expansion chamber C154 contacting the proximal side edge 266 of the positioner members C222.

Once the shank capture structure C106 is coupled with the retainer C112, the shank C102 and retainer C112, now coupled, may be distally displaced relative to the receiver C110, as seen in FIG. 130. As seen in the figure, the positioner members C222 remain in the expansion chamber C154 as it may prevent proximal displacement of the retainer C112 while allowing distal displacement. When distally displaced, the pegs C420 of the retainer C112 may be caused to be positioned within the bores C446, and the outer spherical surface C418 of the retainer and/or spherical surfaces of the proximal end C218 of the shank C102 may be positioned adjacent or abutting the spherical inner surface C320 of the spherical segment C312 (not shown in FIG. 130) of the receiver C110.

Next, the insert C114 may be distally displaced relative to the receiver C110, as seen in FIG. 131, which depicts the positioner members C222 in a state of expansion. As the insert C114 is distally displaced, a distal edge C464 of the insert C114 exerts a force on the ramped surface C238 of the tab members C236, which causes the radial ends C232 to expand outwardly and into the expansion chamber C154 until a tip C466 of the tab members C236 contacts and rides along an outer surface C468 of the insert C114, as seen in FIG. 131. As the insert C114 is distally advanced further, as seen in FIG. 132, the tab members C236 may compress and engage with the recess or notch C212. At this point, proximal retraction of the insert C114 may be limited or restricted because of the positioner members C222 being constrained from movement (i.e., proximal or distal) by the proximal and distal planar steps C158, C160 of the expansion chamber C154. It is also noted that, when the insert C114 is coupled with the positioner C108, the protrusion C150 is now received within the lower notch C148.

Reference is made to FIGS. 133 and 134, which depict, respectively, side views of the mono-planar bone anchor C400 with the shank C102 in a first position and a second position, relative to the head assembly C262. As seen in FIG. 133, the longitudinal axis CLAXS of the shank C102 is generally parallel and coaxial with the longitudinal axis CLAXR of the receiver C110. As seen in the figure, the proximal and distal cylindrical surfaces C424, C428 of the pegs C420 are positioned adjacent the cylindrical inner surface C450 of the bores C446. As described previously, the spherical inner surface C320 of the spherical segment C312 (not seen in FIGS. 133, 1334) may be in bearing contact with the external surface C418 of the retainer C112 and/or the proximal end C128 of the shank C102. And, as long as angling of the shank C102 is about the axis CAX1 extending through the pegs C420, the proximal and distal cylindrical surfaces C424, C428 of the pegs C420 may not provide bearing support for the retainer C112 to rotate. That is, in certain embodiments, the bearing support for the retainer C112 and shank C102 may be only the spherical inner surface C320 of the spherical segment C312 of the receiver C110 when angling of the shank C102 is within the single plane of unrestricted motion.

In these embodiments, when the shank C102 is attempted to angle outside the plane of allowable or unrestricted motion, the flat sides C242 of the shank C102 may contact one or both of the planar faces C454 of the inwardly projecting guides C452, and the proximal and/or distal cylindrical surfaces C424, C428 of the pegs C420 may also contact the cylindrical surfaces C450 of the bores C446. In this way, both of the inwardly projecting guides C452 and the bores C446 may act on the pegs C420 of the retainer C112 and the shank C102, respectively, to limit motion/angling of the shank C102 to a single plane. Additionally, as seen in FIG. 132, for example, when the shank C102 is attempted to angle outside the plane of allowable or unrestricted motion, the flat sides C242 of the shank C102 may contact one or both of the planar faces C454 of the inwardly projecting guides C452. In this instance, the point of contact between the shank C102 and the inwardly projecting guides C452 may act as a point of rotation, which causes the proximal end C218 of the shank C102 to want to be rotated about this point, instead of its normal point of rotation within the receiver C110. This new point of rotation may cause the proximal end C218 of the shank C102 to be pushed against an inner surface of the receiver C110 (e.g., surface C450 of the bores C446), which causes a lateral force (i.e., generally perpendicular to the longitudinal axis CLAXR of the receiver C110) that tends to want to spread apart the distal opening C180 of the receiver C110. Including the pegs C420 on the retainer C112 may tend to convert this lateral force into a vertical or distal force, via the proximal and/or distal cylindrical surfaces C424, C428 of the pegs C420 contacting the cylindrical surfaces C450 of the bores C446, which has less of a tendency to cause splay or spreading apart of the distal opening C180 of the receiver C110. Thus, the collective effort of the pegs C420 and its contact with the surface C450 of the bores C466 may be to convert out of plane motion into a downward force vector, which would otherwise cause a lateral force vector tending to spread apart or splay the distal opening C180 of the receiver C110.

In certain embodiments, the proximal and distal cylindrical surfaces C424, C428 of the pegs C420 may be in bearing contact with the cylindrical surfaces C450 of the bores C446.

Reference is made to FIG. 134, which depicts the longitudinal axis CLAXS of the shank C102 angled relative to the longitudinal axis CLAXR of the receiver C110 by an angle CANS, which may be about 20 degrees. In certain embodiments, the angle CANS may be about 10 degrees. In certain embodiments, the angle CANS may be about 15 degrees. In certain embodiments, the angle CANS may be about 25 degrees. In certain embodiments, the angle CANS may be about 30 degrees. As seen in FIG. 134, when the shank C102 is pivoted the angle CANS about the axis CAX1, the distal projection C456 may contact the proximal end C218 of the shank C102 at, for example, the cylindrical neck section C416. In this way, the distal projection C456 may restrict or limit angling or pivoting of the shank C102 within the plane of allowable motion. FIG. 135 is a non-close-up view of FIG. 134 depicting the entire shank C102, head assembly C262, rod C118, and closure structure C116. The rod C118 and closure structure C116 may be engaged with the head assembly C262 as previously described. As seen in the figure, a longitudinal axis CLAXD of the rod C118 is within the allowable plane of motion/angling of the shank C102. Thus, in the context of surgical bone screws or, more particularly, spinal bone screws, the bone anchor C400 of the figure may be considered a sagittal mono-planar bone screw C400.

It is noted that the head assemblies C262, containing the receivers C110, positioners C108, retainers C112, and inserts C114, discussed in the present disclosure may be combined into a kit. For example, as seen in FIG. 136, the head assemblies C262 described in reference to FIGS. 105, 120, and 128 may be packaged together in a kit C500. The kit C500 may include, for example, multiple head assemblies C262x, C262y, C262z, instructions C502, and packaging C504. Head assembly C262x may be a favored angle multi-planar assembly that may couple with a universal shank C102. Head assembly C262y may be a multi-planar assembly that may couple with the universal shank C102. Head assembly C262z may be a mono-planar assembly that may couple with the universal shank C102. The kit C500 may be packaged with the shanks C102, or the shanks C102 may be packaged separately in another kit. By packaging multiple head assemblies C262 of different varieties C262x, C262y, C262z together in a kit C500 that is separate from the universal shanks C102, the total number of assembled bone anchors may be reduced because the bone anchors may be assembled as needed instead of having all of the bone anchors fully, pre-assembled. It is noted that the discussion of the various embodiments of the head assemblies C262 described various different shank capture structures C106 of the shank C102, as well as differently configured retainers C112. For example, conical, spherical, and cylindrical shank capture structures C106, among others, are discussed herein. And, corresponding conical, spherical, and cylindrical retainers C112, among others, were also discussed. These are merely examples of capture structures C106 and mating retainers C112. The kits C500 of multiple head assemblies C262 may include retainers C112 having the same or similar inner surface features (e.g., conical, spherical, cylindrical, curvate, stepped) such that any of the head assemblies C262x, C262y, C262z may be coupled with a universal shank C102 having a corresponding capture structure C106 (e.g., conical, spherical, cylindrical, curvate, stepped). For example, all retainers C112 in the head assemblies C262x, C262y, C262z of the kit C500 may be retainers C112 with conical inner surfaces (e.g., such as shown in FIGS. 72-75 and 94-95). The universal shanks C102 in such an example may include corresponding capture structures C106 that are conical (e.g., FIGS. 64-65 and 94-95). As another example, all retainers C112 in the head assemblies C262x, C262y, C262z of the kit C500 may be retainers C112 with spherical or curvate inner surfaces (e.g., such as shown in FIG. 22). The universal shanks C102 in such an example may include corresponding capture structures C106 that are spherical or curvate (e.g., FIG. 21).

The instructions C502 may be included within the packaging C504, on the packaging C504, or may be included outside the packaging C504. Alternatively, the instructions C502 may be provided electronically, for example, online and possibly downloadable via a website. The packaging C504 may be vacuum sealed packaging and may be see-through. A tray (not shown) may optionally be included with the kit C500.

Reference is made to FIG. 137, which depicts an isometric view of another embodiment of a receiver C600 having a pair of break-off reduction tabs C602. The receiver C600 is the same as the receiver C110 shown in FIGS. 94-96B, except the upwardly extending arms C134, C136 are respectively coupled with the break-off reduction tabs C602. As seen in FIG. 137, the break-off reduction tabs C602 are coextensive with the upwardly extending arms C134, C136 and include a cylindrical bore C604 and a threaded section C606 that cooperates with the threaded section C140 of the receiver C600 such that a closure structure C116, as seen in FIG. 138, among others, may be continually and threadably engaged through the threaded section C606 of the break-off reduction tabs C602 and into engagement with the threaded section C140 of the receiver C600. Once the closure structure C116 is distally advanced or displaced against a rod (not shown) such that the closure structure C116 is positioned within the threaded section C140 of the receiver C600, the break-off reduction tabs C602 may be snapped, broken, or cut off at the break line C610. The break line C610 may be a reduced thickness between the outer surface C448 of the receiver C600 and the inner threads of the threaded sections C606, C140.

Such a receiver C600 may be useful during a particular medical procedure to provide a mechanical advantage when bending and positioning the rod within the U-shaped channels C168. Thus, the rod may initially be positioned at any distal-proximal position between the upwardly extending arms C134, C136 or the break-off reduction tabs C602. Then, the closure structure C116 may be threadably engaged with the threaded section C606 of the break-off reduction tabs C602 and distally advanced until the closure structure C116 begins to contact and force the rod distally. Further distal displacement of the closure structure C116 may cause the rod to be further distally displaced until the rod is fully seated at the base of the U-shaped channel C168.

As seen in FIG. 138, which is an isometric view of the closure structure C116, the structure includes the outer fastener C164 and the inner set screw C166. The set screw C166 includes an inner feature C168 (not shown in FIG. 138), such as an inner hexagonal faceted surface, for engaging with a tooling head (not shown) to rotationally and distally-proximally displace the set screw C166 relative to the outer fastener C164. The outer fastener C164 cooperates with the receiver C600 and the break-off reduction tabs C602, of FIG. 137, of a bone screw assembly to close the head U-shaped channel C168 and to clamp the spinal fixation rod within the bone screw head or receiver C600. The outer fastener C164 includes the structure C170 with slots C172 sized and shaped for engagement with a suitable tool (not shown) for installing the outer fastener C164 to the bone screw head or receiver C110. Thereafter, the inner set screw C166 is displaced until the distal end C608 of the set screw C166 contacts the rod C118. As seen in FIG. 138, the distal end C608 of the set screw C166 may include a bottom surface C612 that extends entirely across a diameter thereof. In certain embodiments, as seen in the figure, the bottom surface C612 may be flat, or may include another surface profile.

Reference is made to FIG. 139, which depicts an isometric view of another embodiment of a head assembly C702 of a bone anchor that facilitates mono-planar or uni-planar motion of a shank coupled with the head assembly C702. The head assembly C702 includes a receiver C110, a retainer C112, and a multi-piece positioner C108. The retainer C112 is similar to the retainer C112 discussed in reference to FIGS. 122-124A, among others, in that it includes a pair of pegs, protrusions, or members C420 extending from opposite sides of the exterior surface C418 of the retainer C112. The pegs C420 in the present embodiment are proximally offset (i.e., not centered) from the proximal and distal surfaces C426, C434 such that the proximal surface C426 is recessed from the proximal surface C422 of the pegs C420.

As seen in FIG. 140A, which is an isometric view of the positioner C108, it includes two positioner members C222 that may be mirror images of each other. That is, in certain embodiments the positioner members C222 may not be identical, but may be mirror images of each other. Each of the positioner members C222 may include a convex, cylindrical outer surface C224 and a concave, cylindrical inner surface C234 opposite the outer surface C224. Each positioner member C222 also includes a pair of tab members C236 extending from the inner surface C234 and positioned at the radial ends C232. The positioner members C222 of the present discussion differ from the positioner members C222 discussed in reference to FIGS. 98-99 in that they include a rib, ridge, or member C704 on the inner surface C234 that extends from a proximal edge C706 to a distal edge C708. As seen in FIG. 140A, the ribs C704 are positioned closer to one of the radial ends C232 in a mirror image fashion. The ribs C704 may contact or abut a portion of the retainer C112, as seen in FIG. 140B, when positioned adjacent each other (e.g., in the shipping state), and inhibit or prevent rotation of the retainer C112 within the receiver C110. Because of the mirror image nature of the positioner members C222, rotation of the retainer C112 is inhibited or prevented in two directions, as evident in FIG. 140B. On the external surface C224 of each positioner member C222 and positioned centrally between the radial ends C232 is a protrusion C710 extending normally or generally perpendicularly from the external surface C224. As seen in FIGS. 140A-140B, the protrusion C710 is rectangular in shape with a distal surface C712, a pair of lateral surfaces C714 opposite each other and adjacent the distal surface C712, a proximal surface C715 opposite the distal surface C712, and a medial surface C713.

During assembly of the head assembly C702, each of the protrusions C710 of the positioner members C222 may be press-fit or interference fit with opposing sides of a slot or bore C716 in the receiver C110. That is, the positioner members C222 may be mechanically coupled or fastened together with the receiver C110 by the protrusions C710 being pushed or forced through the slots C716. Once the protrusions C710 are positioned within the slots C716, the positioner members C222 are effectively coupled and are prevented from being uncoupled due to the interference fit. In certain embodiments, the positioner members C222 may be uncoupled from the press-fit with the receiver C110. As seen in FIG. 139, the slots C716 are pill or stadium shaped with semi-cylindrical distal and proximal ends and parallel sides extending between the semi-cylindrical ends. Other shapes, however, are possible and contemplated herein.

Reference is made to FIG. 141, which is an isometric cross-sectional view of the receiver C110 with the positioner members C222 positioned within the receiver C110. As seen in the figure, the receiver C110, and the head assembly C262 generally, is similar to the receiver C110 described in reference to FIGS. 125-135 in that it may facilitate monoplanar motion of a universal shank coupled with the head assembly C262. Moving proximal to distal, the receiver C110 may include a threaded section C140, a cylindrical throat section C142, an expansion chamber C154, a spherical segment C312 having a spherical bearing surface C320, and a cylindrical segment C314 that daylights into the distal opening C180. In addition to providing a press-fit between the protrusions C710 and the receiver C110, the slots C716 in the receiver C110 also function to support the pegs C420 of the retainer C112, as similarly described in reference to FIGS. 125-135. More particularly and as seen in FIG. 143, which is an isometric view of the bone anchor C700 with the receiver C110 viewed in cross-section and the rod hidden from view, the pegs C420 of the retainer C112 may be supported on a distal portion C718 of the slots C716 while the protrusions C710 of the positioner C108 may be press-fit to the receiver C110 on a proximal portion C720 of the slots C716. The protrusions C710 may additionally encourage expansion of the positioner members C222 to be on either side of the protrusions C710 and at the radial ends C232.

Referring back to FIG. 141, assembly of the head assembly C262 may involve the positioner members C222 of the positioner C108 being received within an inner volume of the receiver C110 through the proximal end C318 and into the expansion chamber C154 such that the protrusions C710 are received within the slots C716 in a press-fit manner. This may be accomplished by a machine or by hand. Next, the retainer C112 may be delivered into the inner volume of the receiver C110 via the proximal end C318, as seen in FIG. 142, which is an isometric cross-sectional view of the receiver C110 with the positioner members C222 and the retainer C112 positioned with in the receiver C110. This is the shipping state or shipping orientation of the head assembly or receiver assembly/subassembly C262. At this point, the head assembly C262 is ready and configured to couple with a universal shank C102, shown in FIG. 143. The head assembly C262, as shown in FIG. 142, may be coupled with other head assemblies C262 described herein to form a kit. While the assembly is described as first delivering the positioner C108 into the receiver C110, followed by the retainer C112, the assembly may involve initial delivery of the retainer C112 into the receiver, followed by delivery of the positioner C108 into the receiver C110.

As seen in FIG. 142, the tab members C236 of the positioner members C222 abut or contact the proximal edge C260 of the retainer C112 and prevent or inhibit the retainer C112 from displacing proximally within the receiver C110. And, the ribs C704 on the inner surface C234 of the positioner C222 abut or contact the pegs C420 of the retainer C112 and prevent or inhibit rotation of the retainer C112 within the receiver C110. Additionally, the positioner members C222 maintain axial alignment of the retainer C112 (i.e., by inhibiting or preventing proximal displacement) such that it is in position to receive the proximal end of a shank so as to couple with a shank capture structure of the shank.

As seen in FIG. 143, the shank C102 may be coupled with the head assembly C262 to form the bone anchor C700. The shank C102 may be any universal shank described herein or otherwise known in the art. Coupling of the shank C102 with the head assembly C262 may be accomplished via similar methods described previously. In general, the proximal end C218 of the shank C102 having the capture structure C106 may be bottom-loaded through the distal opening C180 of the receiver C110 so as to expand the retainer C112 and the positioner C108 (e.g., the radial ends C232) and cause the retainer C112 to snap-on or couple with the capture structure C106 of the shank C102 thereby preventing the shank C102 from distally exiting the distal opening C180 of the receiver C110. The retainer C112 may limit motion or angling of the shank C102 to a single plane of motion, similar to the retainer C112 and receiver C110 described in reference to FIGS. 122-135. That is, when movement of the shank C102 is attempted outside of the plane of allowable motion/ angling, the pegs C420 of the retainer C112 may come into contact with the inner surface C450 of the slots C716 and, thus, prevent the shank C102 from such motion/angling. The retainer C110 may additionally include inwardly projecting guide members, as described in previous embodiments, to aid in limiting the shank C102 to motion in a single plane.

Once the shank C102 is coupled with the retainer C112, a rod (not shown in order to see the other portions of the assembly) may be positioned within the U-shaped channels C168 in the receiver C110 and driven distally via the closure structure C116 until the surface of the rod is in contact with the proximal end C218 of the shank C102 so as to prevent further adjustment of the shank C102 relative to the head assembly C262. That is, the bone anchor C700 may not include an insert, such as, for example, the insert C114 described in reference to FIGS. 122 and 128-132. Rather, the rod may contact the top portion of the proximal end C218 of the shank C102 and be secured in place via the closure structure C116, which, as seen in FIG. 143, is a single piece structure with an external surface C174 that is threaded and threadably engages the threaded section C140 of the receiver C110. A distal end of the closure structure C116 may be pointed or flat across a diameter thereof.

Because the positioner members C222 are coupled to the receiver C110 via a press-fit arrangement, they are prevented from displacing within or out of the receiver C110 without an insert C114. And, the positioner members C222 are positioned such that the shank C102 and retainer C112 may rotate or pivot within the confines of the receiver C110 without being obstructed by the positioner members C222. It is foreseen that this type of bone anchor C700 may be suitable for use with an insert, as well.

It is foreseen that other closure structures C116 may be used with the bone anchor C700 without departing from the teachings of the present disclosure. Additionally, receivers C110 and retainers C112 having different geometries and configurations may be used with the positioner members C222, of FIGS. 139-143, to facilitate head assemblies C262 configured for multi-planar or favored angle orientations. Stated differently, although the head assembly C262 of FIGS. 139 and 142-142 is described as facilitating monoplanar motion/angling of a shank C102, other embodiments of a head assembly C262 may similar utilize a positioner C108 that is press-fit with a receiver C110 to facilitate multi-planar or favored angle orientations.

It is noted that features of each of the various embodiments of the bone anchors, including but not limited to the receiver, positioner, retainer, insert, and closure structure, may be combined with other embodiments without limitation.

In general, while the discussion has been described with reference to particular embodiments, modifications can be made thereto without departing from the spirit and scope of the disclosure. Note also that the term "including" as used herein is intended to be inclusive, i.e. "including but not limited to."

It is to be understood that while certain forms of the present disclosure have been illustrated and described herein, it is not to be limited to the specific forms or arrangement of parts described and shown.

What is claimed is:

1. A pivotal bone anchor assembly for securing an elongate rod to a bone, the bone anchor assembly comprising:
    a bone anchor having a capture portion and an integral anchor portion extending distally from the capture portion for fixation to the bone; and
    a receiver assembly in a pre-assembled configuration prior to receiving the capture portion of the bone anchor, the receiver assembly including:
        a receiver comprising a base defining an internal cavity having a bottom opening in communication with a bottom surface of the base and a pair of integral arms extending upwardly from the base to define a U-shaped channel configured to receive the elongate rod, the U-shaped channel being in communication with the cavity and the cavity including an upper portion with a recess having a downwardly-facing surface spaced above the bottom opening;
        a retainer expandable within the receiver cavity recess and having an inner surface operable to capture the bone anchor capture portion;
        a pressure insert disposed within the U-shaped channel and having an upper surface operable to engage the elongate rod; and
        a positioner disposed within the receiver cavity recess and engaged with the retainer to stabilize and centralize the retainer within the receiver cavity recess above the bottom opening,
    wherein, upon insertion of the bone anchor capture portion into the receiver cavity through the bottom opening, the retainer is released from the positioner to allow the retainer inner surface to capture and hold the bone anchor capture portion within the receiver cavity.

2. The bone anchor assembly of claim 1, wherein upon capture of the bone anchor capture portion by the retainer inner surface, the positioner is configured to engage the pressure insert.

3. The bone anchor assembly of claim 1, wherein the positioner further comprises a single piece member.

4. The bone anchor assembly of claim 1, wherein the positioner further comprises a multi-piece member.

5. The bone anchor assembly of claim 1, wherein the retainer is pivotable with respect to the receiver prior to locking the bone anchor assembly.

6. The bone anchor assembly of claim 1, wherein the receiver cavity recess includes an upwardly-facing surface that, together with the downwardly facing surface, engage a bottom surface and a top surface of the positioner, respectively, to restrict axial displacement of the positioner relative to the receiver.

7. The bone anchor assembly of claim 1, wherein a lower portion of the insert is configured to engage an upper portion of the positioner to center the positioner within the cavity when the retainer is stabilized and centralized above the bottom opening.

8. The bone anchor assembly of claim 1, wherein the positioner further comprises at least one flange projecting radially inward from a positioner inner surface.

9. The bone anchor assembly of claim 8, wherein an inner cylindrical surface of the at least one flange is configured to engage an outer surface of the bone anchor capture portion upon insertion of the bone anchor capture portion into the cavity to release the retainer and captured bone anchor capture portion.

10. The bone anchor assembly of claim 8, wherein a bottom surface of the at least one flange is configured to engage a top surface of the retainer when the retainer is stabilized and centralized above the bottom opening.

11. The bone anchor assembly of claim 1, wherein the bone anchor is cannulated.

12. The bone anchor assembly of claim 1, wherein the retainer further comprises a split ring.

13. The bone anchor assembly of claim 1, wherein the positioner further comprises a discontinuous ring structure having a gap extending from an interior surface to an exterior surface.

14. The bone anchor assembly of claim 1, wherein the retainer is non-pivotable with respect to a lower cavity locking portion prior to locking the bone anchor assembly.

15. The bone anchor assembly of claim 14, wherein the lower cavity locking portion further comprises a stepped annular seating surface that engages an annular bottom surface and cylindrical outer surface of the retainer.

16. A pivotal bone anchor assembly for securing an elongate rod to a bone, the bone anchor assembly comprising:
- a bone anchor having a capture portion and an integral anchor portion extending distally from the capture portion for fixation to the bone;
- a receiver comprising a base defining a cavity having a bottom opening in communication with a bottom surface of the base and a pair of integral arms extending upwardly from the base to define a U-shaped channel configured to receive the elongate rod, the U-shaped channel being in communication with the cavity and the cavity having an internal circumferential recess above the bottom opening;
- a retainer expandable within the circumferential recess and having an inner surface operable to capture the bone anchor capture portion; and
- a positioner disposed within the receiver cavity and engaged with the retainer to stabilize and centralize the retainer within the receiver cavity above a lower portion of the cavity adjacent the bottom opening and entirely spaced from internal surfaces of the receiver cavity, prior to receiving the capture portion of the bone anchor,
- wherein, upon insertion of the bone anchor capture portion into the receiver cavity through the bottom opening, the retainer is released from the positioner and moved to the lower portion of the cavity, thereby allowing the retainer inner surface to capture and hold the bone anchor capture portion within the receiver cavity.

17. The bone anchor assembly of claim 16, further comprising a pressure insert disposed within the U-shaped channel and having an upper surface operable to engage the elongate rod.

18. The bone anchor assembly of claim 17, wherein a lower portion of the insert is configured to engage an upper portion of the positioner to center the positioner within the cavity when the retainer is stabilized and centralized above the bottom opening.

19. The bone anchor assembly of claim 17, wherein upon capture of the bone anchor capture portion by the retainer inner surface, the positioner is configured to engage the pressure insert.

20. The bone anchor assembly of claim 16, wherein the circumferential recess includes an upper abutment surface and a lower abutment surface that engage a top surface and a bottom surface of the positioner, respectively, to restrict axial displacement of the positioner relative to the receiver.

21. The bone anchor assembly of claim 16, wherein the positioner further comprises at least one flange projecting radially inward from a positioner inner surface.

22. The bone anchor assembly of claim 21, wherein an inner cylindrical surface of the at least one flange is configured to engage an outer surface of the bone anchor capture portion upon insertion of the bone anchor capture portion into the cavity to release the retainer and captured bone anchor capture portion.

23. The bone anchor assembly of claim 21, wherein a bottom surface of the at least one flange is configured to engage a top surface of the retainer when the retainer is stabilized and centralized above the bottom opening.

24. The bone anchor assembly of claim 16, wherein the positioner prevents the retainer from returning to the recess after capturing the bone anchor upper capture portion and moving to the lower portion of the cavity.

\* \* \* \* \*